United States Patent
Yamamoto et al.

(10) Patent No.: US 6,852,734 B2
(45) Date of Patent: Feb. 8, 2005

(54) INDOLE DERIVATIVES EXHIBITING CHYMASE-INHIBITORY ACTIVITIES AND PROCESS FOR PREPARATION THEREOF

(75) Inventors: Yasuo Yamamoto, Yokohama (JP); Kenzo Hariyama, Yokohama (JP); Yumiko Yanagisawa, Yokohama (JP); Sojiro Shiokawa, Yokohama (JP); Takumi Takeyasu, Hino (JP); Osami Takenouchi, Hino (JP); Hidenori Kasai, Hino (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 0 days.

(21) Appl. No.: 10/275,111

(22) PCT Filed: May 1, 2001

(86) PCT No.: PCT/JP01/03774
§ 371 (c)(1),
(2), (4) Date: Jan. 10, 2003

(87) PCT Pub. No.: WO01/83471
PCT Pub. Date: Nov. 8, 2001

(65) Prior Publication Data
US 2004/0058963 A1 Mar. 25, 2004

(30) Foreign Application Priority Data
May 2, 2000 (JP) ........................................ 2000-133106

(51) Int. Cl.[7] ...................... A61K 31/47; C07D 515/02; C07D 491/02; C07D 215/16; C07D 209/02
(52) U.S. Cl. ...................... 514/312; 546/155; 546/114; 546/120; 548/454; 548/465
(58) Field of Search .................. 514/312; 546/155, 546/114, 120; 548/454, 465

(56) References Cited

U.S. PATENT DOCUMENTS 6,432,978 B1 * 8/2002 Tani et al. .................. 514/312

FOREIGN PATENT DOCUMENTS

| WO | WO 93/25574 | * 12/1993 |
| WO | WO 00/32587 | * 6/2000 |

* cited by examiner

*Primary Examiner*—D. Margaret Seaman
(74) *Attorney, Agent, or Firm*—Stites & Harbison PLLC; B. Aaron Schulman

(57) ABSTRACT

According to this invention, there is provided an indole derivative having the general formula (I)

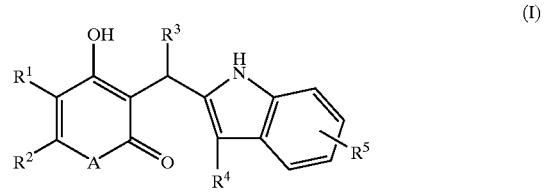

wherein A is an oxygen atom or a nitrogen atom which nitrogen atom is optionally substituted with an alkyl group, and (i) $R^1$ and $R^2$ each stand for a hydrogen atom or an alkyl group, independently, or (ii) $R^1$ and $R^2$ as taken together form a cycloalkyl group or an aromatic ring, or (iii) $R^1$ and $R^2$ as taken together form a heterocyclic ring, and $R^3$ is a hydrogen atom, a $(C_1-C_{10})$alkyl group or others, $R^4$ is a substituted alkyl group and $R^5$ is a hydrogen atom, a halogen atom, an alkyl group or an alkoxy group and so on, as novel compounds by a novel chemical synthetic process. The indole derivative of formula (I) exhibits a useful chymase inhibitory activity.

18 Claims, No Drawings

INDOLE DERIVATIVES EXHIBITING CHYMASE-INHIBITORY ACTIVITIES AND PROCESS FOR PREPARATION THEREOF

TECHNICAL FIELD

This invention relates to a novel indole derivative having a high inhibitory activity to an enzyme, chymase, as well as to a process for the preparation of said indole derivative. This invention further relates to novel synthetic processes for the preparation of SF2809-I, -II, -III, -IV, -V and -VI substances which have earlier been obtained by the inventors of this invention each as a compound having an inhibitory activity to the enzyme chymase.

BACKGROUND ART

The enzyme chymase, which is mentioned simply as chymase sometime hereinafter, is a chymotripsin-like serine protease. Chymase is mainly stored in mast cells and can be secreted in tissues of heart, blood vessel, skin and others. As one of the main actions of chymase, it is known that chymase has such action as to produce angiotensin II from angiotensin I which is a substrate. Angiotensin II is known to exhibit a strong constrictive activity on vascular smooth muscle cells, leading to hypertension and cardiac insufficiency. It has hitherto been thought that the production of angiotensin II is affected mainly by the participation and action of angiotensin-converting enzyme (ACE).

Recently, however, there has been suggested newly that another physiological mechanism exists for the production of angiotensin II in local tissues as induced by serine proteinase, which is different from that by ACE. Reference is made specifically to some reports which reveal that angiotensin II as produced in human heart and blood vessel systems is mainly resulted from the conversion of angiotensin I by a chymase rather than the conversion of angiotensin I by ACE [see "Biochem. Biophys. Res. Coummun.", 1987, No.149, p.1186; and "Circ. Res.", 1990, No.66, p.883]. Other literatures have reported that chymase has many functions, including promotion of the degranulation of mast cell, activation of interleukin-1β, conversion of endoserine, and so on.

In view of these facts, it is expected that a compound capable of inhibiting the enzymatic activity of a human chymase, that is, a human chymase inhibitor is useful as new medicines for the therapeutic or prophylactic treatment of diseases in the cardiovascular system, such as hypertension, cardiac insufficiency, and of allergic diseases such as asthma, rheumatism, atopic dermatitis and others.

Until now, there are known several compounds having a chymase inhibitory activity. For example, we, the inventors of this invention, have already found that the cultivation of a microbial strain, SF2809 of a family *Micromonosporaceae*, which is a new microorganism as isolated by us from a soil sample collected at Hachijo Island, Tokyo, produces six compounds each having a chymase inhibitory activity in the resulting culture. Then, we have succeeded in isolating these six compounds from the culture and determined fully their chemical structures. As a result, we have recognized that all the six compounds are to be novel compounds hitherto unknown, and we have designated them as SF2809-I substance, SF2809-II substance, SF2809-III substance, SF2809-IV substance, SF2809-V substance and SF2809-VI substance, respectively. These SF2809-I, -II, -III, -IV, -V and -VI substances each are compounds which are represented by the following formula (A), formula (B), formula (C), formula (D), formula (E) and formula (F).

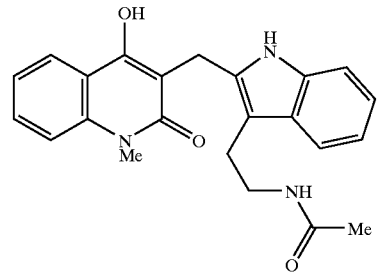

(A)

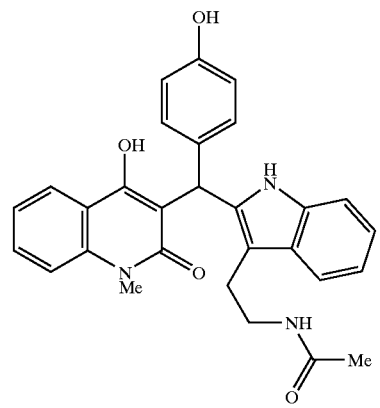

(B)

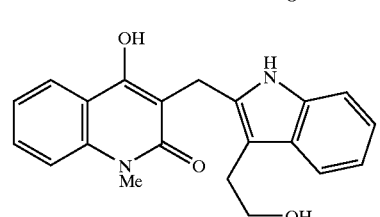

(C)

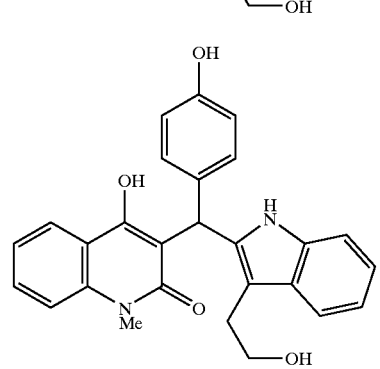

(D)

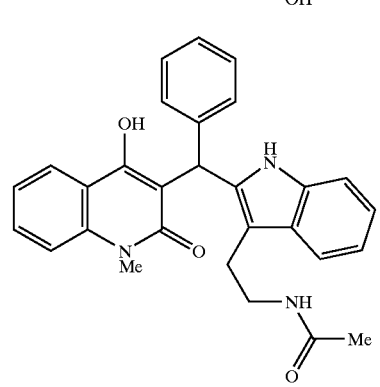

(E)

-continued

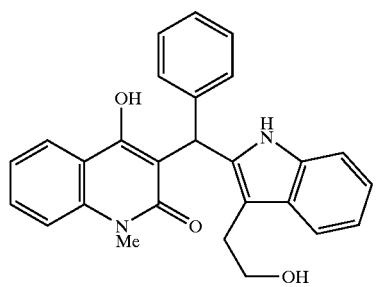

(F)

It has been confirmed that each of the substances SF2809-I, -II, -III, -IV, -V and -VI above-mentioned, as novel compounds, has a chymase inhibitory activity (refer to the specification of PCT application No. PCT/JP99/06738 filed on Dec. 1, 1999 and laid open under an international publication WO 00/32587 on Jun. 8, 2000).

On the other hand, there are disclosed peptide-type compounds having an inhibitory activity to human chymase in the specifications of the publications WO95/27053 and WO95/27055, and non-peptide-type chymase inhibitors in the specifications of the publication WO96/04248 and Japanese Patent Application publication Kokai Hei-10-87567. Furthermore, several chymase inhibitory compounds originated from a microorganism metabolite are disclosed in Japanese Patent Application publication Kokai Hei-10-101666. Up to now, however, these known compounds having a chymase inhibitory activity have not yet been utilized clinically in therapeutic and prophylactic treatments of the various diseases as above-mentioned in which a chymase can participate.

Thus, at present, there occurs a keen demand in the art to provide such new compounds which have a high chymase inhibitory activity with low toxicity against mammals.

While, the chemical structures of SF2809-I, -II, -III, -IV, -V and -VI substances of the formulae (A)-(F) given above, respectively, which have been provided by us, differ from those of the already known chymase inhibitors, and it has been expected that SF2809-I to IV substances are useful as chymase inhibitors usable for elucidation of the mechanism of the chymase inhibitory activity and also for studying the physiological activities other than the chymase inhibitory activity. However, SF2809-I to VI substances which are the metabolic products of a microorganism have such disadvantage that the steps of the process required for their isolation and purification are complicated when the SF2809-I to VI substances are to be isolated from their culture broth of the SF-2809-I to VI-producing microorganism. Another disadvantage is in that the amounts of SF2809-I to VI substances so produced by cultivation of said microorganisms are only very small.

Accordingly, so far as there is used the process for the production of SF2809-I to VI substances by a small scale cultivation of the SF2809 strain belonging to *Micromonosporaceae* as above-mentioned, there necessarily exists such problem that the amount produced of each of SF2809-I to VI substances is much poorer than the amount which will be required to be employed for carrying out further investigations on the progress of chemical syntheses for producing novel derivatives from the SF2809 substances in order to improve their physiological activities and also will be required to be employed for studying the utilizability of the SF2809 substances as a chymase-inhibitor.

It is now strongly demanded to develop and provide such new chemical synthetic processes for producing SF2809-I to VI substances, which can make it possible to produce each of SF2809 substances in ample amount and in an efficient way. However, there was no available chemical process in the prior art which can be utilized directly to develop new chemical synthetic process for producing the SF2809-I to VI substances.

We, the inventors of this invention, have made search in a lot of chemical literature, with our intention of finding out some chemical reactions which are utilizable to create and develop novel processes for chemical synthetic production of the SF2809-I to VI substances. According to this search, we have now found that, in respect of the processes for chemical synthesis of bis-indole derivatives having two indole groups bonded together via a methylene group, there is known a process of synthesizing a symmetric bis-indole derivative of the undermentioned formula (J) in which process two molecules of an indole compound of the undermentioned formula (G) are subjected to a condensation reaction with a benzaldehyde derivative of the undermentioned formula (H) according to the following reaction equation (A):

Reaction Equation (A)

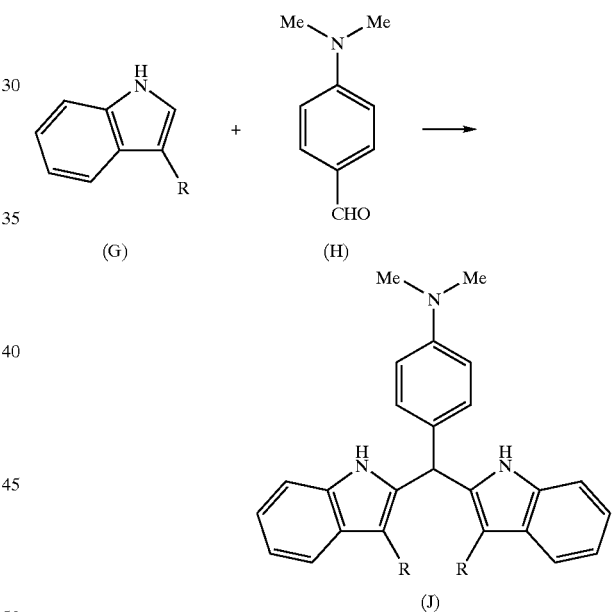

wherein R stands for phenyl group, hydroxymethyl methyl group, formyl group, cyano group, acetyl group, or dimethylaminomethyl group [see Ulf Pindur, "Arch. Pharma." (published from Weinheim), Vol.317, pp.502–505 (1984)].

There is also known a chemical synthetic process for producing a bis-quinol derivative having two 4-hydroxy-1-methyl-2-quinoline moieties bonded together via a methylene group, in which process two molecules of 4-hydroxy-1-methyl-2-quinoline of the undermentioned formula (K) are subjected to a condensation reaction with an imilidene compound of the undermentioned formula (L) so as to synthesize the symmetric bis-quinol derivative of the undermentioned formula (M), according to the following reaction equation (B):

Reaction equation (B)

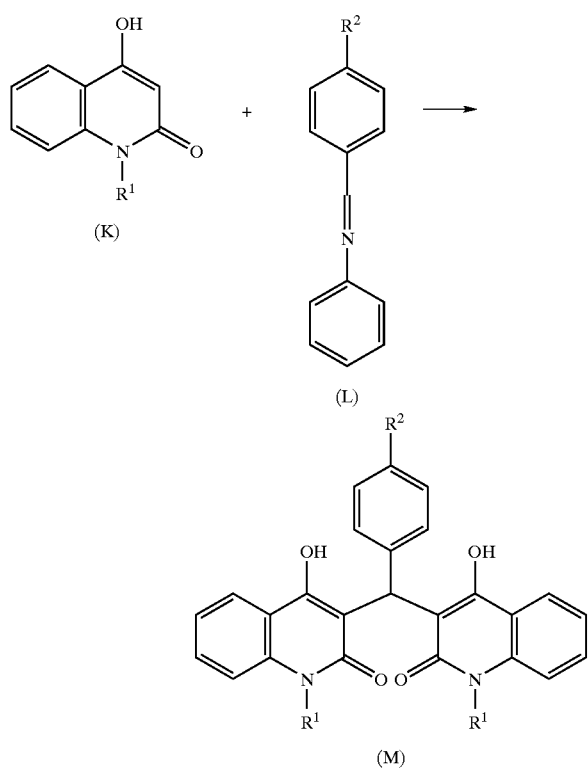

wherein $R^1$ stands for methyl group or phenyl group and $R^2$ stands for hydrogen atom, chlorine atom, methyl group, methoxy group or nitro group [see V Sudhakarrao and Malleshwar Daebarwar, "Indian Journal of Chemistry" Vol.25B, pp.540–541 (1986)].

Furthermore, there is known a chemical synthetic process for producing an indole derivative having an oxolane ring bonded to an indol-3-yl group via a methylene group, in which process an indole compound of the undermentioned formula (G'), paraformaldehyde of the formula (N) and an oxolane derivative of the formula (O) are simultaneously subjected to condensation reaction by a single step reaction of multicomponents so as to synthesize an indole derivative of the undermentioned formula (O), according to the following reaction equation (C):

Reaction equation (C)

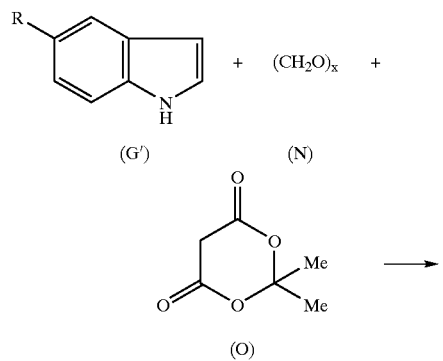

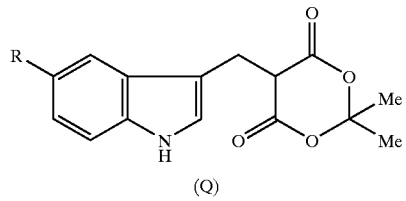

wherein R stands for a group selected from hydrogen atom, bromine atom, methyloxy group, cyano group and phthaliminomethyl group and X stands for an integer of 1 or higher [see "Synthesis" p.254 (1999)].

However, it is to be noticed that in this process, the 3-position of the indole compound of formula (G') is the site of the reaction with the compound of formula (N), and so the 2-position of the indole ring of formula (G') does not participate in the reaction as concerned, and that the yield of the compound of formula (Q) as produced in said single step reaction of the multicomponents is not so good.

We have once presumed that, with reference to the process of the reaction equation (A), the process of the reaction equation (B) and the process of the reaction equation (C) as subjected to our above examination, it would be difficult to foresee and predict any appropriately devised chemical process which can produce, through a chemical synthetic route, each of the SF2809-I to VI substances having the unique structures of the above-mentioned formulae (A) to (F).

On the other hand, in recent years, there has been developed noticeably "combinatorial chemistry" as a novel technique capable of speeding up the generation of lead compounds and the optimization of these lead compounds and capable of reducing the period of time required for searching prospective compounds usable for new medicines, in the field of the development of medicine [refer to "Molecular Diversity and Combinatorial Chemistry", written by I. M. Chaikin and K. D. Janda, and published by American Chemical Society in 1996; and "J. Med. Chem.", Vol.37, p.1233 (1994); and "Chem. Rev.", Vol.96, p.555 (1996)]. One of the core techniques of "combinatorial chemistry" is a combinatorial synthesis in which a compound library comprising many compounds is prepared rapidly. In the process of combinatorial synthesis, there are included a solid phase synthesis wherein the synthesis of a compound is carried on an insoluble solid polymeric support, called as a solid phase, as well as a liquid phase synthesis wherein the synthesis of an aimed compound is carried out in a solution, which liquid phase synthesis has been used much prominently [see "A Practical Guide to Combinatorial Chemistry", written by A. W. Czarnik and S. H. DeWitt, and published by American Chemical Society (1997)]. Among the known processes for the combinatorial liquid phase synthesis as mentioned above, a superior process is a multicomponent single step reaction procedure in which a compound is synthesized by reactions of multiple (3 or more) and different reaction component compounds in a single reaction step for rapid preparation of a compound library, resulting in a merit such that the library of compounds can be prepared much more speedily, as compared with such a synthetic method in which the multiple and different reaction component compounds are reacted successively in multi-reaction steps. As examples of the multicomponent single step reaction procedure, there are known Ugi reaction [see "Angew. Chem. Int. Ed. Engl.", Vol.34, p.2280 (1995)] and Mannich-type reaction [see "Synthesis", p.1401 (1999)].

DISCLOSURE OF INVENTION

A primary object of this invention is to provide novel compounds having a chymase inhibitory activity higher than those of the already known chymase inhibitors. A second object of this invention is to provide a chemical synthetic process which can synthesize in a facile and efficient way the novel compounds having such chymase inhibitory activity. A third object of this invention is to provide new chemical synthetic processes which can produce the above-mentioned SF2809-I to VI substances, in a facile and efficient way.

We have paid our attention to the combinatorial liquid phase synthetic process comprising the multicomponent single step reaction, and we have first investigated new processes which can synthesize in a facile way the SF2809-I to VI substances of the formulae (A)–(F) having the chymase inhibitory activity (see the PCT Application No. PCT/JP99/06738 application) according to the combinatorial liquid phase process.

First of all, we have carried out our investigations with our intention of chemically synthesizing SF2809-V substance of the formula (E). As a result, we have now found that SF2809-V substance of the following formula (E)

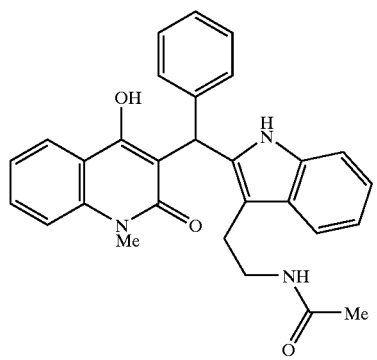

(E)

can be synthesized by effecting a single step reaction of three reaction components consisting of, 4-hydroxy-1-methyl-2-quinolinone of the formula (α)

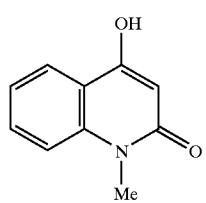

(α)

and benzaldehyde of the formula (γ-3)

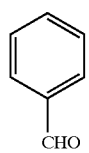

(γ-3)

and 3-(2-acetaminoethyl)indole of the formula (β-1)

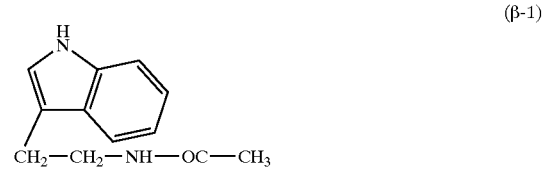

(β-1)

in a solvent, for example, benzene or toluene in the presence of a substance capable of acting as an acid such as acetic acid or trichloroacetic acid, or in a substance capable of acting both as an acid and as a solvent, for example, acetic acid.

We have further continued our studies, and as a result we have now found that SF2809-I substance of the formula (A)

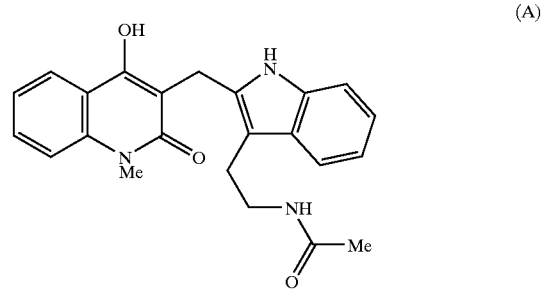

(A)

can be synthesized by effecting a single step reaction of three components consisting of 4-hydroxy-1-methyl-2-quinolinone of the formula (α)

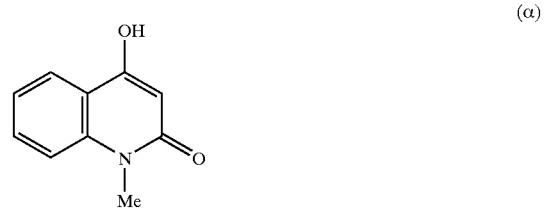

(α)

and formaldehyde

HCHO  (γ-1)

and 3-(2-acetaminoethyl)indole of the formula (β-1)

(β-1)

in an organic solvent or an aqueous solvent in the presence of a substance capable of acting as an acid; and further that SF2809-II substance of the formula (B)

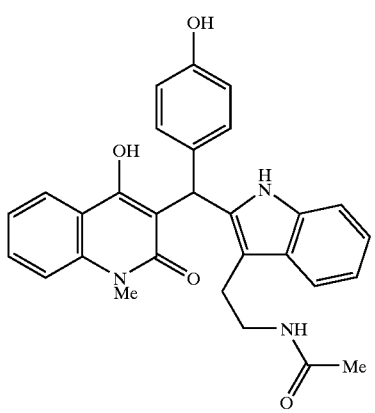
(B)

can be produced by effecting a single step reaction of three components consisting of 4-hydroxy-1-methyl-2-quinolinone of the formula (α)

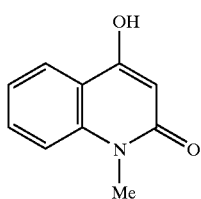
(α)

and 4-hydroxybenzaldehyde of the formula (γ-2)

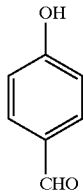
(γ-2)

and 3-(2-acetaminoethyl)indole of the formula (β-1)

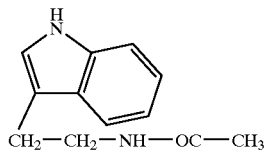
(β-1)

in an organic solvent or an aqueous solvent in the presence of a substance capable of acting as an acid.

We have further found that SF2809-III substance of the formula (C)

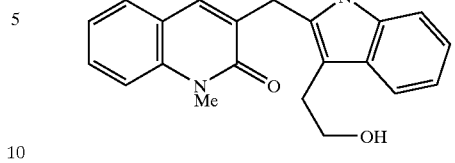
(C)

can be produced by effecting a single step reaction of three components consisting of 4-hydroxy-1-methyl-2-quinolinone of the formula (α)

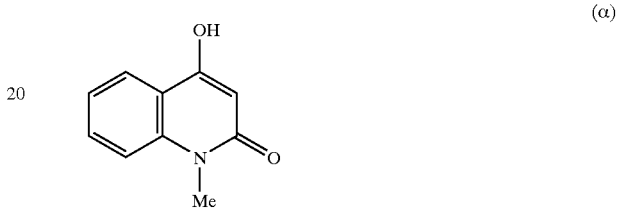
(α)

and formaldehyde of the formula (γ-1)

HCHO  (γ-1)

and 3-(2-hydroxyethyl)indole of the formula (β-2)

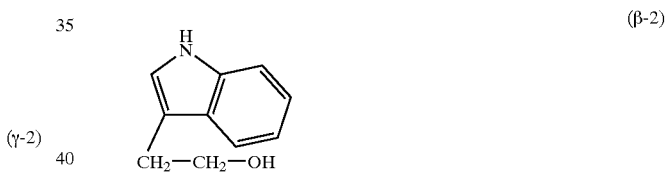
(β-2)

in an organic solvent or an aqueous solvent in the presence of a substance capable of acting as an acid.

We have also found that SF2809-IV substance of the formula (D)

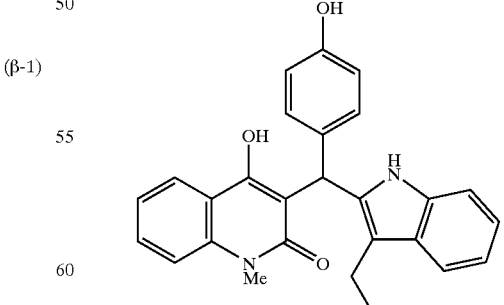
(D)

can be produced by effecting a single step reaction of three components consisting of 4-hydroxy-1-methyl-2-quinolinone of the formula (α)

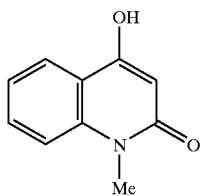

(α)

and 4-hydroxybenzaldehyde of the formula (γ-2)

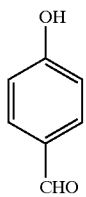

(γ-2)

and 3-(2-hydroxyethyl)indole of the formula (β-2)

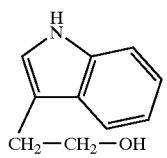

(β-2)

in an organic solvent or an aqueous solvent in the presence of a substance capable of acting as an acid.

We have moreover found that SF2809-VI substance of the formula (F)

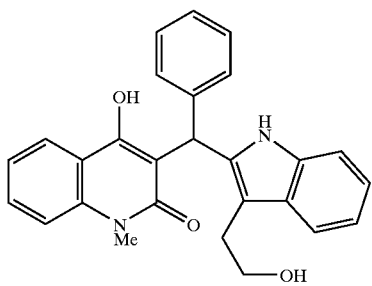

(F)

can be produced by effecting a single step reaction of three components consisting of 4-hydroxy-1-methyl-2-quinolinone of the formula (α)

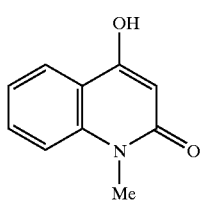

(α)

and benzaldehyde of the formula (γ-3)

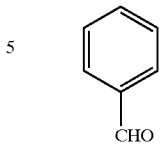

(γ-3)

and 3-(2-acetaminoethyl)indole of the formula (β-1)

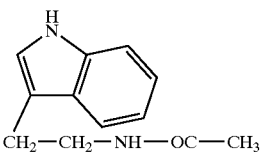

(β-1)

in an organic solvent or an aqueous solvent in the presence of a substance capable of acting as an acid.

As described above, we have thus succeeded in synthesizing the SF2809-I to VI substances by using the technique of the multicomponent single step reaction.

Yet further, we have proceeded another investigations. As a result, we have now found that in general, a variety of such novel indole derivatives, which are represented collectively by the general formula (I) given hereinafter, can be efficiently synthesized with success, when a compound of the general formula (II)

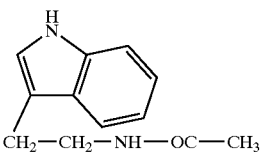

(II)

wherein A, $R^1$ and $R^2$ have the same meanings as defined in the general formula (I) given hereinafter is used in place of the 2-quinolinone compound of the formula (α) above, and also when an aldehyde compound of the general formula (III)

$R^3$—CHO    (III)

wherein $R^3$ has the same meaning as defined below in the under-mentioned general formula (I) is used, or such a compound which is chemically equivalent to said aldehyde compound (III) and is represented by the general formula (III')

$R^3$—CH=N—$R^9$    (III')

wherein $R^3$ has the same meaning as defined below and $R^9$ is an alkyl group or other is used in place of the aldehyde compound of the formula (γ-1), (γ-2) or (γ-3) above, and when concurrently an indole compound of the general formula (IV)

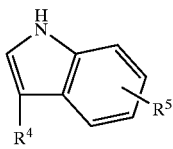

(IV)

wherein $R^4$ and $R^5$ have the same meanings as defined in the undermentioned general formula (I) is used in place of the 3-(2-acetaminoethyl or 2-hydroxyethyl)indole of the formula (β-1) or (β-2) above, thus resulting in that the compound of the general formula (II) and the compound of the general formula (III) or (III') and the compound of the general formula (IV) are simultaneously subjected to a multicomponent single step reaction in solution in an organic solvent or an aqueous solvent in the presence of a substance capable of acting as an acid.

Furthermore, we have found that each of the indole derivatives having the general formula (I) exhibits a high chymase inhibitory activity. On the basis of our findings as above-mentioned, this invention has been completed.

In a first aspect of this invention, therefore, there is provided an indole derivative which is a compound represented by the general formula (I)

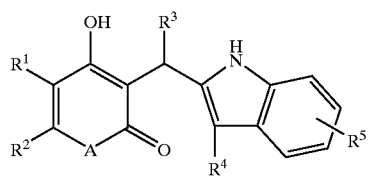

(I)

wherein A is an oxygen atom or a nitrogen atom to which nitrogen atom is bonded a hydrogen atom or such a $(C_1-C_{10})$ alkyl group which is, in turn, optionally substituted by a substituent selected from a halogen atom, a $(C_1-C_{10})$alkyl group, a $(C_1-C_{10})$alkoxy group and an acyl group, particularly an alkanoyl group or an aroyl group;

(i) $R^1$ and $R^2$ each stand for a hydrogen atom or an optionally substituted $(C_1-C_{10})$alkyl group, independently, or (ii) $R^1$ and $R^2$ as taken together form an optionally substituted $(C_5-C_{10})$cycloalkyl group or an optionally substituted $(C_6-C_{20})$aromatic ring, particularly a benzene ring, or (iii) $R^1$ and $R^2$ as taken together form an optionally substituted, saturated or unsaturated heterocycric ring containing one or more nitrogen, oxygen or sulfur atom(s), provided that the possible substituent(s) optionally present on the said optionally substituted alkyl group or cycloalkyl group or aromatic ring or heterocyclic ring may be one or more and is or are selected from a halogen atom, a $(C_1-C_{10})$ alkyl group and a $(C_1-C_{10})$alkoxy group;

$R^3$ stands for a hydrogen atom, an optionally substituted $(C_1-C_{10})$alkyl group, an optionally substituted $(C_5-C_{10})$ cycloalkyl group or an optionally substituted $(C_6-C_{20})$aryl group, particularly a phenyl group, or $R^3$ stands for an optionally substituted, saturated or unsaturated heterocyclic group containing one or more nitrogen, oxygen or sulfur atom(s), provided that the possible substituent(s) optionally present on the said optionally substituted alkyl group or cycloalkyl group or aryl group or heterocyclic group may be one or more and is or are selected from a halogen atom, a $(C_1-C_{10})$alkyl group, a $(C_1-C_{10})$alkoxy group, a halogenated $(C_1-C_{10})$alkyl group and a halogenated $(C_1-C_{10})$ alkoxy group, and that two or more of the said possible substituents as selected may be combined together to form one cyclic group;

$R^4$ stands for an optionally substituted $(C_1-C_{10})$alkyl group where the possible substituent(s) optionally present on the said alkyl group may be one or more and is or are selected from a hydroxyl group, an acyl group, particularly an alkanoyl group or an aroyl group, a $(C_1-C_{10})$ alkyloxycarbonyl group, a cyano group, an amino group, an acylamino group, particularly an alkanoylamino group or an aroylamino group, an acyloxy group, particularly an alkanoyloxy group, an ureido group and a sulfonylamino group, and where the said possible substituent(s) is or are optionally further substituted by one or more of a halogen atom, a $(C_1-C_{10})$alkyl group, a $(C_1-C_{10})$alkoxy group, a $(C_6-C_{20})$aryl group, particularly a phenyl group, an acyl group, particularly an alkanoyl group or an aroyl group, an acylamino group, a halogenated $(C_1-C_{10})$alkyl group and a halogenated $(C_1-C_{10})$ alkoxy group;

$R^5$ stands for a hydrogen atom, a halogen atom, a $(C_{1-10})$ alkyl group or a $(C_1-C_{10})$alkoxy group;

but with such provisos that, in the general formula (I), (i) when A is a methylated nitrogen atom and also $R^1$ and $R^2$ as taken together form a benzene ring in association with the ring-forming carbon atoms to which $R^1$ and $R^2$ are bonded, there is excluded the case where $R^3$ is hydrogen atom, $R^4$ is 2-acetaminoethyl group and $R^5$ is hydrogen atom;

(ii) when A is a methylated nitrogen atom and also $R^1$ and $R^2$ as taken together form a benzene ring in association with the ring-forming carbon atoms to which $R^1$ and $R^2$ are bonded, there is excluded the case where $R^3$ is 4-hydroxyphenyl group, $R^4$ is 2-acetaminoethyl group and $R^5$ is hydrogen atom;

(iii) when A is a methylated nitrogen atom and also $R^1$ and $R^2$ as taken together form a benzene ring in association with the ring-forming carbon atoms to which $R^1$ and $R^2$ are bonded, there is excluded the case where $R^3$ is hydrogen atom, $R^4$ is 2-hydroxyethyl group and $R^5$ is hydrogen atom;

(iv) when A is a methylated nitrogen atom and also $R^1$ and $R^2$ as taken together form a benzene ring in association with the ring-forming carbon atoms to which $R^1$ and $R^2$ are bonded, there is excluded the case where $R^3$ is 4-hydroxyphenyl group, $R^4$ is 2-hydroxyethyl group and $R^5$ is hydrogen atom;

(v) when A is a methylated nitrogen atom and also $R^1$ and $R^2$ as taken together form a benzene ring in association with the ring-forming carbon atoms to which $R^1$ and $R^2$ are bonded, there is excluded the case where $R^3$ is phenyl group, $R^4$ is 2-acetaminoethyl group and $R^5$ is hydrogen atom; and (vi) when A is a methylated nitrogen atom and also $R^1$ and $R^2$ as taken together form a benzene ring in association with the ring-forming carbon atoms to which $R^1$ and $R^2$ are bonded, there is excluded the case where $R^3$ is phenyl group, $R^4$ is 2-hydroxyethyl group and $R^5$ is hydrogen atom;

or a pharmaceutically acceptable salt or a solvate thereof.

Further, according to a first preferred embodiment of the first aspect of this invention, the compound of the general formula (I) above may include an indole derivative which is a compound having the general formula (Ia)

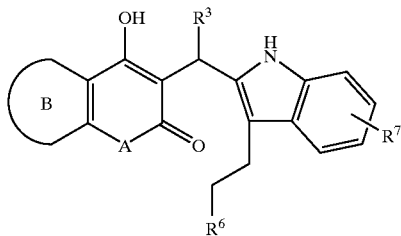

(Ia)

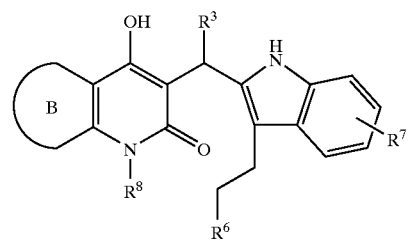

(Ib)

wherein A has the same meaning as defined above;

B stands for a cyclic group, which cyclic group B either stands for an optionally substituted $(C_6$–$C_{20})$aromatic ring, particularly a benzene ring, or the cyclic group B stands for an optionally substituted, saturated or unsaturated heterocyclic ring containing one or more nitrogen, oxygen or sulfur atom(s), provided that the possible substituent(s) optionally present on the said optionally substituted aromatic ring or heterocyclic ring is or are selected from a halogen atom, a $(C_1$–$C_{10})$alkyl group, a $(C_1$–$C_{10})$alkoxy group, a halogenated $(C_1$–$C_{10})$alkyl group and a halogenated $(C_1$–$C_{10})$alkoxy group and the said possible substituent(s) may be either single or plural ones;

$R^3$ has the same meaning as defined above;

$R^6$ stands for a hydroxyl group, an optionally substituted acyl group, particularly an alkanoyl group or an aroyl group, an optionally substituted $(C_1$–$C_{10})$alkyloxycarbonyl group, a cyano group, an optionally substituted amino group, particularly an acylamino group, particularly an alkanoylamino group or an aroylamino group, an optionally substituted acyloxy group, particularly an alkanoyloxy group, an optionally substituted ureido group or an optionally substituted sulfonylamino group, provided that the possible substituent(s) optionally present on the said optionally substituted groups is or are selected from a halogen atom, a $(C_1$–$C_{10})$alkyl group, a $(C_1$–$C_{10})$alkoxy group, a $(C_6$–$C_{20})$ aryl group, particularly a phenyl group, an acyl group, particularly an alkanoyl group, an acylamino group, a halogenated $(C_1$–$C_{10})$alkyl group, a halogenated $(C_1$–$C_{10})$ alkoxy group and a halogenated acyl group;

$R^7$ stands for a hydrogen atom, a halogen atom, a $(C_1$–$C_6)$ alkyl group or a $(C_1$–$C_6)$ alkoxy group;

but with such provisos that, in the general formula (Ia),
(i) when A is a methylated nitrogen atom and B is a benzene ring, there is excluded the case where $R^3$ is hydrogen atom, $R^6$ is acetamino group and $R^7$ is hydrogen atom;
(ii) when A is a methylated nitrogen atom and B is a benzene ring, there is excluded the case where $R^3$ is 4-hydroxyphenyl group, $R^6$ is acetamino group and $R^7$ is hydrogen atom;
(iii) when A is a methylated nitrogen atom and B is a benzene ring, there is excluded the case where $R^3$ is hydrogen atom, $R^6$ is hydroxyl group and $R^7$ is hydrogen atom;
(iv) when A is a methylated nitrogen atom and B is a benzene ring, there is excluded the case where $R^3$ is 4-hydroxylphenyl group, $R^6$ is hydroxyl group and $R^7$ is hydrogen atom;
(v) when A is a methylated nitrogen atom and B is a benzene ring, there is excluded the case where $R^3$ is phenyl group, $R^6$ is acetamino group and $R^7$ is hydrogen atom; and
(vi) when A is a methylated nitrogen atom and B is a benzene ring, there is excluded the case where $R^3$ is phenyl group, $R^6$ is hydroxyl group and $R^7$ is hydrogen atom.

Further, according to a second preferred embodiment of the first aspect of this invention, the compound of the general formula (I) above may include an indole derivative which is a compound having the general formula (Ib)

wherein B, $R^3$, $R^6$ and $R^7$ have the same meanings as defined above, respectively;

$R^8$ stands for a hydrogen atom or a straight or branched $(C_1$–$C_{10})$alkyl group;

but with such provisos that in the general formula (Ib), (i) when B is a benzene ring and $R^8$ is methyl group, there is excluded the case where $R^3$ is hydrogen atom, $R^6$ is acetamino group and $R^7$ is hydrogen atom;
(ii) when B is a benzene ring and $R^8$ is methyl group, there is excluded the case where $R^3$ is 4-hydroxyphenyl group, $R^6$ is acetamino group and $R^7$ is hydrogen atom;
(iii) when B is a benzene ring and $R^8$ is methyl group, there is excluded the case where $R^3$ is hydrogen atom, $R^6$ is hydroxyl group and $R^7$ is hydrogen atom;
(iv) when B is a benzene ring and $R^8$ is methyl group, there is excluded the case where $R^3$ is 4-hydroxyphenyl group, $R^6$ is hydroxyl group and $R^7$ is hydrogen atom;
(v) when B is a benzene ring and $R^8$ is methyl group, there is excluded the case where $R^3$ is phenyl group, $R^6$ is acetamido group and $R^7$ is hydrogen atom; and
(vi) when B is a benzene ring and $R^8$ is methyl group, there is excluded the case where $R^3$ is phenyl group, $R^6$ is hydroxyl group and $R^7$ is hydrogen atom.

Of course, it is clear that from the indole derivatives of the general formula (I), of the general formula (Ia) and of the general formula (Ib), respectively, there are excluded those substances of SF2809-I to VI which are disclosed in the specification of the aforesaid PCT application No. PCT/JP99/06738 [because of the definitions given in the provisios of (i), (ii), (iii), (iv), (v) and (vi) as shown in the "provisos" requirements prescribed for the general formulae (I), (Ia) and (Ib) given hereinbefore].

So far as the indole derivative of the general formula (I), or the indole derivative of the general formula (Ia) or (Ib) according to the first aspect of this invention is concerned with, a halogen atom given in the general formula (I), (Ia) or (Ib) means a fluorine, chlorine, bromine or iodine atom.

Further, in the general formula (I), (Ia) or (Ib), an alkyl group which $R^1$ to $R^4$ may denote a straight or branched $(C_1$–$C_{10})$alkyl group. As such alkyl group, there are exemplified straight chain alkyl groups, e.g. methyl group, ethyl group and n-butyl group, as well as branched chain alkyl groups, e.g. isopropyl group, isobutyl group, t-butyl group or 2,2-dimethylpropyl group.

As a $(C_5$–$C_{10})$cycloalkyl group which $R^1$, $R^2$ and $R^3$ may denote, there may be exemplified cyclopentyl group or cyclohexyl group.

As a $(C_6$–$C_{20})$aryl group which $R^3$ may denote, or $(C_6$–$C_{20})$aryl group which may optionally be born on the alkyl group $R^4$, there may be exemplified phenyl group, naphthyl group or anthracenyl group.

Alkyloxycarbonyl group as above-mentioned may include, for example, methyloxycarbonyl group or benzyloxycarbonyl group.

Acyloxy group as above-mentioned may include an alkanoyloxy group or an aroyloxy group, for example, acetyloxy group, ethylcarbonyloxy group, cyclohexylcarbonyloxy group, benzoyloxy group, benzylcarbonyloxy group or undecanoylcarbonyloxy group and others.

Examples of an alkoxy group above-mentioned are methoxy group or trifluoromethoxy group and others.

Acyl group above-mentioned may be an alkanoyl group or an aroyl group, typical examples of which are acetyl group, propionyl group, benzylcarbonyl group, benzoyl group and others.

As the acylamino group above-mentioned, there may be exemplified an alkanoylamino group or an aroylamino group, typical examples of which are acetylamino group, propionylamino group, cyclohexylcarbonylamino group, benzoylamino group, benzylcarbonylamino group or undecanoylcarbonylamino group and others.

As carbamoyl groups above-mentioned, there may be exemplified methyloxycarbonylamino group, benzyloxycarbonylamino group, t-butyloxycarbonylamino group or allyloxycarbonylamino group and others.

Examples of an ureido group above-mentioned are aminocarbonylamino group, N'-methylaminocarbonylamino group, piperidinocarbonylamino group, morpholinocarbonylamino group, N'-methyl-N'-phenylaminocarbonylamino group and others.

Further, the sulfonylamino group above-mentioned may include butylsulfonylamino group, phenylsulfonylamino group, benzylsulfonylamino group and naphthylsulfonylamino group, and so on.

In the general formula (I), by a cycloalkyl group which may be constituted by $R^1$ and $R^2$ taken together is meant a residue of a saturated cycloalkane such as cyclopentane ring and cyclohexane ring. Also in the general formula (I), examples of an aromatic ring or a heterocyclic ring which can be constituted by $R^1$ and $R^2$ taken together may include an aromatic ring such as benzene ring, naphthalene ring and the like, as well as or saturated heterocyclic ring such as tetrahydrofuran ring, pyrrolidine ring and the like, and an unsaturated heterocyclic ring such as pyrazole ring, thiazole ring and the like.

In the general formula (I), (Ia) or (Ib), by a $(C_6-C_{20})$aryl group for $R^3$ is meant an aromatic hydrocarbon ring such as phenyl group, naphthyl group and anthracenyl group.

As examples of an optionally substituted heterocyclic ring containing one or more nitrogen atom(s), oxygen atom(s) or sulfur atom(s) which may be formed by $R^1$ and $R^2$ taken together or which is represented by $R^3$, there may be mentioned a residue of a saturated five-membered heterocyclic ring such as tetrahydrofuran, pyrrolidine, imidazoline or oxazoline; a residue of an unsaturated five-membered heterocyclic ring such as pyrrole, oxazole, imidazole or thiazole; a residue of a saturated six-membered heterocyclic ring such as piperidine, piperazine or morpholine ring; a residue of an unsaturated six-membered heterocyclic ring such as pyridine, pyridazine, pyrimidine or pyrazine ring; and a residue of a condensed heterocyclic ring such as indole, benzoxazole, benzothiazole, coumarin, quinoline, purine or xanthine ring. Further, in the general formula (Ia) or (Ib), the heterocyclic ring which the ring B denotes may be any heterocyclic ring as exemplified in the above.

The indole derivative of the general formula (I) according to the first aspect of this invention may either be in the free form or in the form of a pharmaceutically acceptable salt thereof. As such salts, they may be pharmaceutically acceptable non-toxic salts. Preferably, there may be mentioned the salts with a pharmaceutically acceptable inorganic acid such as a hydrohalogenic acid, e.g. hydrofluoric acid, hydrochloric acid, hydrobromic acid, hydroiodic acid, etc., sulfuric acid, nitric acid, phosphoric acid, hydroperoxy acid, carbonic acid and the like; as well as the salts with a pharmaceutically acceptable organic carboxylic acid such as acetic acid, trichloroacetic acid, trifluoroacetic acid, hydroxyacetic acid, lactic acid, citric acid, tartaric acid, oxalic acid, benzoic acid, mandelic acid, butyric acid, maleic acid, propionic acid, formic acid, malic acid; and the salts with an acidic amino acid such as aspartic acid, glutamic acid; the salts with an alkylsulfonic acids or arylsulfonic acids such as methanesulfonic acid, p-toluenesulfonic acid, and so on. The compound of the formula (I) may also be in the form of a solvate thereof. Typical solvate is hydrate.

The indole derivative having the general formula (I) according to this invention include all the optical isomers and the racemic mixtures thereof.

Processes for the preparation of the indole derivative of the general formula (I) according to the first aspect of this invention will be explained in detail hereinafter.

For exemplary compounds of the indole derivative of the general formula (I) or the indole derivative of the general formula (Ia) or (Ib) according to the first aspect of this invention, they are listed in Table 1-1 to Table 1-7 where 81 compounds are shown by their compound Nos. 003 to 083 along with their chemical structural formulae, as well as in Table 2-1 to Table 2-44 where 530 compounds are shown by their compound Nos. 084 to 613 along with their chemical structural formulae.

TABLE 1-1

Compound No. 003

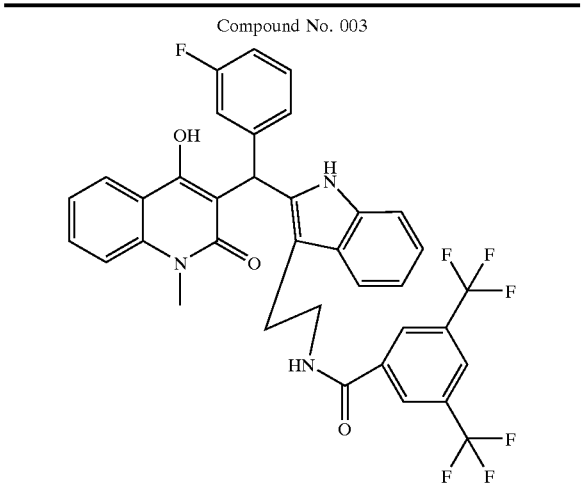

TABLE 1-1-continued
Compound No. 004
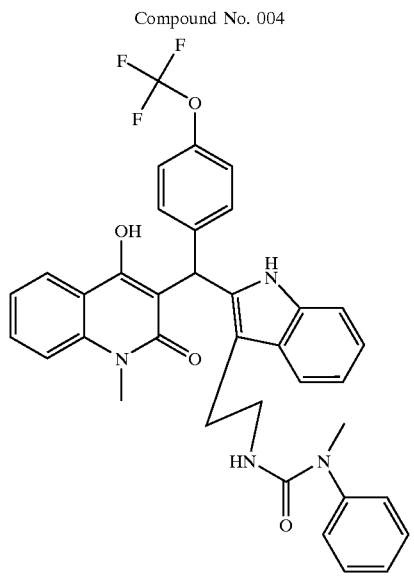
Compound No. 005
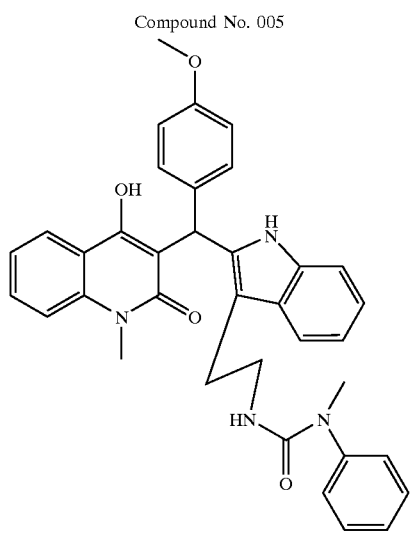
Compound No. 006
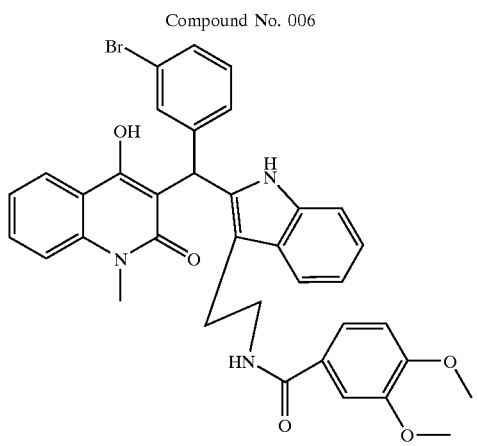
TABLE 1-1-continued
Compound No. 007
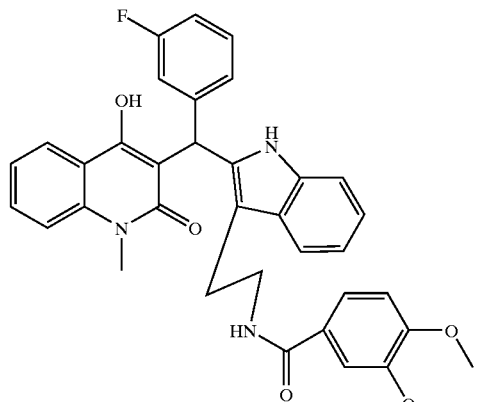
Compound No. 008
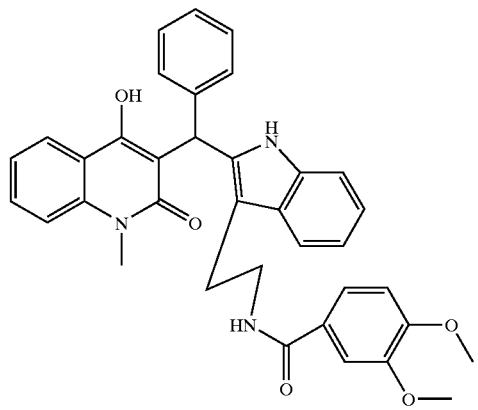
Compound No. 009
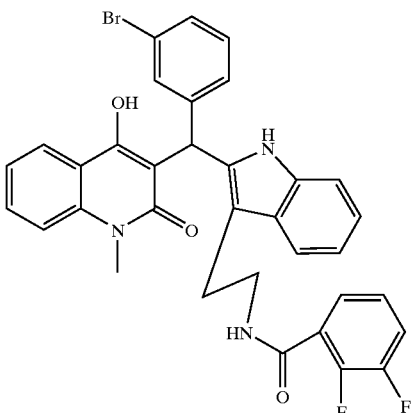

TABLE 1-1-continued
Compound No. 010
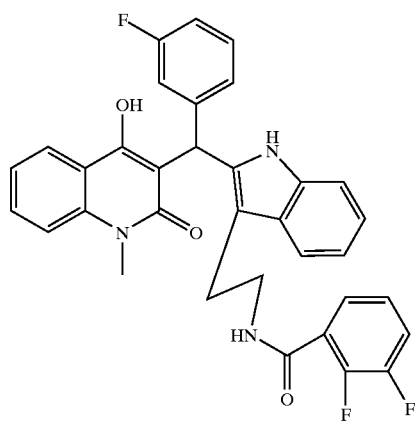
Compound No. 011
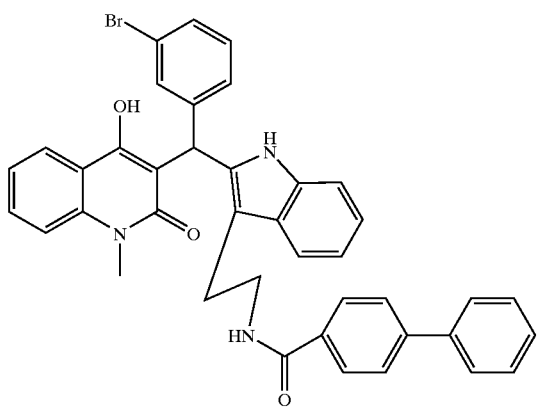
Compound No. 012
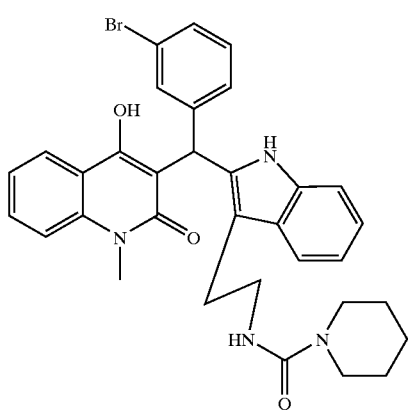
TABLE 1-1-continued
Compound No. 013
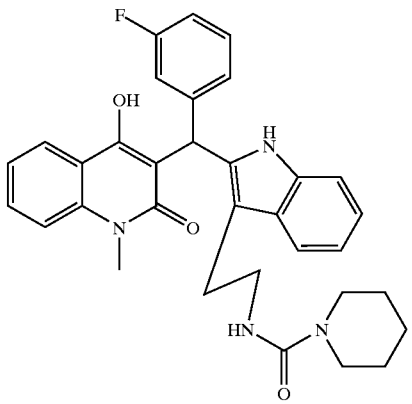
Compound No. 014
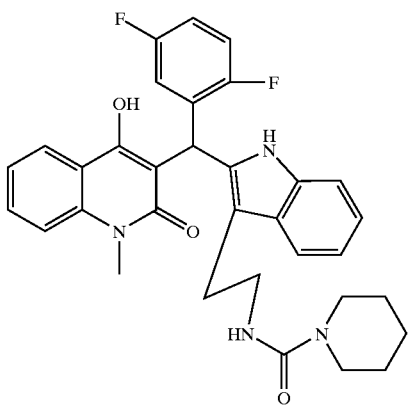
TABLE 1-2
Compound No. 015
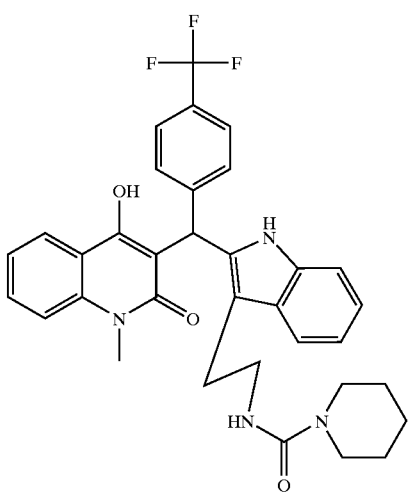

TABLE 1-2-continued
Compound No. 016
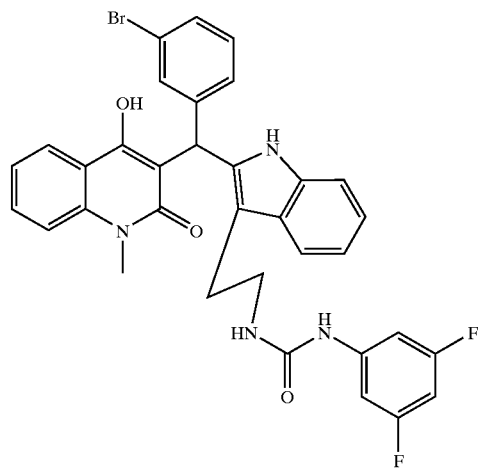
Compound No. 017
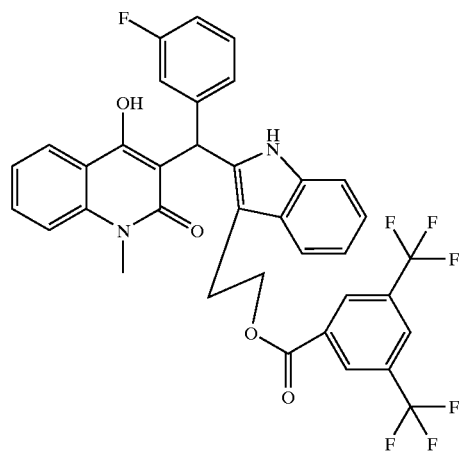
Compound No. 018
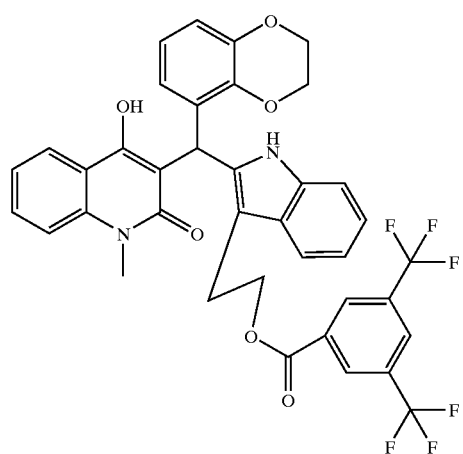
TABLE 1-2-continued
Compound No. 019
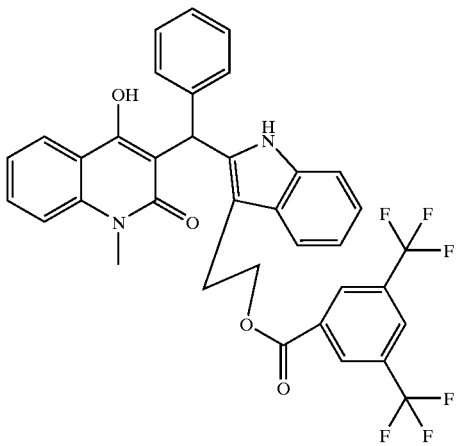
Compound No. 020
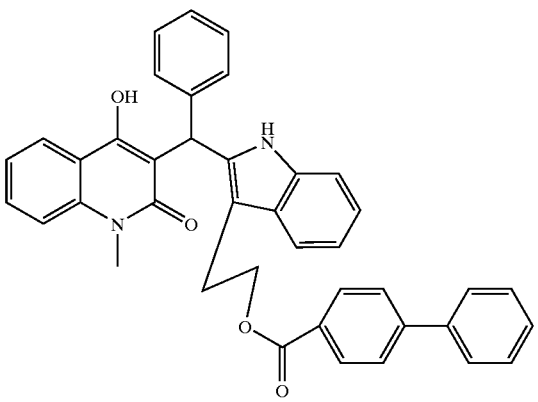
Compound No. 021
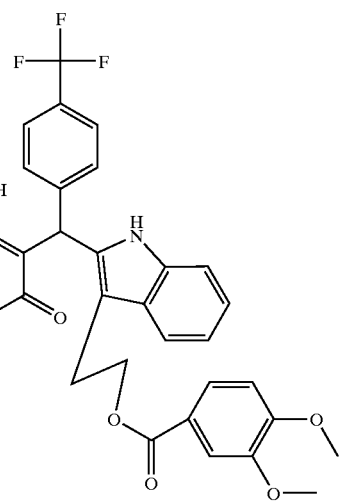

TABLE 1-2-continued
Compound No. 022
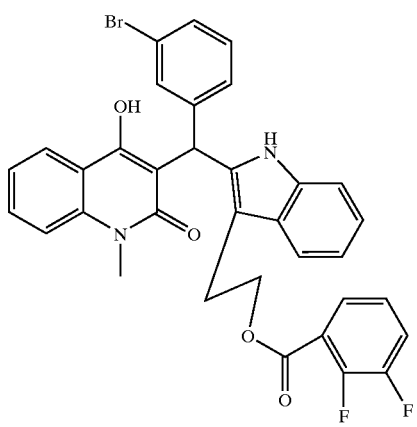
Compound No. 023
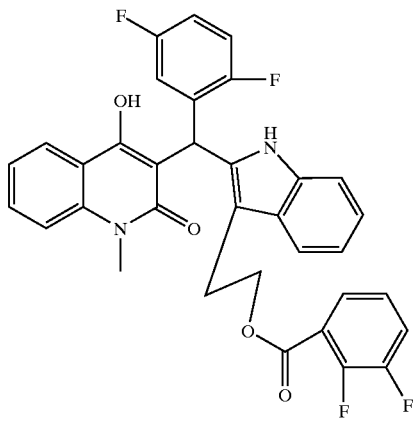
Compound No. 024
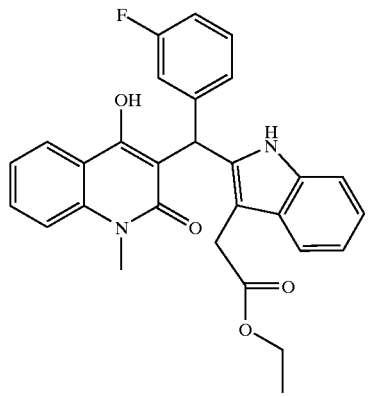
TABLE 1-2-continued
Compound No. 025
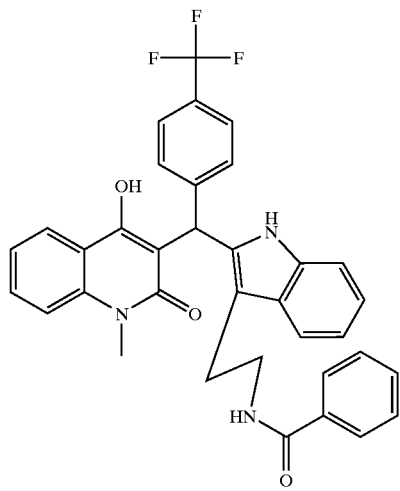
Compound No. 026
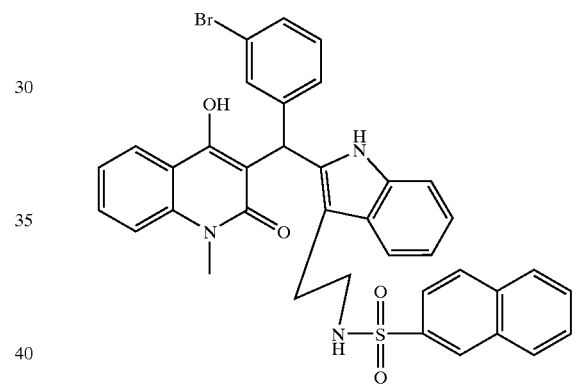
TABLE 1-3
Compound No. 027
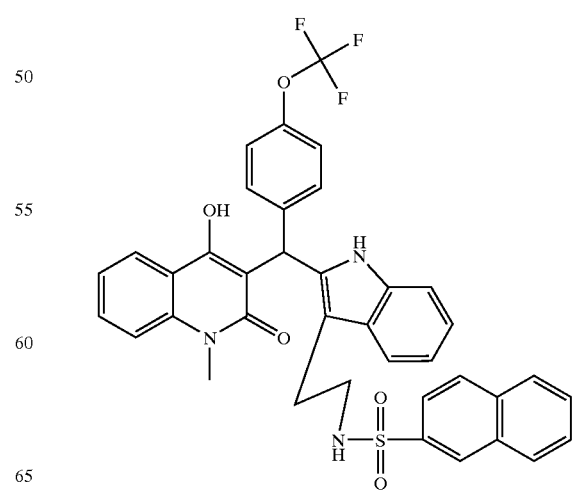

TABLE 1-3-continued
Compound No. 028
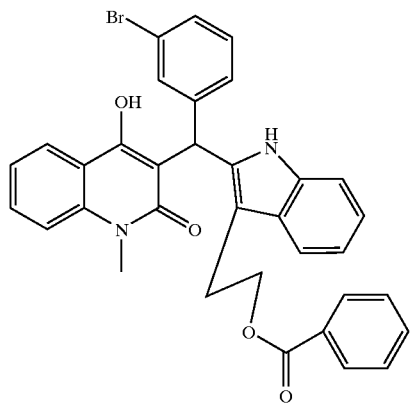
Compound No. 029
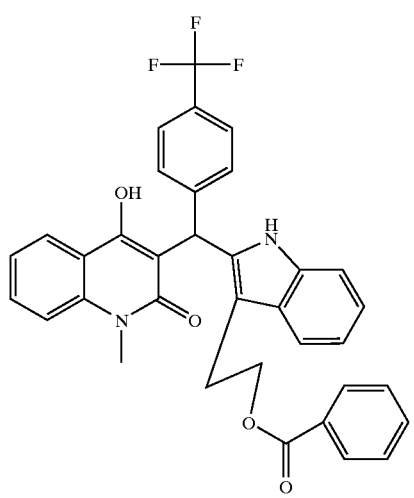
Compound No. 030
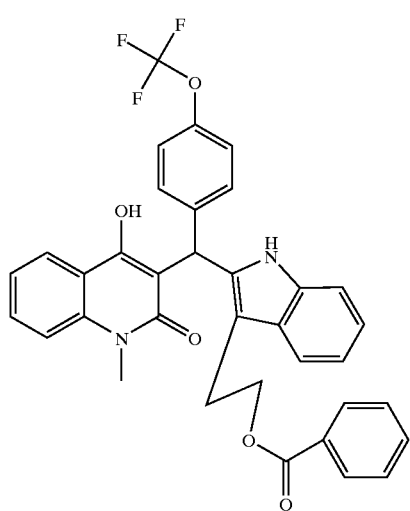
TABLE 1-3-continued
Compound No. 031
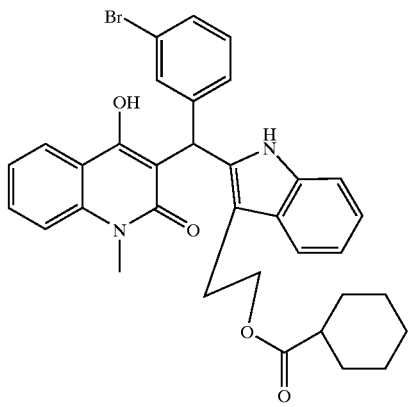
Compound No. 032
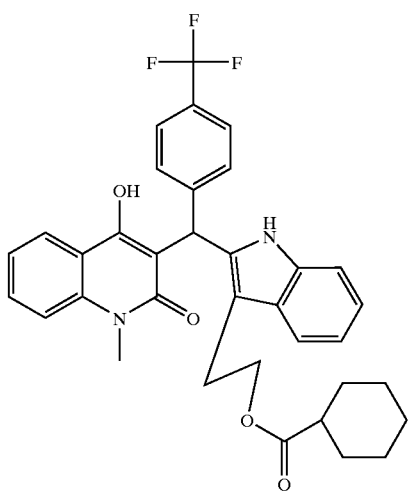
Compound No. 033
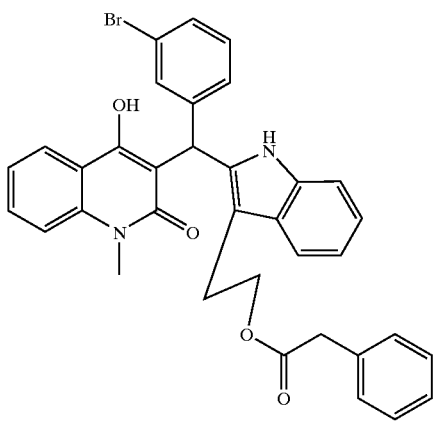

TABLE 1-3-continued
Compound No. 034
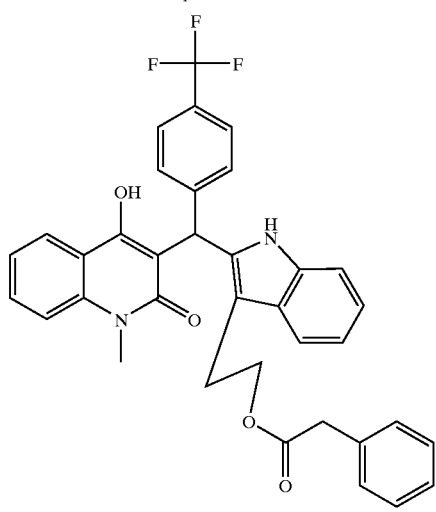
Compound No. 035
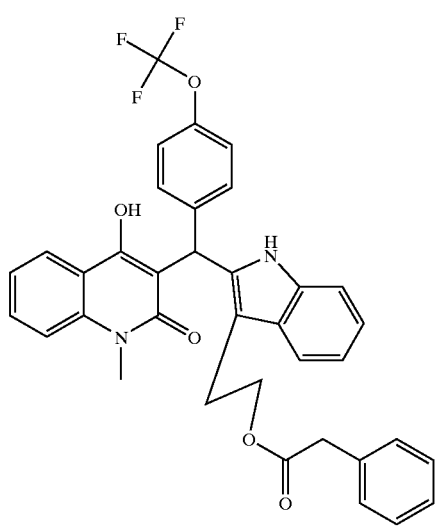
Compound No. 036
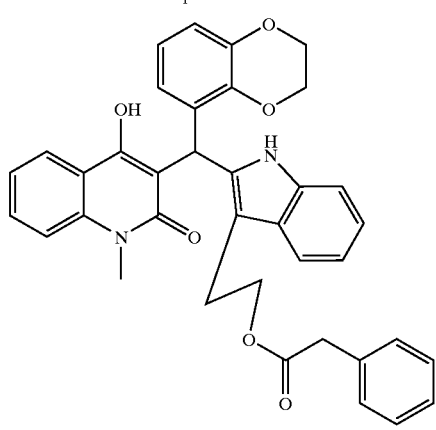
TABLE 1-3-continued
Compound No. 037
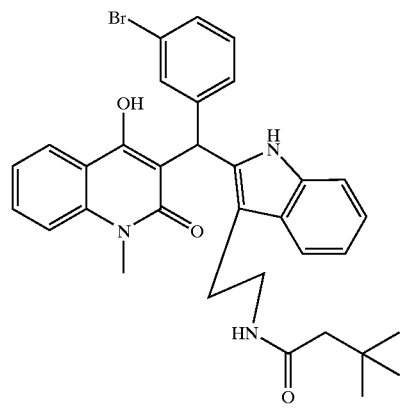
Compound No. 038
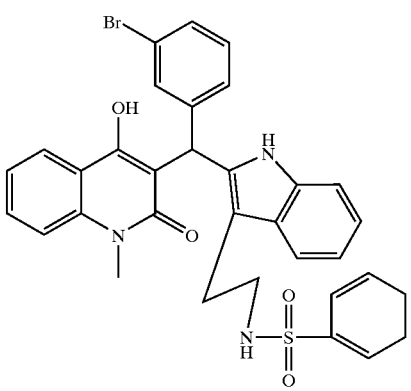
TABLE 1-4
Compound No. 039
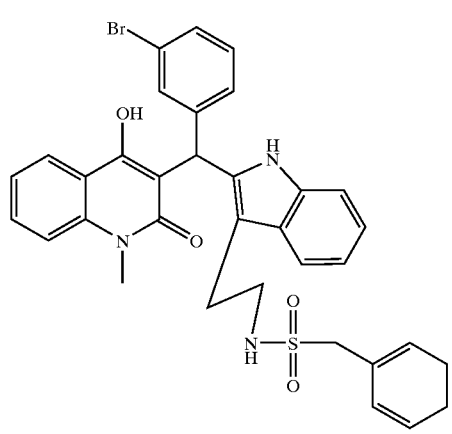

TABLE 1-4-continued
Compound No. 040
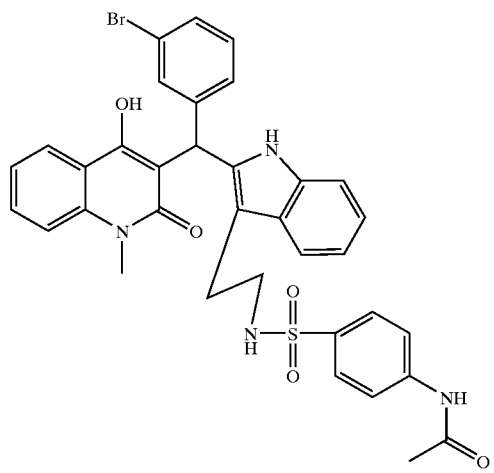
Compound No. 041
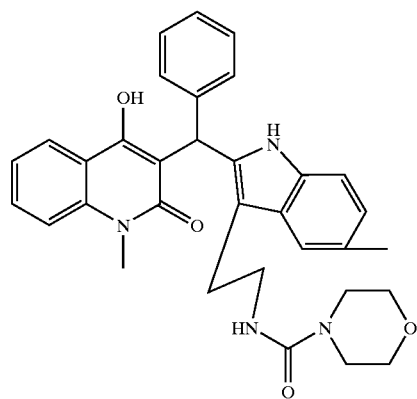
Compound No. 042
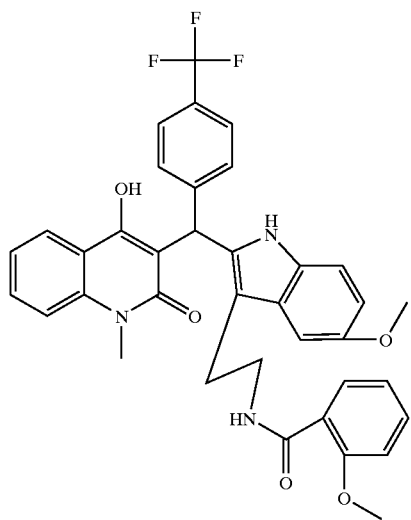
TABLE 1-4-continued
Compound No. 043
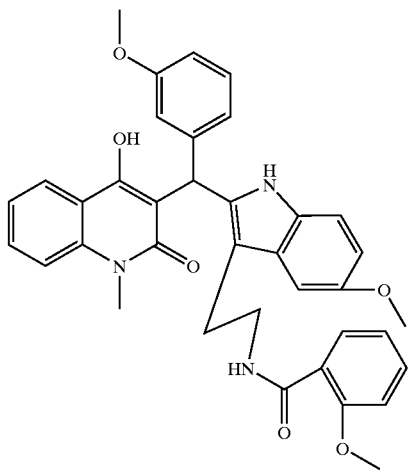
Compound No. 044
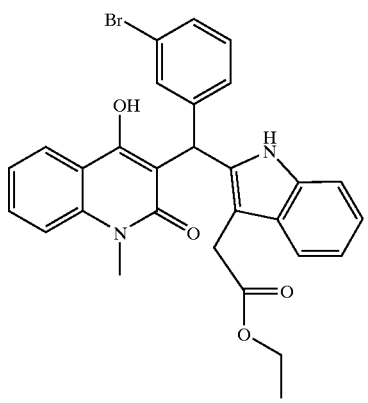
Compound No. 045
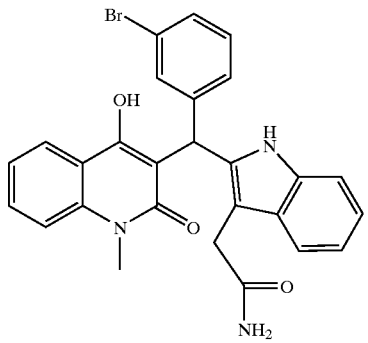

TABLE 1-4-continued
Compound No. 046
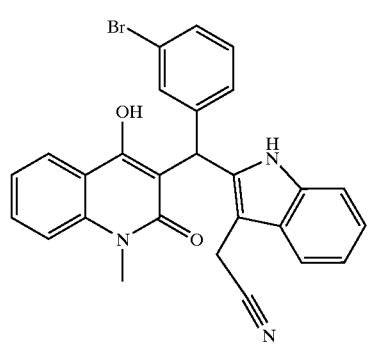
Compound No. 047
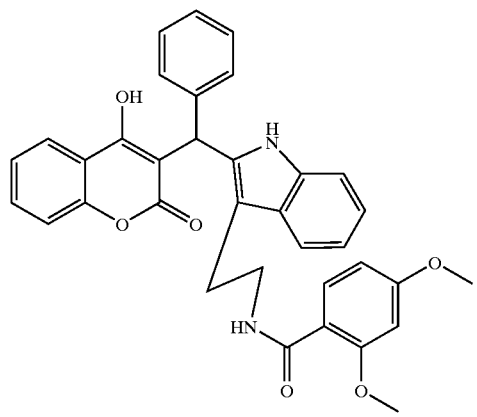
Compound No. 048
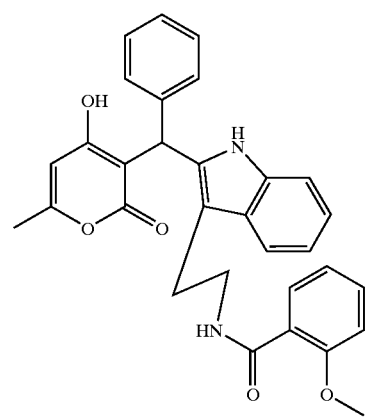
TABLE 1-4-continued
Compound No. 049
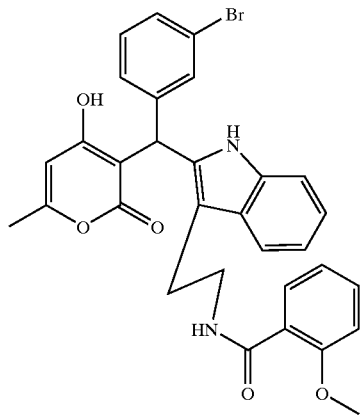
Compound No. 050
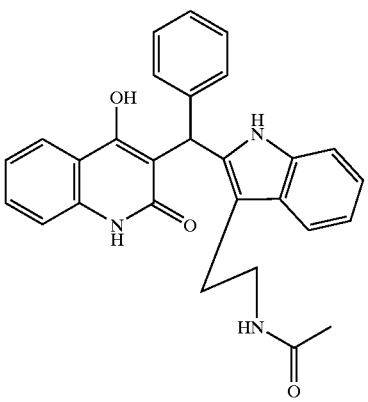
TABLE 1-5
Compound No. 051
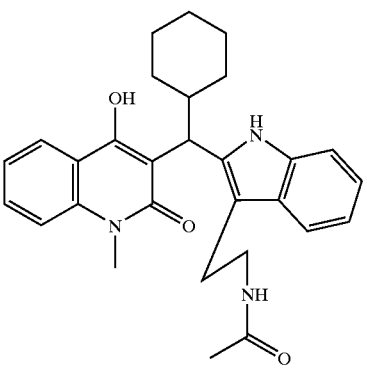

TABLE 1-5-continued
Compound No. 052
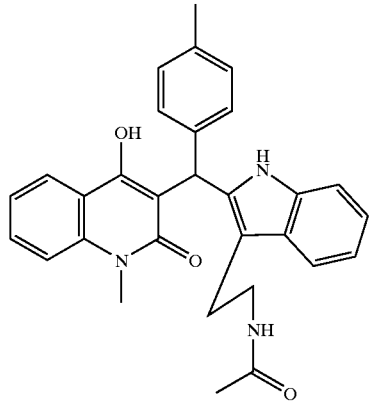
Compound No. 053
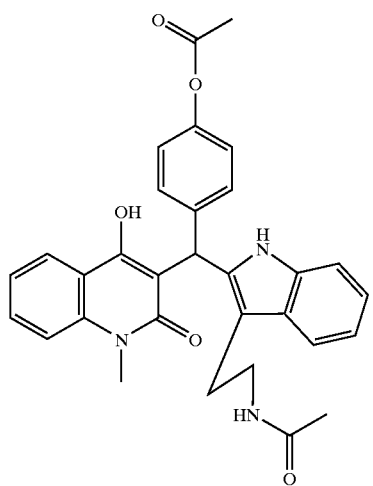
Compound No. 054
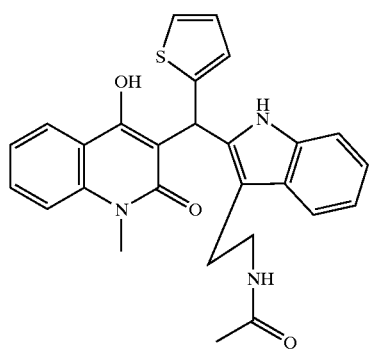
TABLE 1-5-continued
Compound No. 055
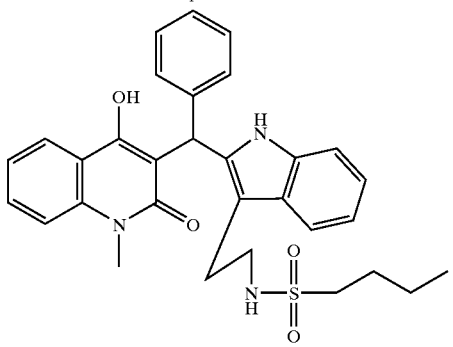
Compound No. 056
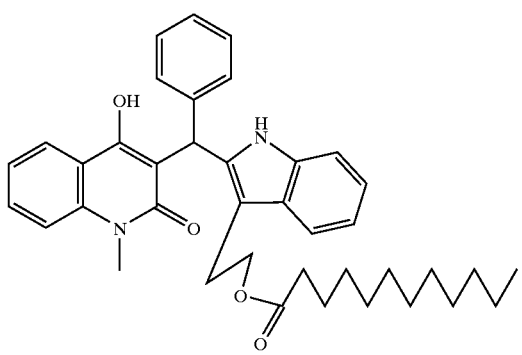
Compound No. 057
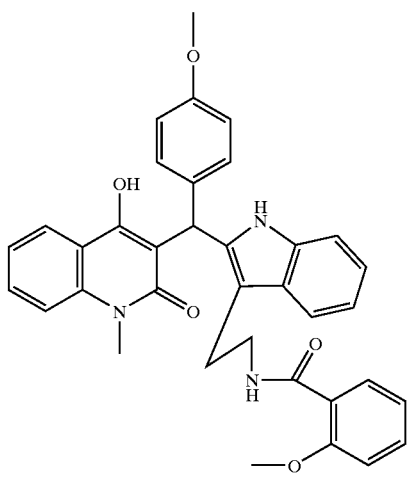
Compound No. 058
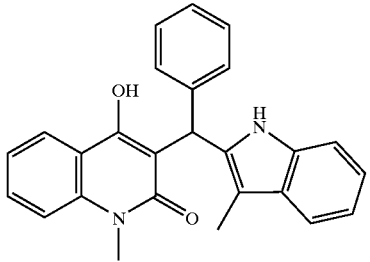

TABLE 1-5-continued
Compound No. 059
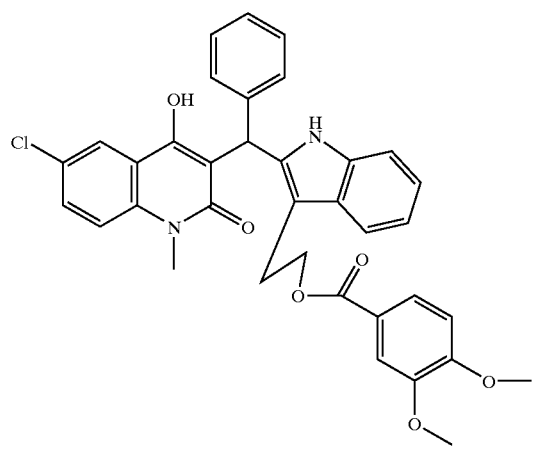
Compound No. 060
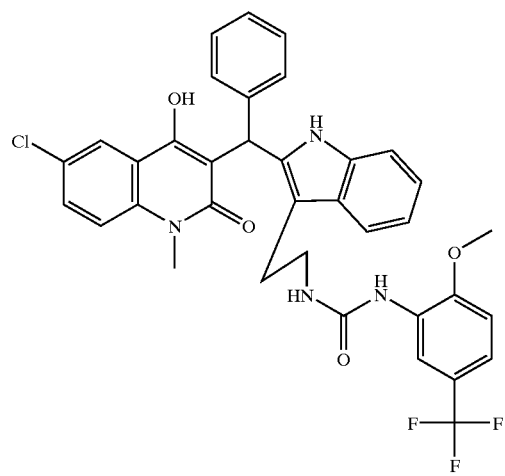
Compound No. 061
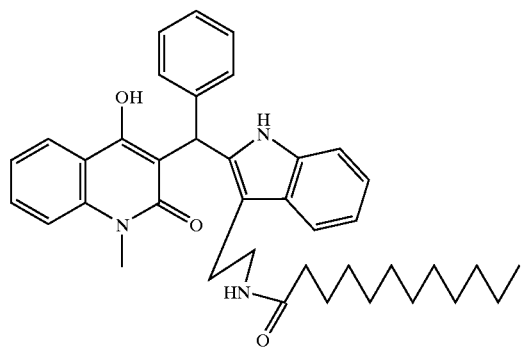
TABLE 1-5-continued
Compound No. 062
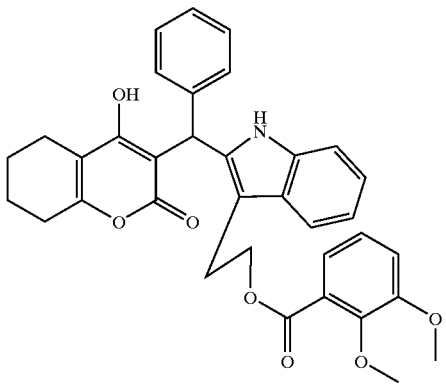
TABLE 1-6
Compound No. 063
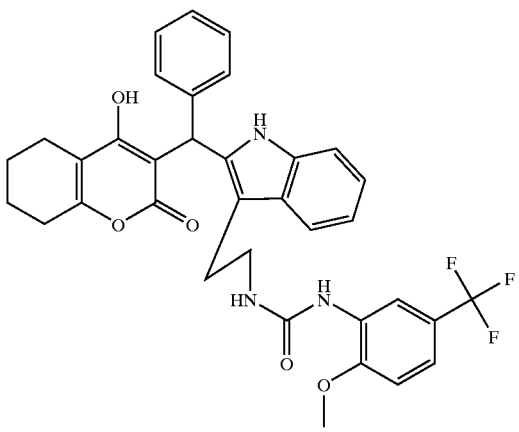
Compound No. 064

TABLE 1-6-continued
Compound No. 065
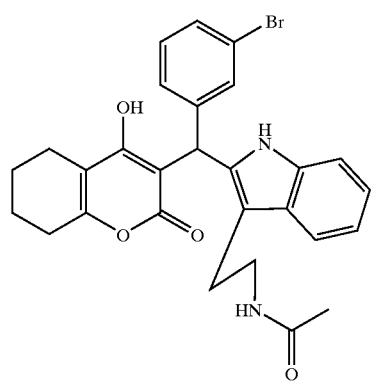
Compound No. 066
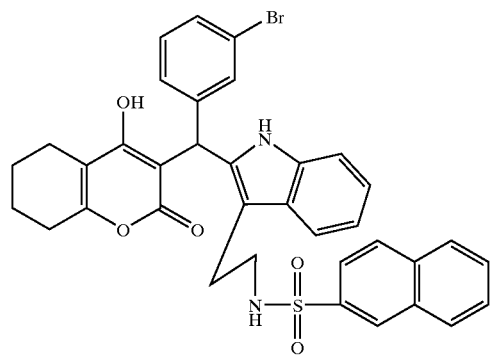
Compound No. 067
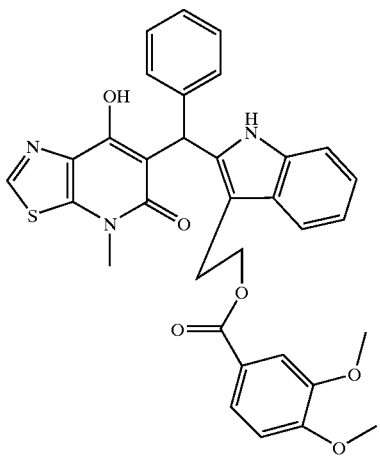
TABLE 1-6-continued
Compound No. 068
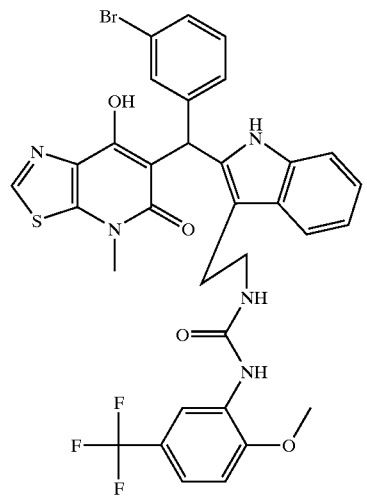
Compound No. 069
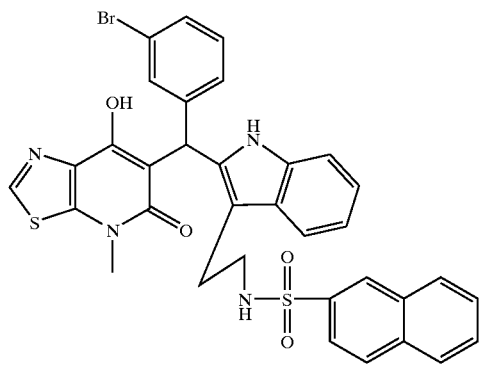
Compound No. 070
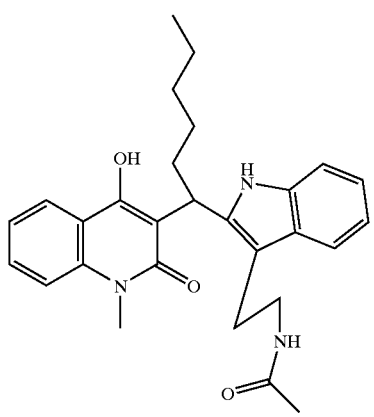

TABLE 1-6-continued
Compound No. 071
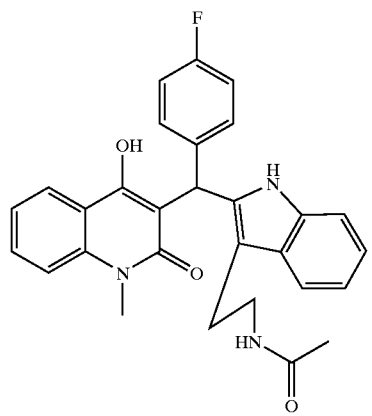
Compound No. 072
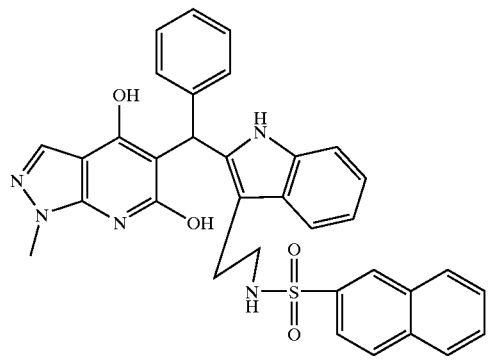
Compound No. 073
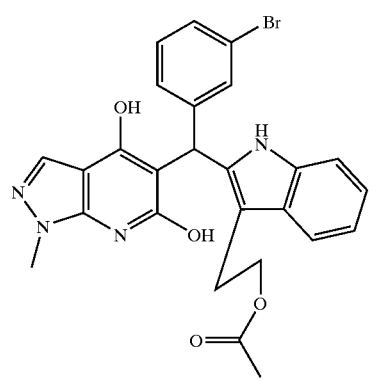
TABLE 1-6-continued
Compound No. 074
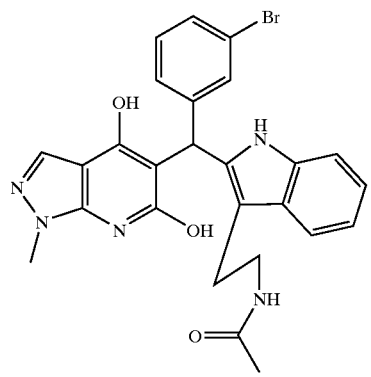
TABLE 1-7
Compound No. 075
Compound No. 076
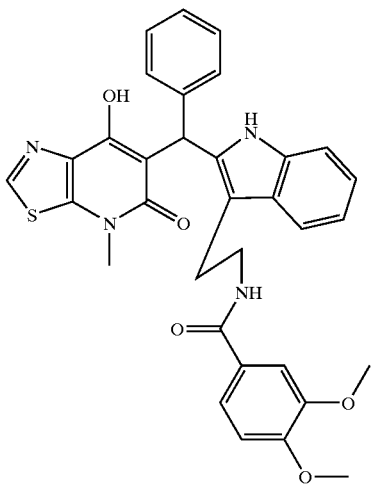
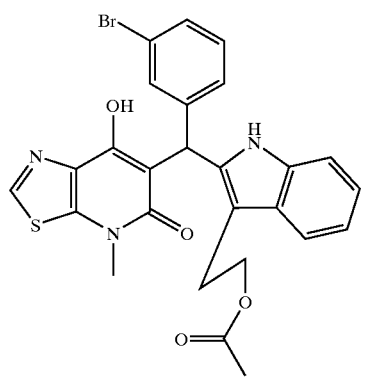

TABLE 1-7-continued
Compound No. 077
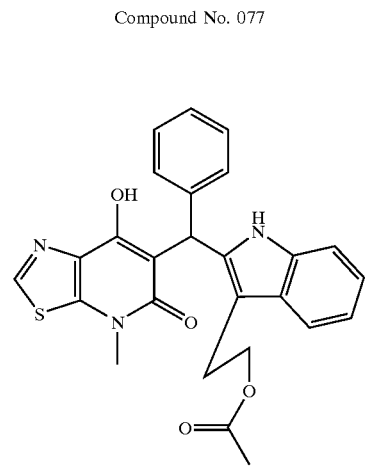
Compound No. 078
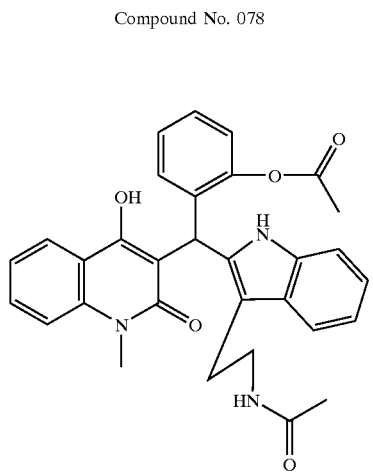
Compound No. 079
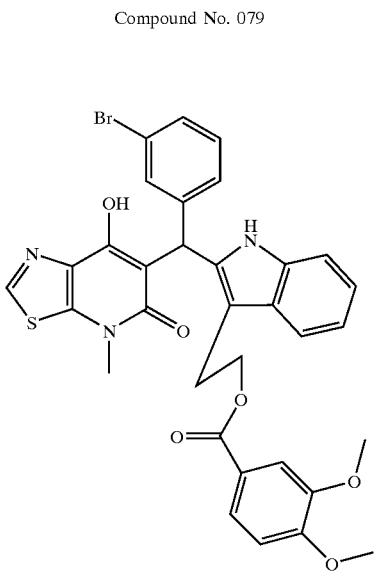
TABLE 1-7-continued
Compound No. 080
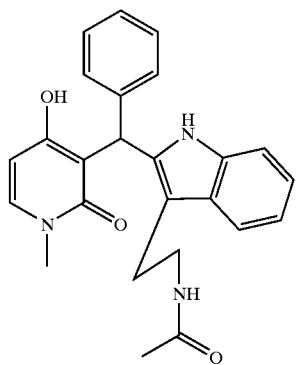
Compound No. 081
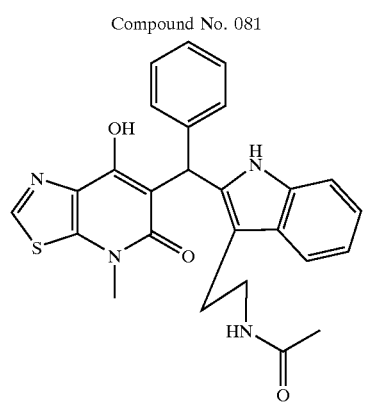
Compound No. 082
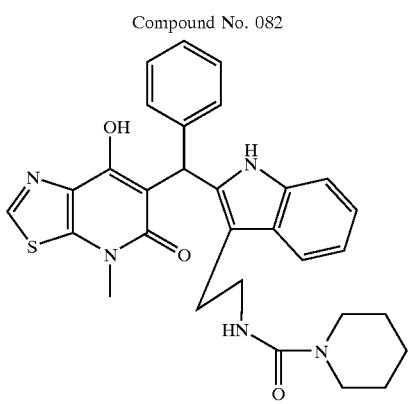
Compound No. 083
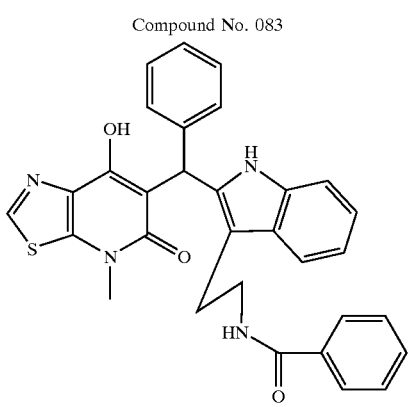

TABLE 2-1
Compound No. 084
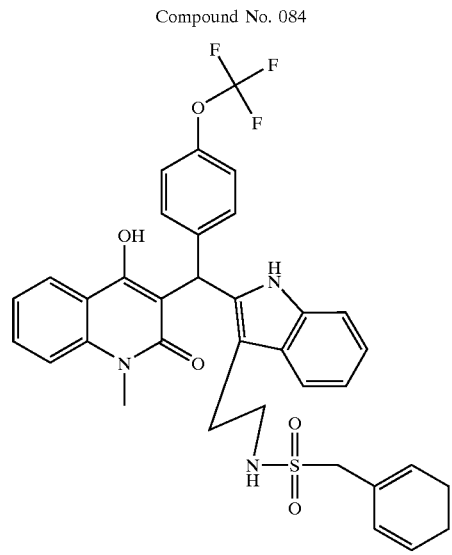
Compound No. 085
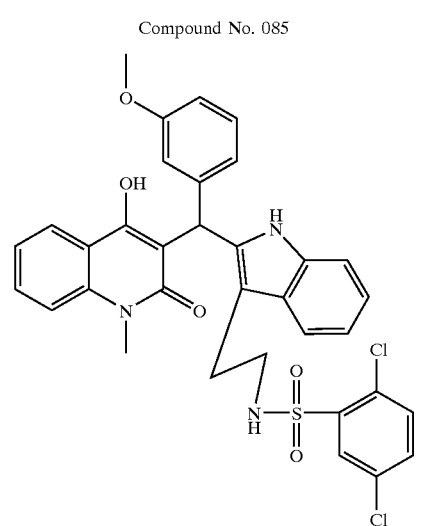
Compound No. 086
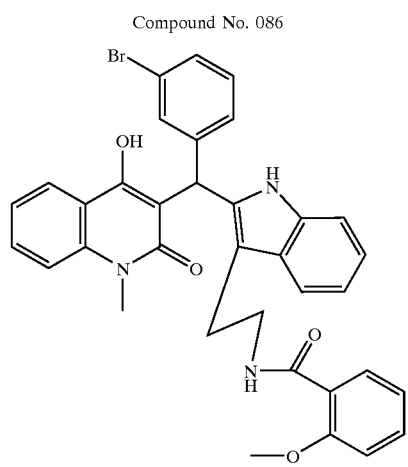
TABLE 2-1-continued
Compound No. 087
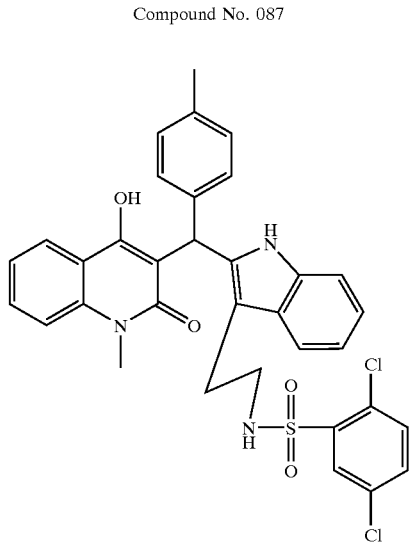
Compound No. 088
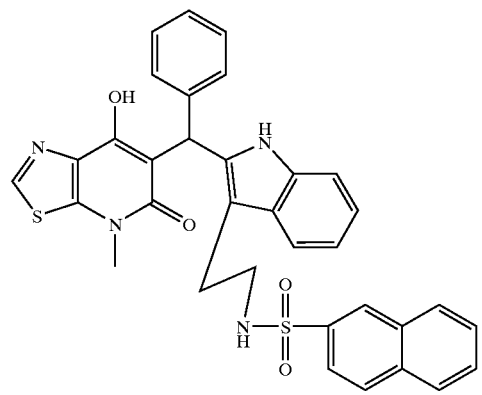
Compound No. 089
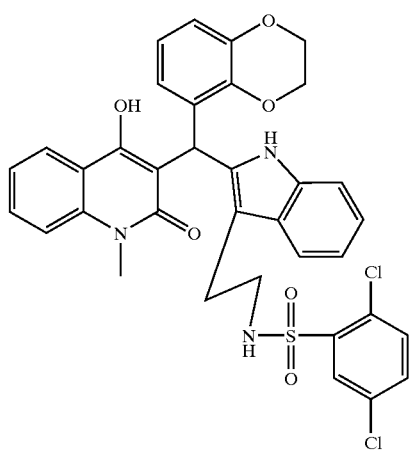

TABLE 2-1-continued
Compound No. 090
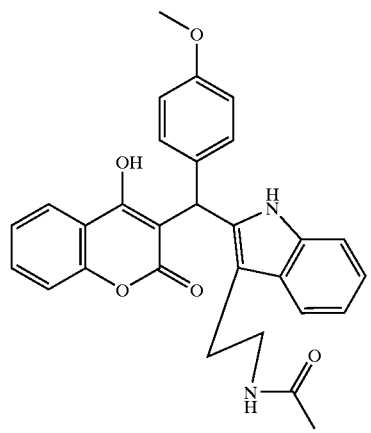
Compound No. 091
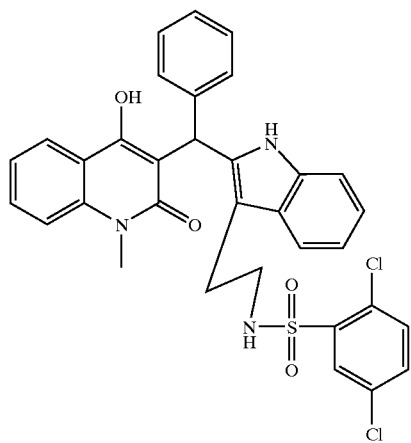
Compound No. 092
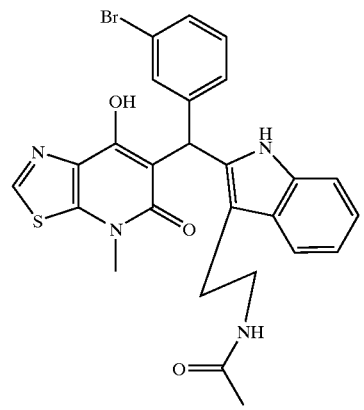
TABLE 2-1-continued
Compound No. 093
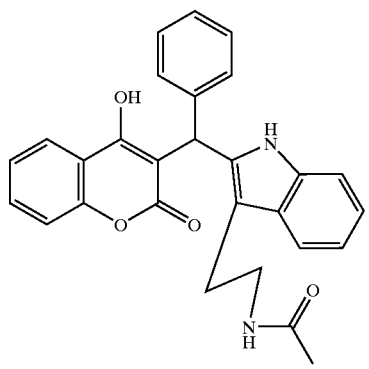
Compound No. 094
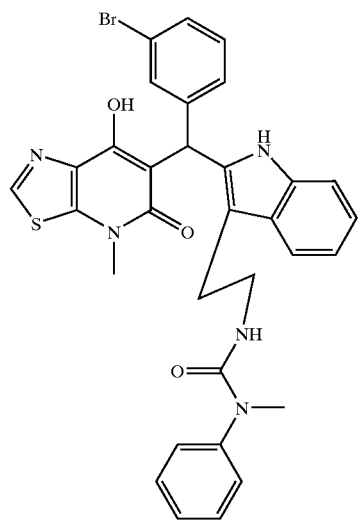
Compound No. 095
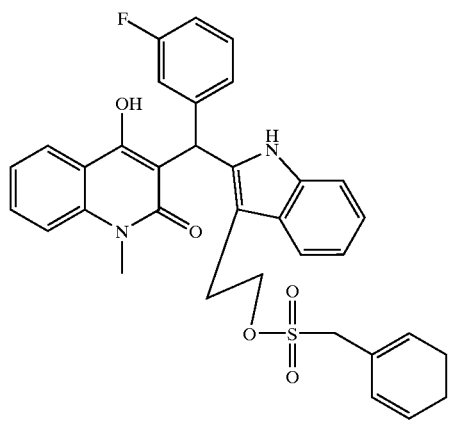

TABLE 2-1-continued
Compound No. 096
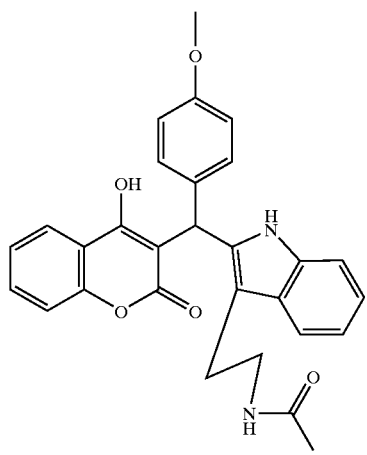
Compound No. 097
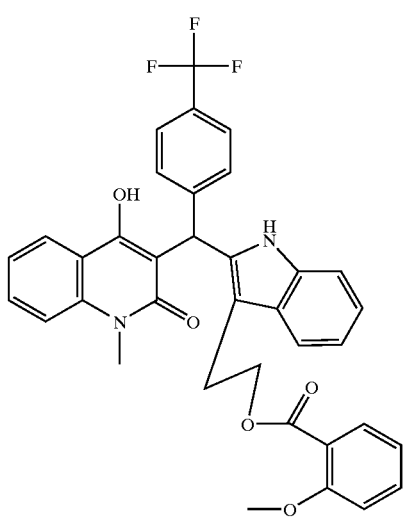
Compound No. 098
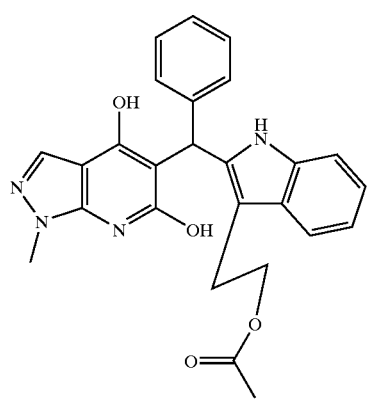
TABLE 2-2
Compound No. 099
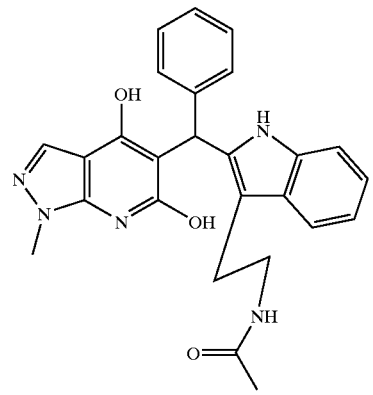
Compound No. 100
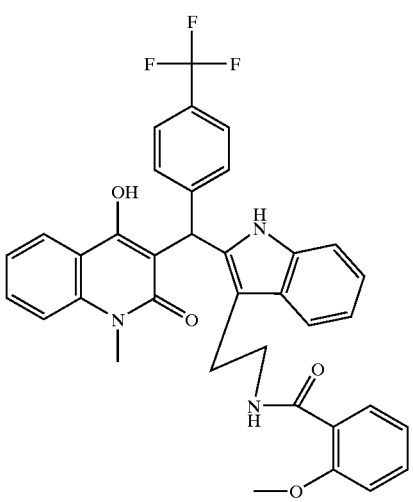
Compound No. 101
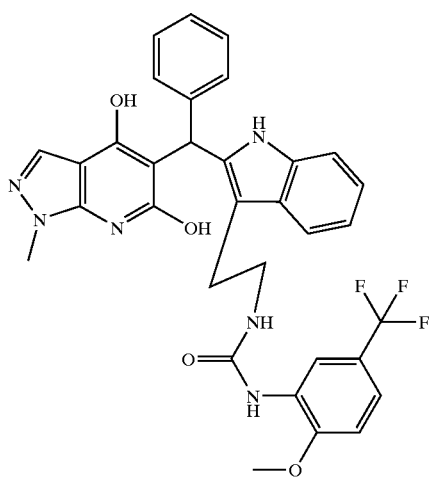

TABLE 2-2-continued
Compound No. 102
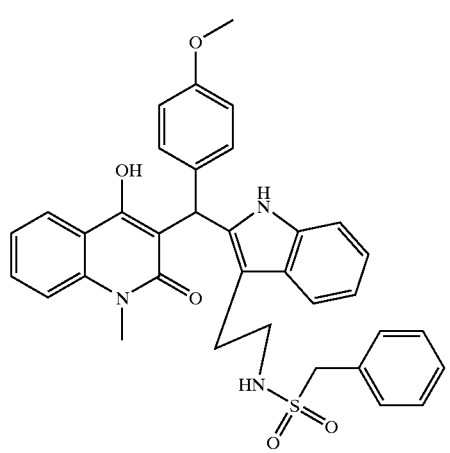
Compound No. 103
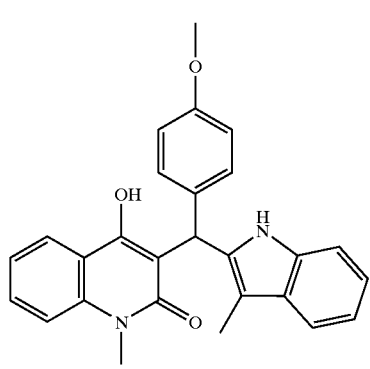
Compound No. 104
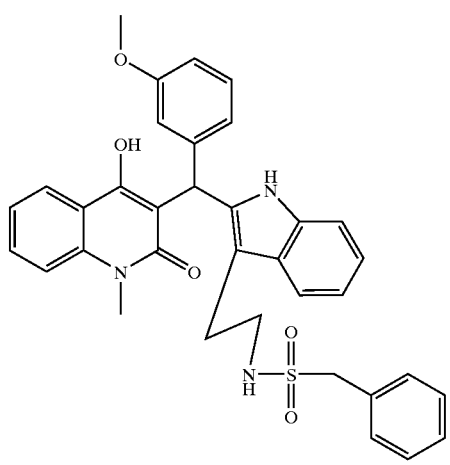
TABLE 2-2-continued
Compound No. 105
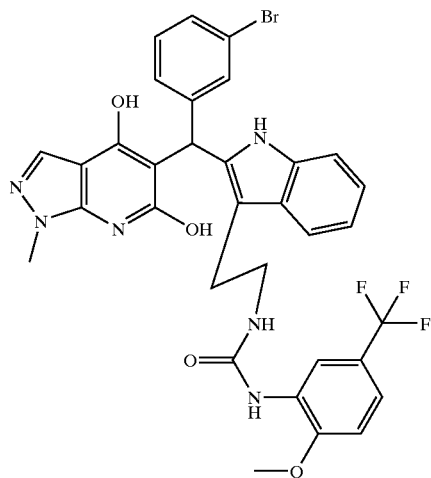
Compound No. 106
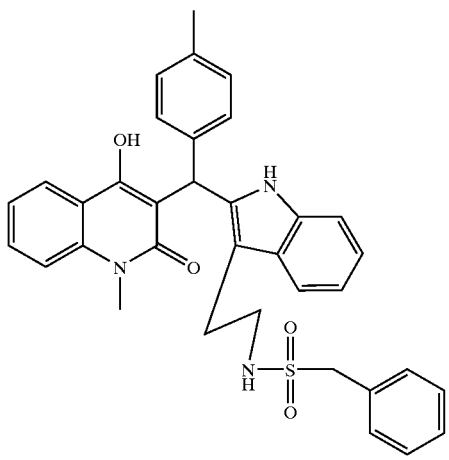
Compound No. 107
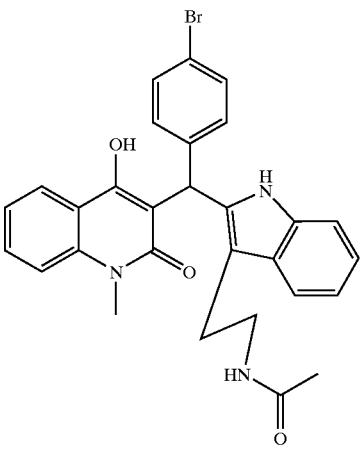

TABLE 2-2-continued
Compound No. 108
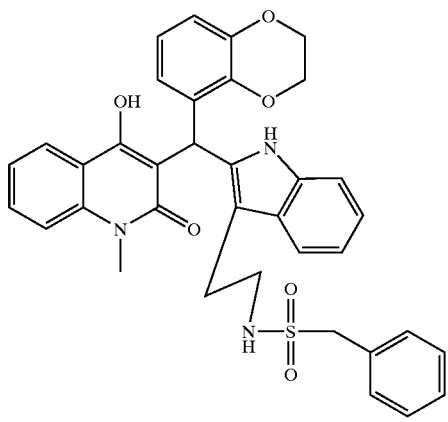
Compound No. 109
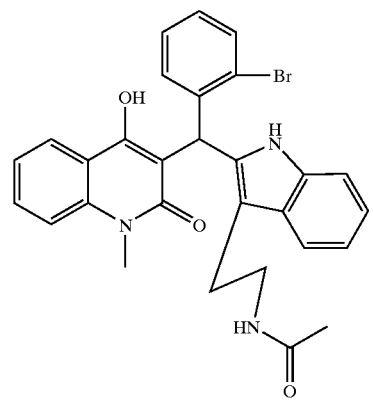
Compound No. 110
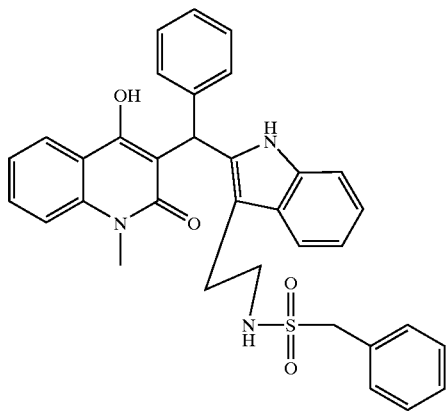
TABLE 2-3
Compound No. 111
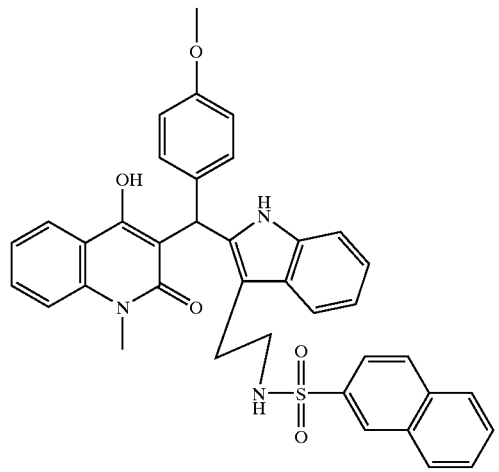
Compound No. 112
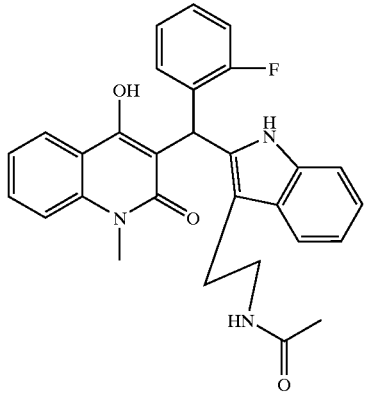
Compound No. 113
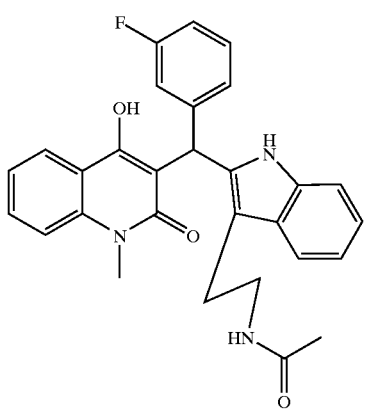

TABLE 2-3-continued
Compound No. 114
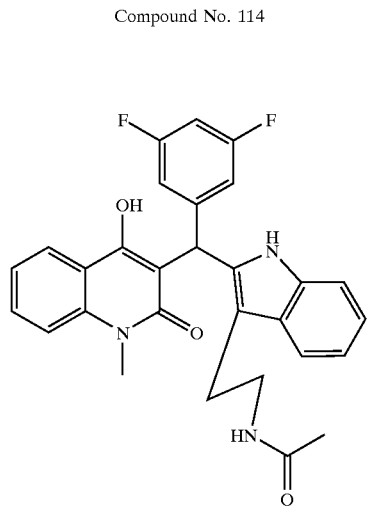
Compound No. 115
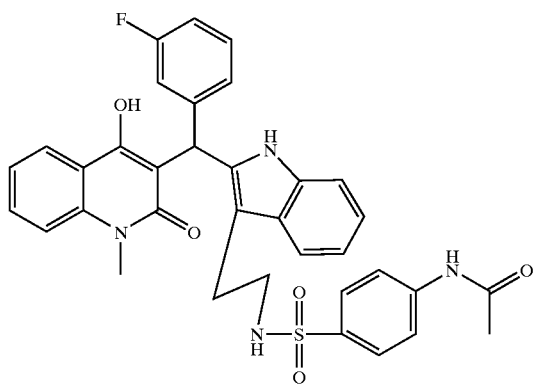
Compound No. 116
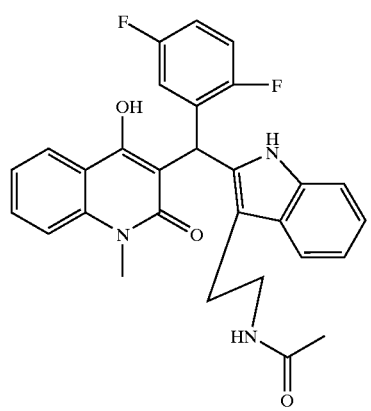
TABLE 2-3-continued
Compound No. 117
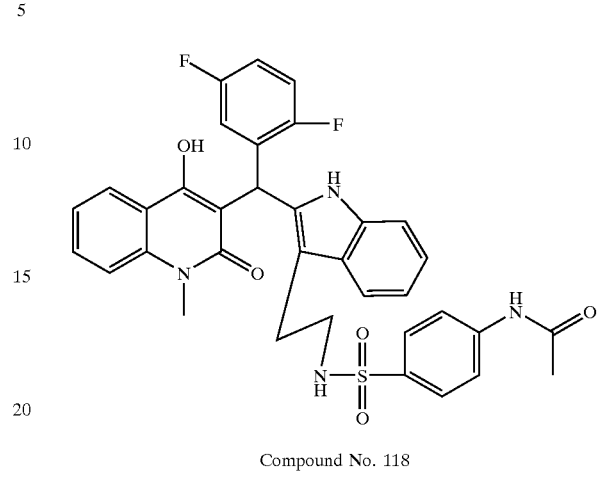
Compound No. 118
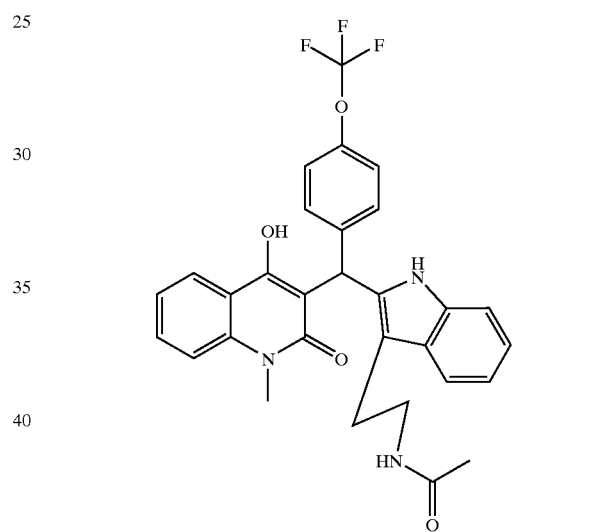
Compound No. 119
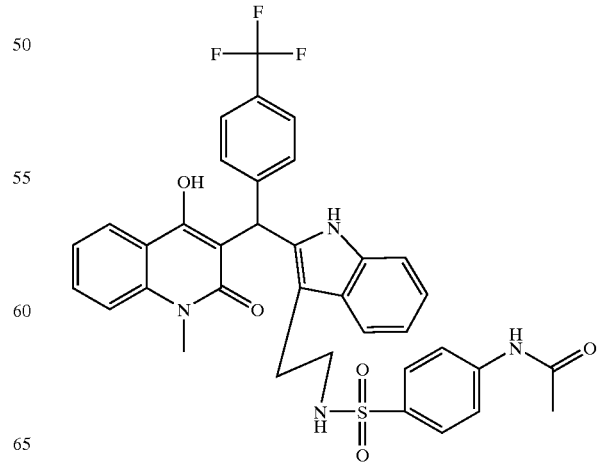

TABLE 2-3-continued
Compound No. 120
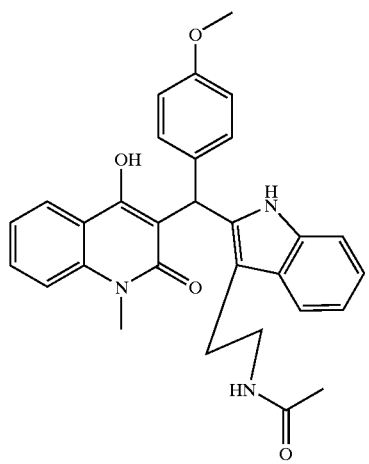
Compound No. 121
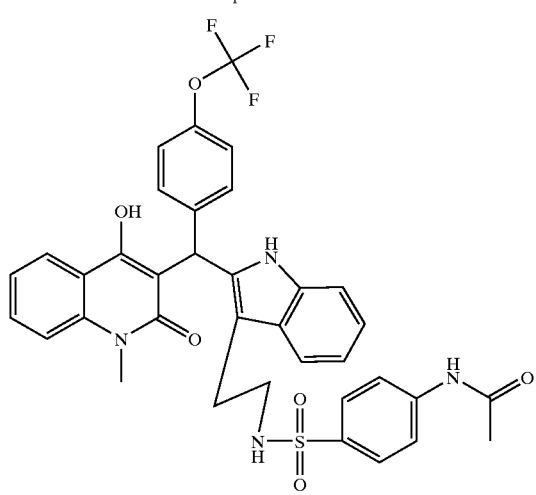
Compound No. 122
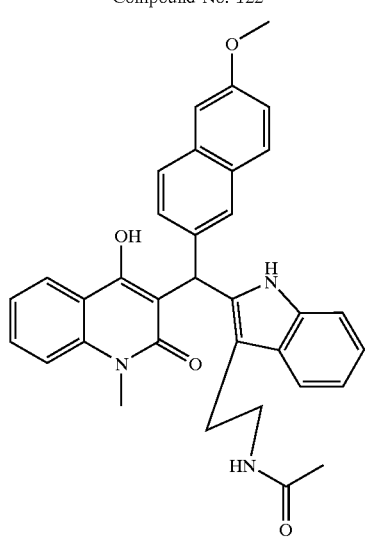
TABLE 2-4
Compound No. 123
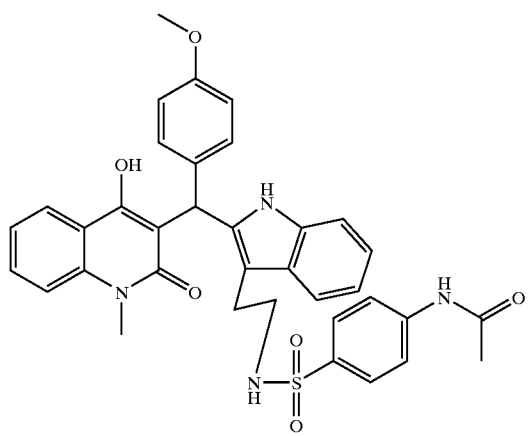
Compound No. 124
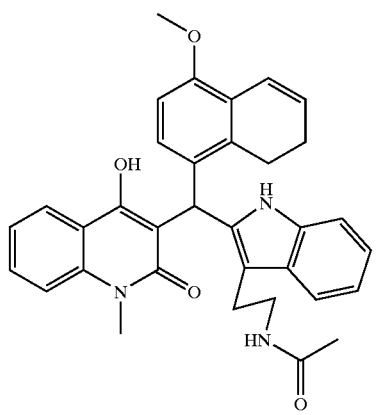
Compound No. 125
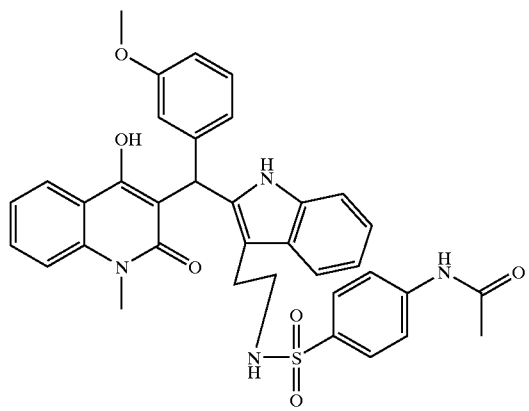

TABLE 2-4-continued
Compound No. 126
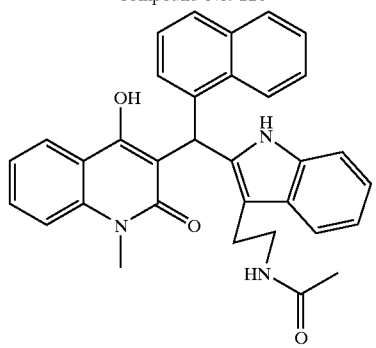
Compound No. 127
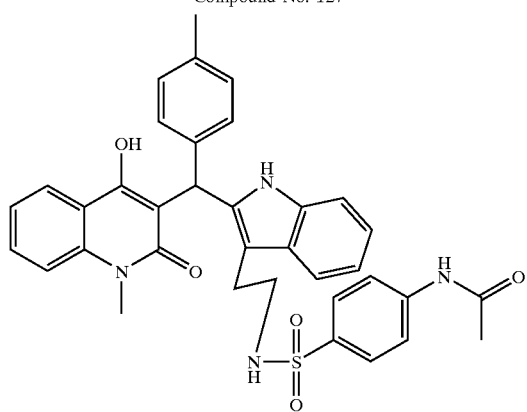
Compound No. 128
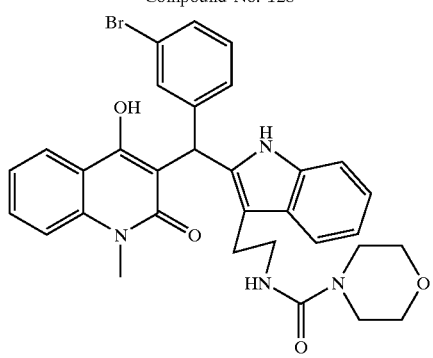
Compound No. 129
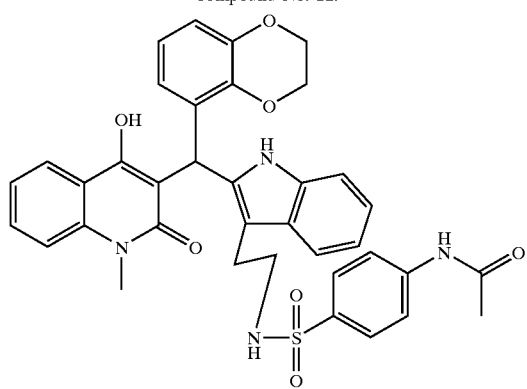
TABLE 2-4-continued
Compound No. 130
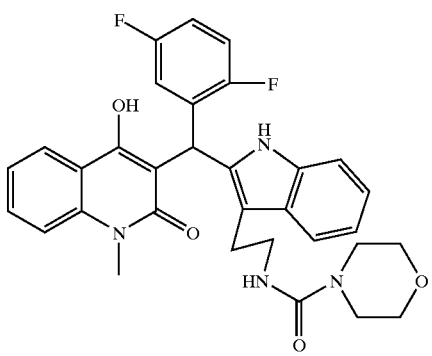
Compound No. 131
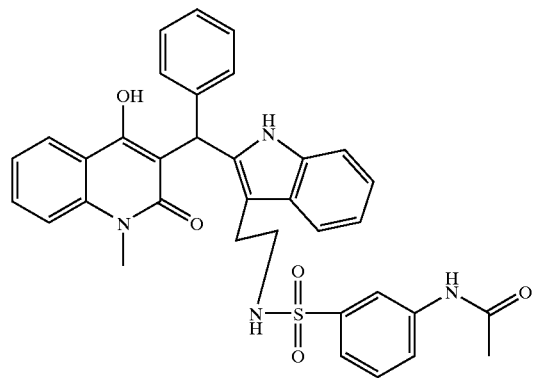
Compound No. 132
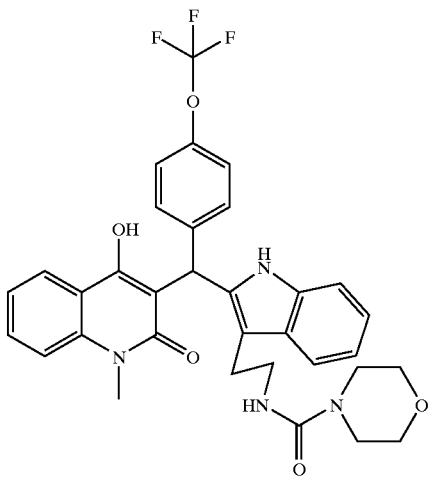

TABLE 2-4-continued
Compound No. 133
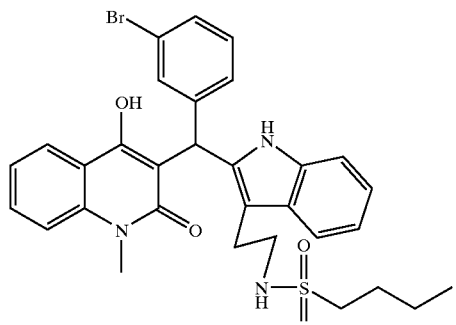
Compound No. 134
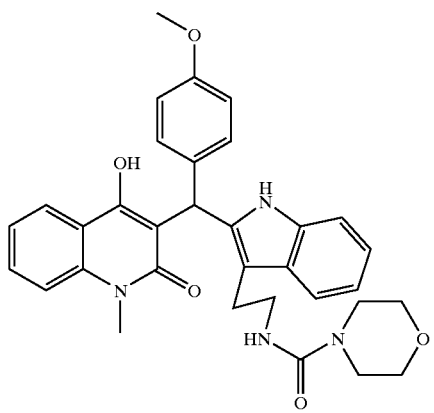
TABLE 2-5
Compound No. 135
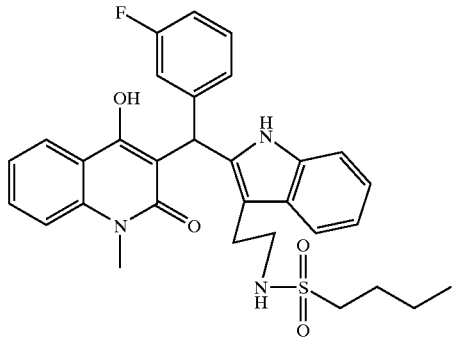
TABLE 2-5-continued
Compound No. 136
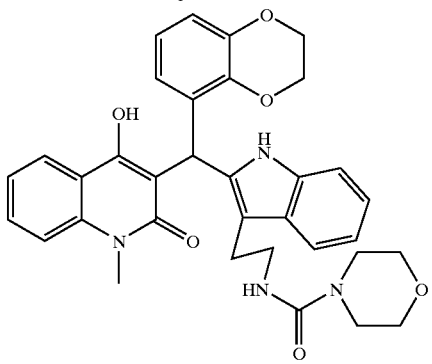
Compound No. 137
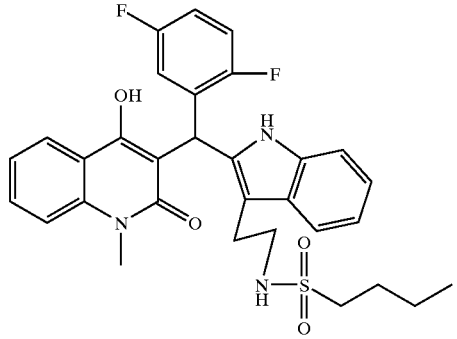
Compound No. 138
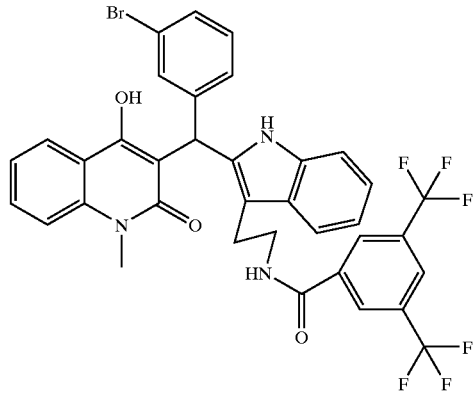
Compound No. 139
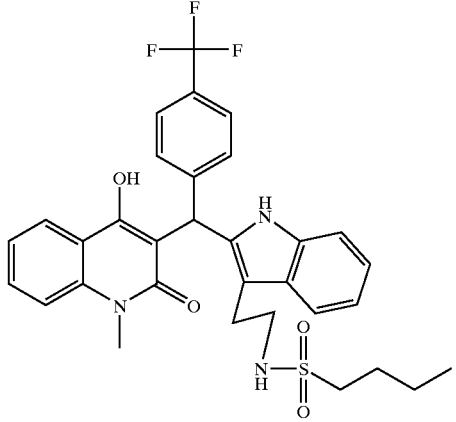

TABLE 2-5-continued
Compound No. 140
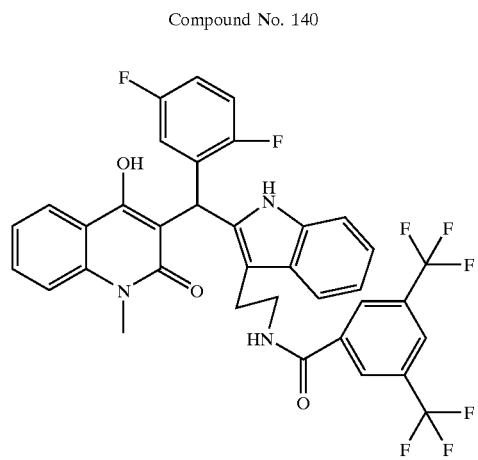
Compound No. 141
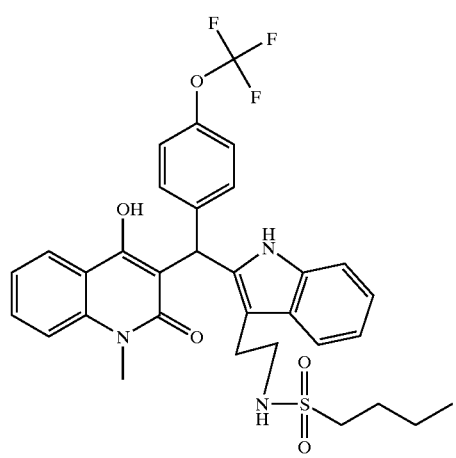
Compound No. 142
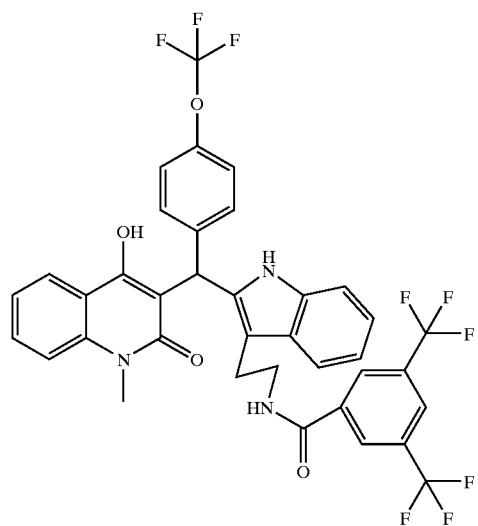
TABLE 2-5-continued
Compound No. 143
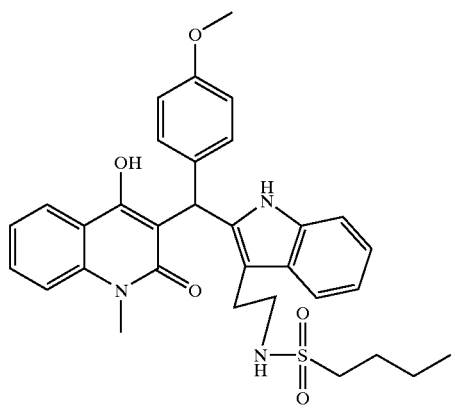
Compound No. 144
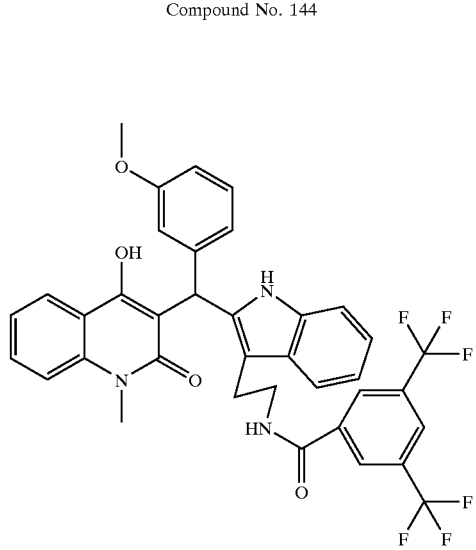
Compound No. 145
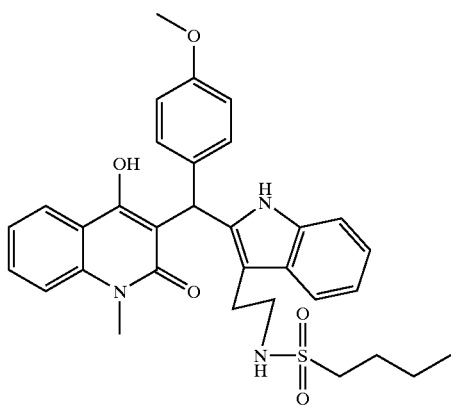

TABLE 2-5-continued
Compound No. 146
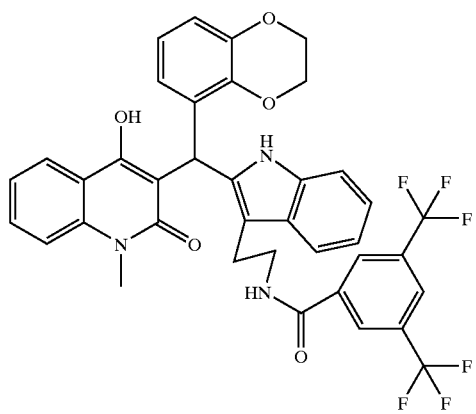
TABLE 2-6
Compound No. 147
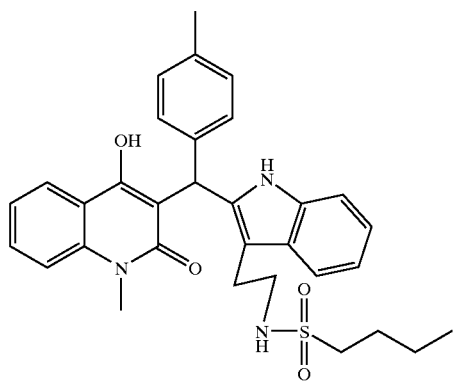
Compound No. 148
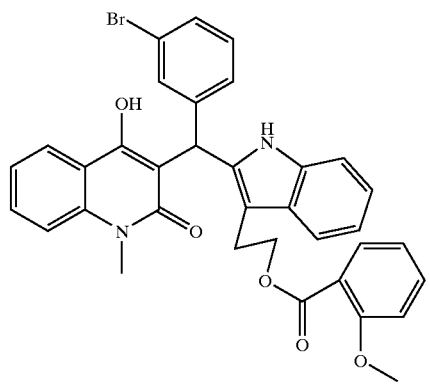
TABLE 2-6-continued
Compound No. 149
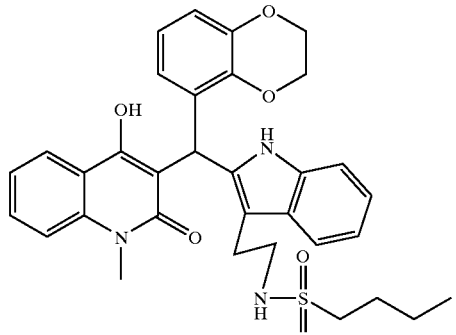
Compound No. 150
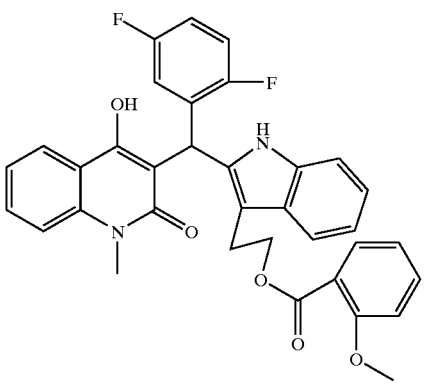
Compound No. 151
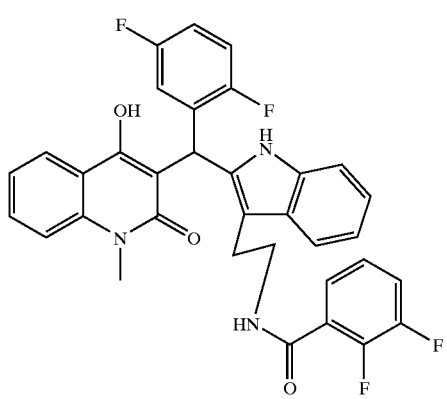

TABLE 2-6-continued
Compound No. 152
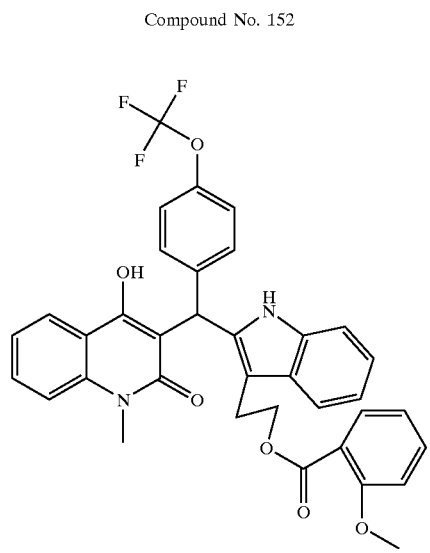
Compound No. 153
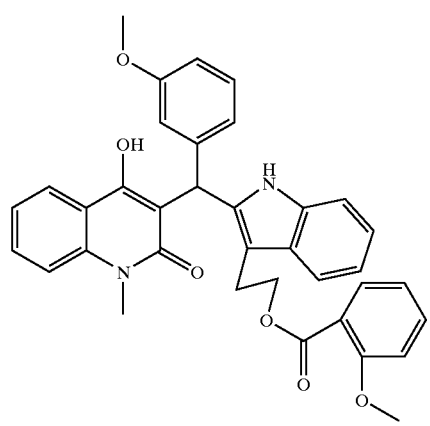
Compound No. 154
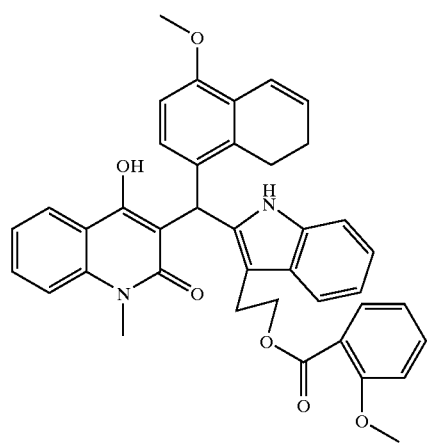
TABLE 2-6-continued
Compound No. 155
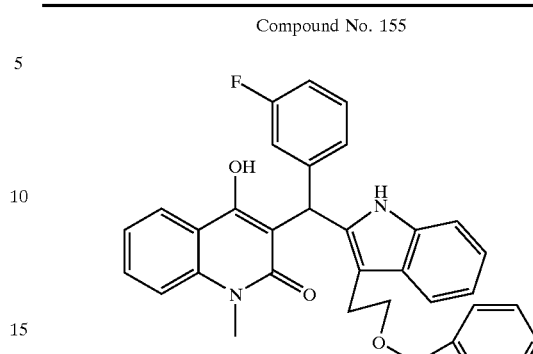
Compound No. 156
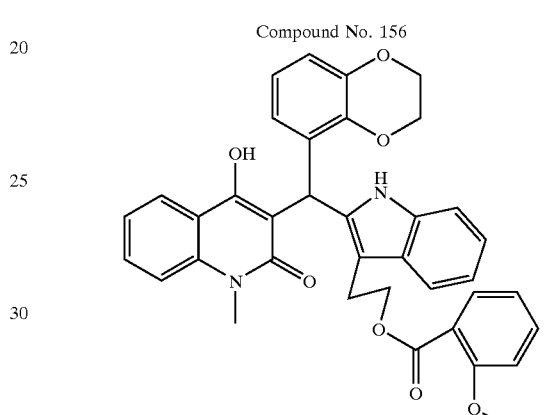
Compound No. 157
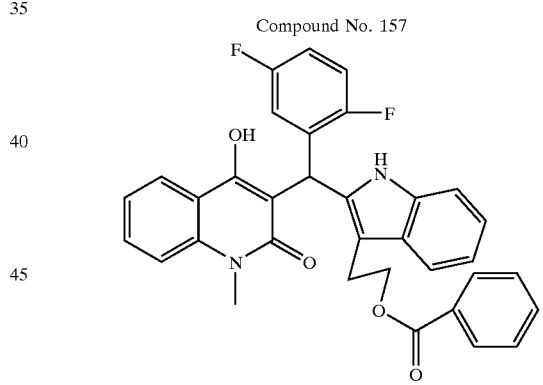
Compound No. 158
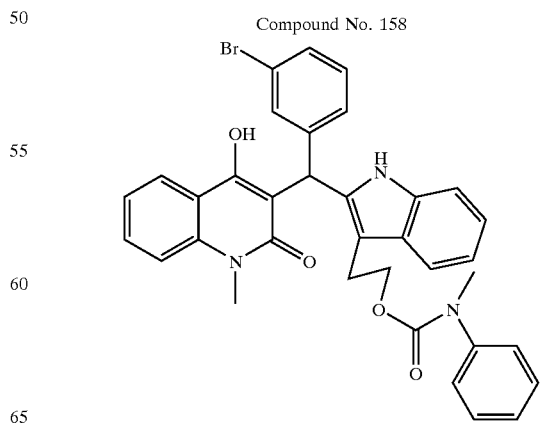

TABLE 2-7

Compound No. 159

Compound No. 160

Compound No. 161

TABLE 2-7-continued

Compound No. 162

Compound No. 163

Compound No. 164

TABLE 2-7-continued
Compound No. 165
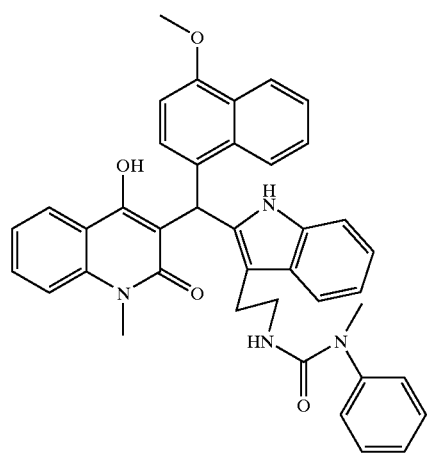
Compound No. 166
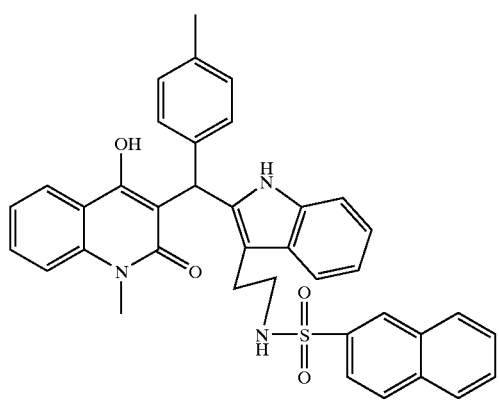
Compound No. 167
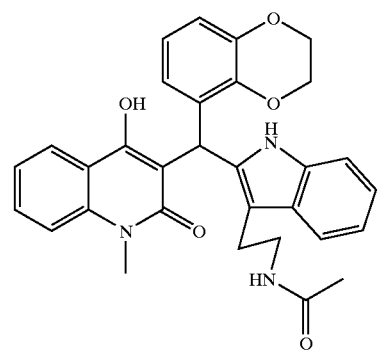
TABLE 2-7-continued
Compound No. 168
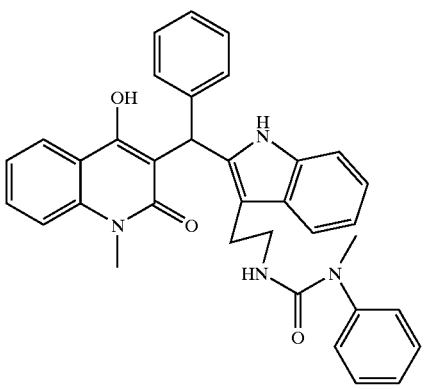
Compound No. 169
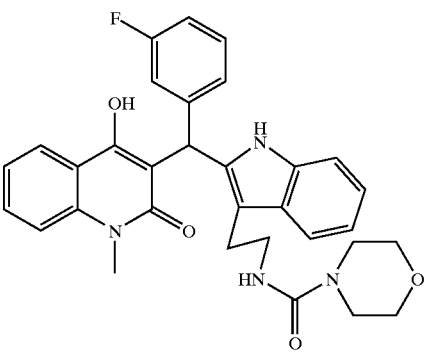
Compound No. 170
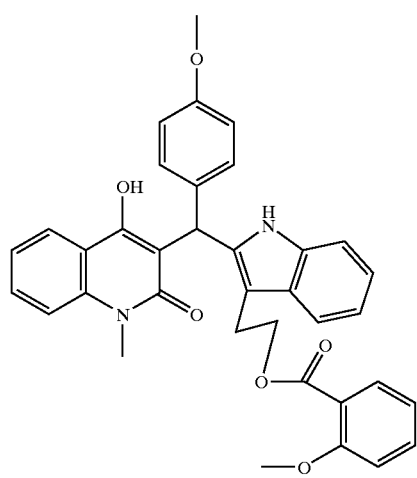

TABLE 2-8
Compound No. 171
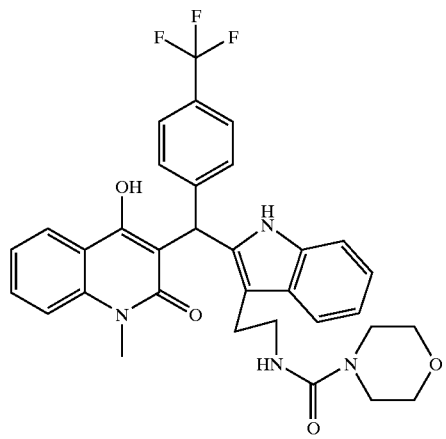
Compound No. 172
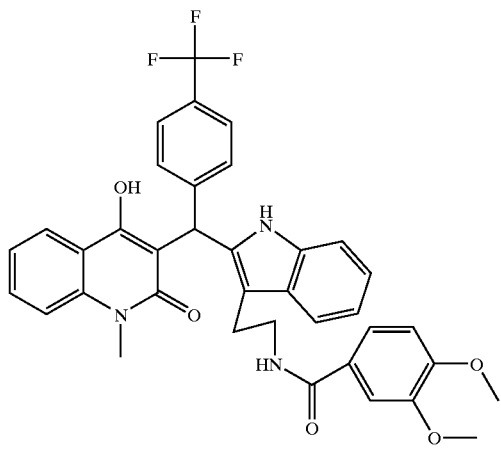
Compound No. 173
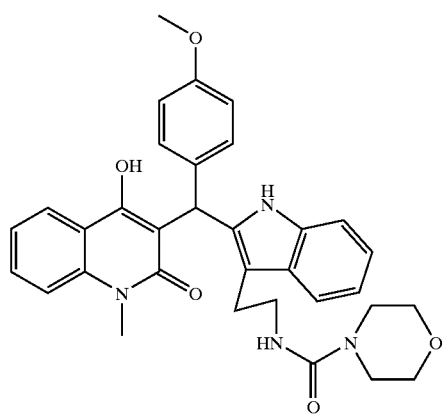
TABLE 2-8-continued
Compound No. 174
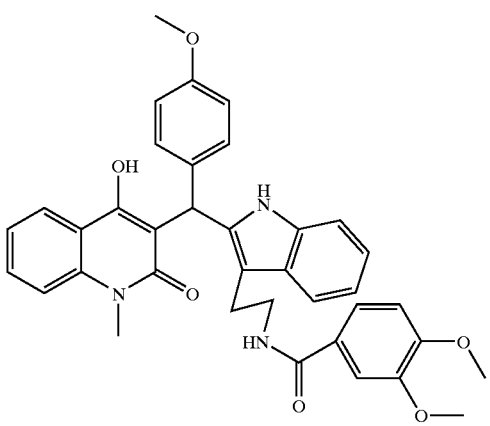
Compound No. 175
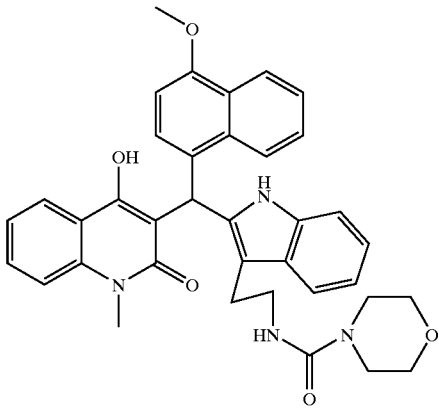
Compound No. 176
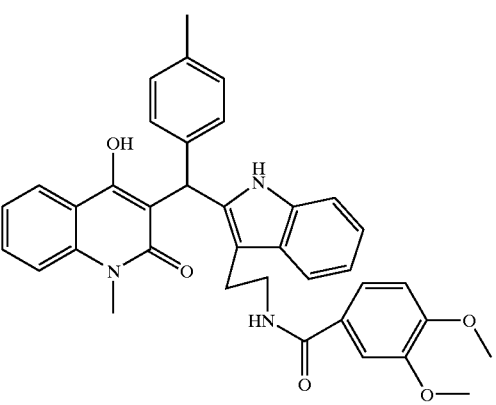

TABLE 2-8-continued
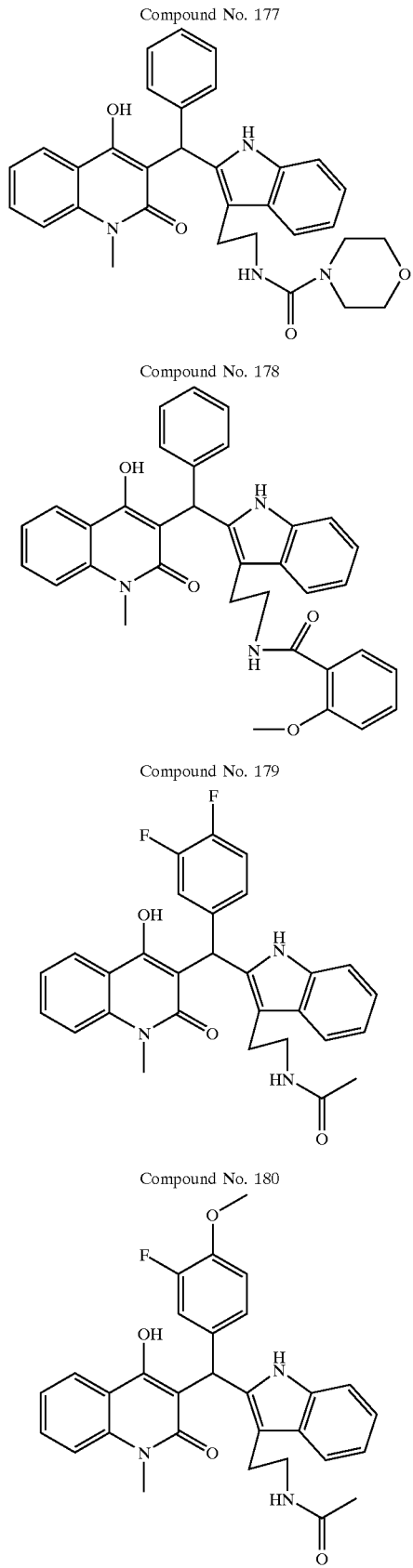
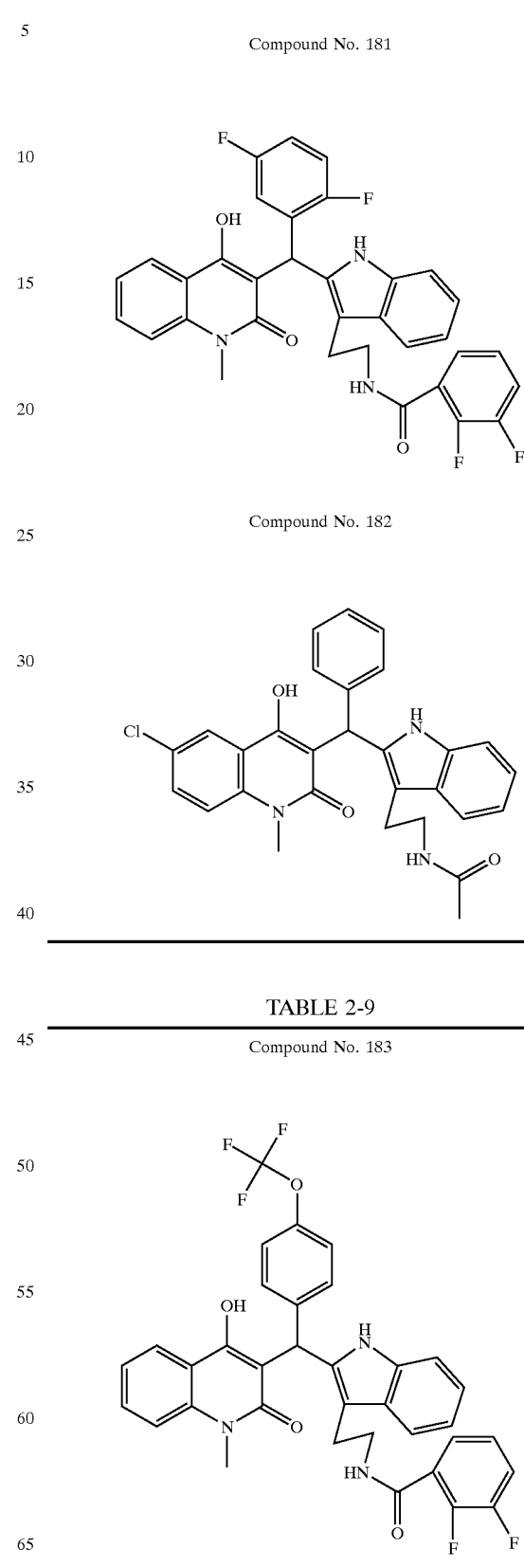

TABLE 2-9-continued
Compound No. 184
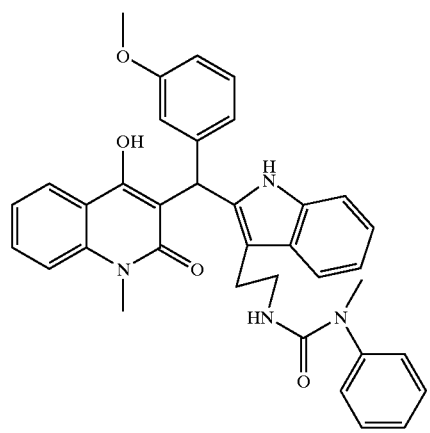
Compound No. 185
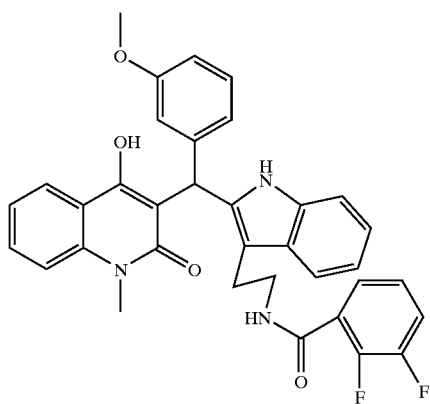
Compound No. 186
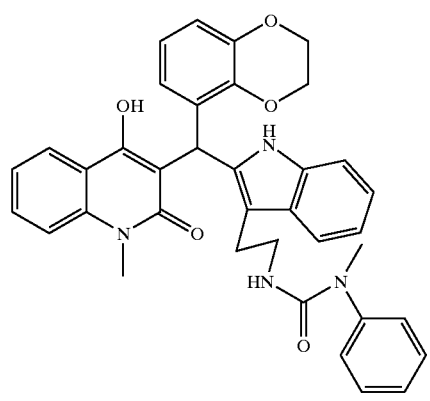
TABLE 2-9-continued
Compound No. 187
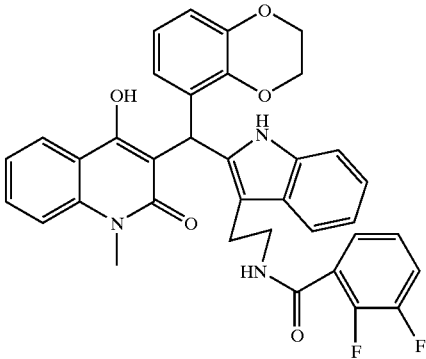
Compound No. 188
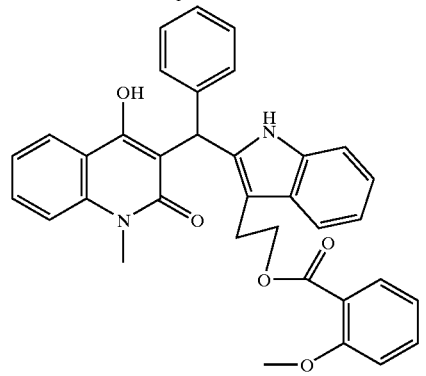
Compound No. 189
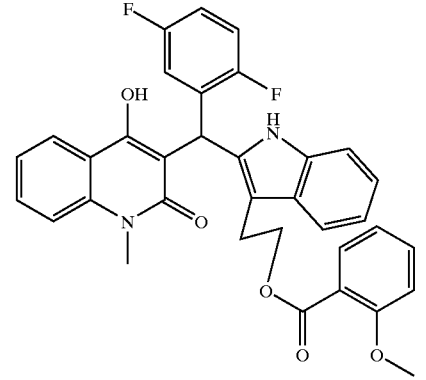
Compound No. 190
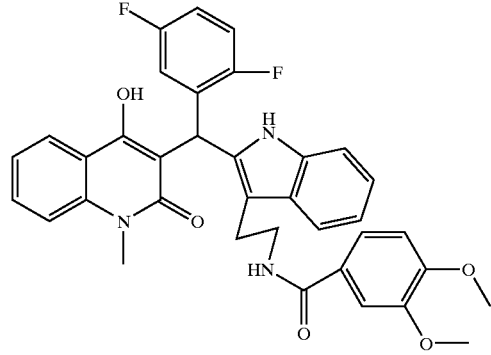

TABLE 2-9-continued
Compound No. 191
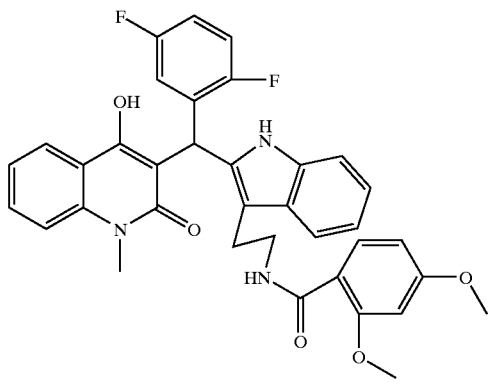
Compound No. 192
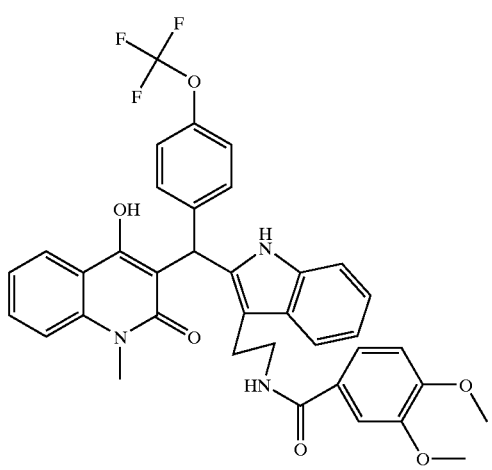
Compound No. 193
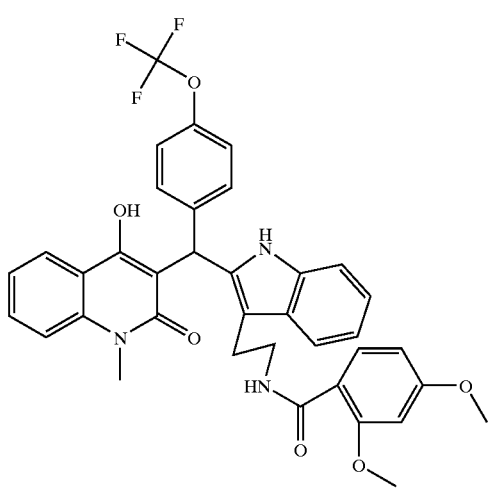
TABLE 2-9-continued
Compound No. 194
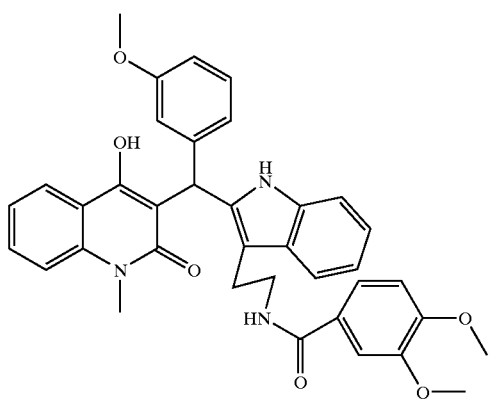
TABLE 2-10
Compound No. 195
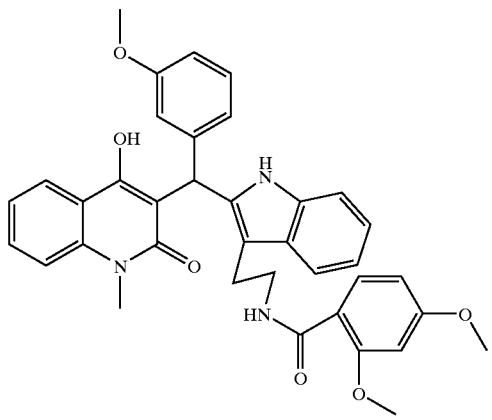
Compound No. 196
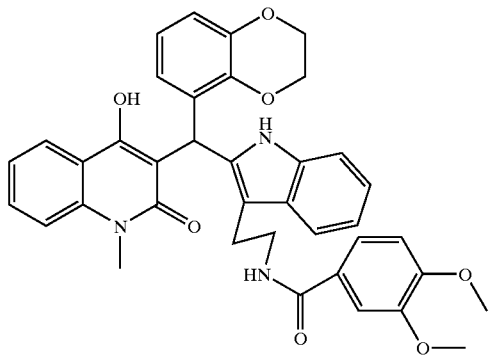

TABLE 2-10-continued
Compound No. 197
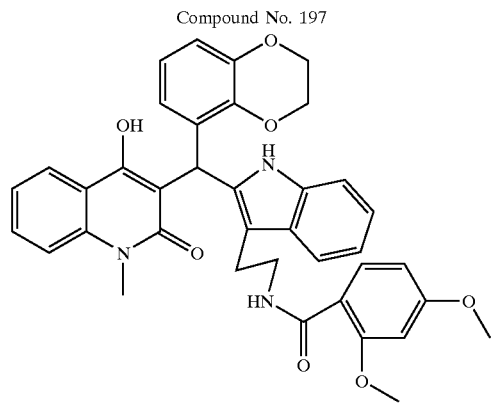
Compound No. 198
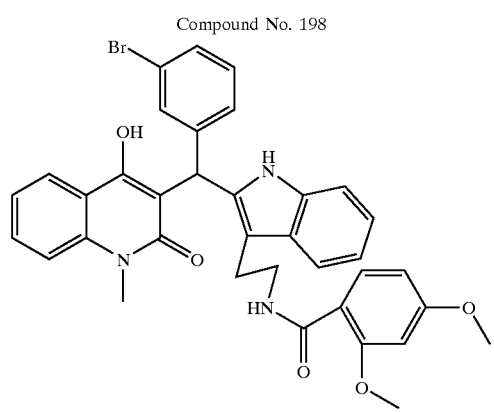
Compound No. 199
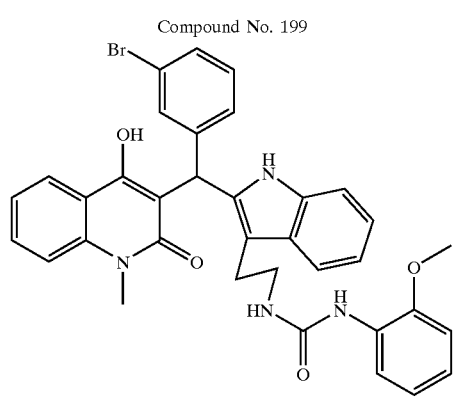
Compound No. 200
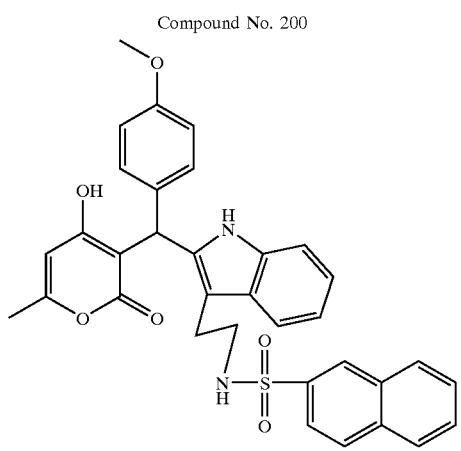
TABLE 2-10-continued
Compound No. 201
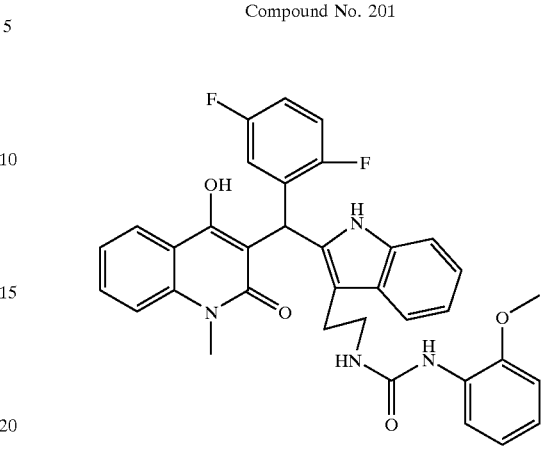
Compound No. 202
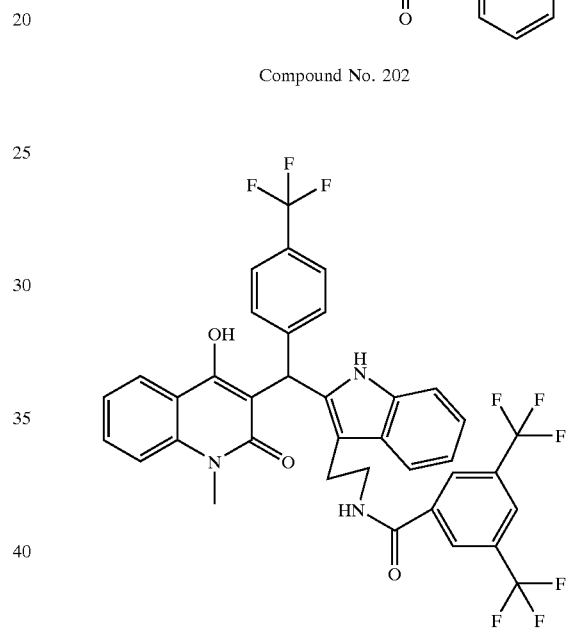
Compound No. 203
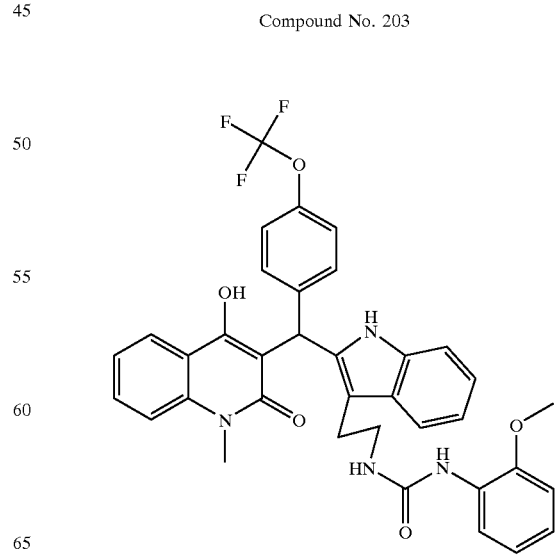

TABLE 2-10-continued
Compound No. 204
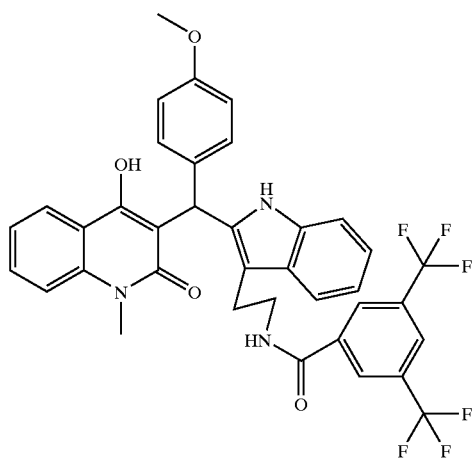
Compound No. 205
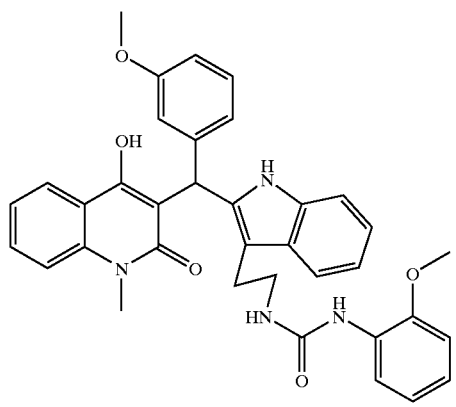
Compound No. 206
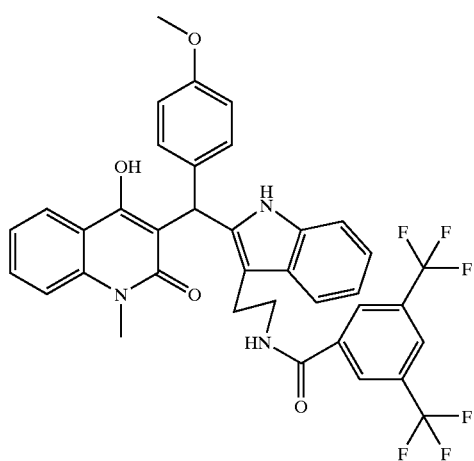
TABLE 2-11
Compound No. 207
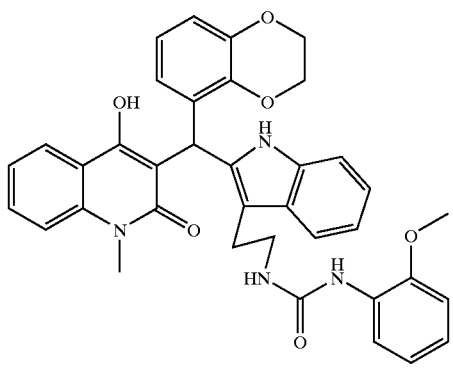
Compound No. 208
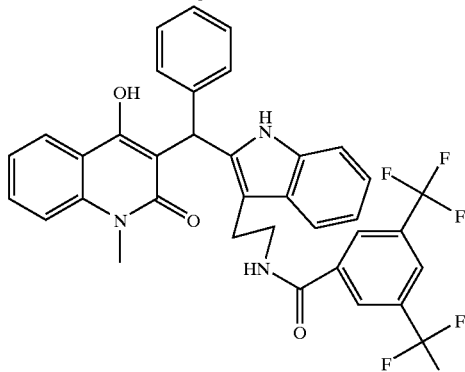
Compound No. 209
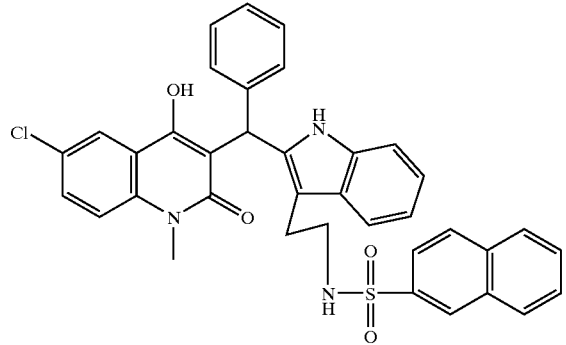
Compound No. 210
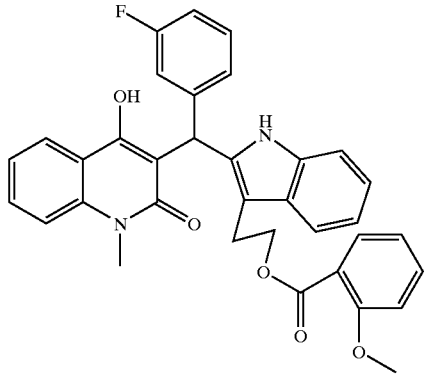

TABLE 2-11-continued
Compound No. 211
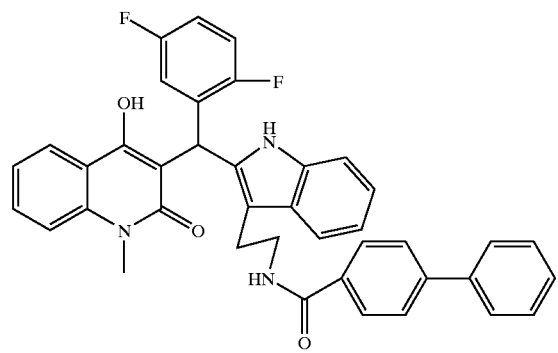
Compound No. 212
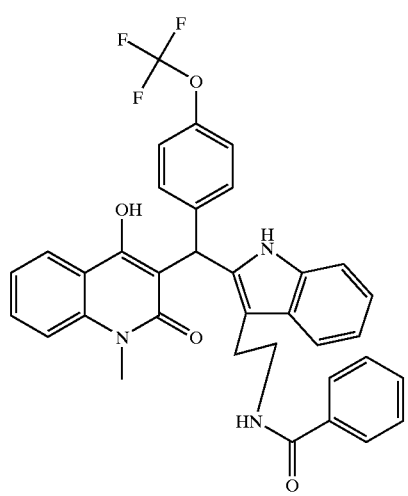
Compound No. 213
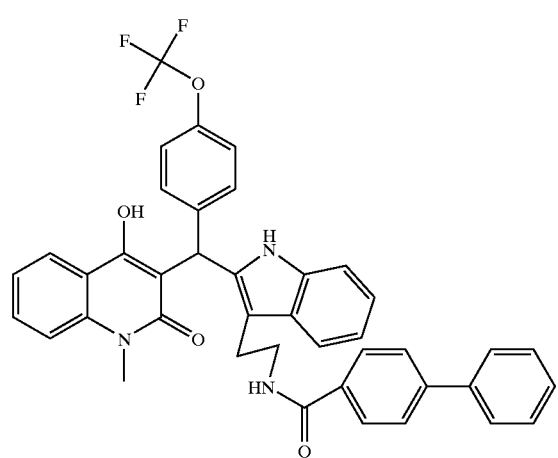
TABLE 2-11-continued
Compound No. 214
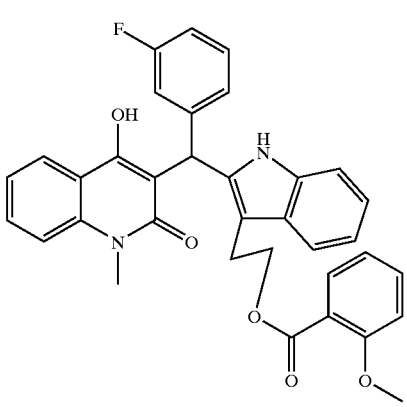
Compound No. 215
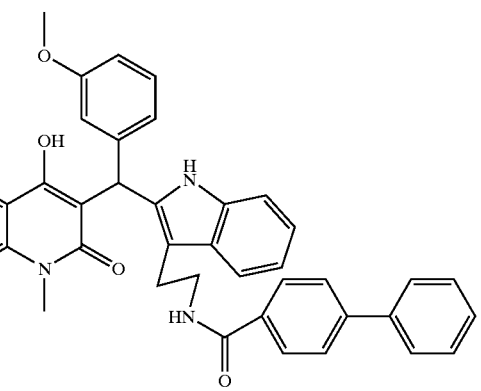
Compound No. 216
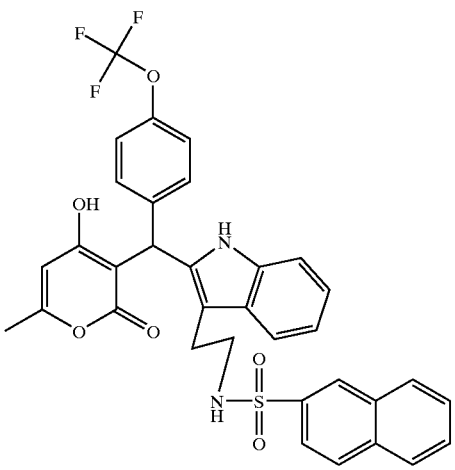

TABLE 2-11-continued
Compound No. 217
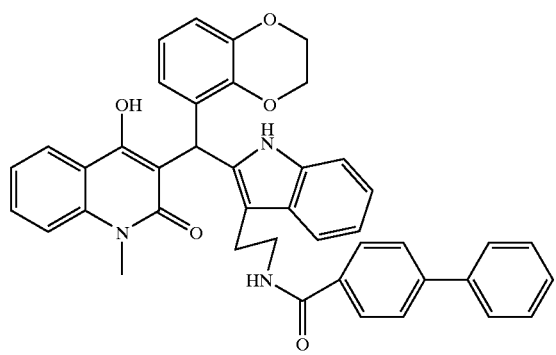
Compound No. 218
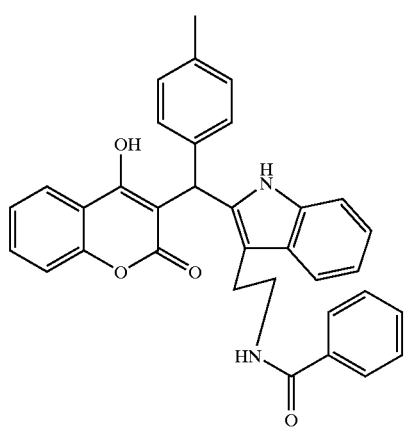
TABLE 2-12
Compound No. 219
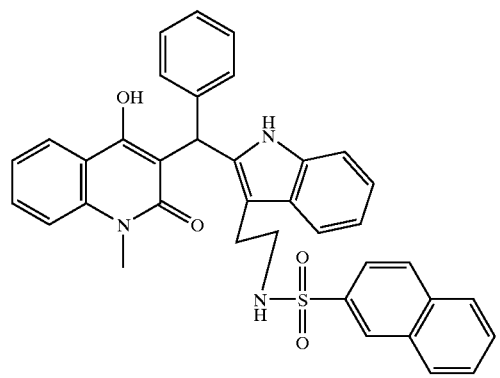
TABLE 2-12-continued
Compound No. 220
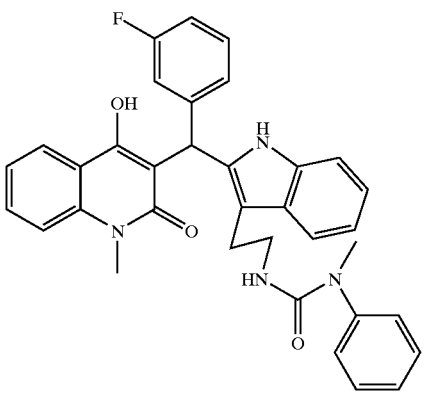
Compound No. 221
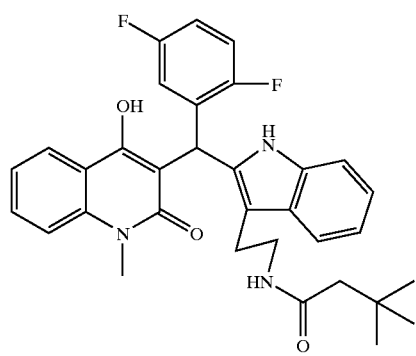
Compound No. 222
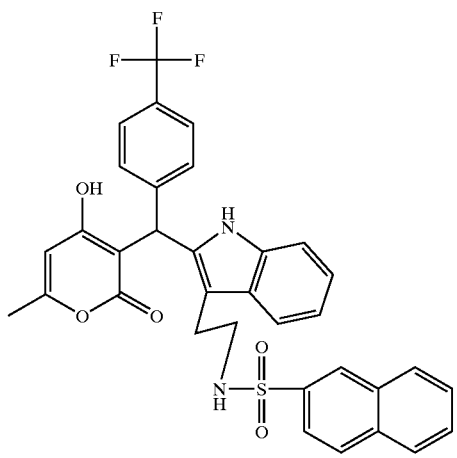

TABLE 2-12-continued
Compound No. 223
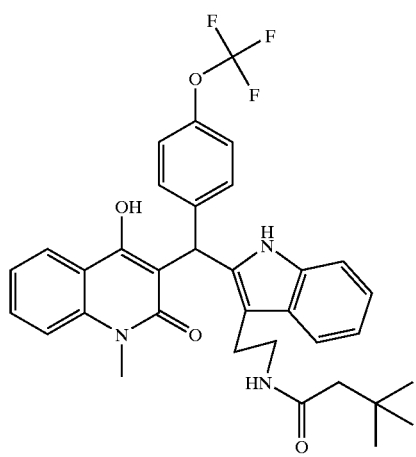
Compound No. 224
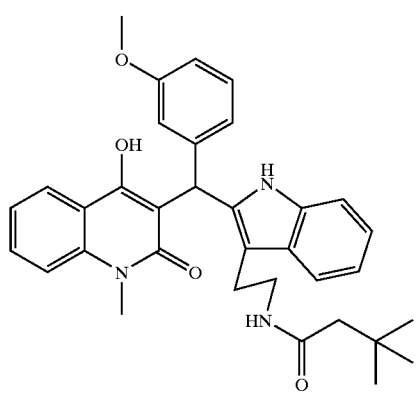
Compound No. 225
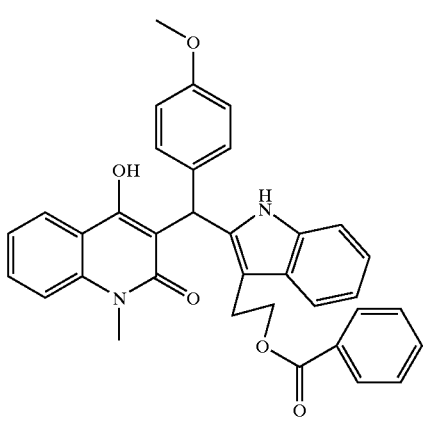
TABLE 2-12-continued
Compound No. 226
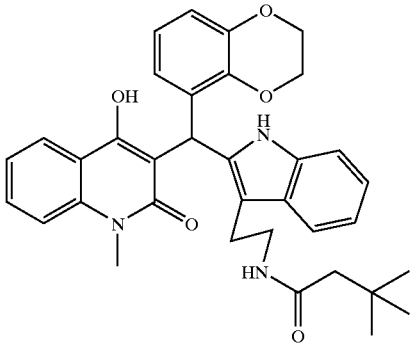
Compound No. 227
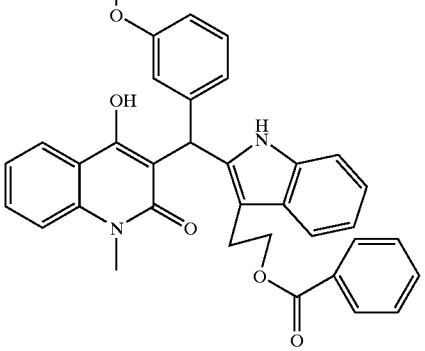
Compound No. 228
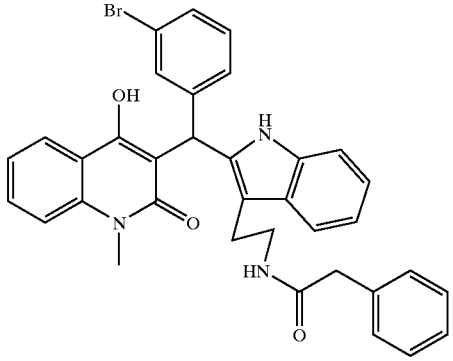
Compound No. 229
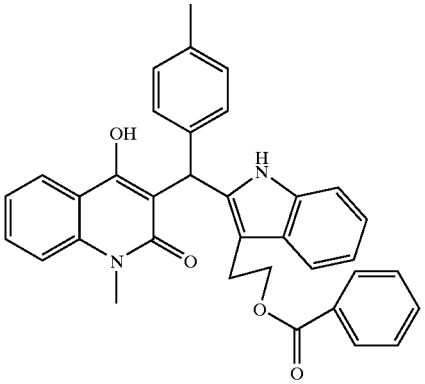

TABLE 2-12-continued
Compound No. 230
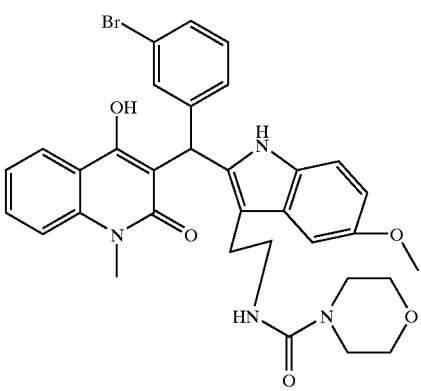
TABLE 2-13
Compound No. 231
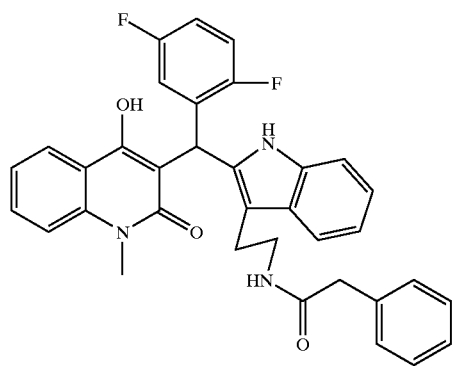
Compound No. 232
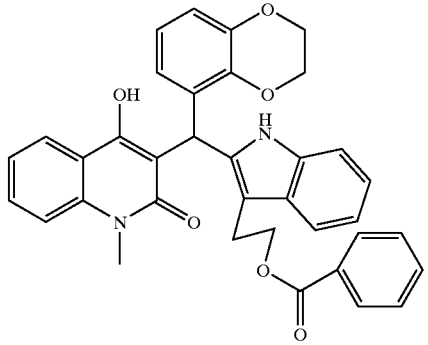
TABLE 2-13-continued
Compound No. 233
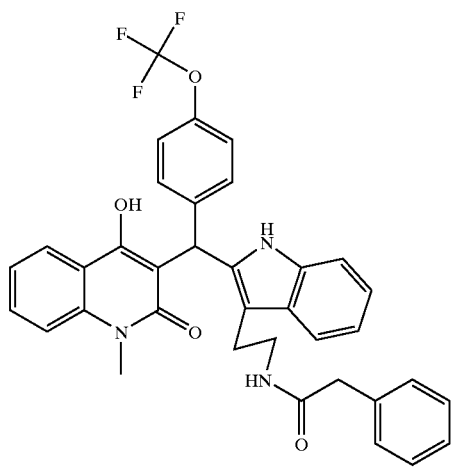
Compound No. 234
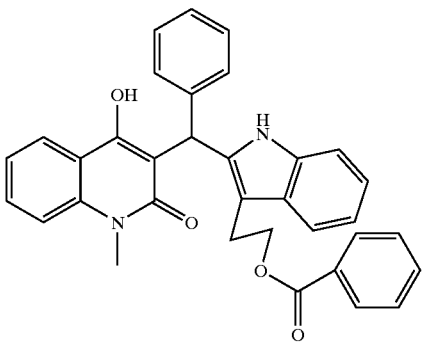
Compound No. 235
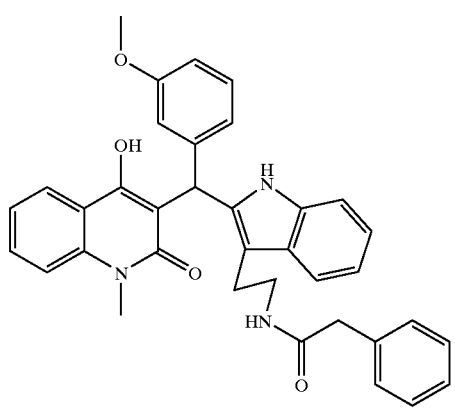

TABLE 2-13-continued
Compound No. 236
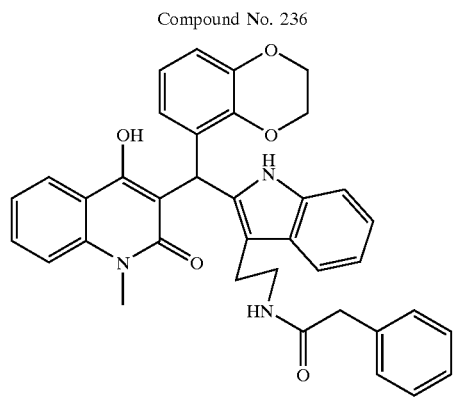
Compound No. 237
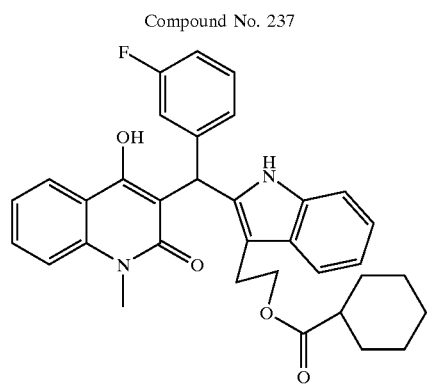
Compound No. 238
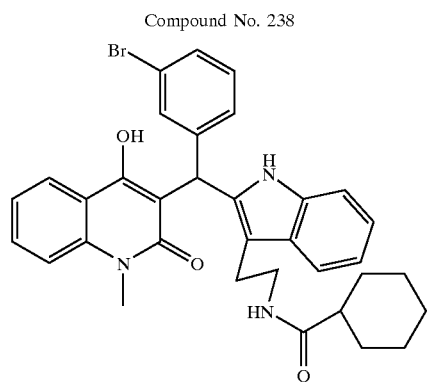
Compound No. 239
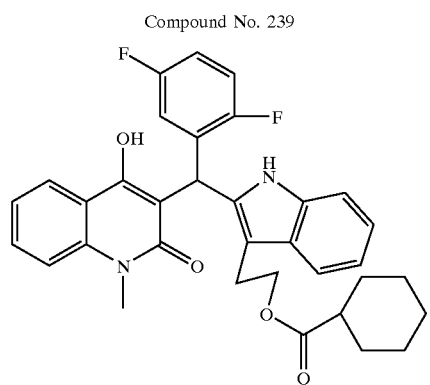
TABLE 2-13-continued
Compound No. 240
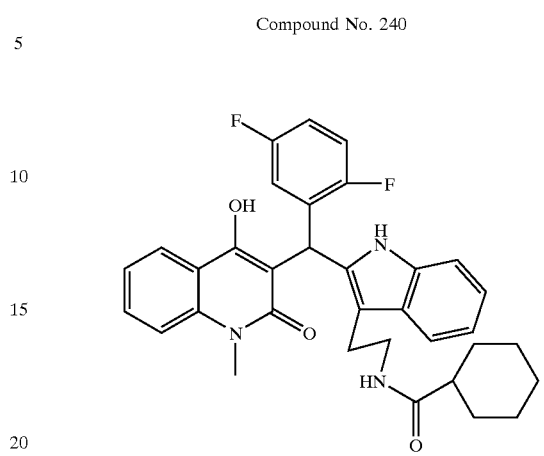
Compound No. 241
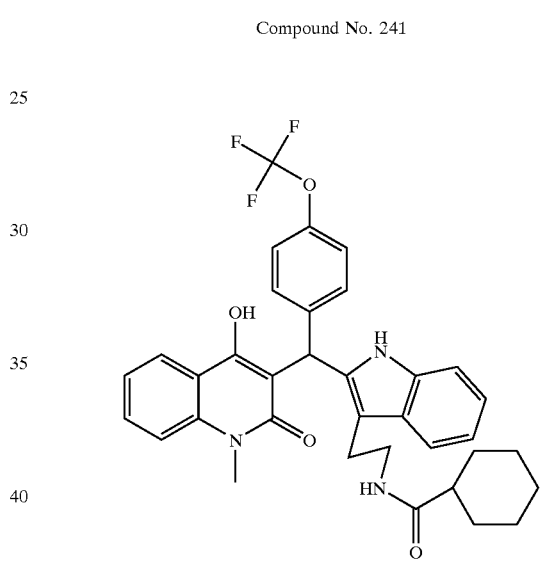
Compound No. 242
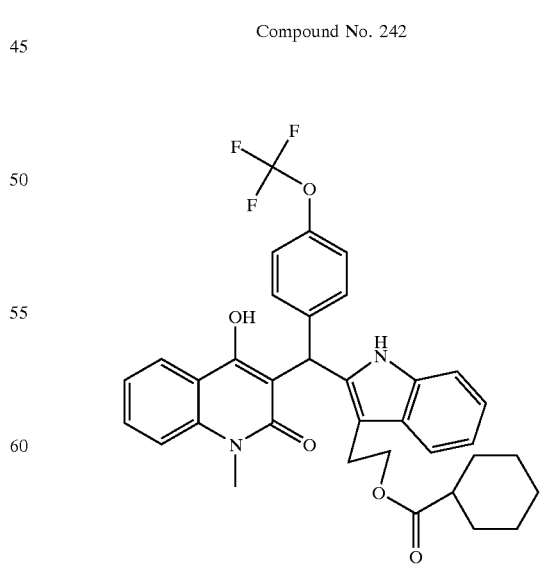

TABLE 2-14
Compound No. 243
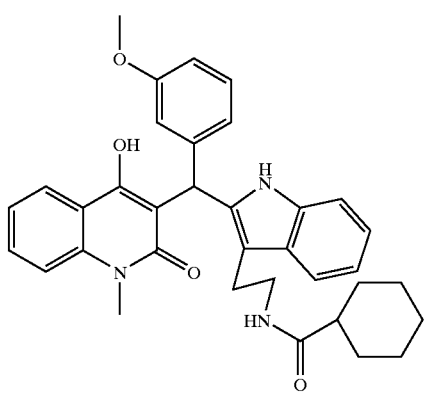
Compound No. 244
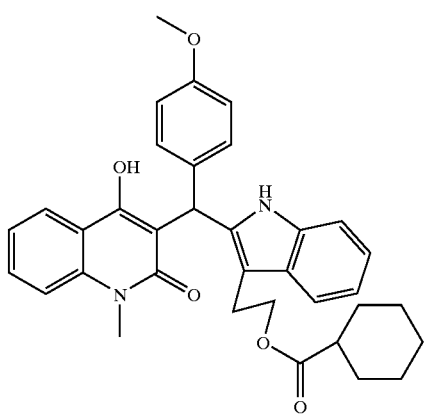
Compound No. 245
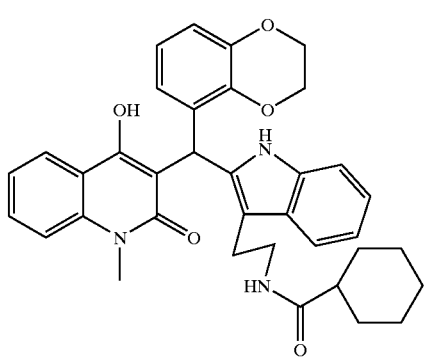
TABLE 2-14-continued
Compound No. 246
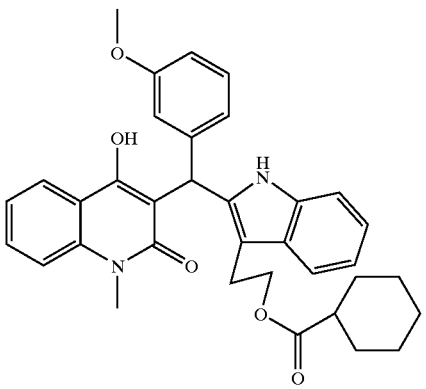
Compound No. 247
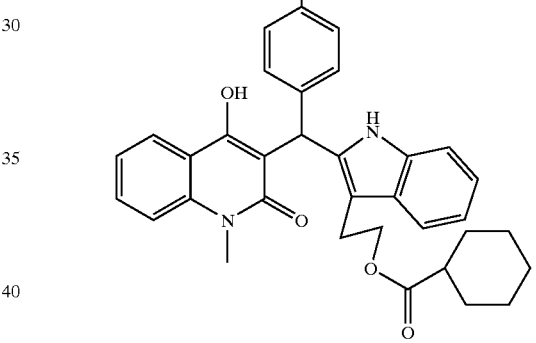
Compound No. 248
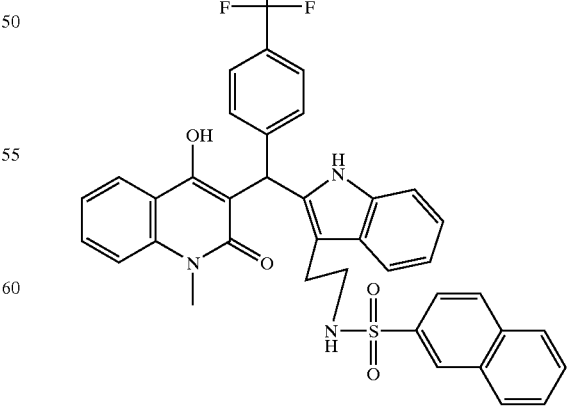

TABLE 2-14-continued
Compound No. 249
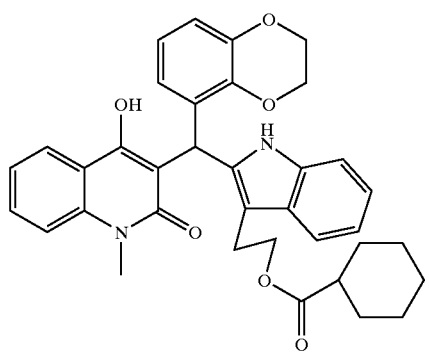
Compound No. 250
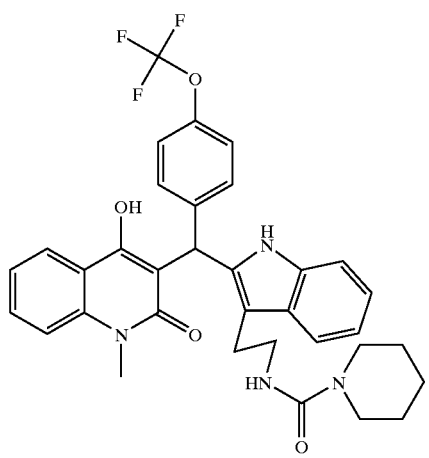
Compound No. 251
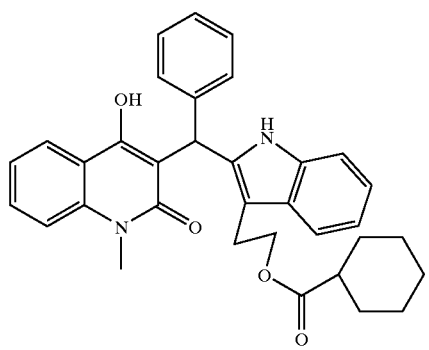
TABLE 2-14-continued
Compound No. 252
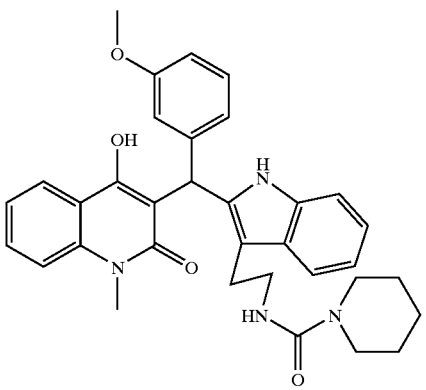
Compound No. 253
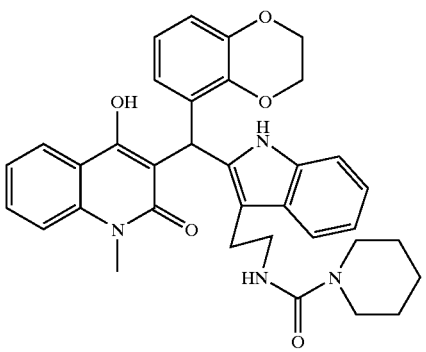
Compound No. 254
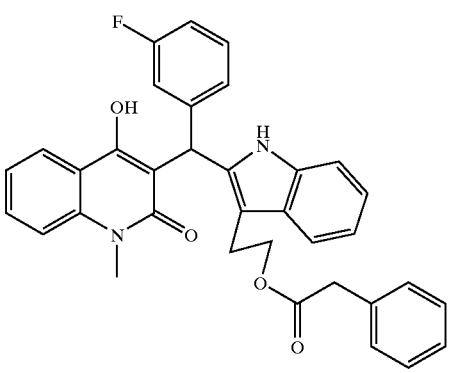

TABLE 2-15
Compound No. 255
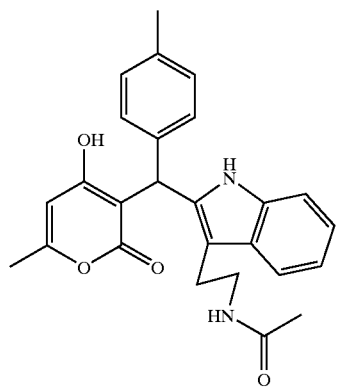
Compound No. 256
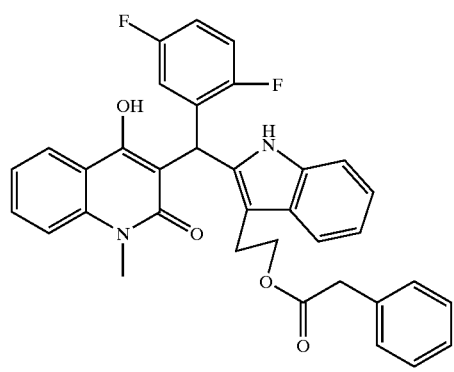
Compound No. 257
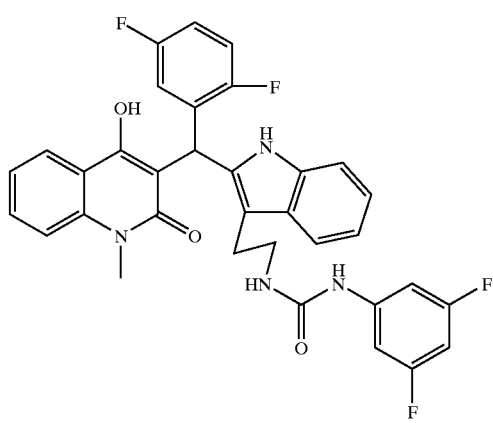
TABLE 2-15-continued
Compound No. 258
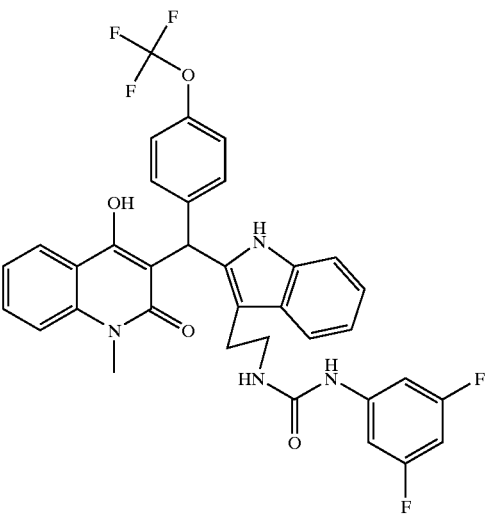
Compound No. 259
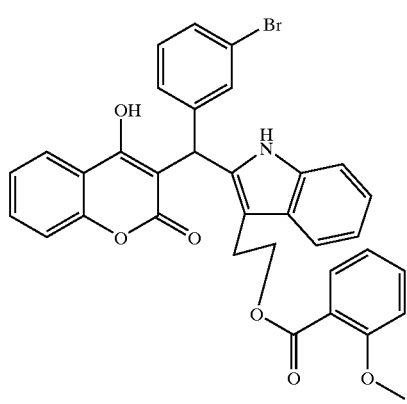
Compound No. 260
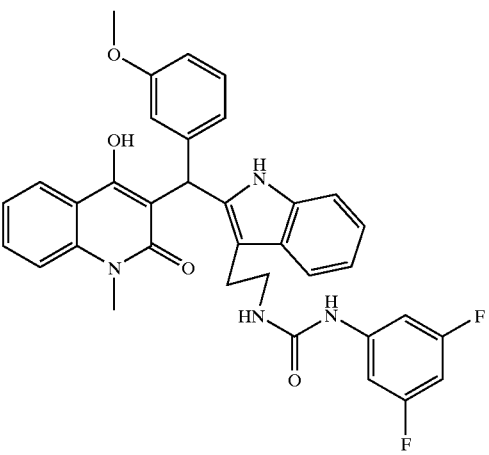

TABLE 2-15-continued
Compound No. 261
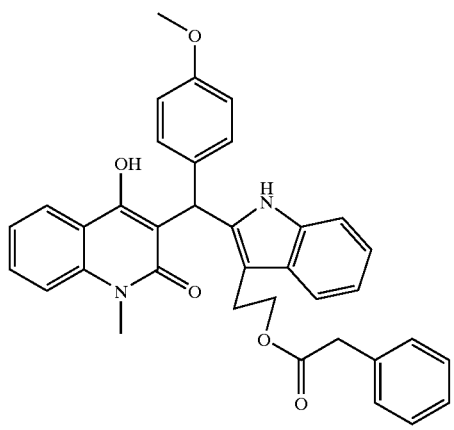
Compound No. 262
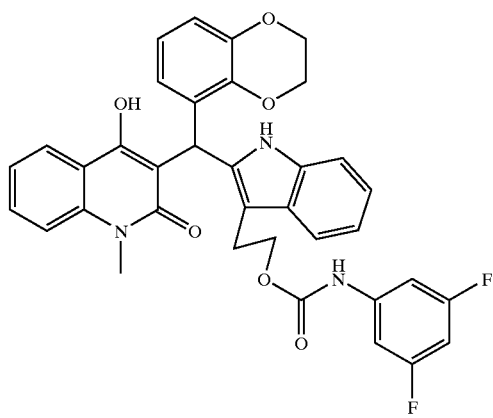
Compound No. 263
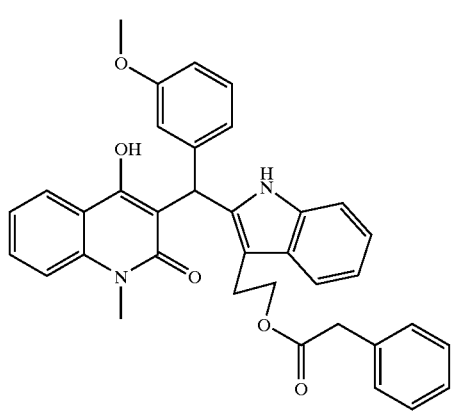
TABLE 2-15-continued
Compound No. 264
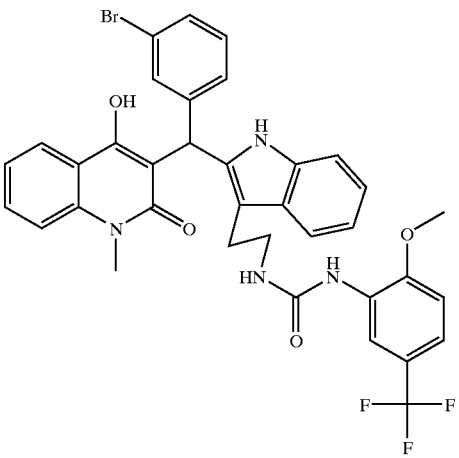
Compound No. 265
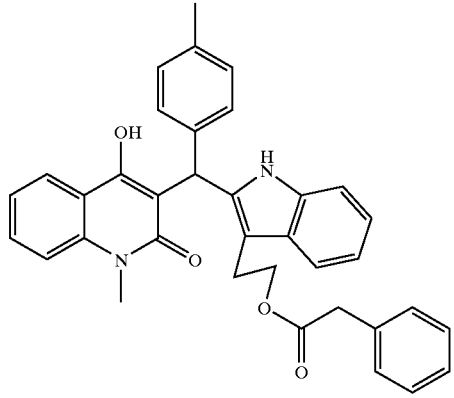
Compound No. 266
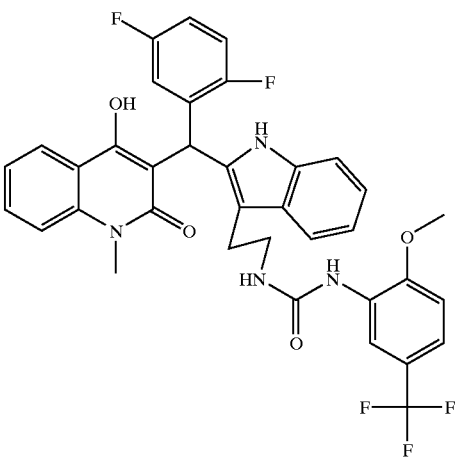

TABLE 2-16
Compound No. 267
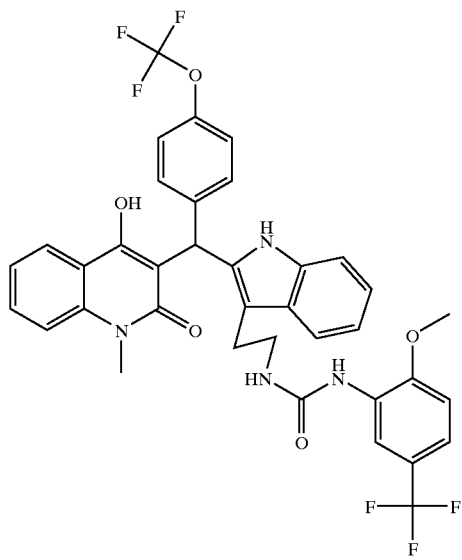
Compound No. 268
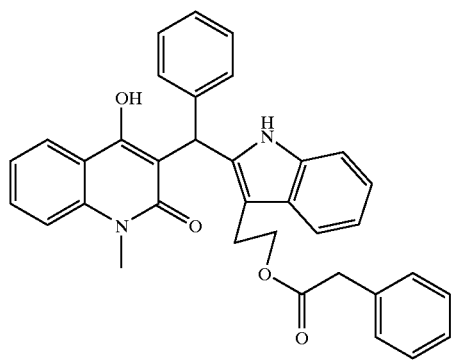
Compound No. 269
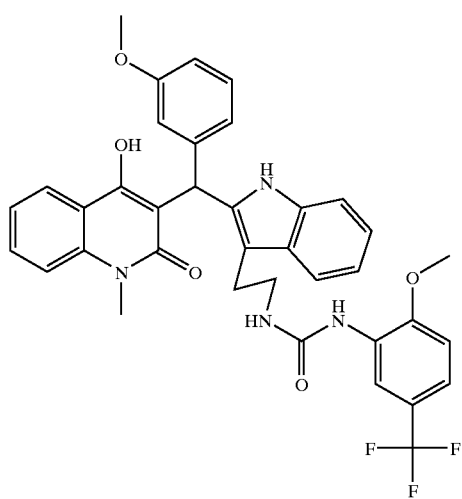
TABLE 2-16-continued
Compound No. 270
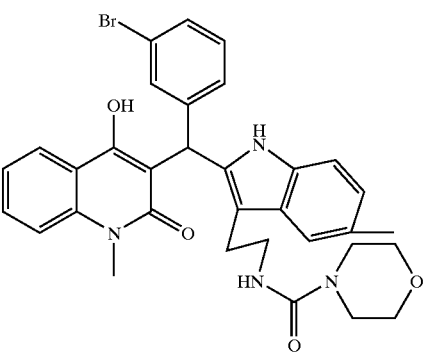
Compound No. 271
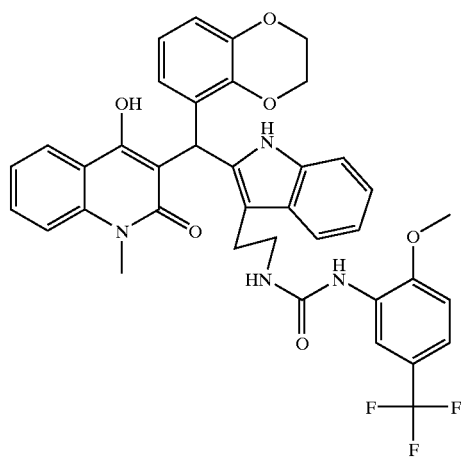
Compound No. 272
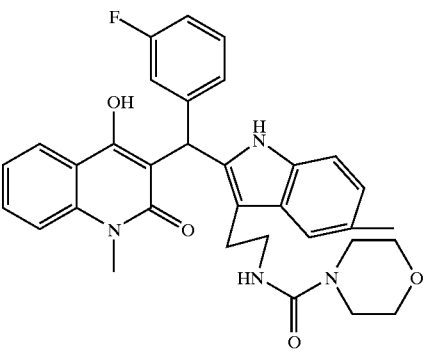

TABLE 2-16-continued
Compound No. 273
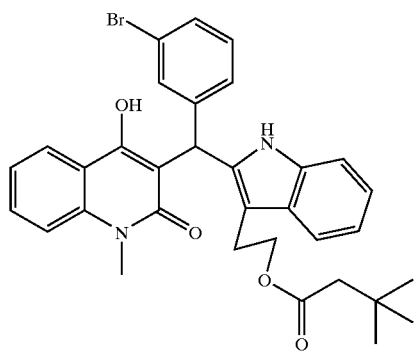
Compound No. 274
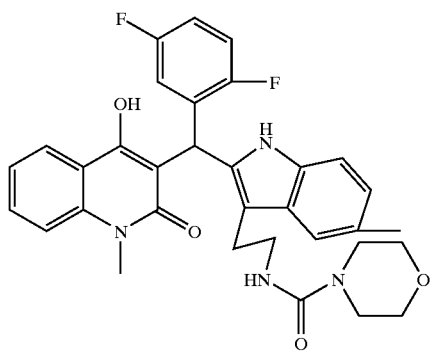
Compound No. 275
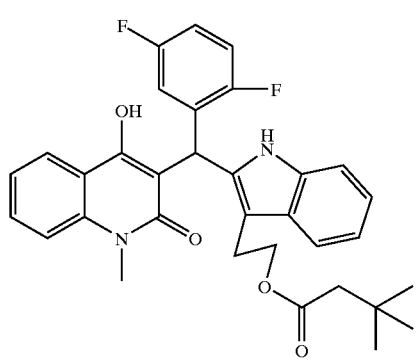
TABLE 2-16-continued
Compound No. 276
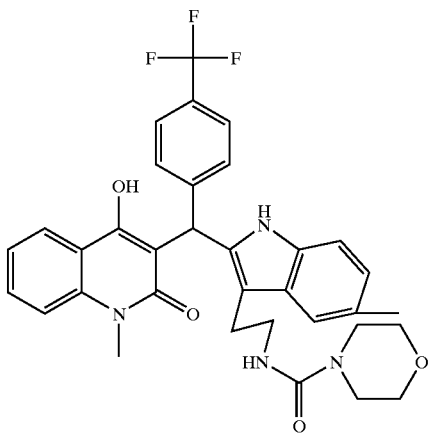
Compound No. 277
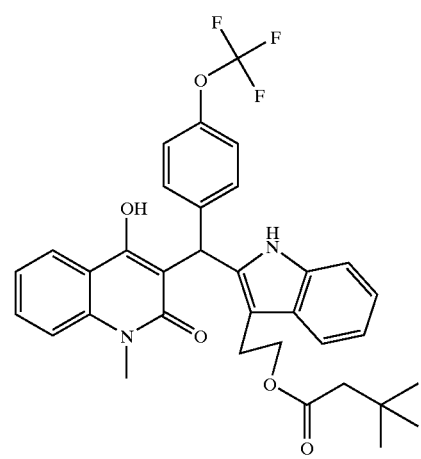
Compound No. 278
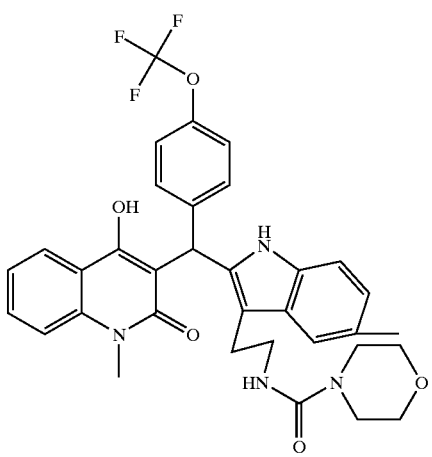

TABLE 2-17
Compound No. 279
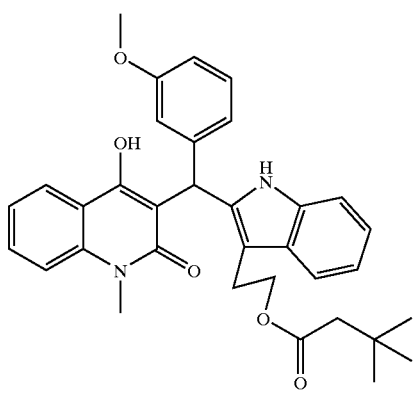
Compound No. 280
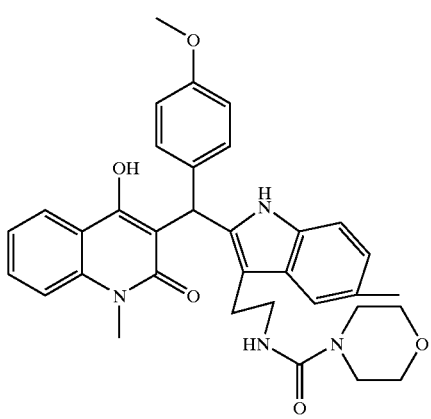
Compound No. 281
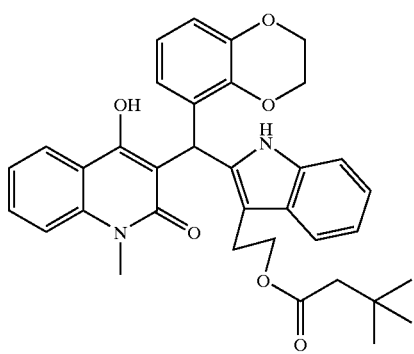
TABLE 2-17-continued
Compound No. 282
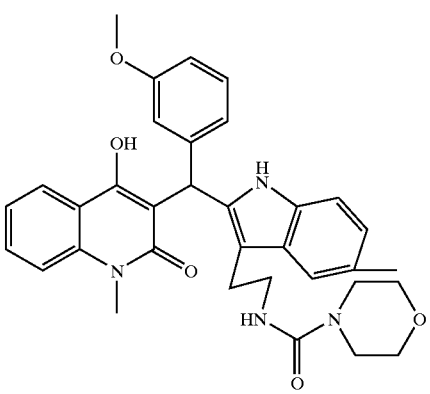
Compound No. 283
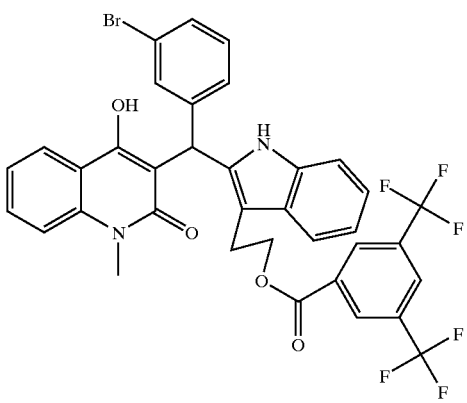
Compound No. 284
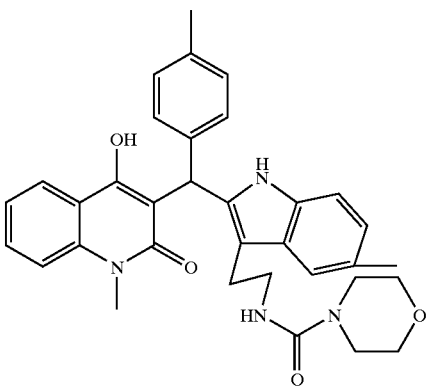

TABLE 2-17-continued
Compound No. 285
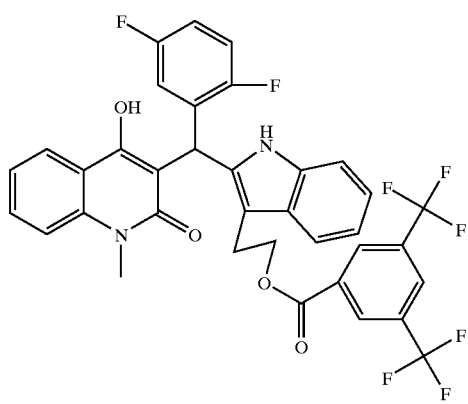
Compound No. 286
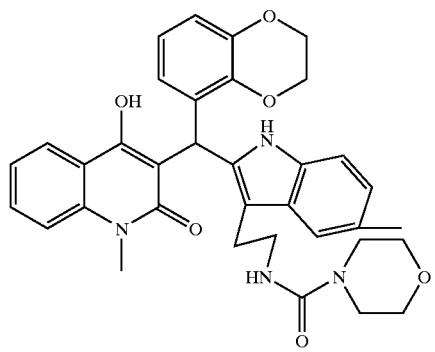
Compound No. 287
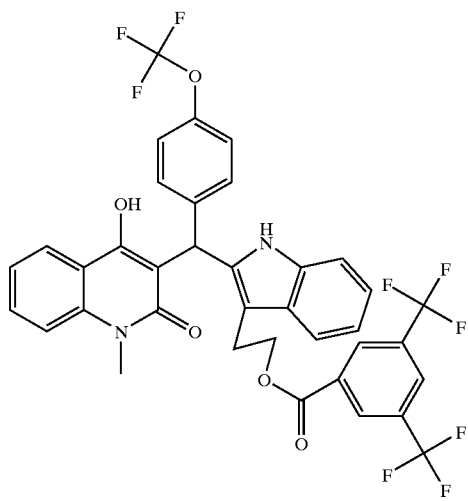
TABLE 2-17-continued
Compound No. 288
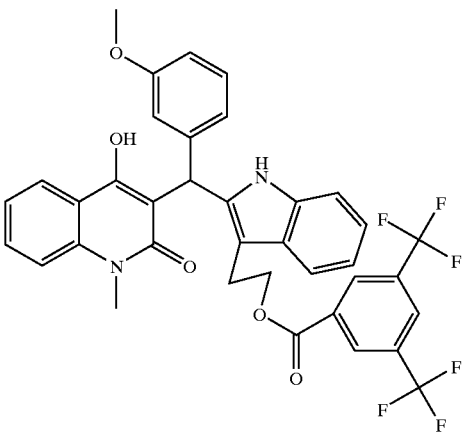
Compound No. 289
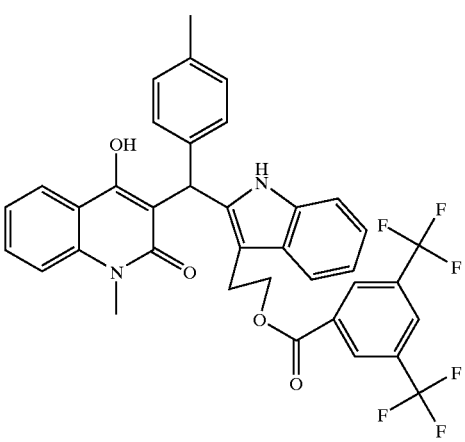
Compound No. 290
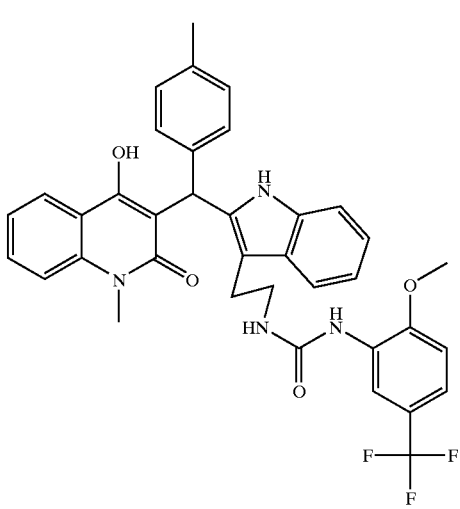

TABLE 2-18
Compound No. 291
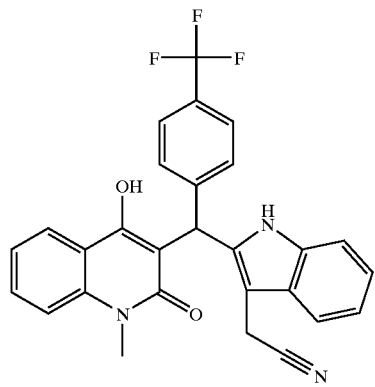
Compound No. 292
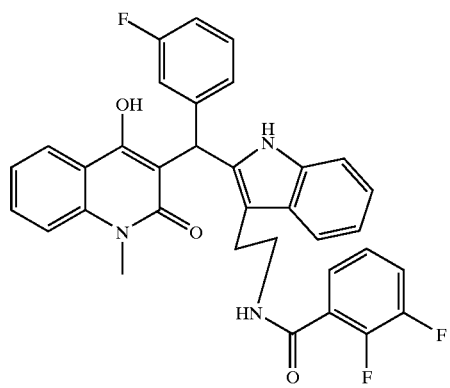
Compound No. 293
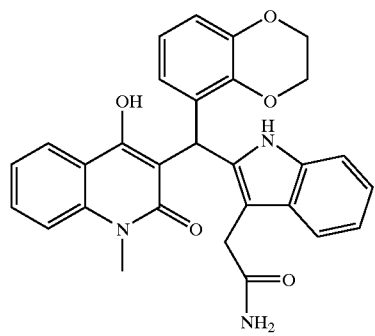
TABLE 2-18-continued
Compound No. 294
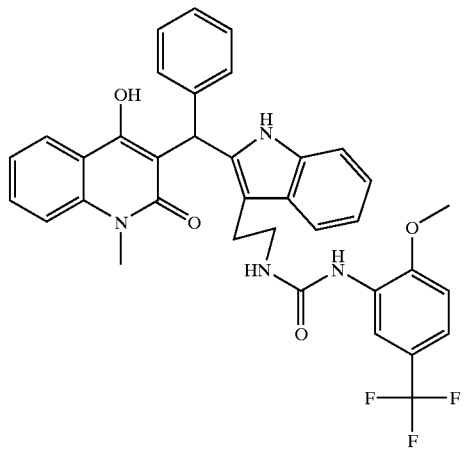
Compound No. 295
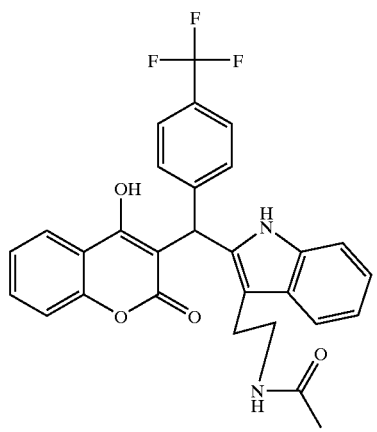
Compound No. 296
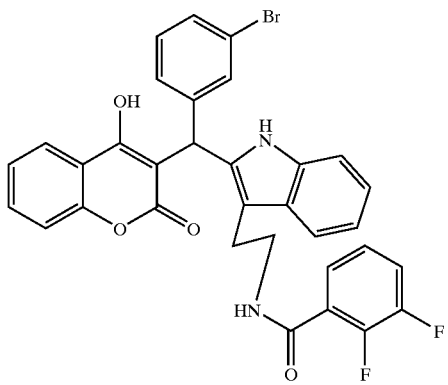

TABLE 2-18-continued
Compound No. 297
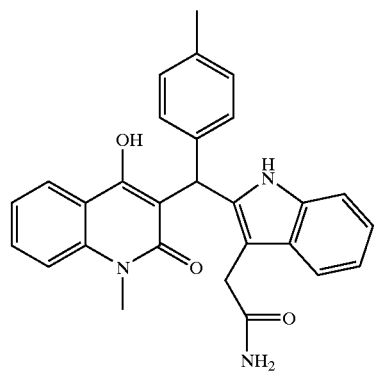
Compound No. 298
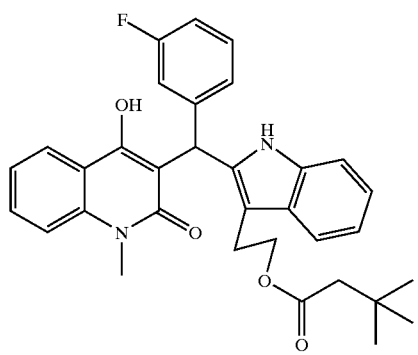
Compound No. 299
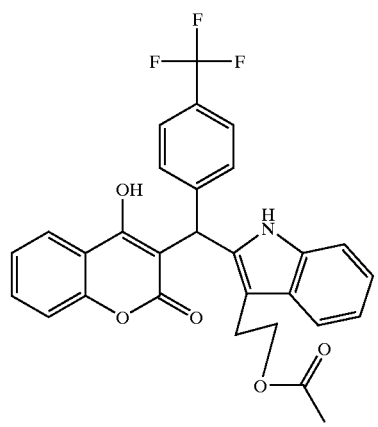
TABLE 2-18-continued
Compound No. 300
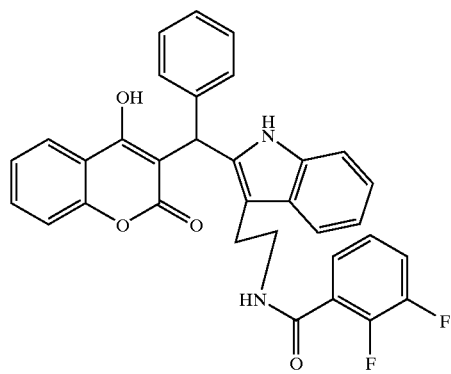
Compound No. 301
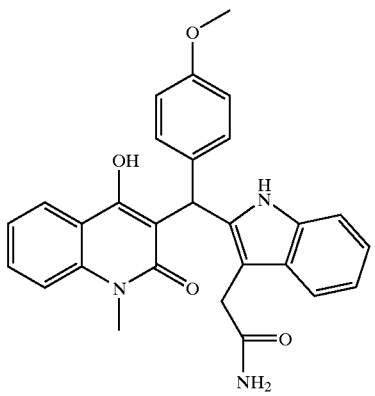
Compound No. 302
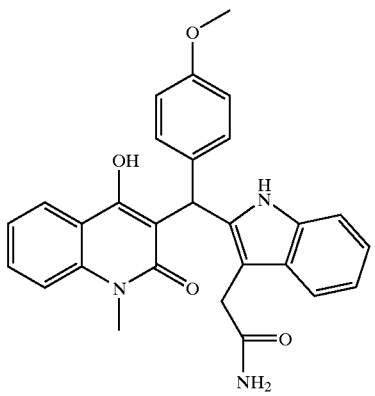

TABLE 2-19
Compound No. 303
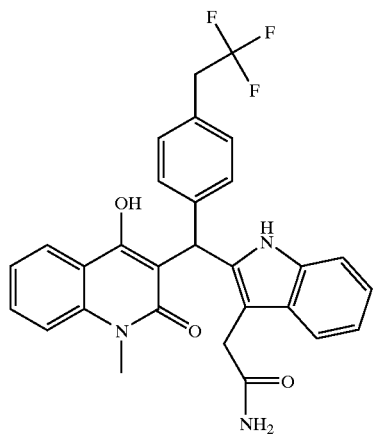
Compound No. 304
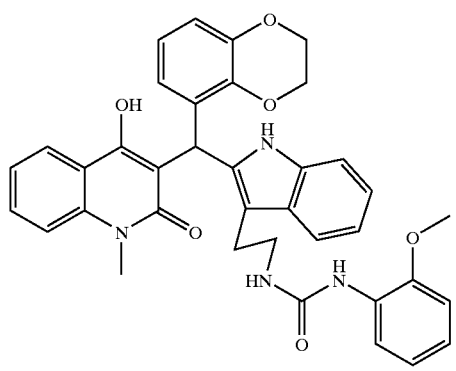
Compound No. 305
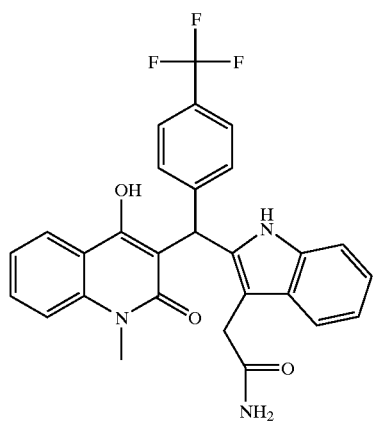
TABLE 2-19-continued
Compound No. 306
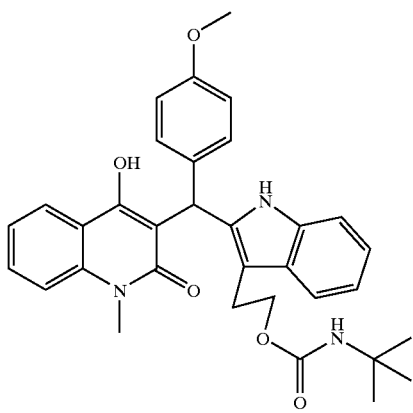
Compound No. 307
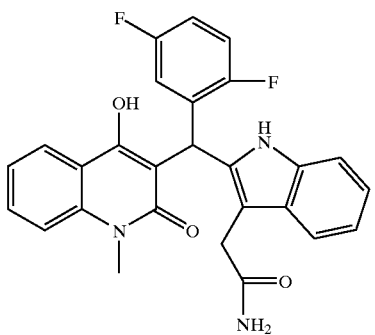
Compound No. 308
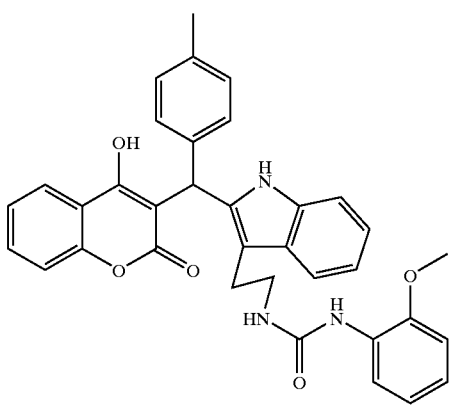

TABLE 2-19-continued
Compound No. 309
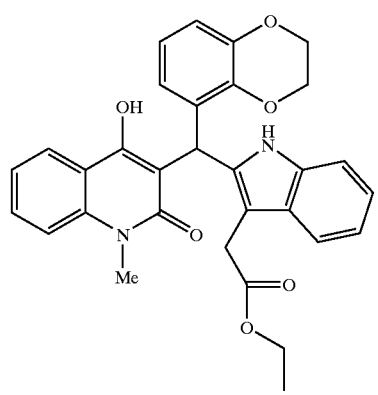
Compound No. 310
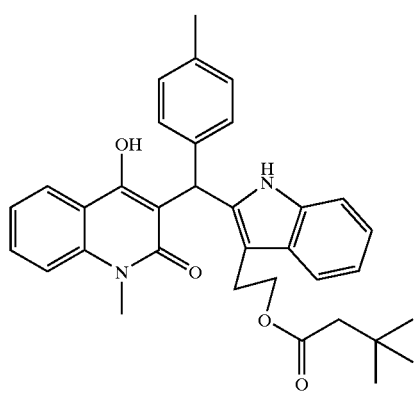
Compound No. 311
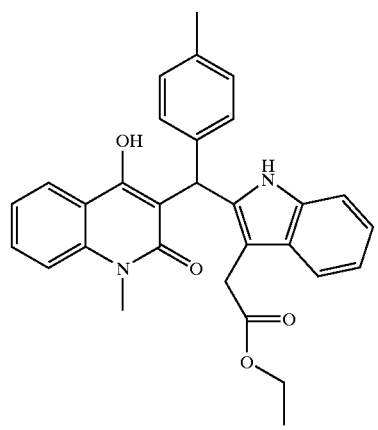
TABLE 2-19-continued
Compound No. 312
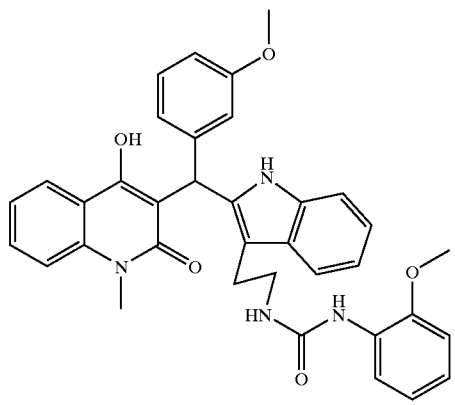
Compound No. 313
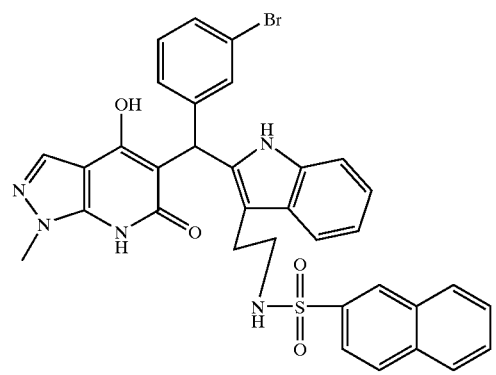
Compound No. 314
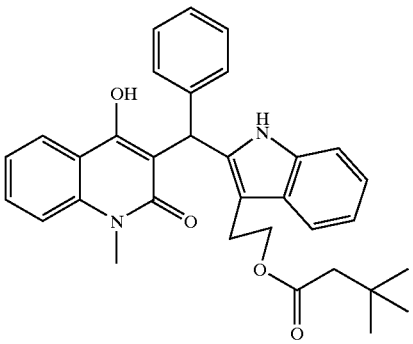

TABLE 2-20
Compound No. 315
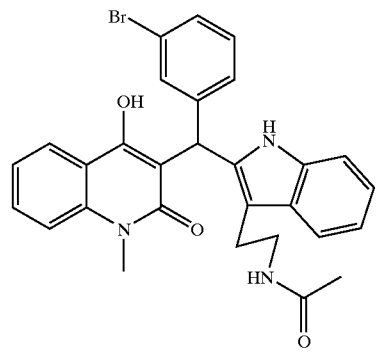
Compound No. 316
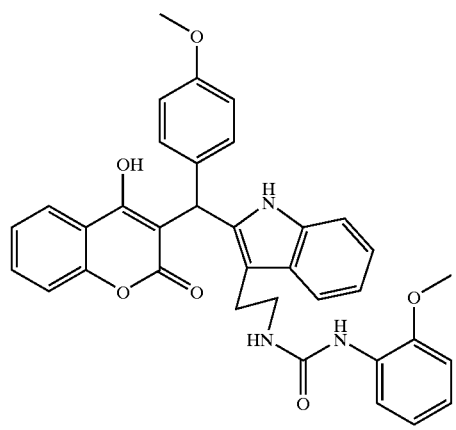
Compound No. 317
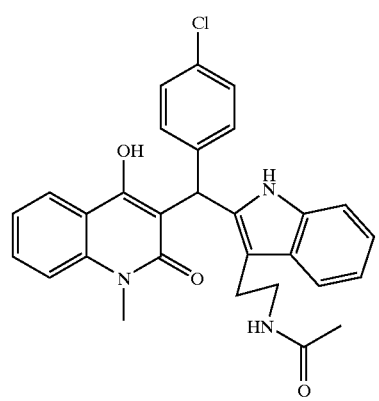
TABLE 2-20-continued
Compound No. 318
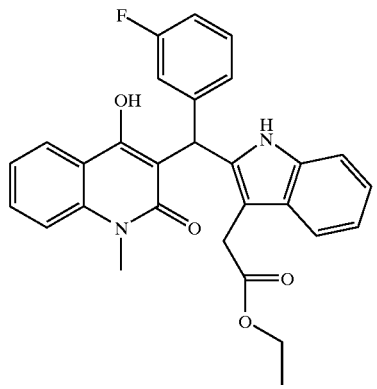
Compound No. 319
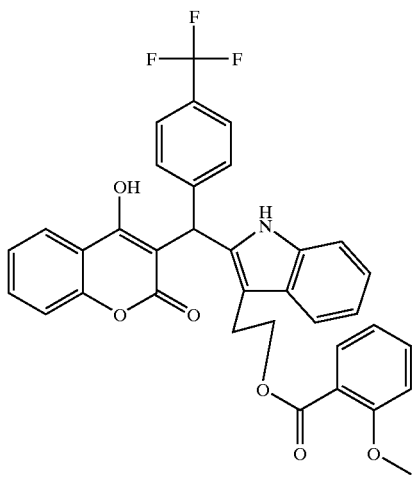
Compound No. 320
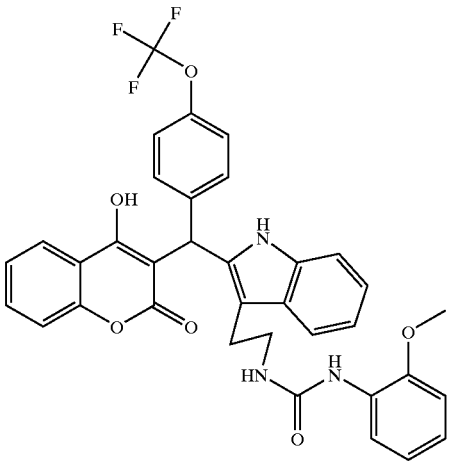

TABLE 2-20-continued
Compound No. 321
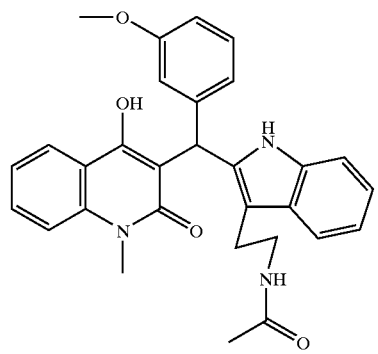
Compound No. 322
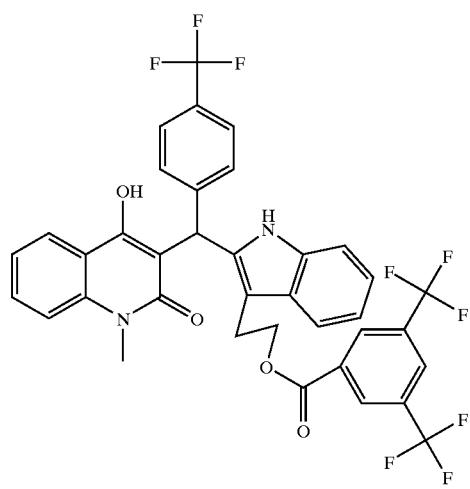
Compound No. 323
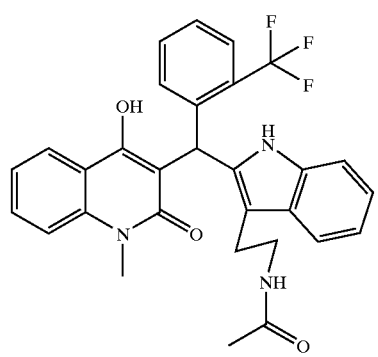
TABLE 2-20-continued
Compound No. 324
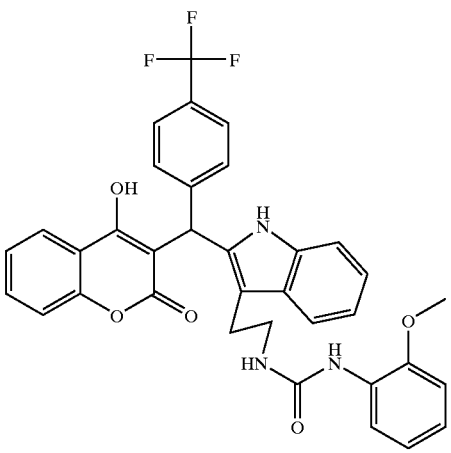
Compound No. 325
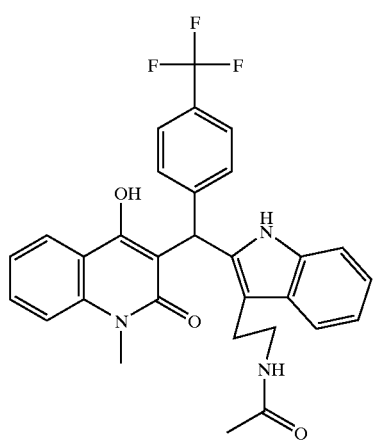
Compound No. 326
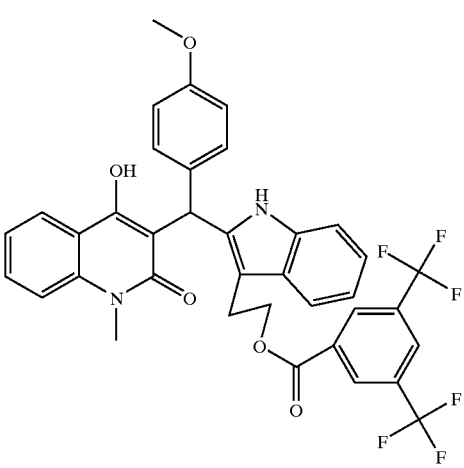

TABLE 2-21
Compound No. 327
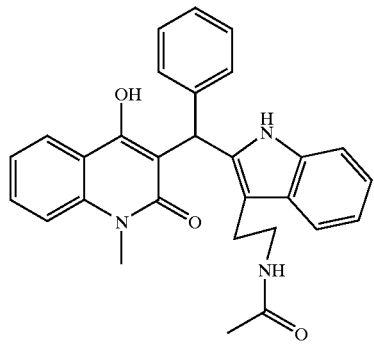
Compound No. 328
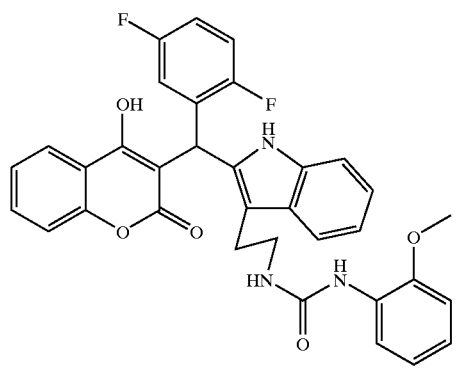
Compound No. 329
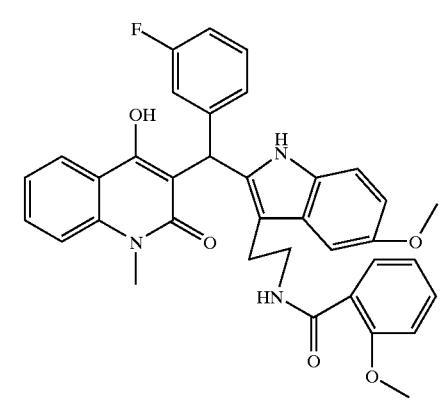
TABLE 2-21-continued
Compound No. 330
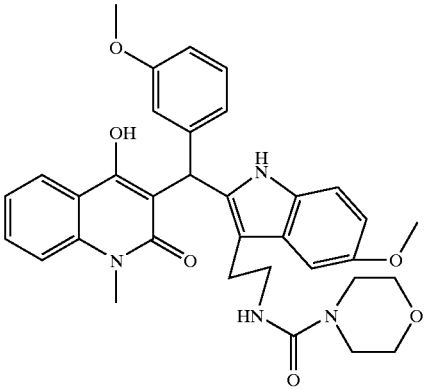
Compound No. 331
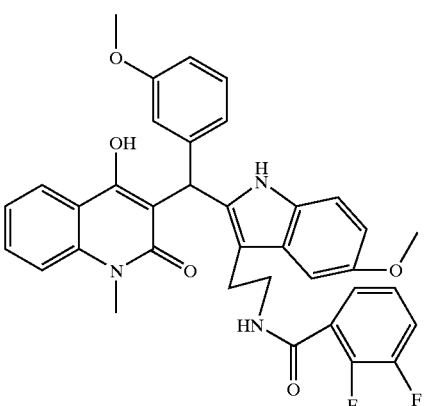
Compound No. 332
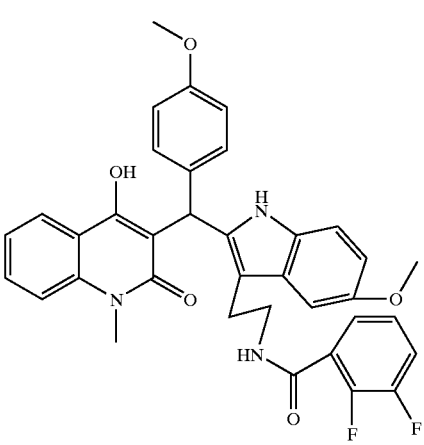

TABLE 2-21-continued
Compound No. 333
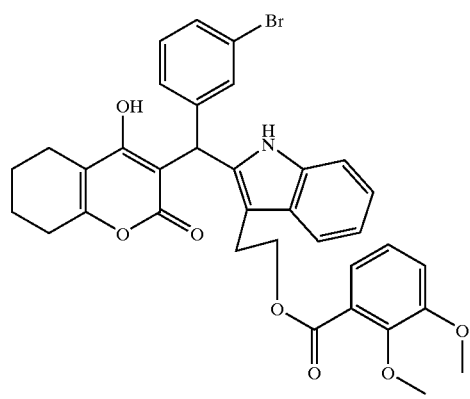
Compound No. 334
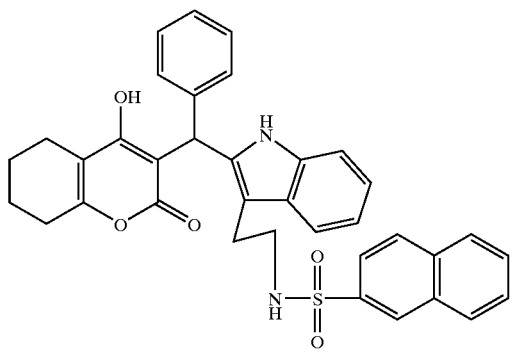
Compound No. 335
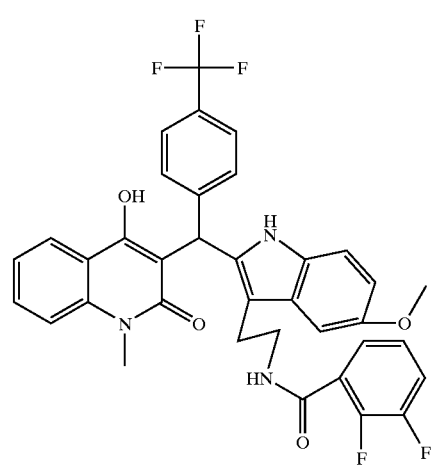
TABLE 2-21-continued
Compound No. 336
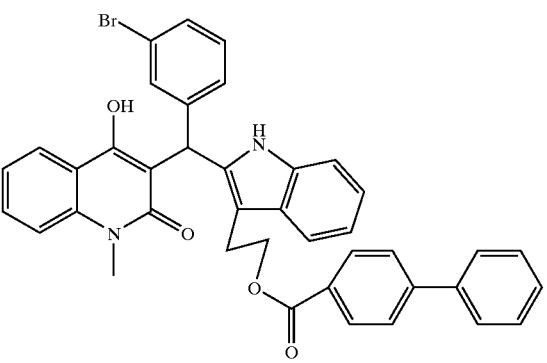
Compound No. 337
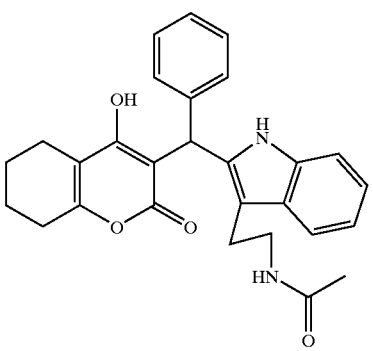
Compound No. 338

TABLE 2-22
Compound No. 339
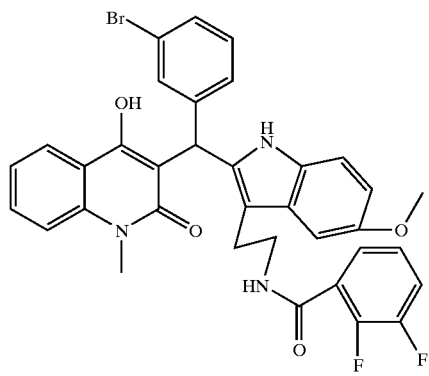
Compound No. 340
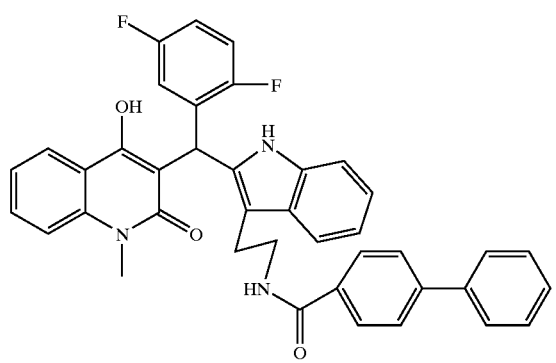
Compound No. 341
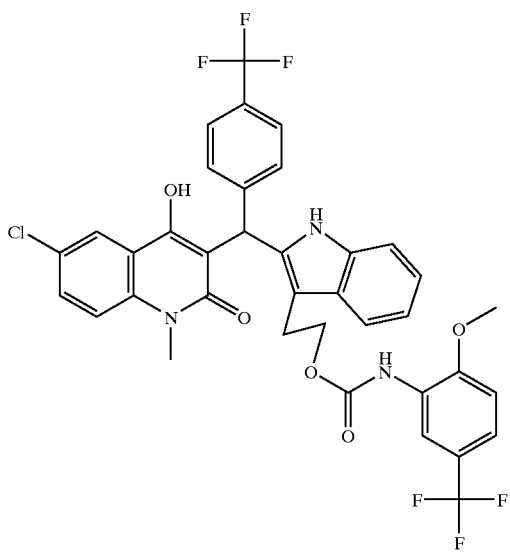
TABLE 2-22-continued
Compound No. 342
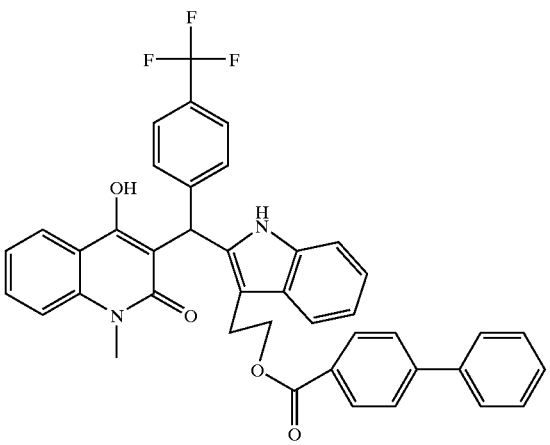
Compound No. 343
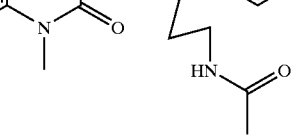
Compound No. 344
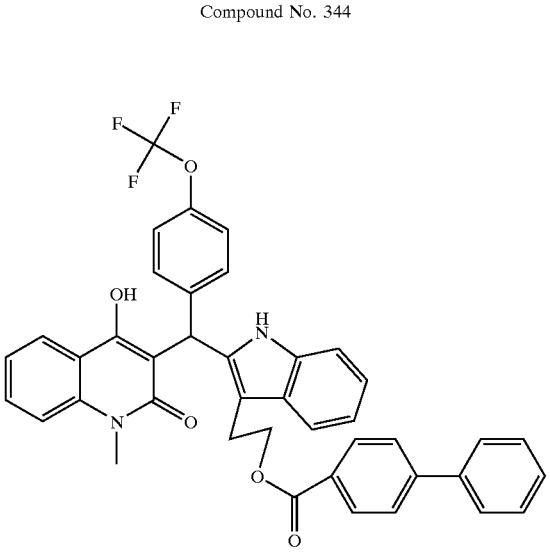

TABLE 2-22-continued
Compound No. 345
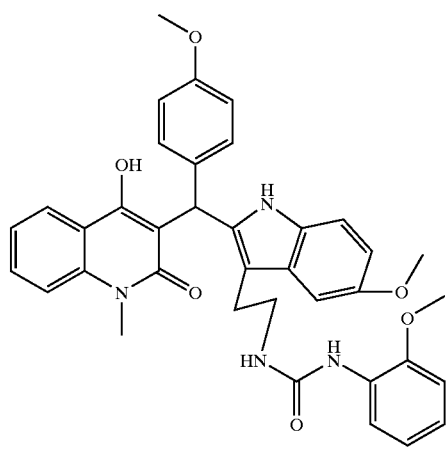
Compound No. 346
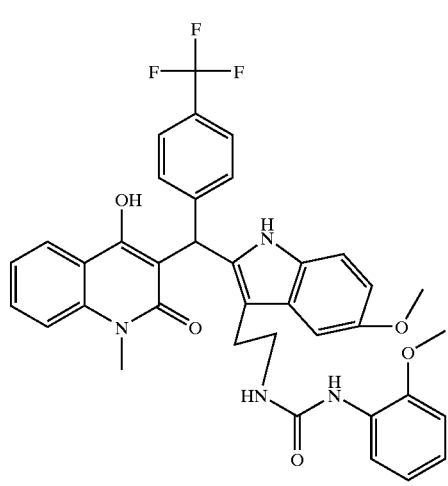
Compound No. 347
Compound No. 348
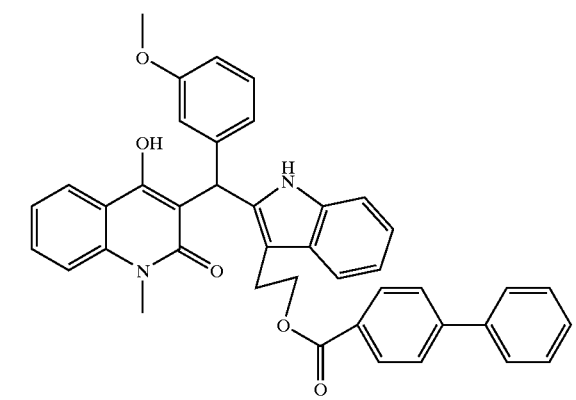
Compound No. 349
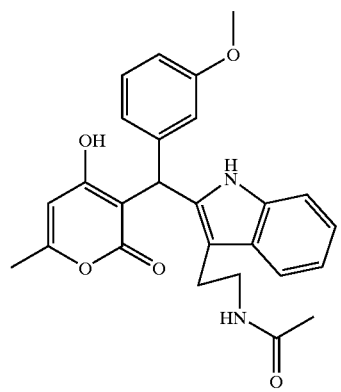
Compound No. 350
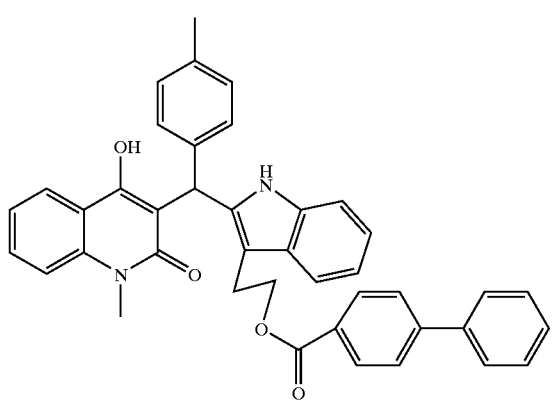
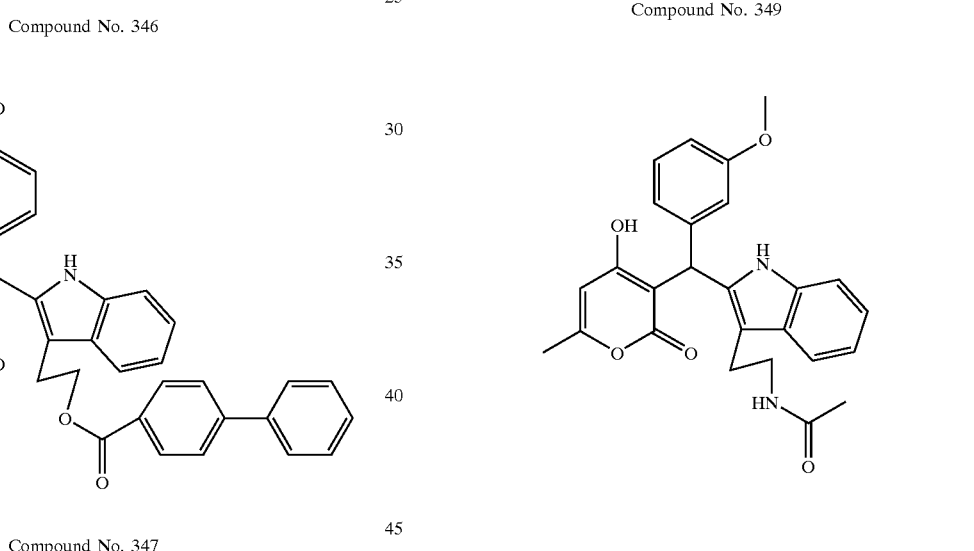

TABLE 2-23
Compound No. 351
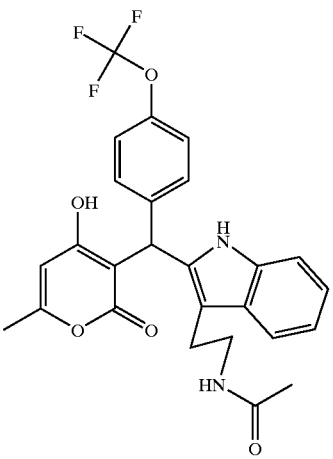
Compound No. 352
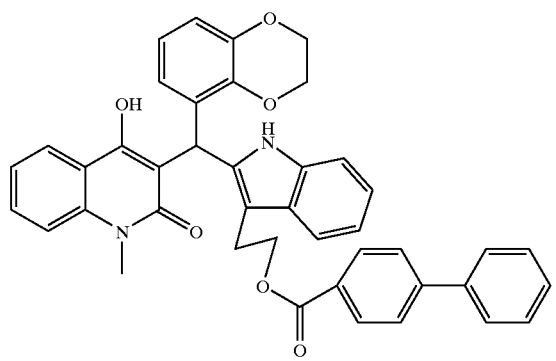
Compound No. 353
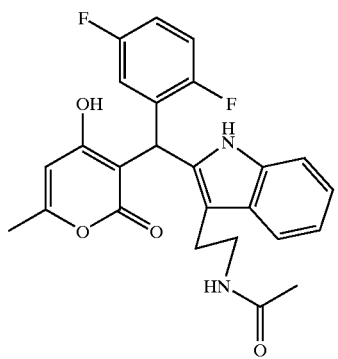
TABLE 2-23-continued
Compound No. 354
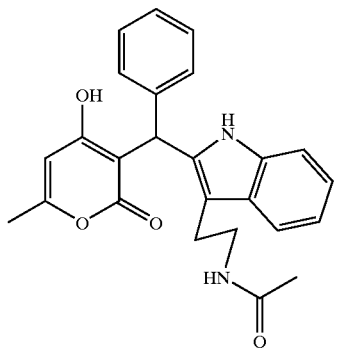
Compound No. 355
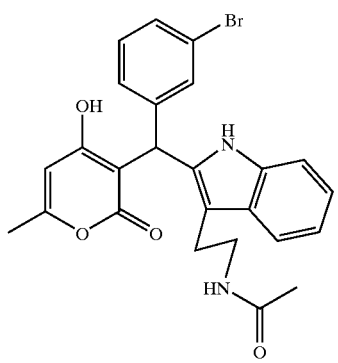
Compound No. 356
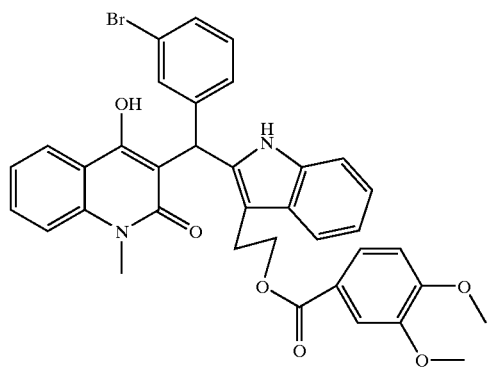
Compound No. 357
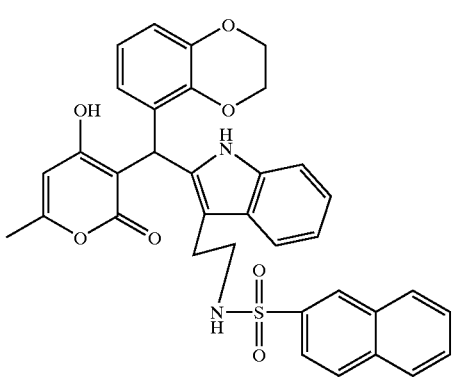

TABLE 2-23-continued
Compound No. 358
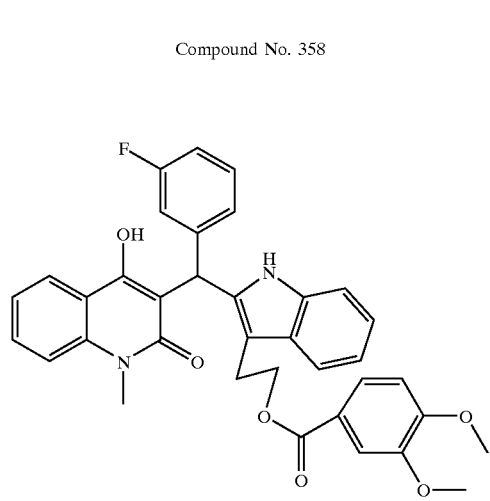
Compound No. 359
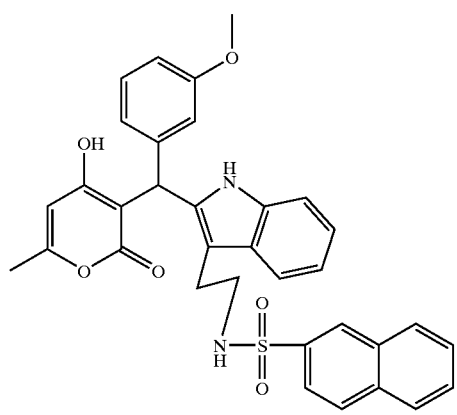
Compound No. 360
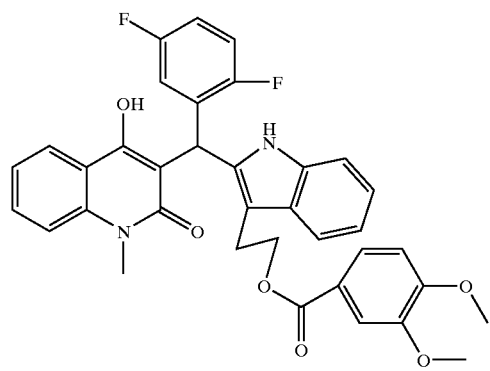
TABLE 2-23-continued
Compound No. 361
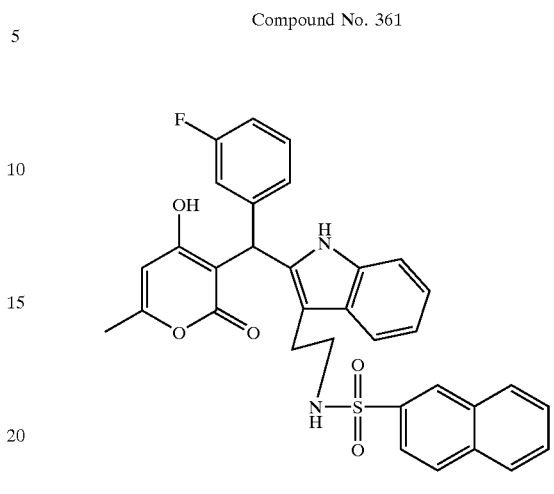
Compound No. 362
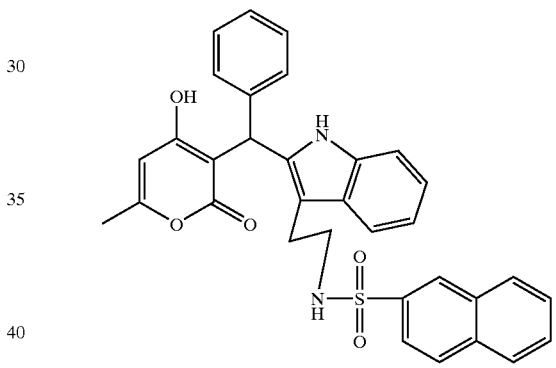
TABLE 2-24
Compound No. 363
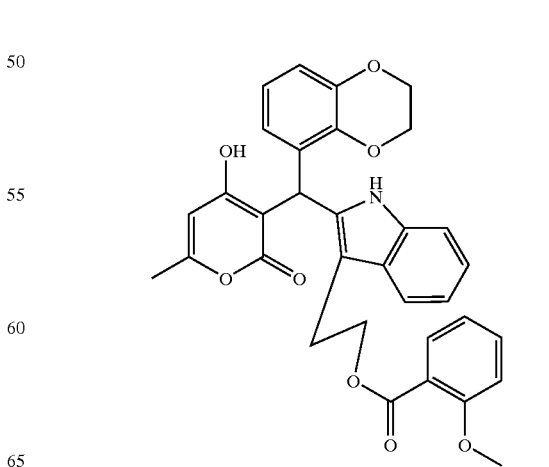

TABLE 2-24-continued
Compound No. 364
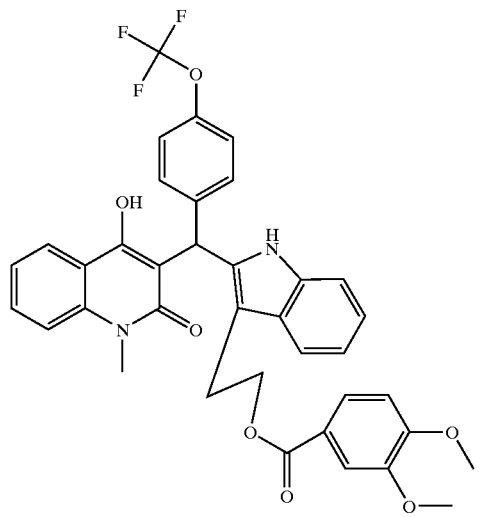
Compound No. 365
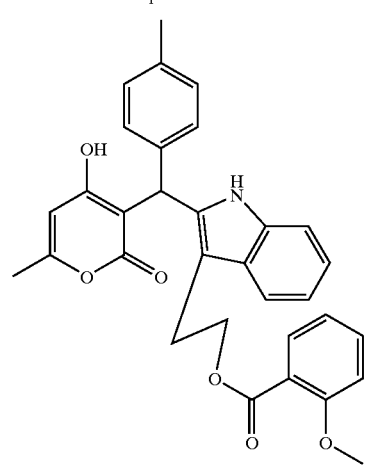
Compound No. 366
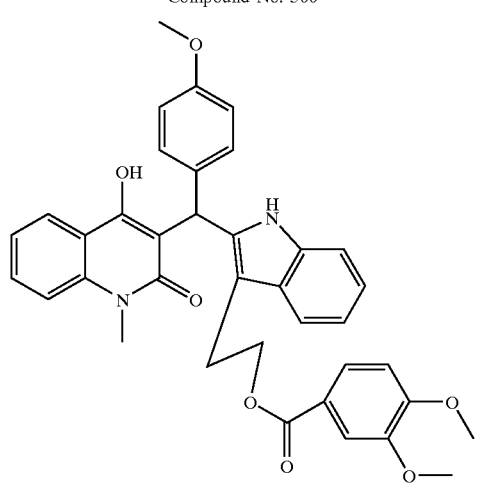
TABLE 2-24-continued
Compound No. 367
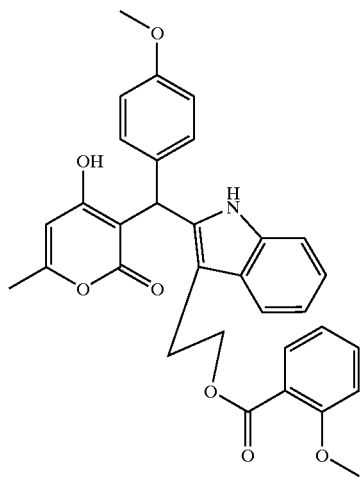
Compound No. 368
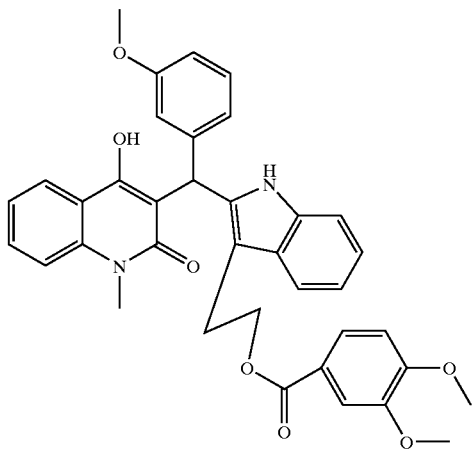
Compound No. 369
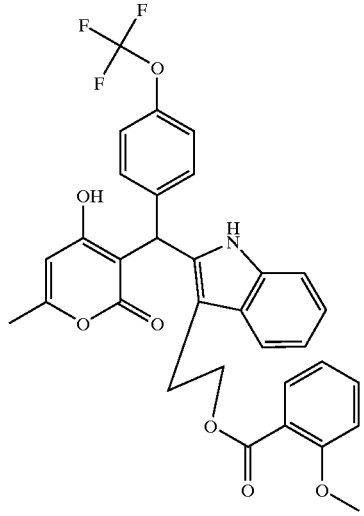

TABLE 2-24-continued
Compound No. 370
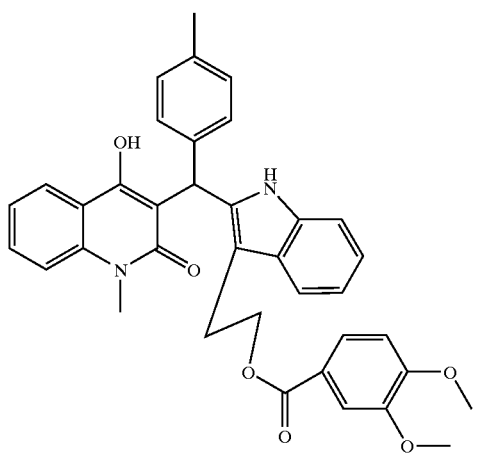
Compound No. 371
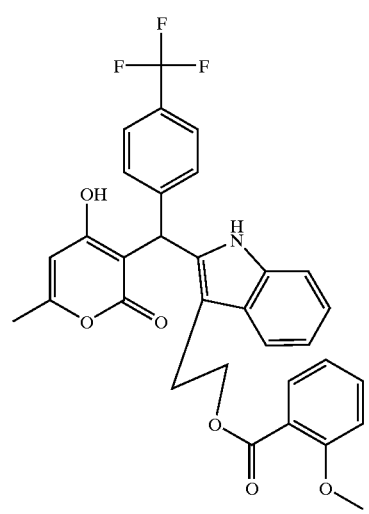
Compound No. 372
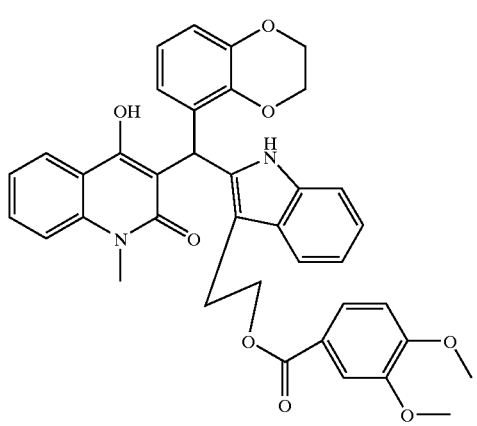
TABLE 2-24-continued
Compound No. 373
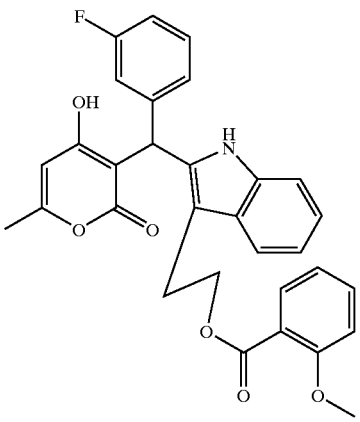
Compound No. 374
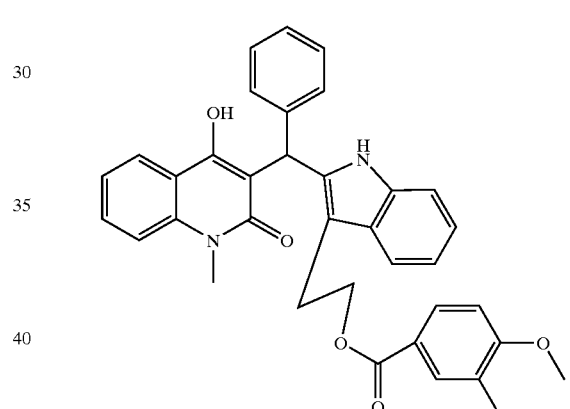
TABLE 2-25
Compound No. 375
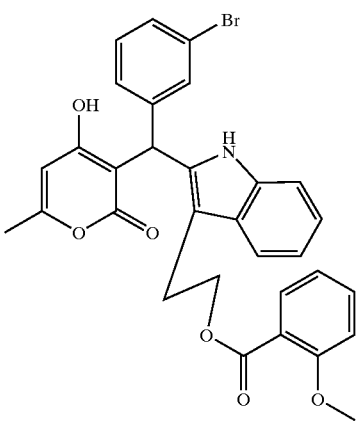

TABLE 2-25-continued
Compound No. 376
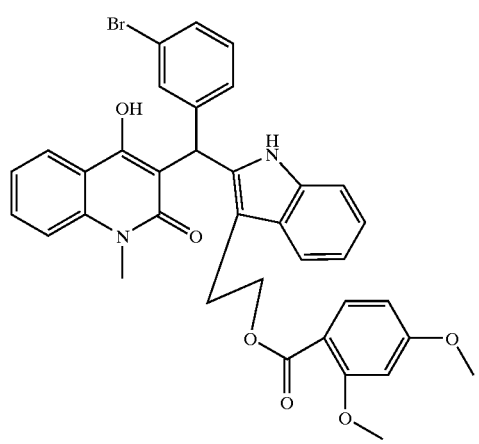
Compound No. 377
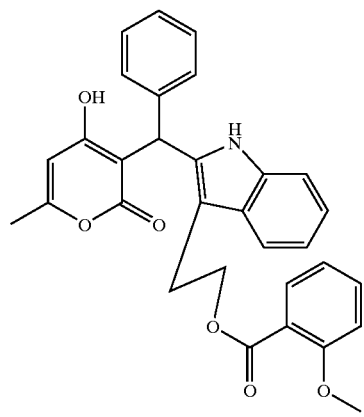
Compound No. 378
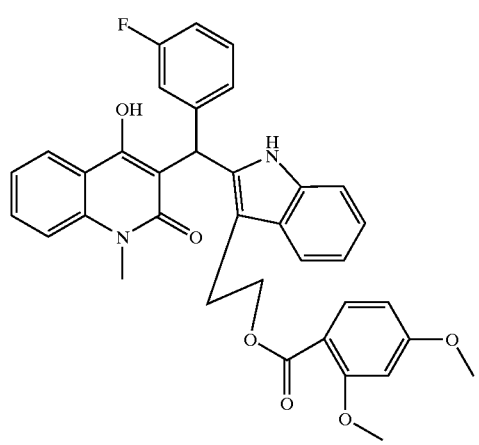
TABLE 2-25-continued
Compound No. 379
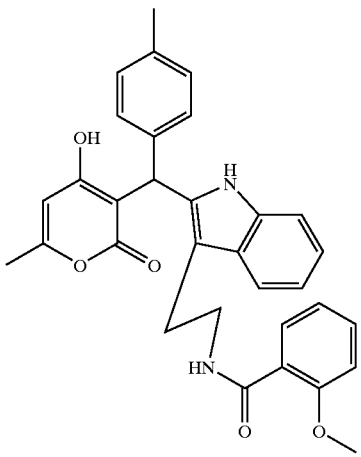
Compound No. 380
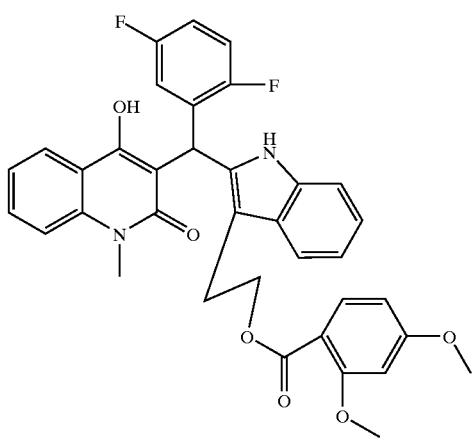
Compound No. 381
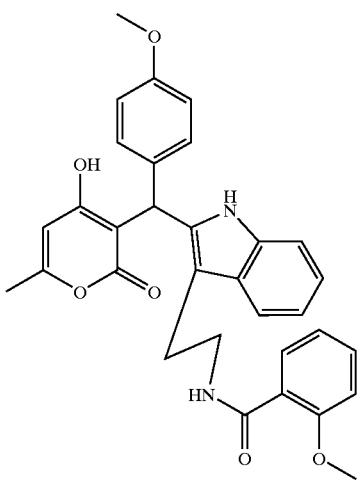

TABLE 2-25-continued
Compound No. 382
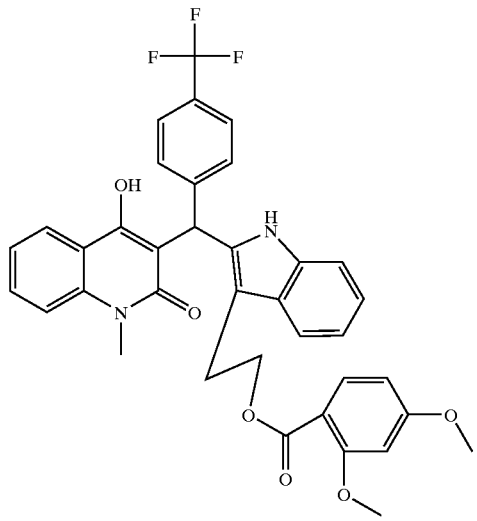
Compound No. 383
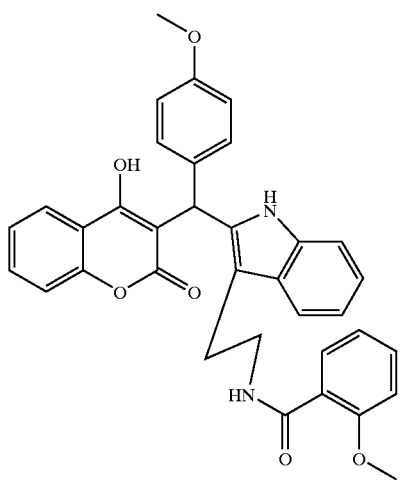
Compound No. 384
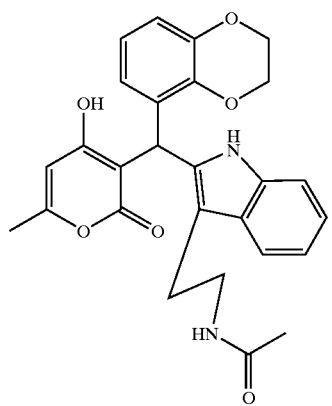
TABLE 2-25-continued
Compound No. 385
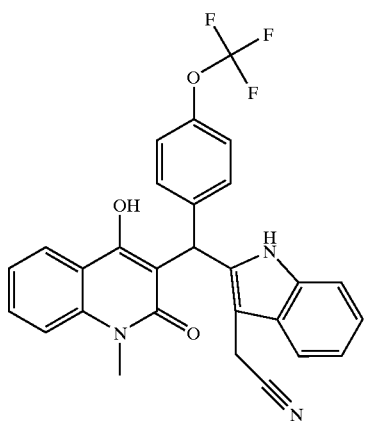
Compound No. 386
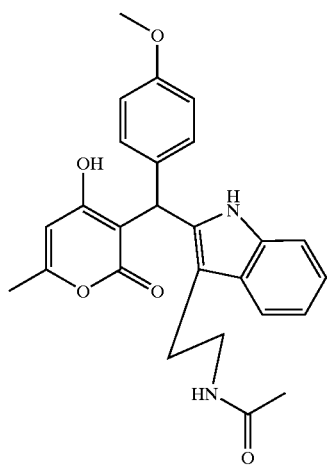
Compound No. 387
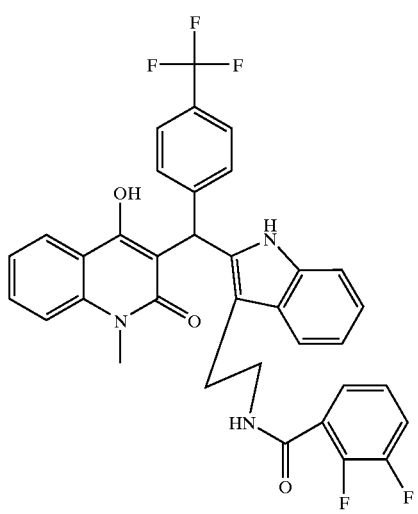

Compound No. 388
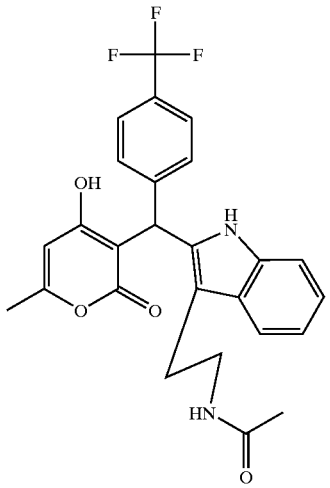
Compound No. 389
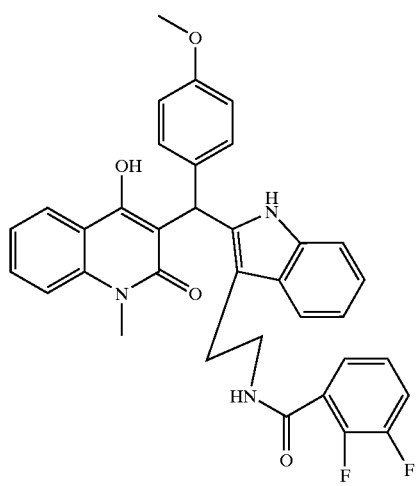
Compound No. 390
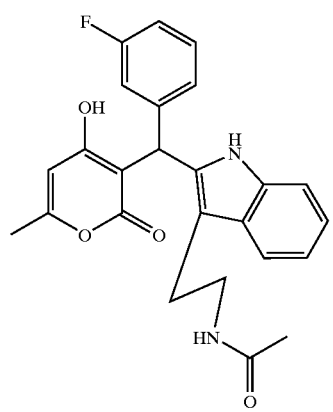
Compound No. 391
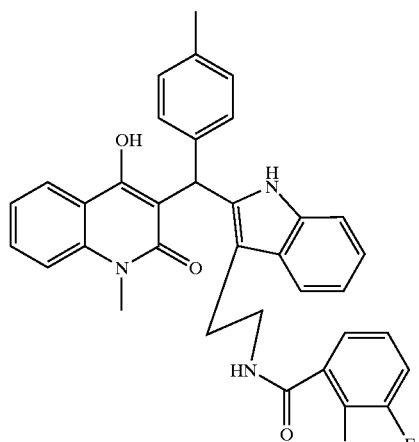
Compound No. 392
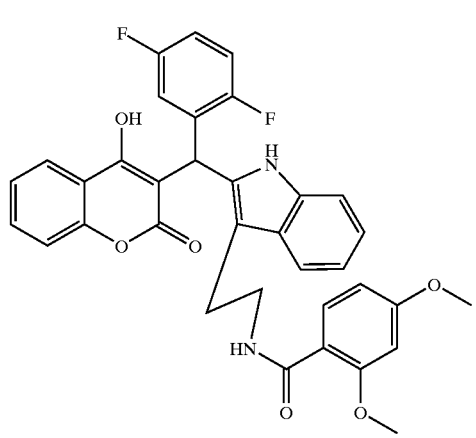
Compound No. 393
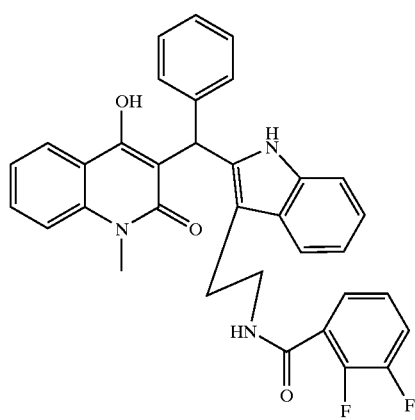

-continued
Compound No. 394
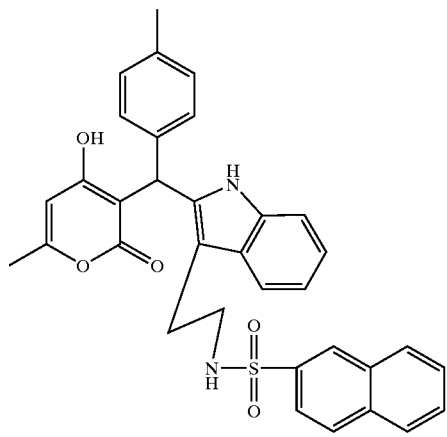
Compound No. 395
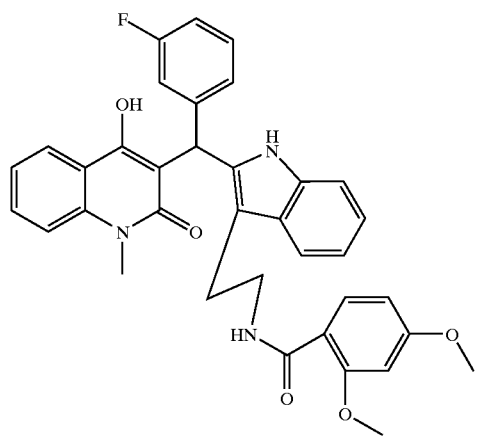
Compound No. 396
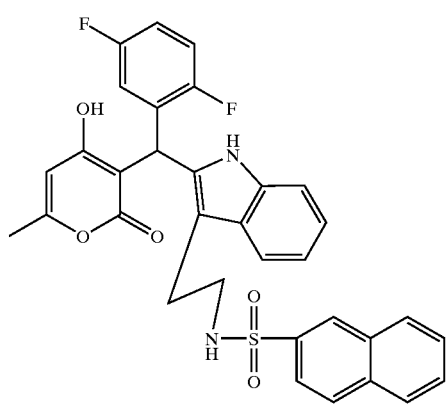
-continued
Compound No. 397
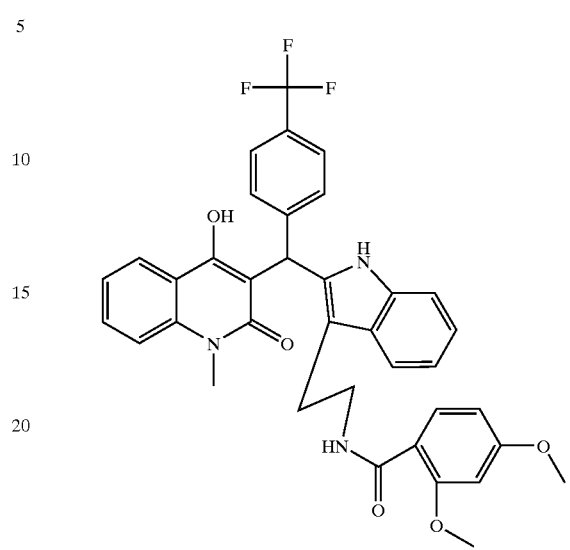
Compound No. 398
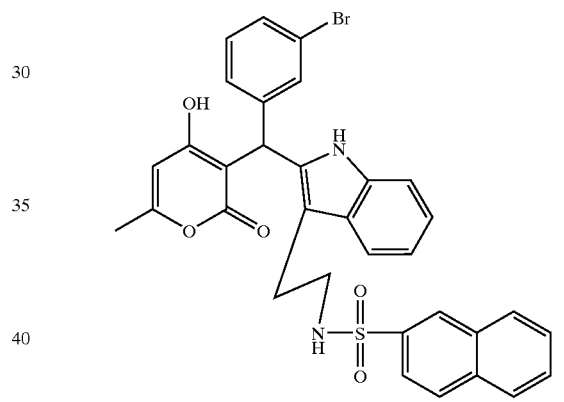
TABLE 2-27
Compound No. 399
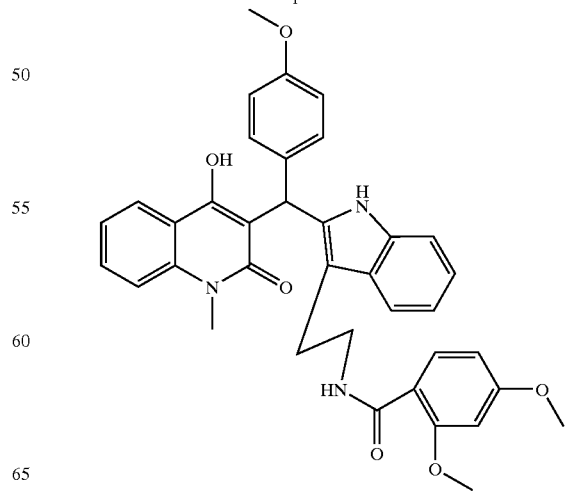

TABLE 2-27-continued
Compound No. 400
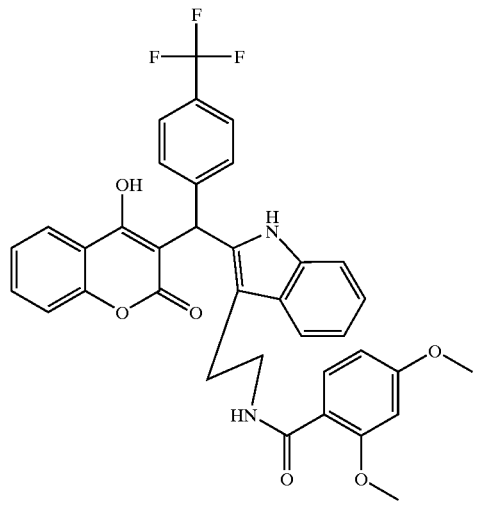
Compound No. 401
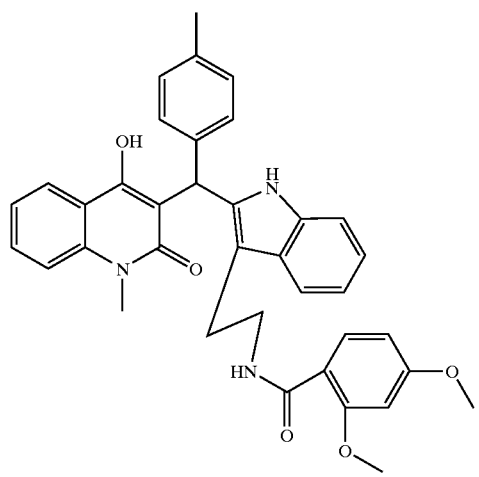
Compound No. 402
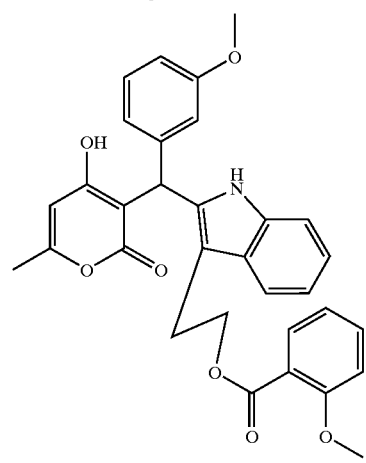
TABLE 2-27-continued
Compound No. 403
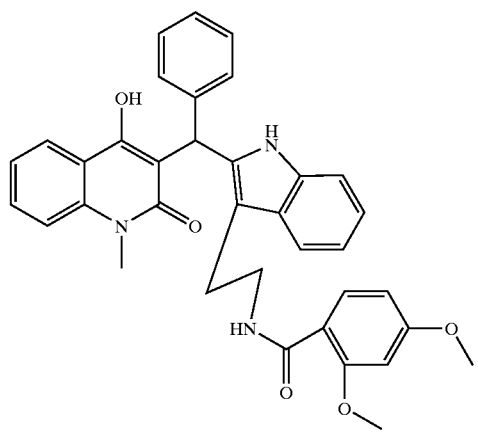
Compound No. 404
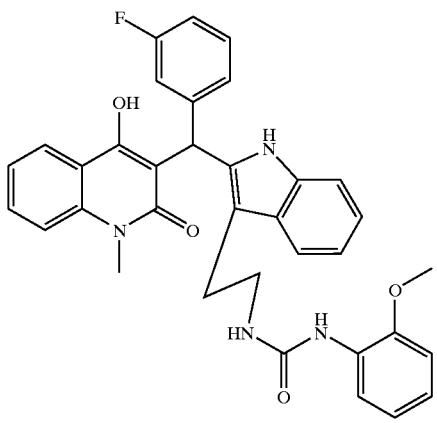
Compound No. 405
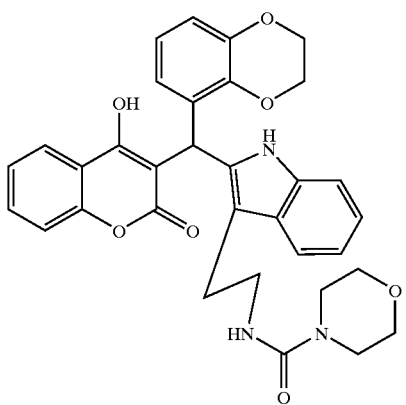

TABLE 2-27-continued
Compound No. 406
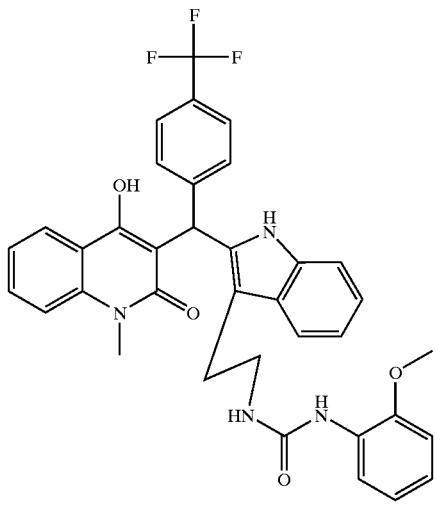
Compound No. 407
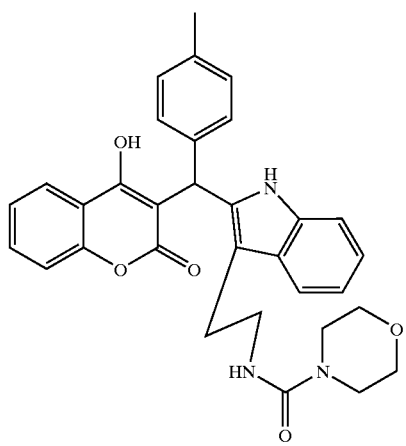
Compound No. 408
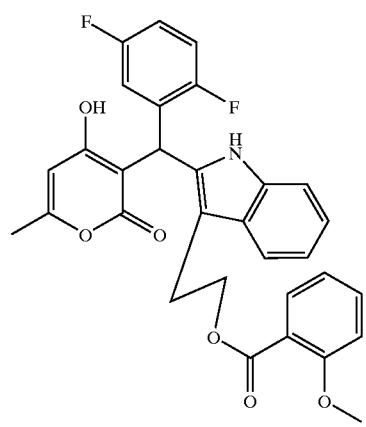
TABLE 2-27-continued
Compound No. 409
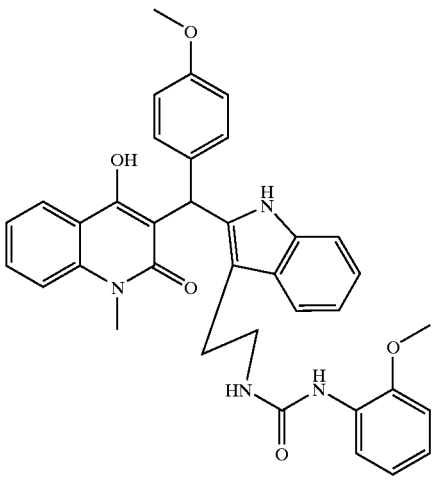
Compound No. 410
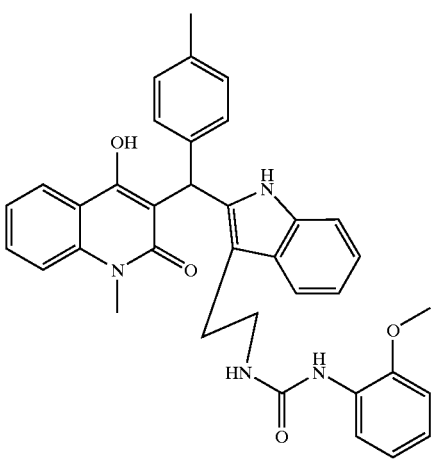
TABLE 2-28
Compound No. 411
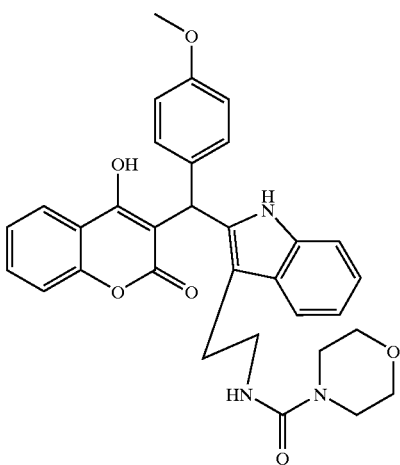

TABLE 2-28-continued
Compound No. 412
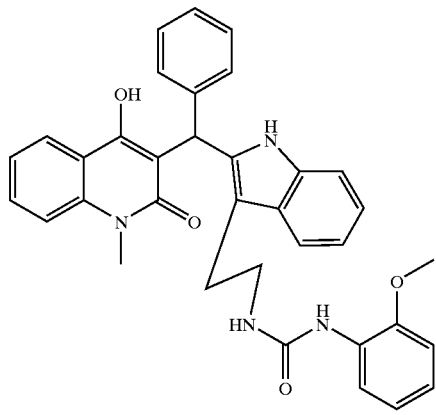
Compound No. 413
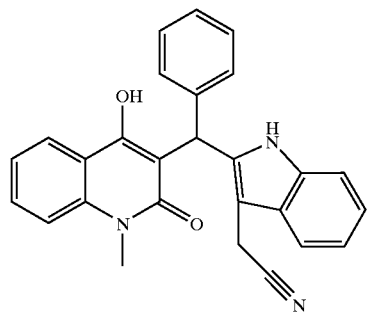
Compound No. 414
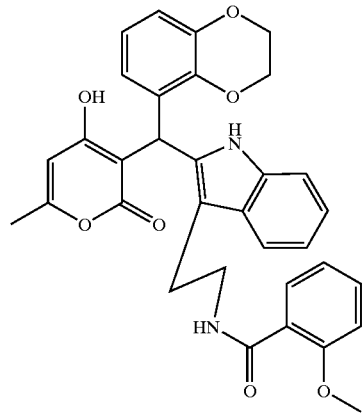
TABLE 2-28-continued
Compound No. 415
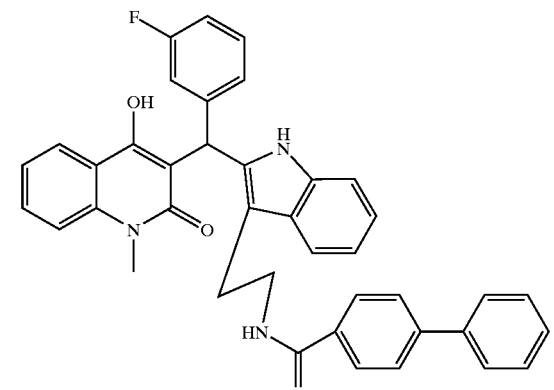
Compound No. 416
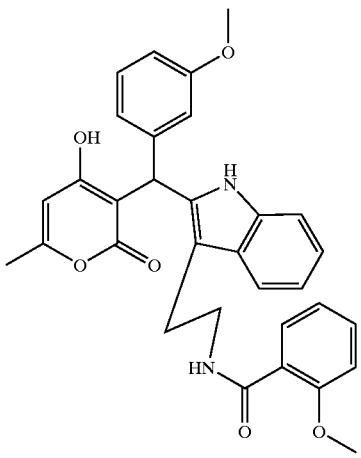
Compound No. 417
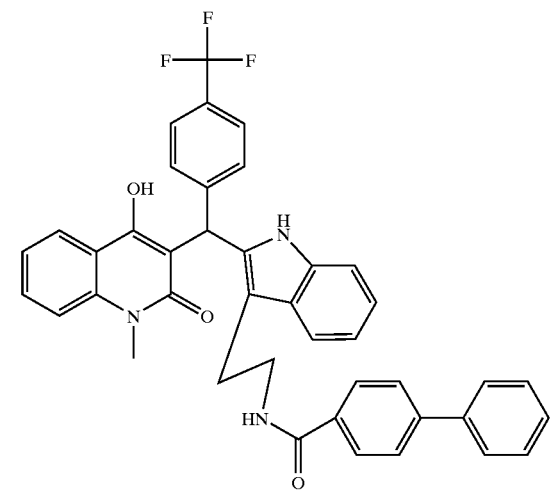

TABLE 2-28-continued
Compound No. 418
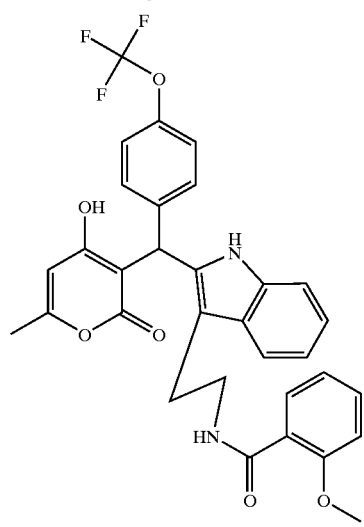
Compound No. 419
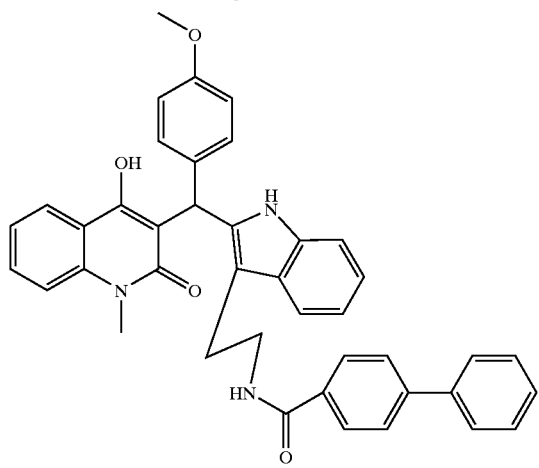
Compound No. 420
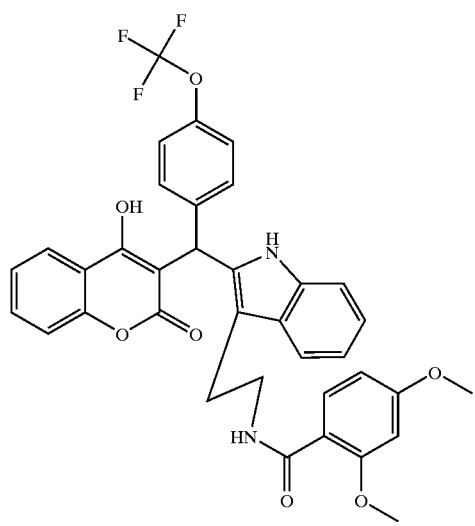
TABLE 2-28-continued
Compound No. 421
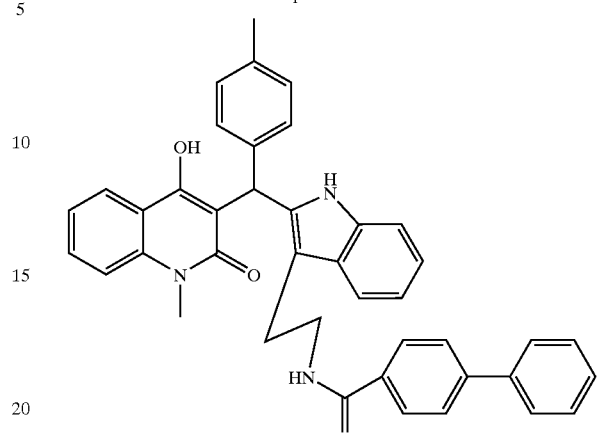
Compound No. 422
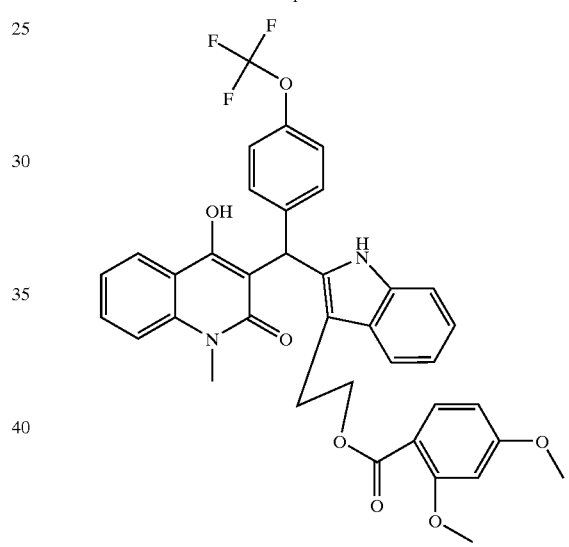
TABLE 2-29
Compound No. 423
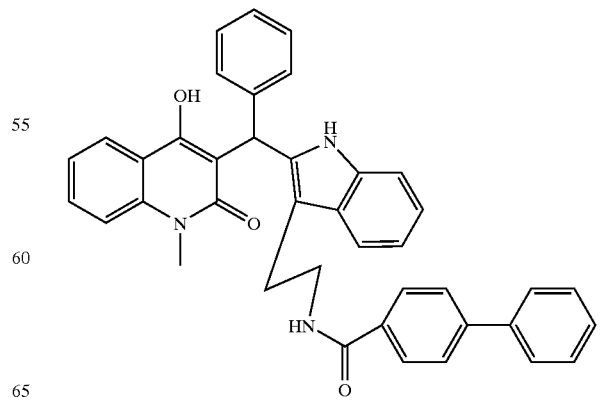

TABLE 2-29-continued
Compound No. 424
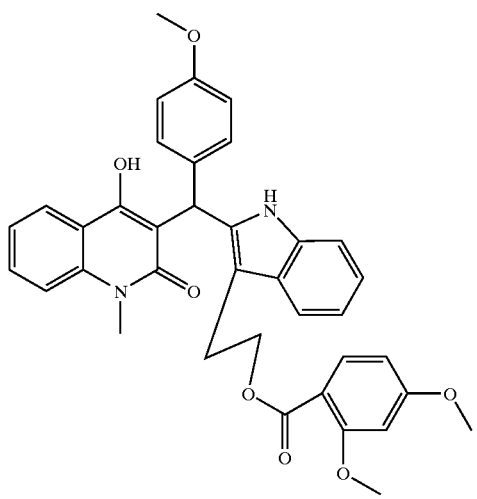
Compound No. 425
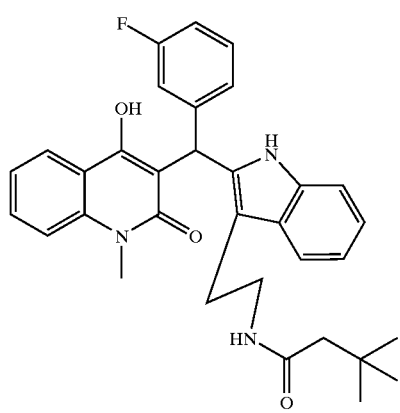
Compound No. 426
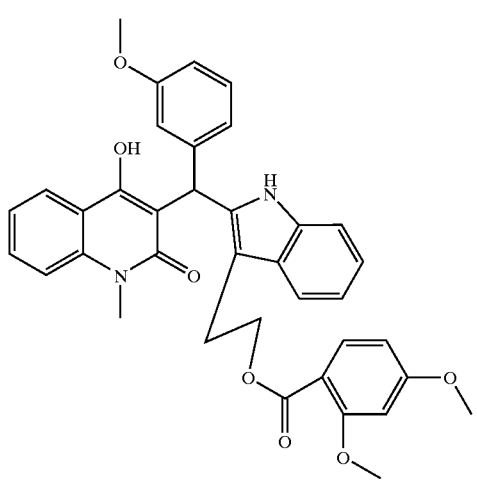
TABLE 2-29-continued
Compound No. 427
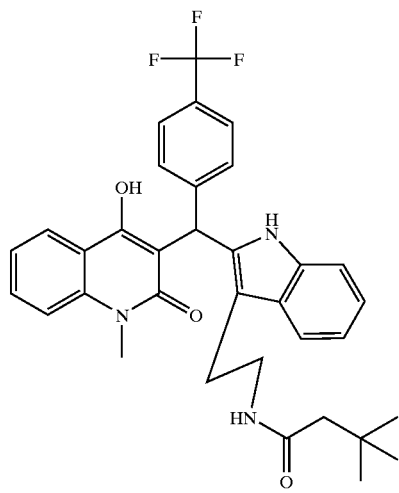
Compound No. 428
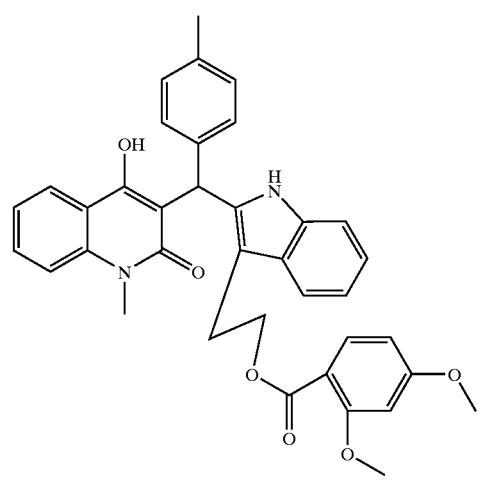
Compound No. 429
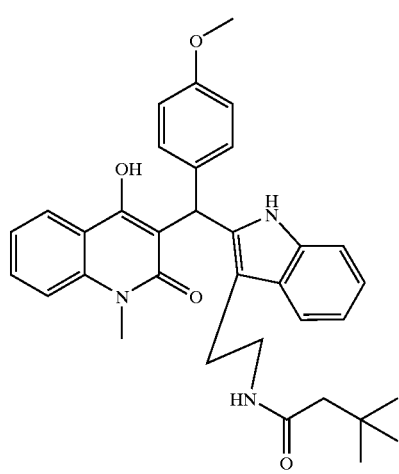

TABLE 2-29-continued
Compound No. 430
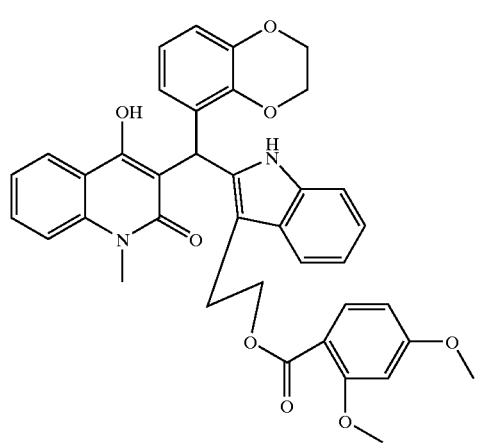
Compound No. 431
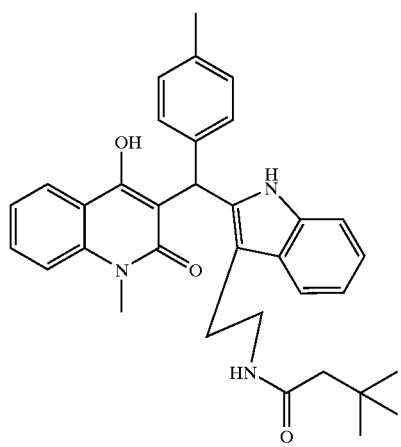
Compound No. 432
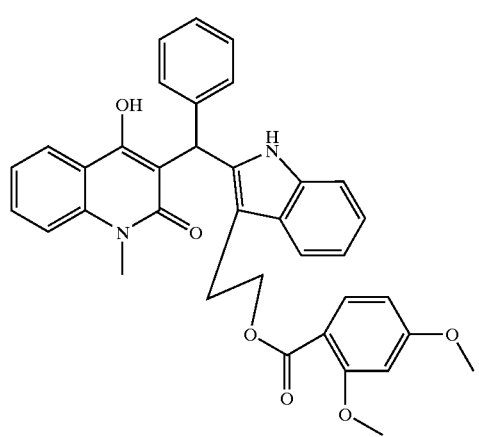
TABLE 2-29-continued
Compound No. 433
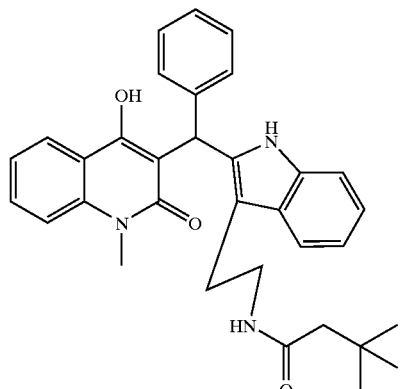
Compound No. 434
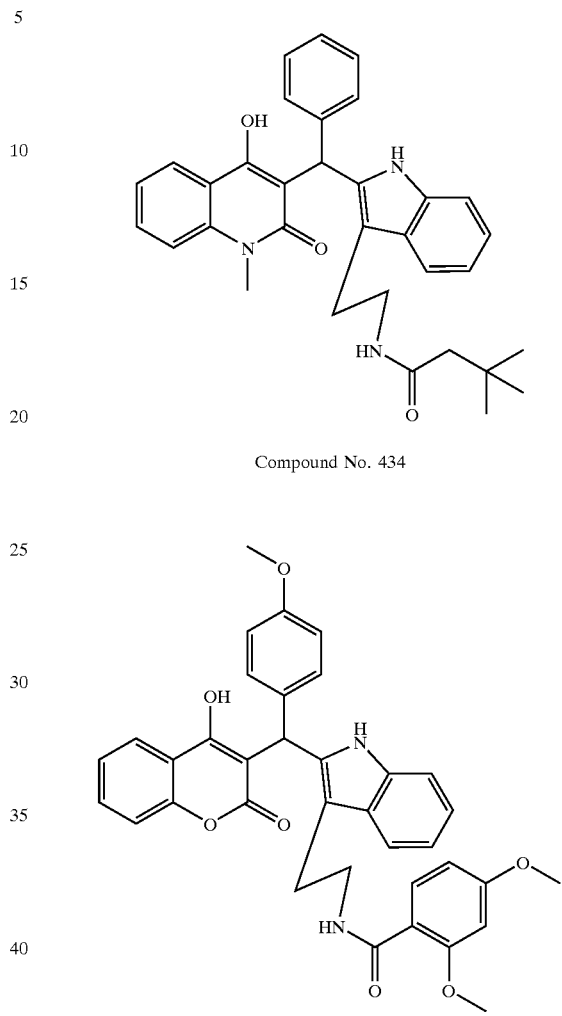
TABLE 2-30
Compound No. 435
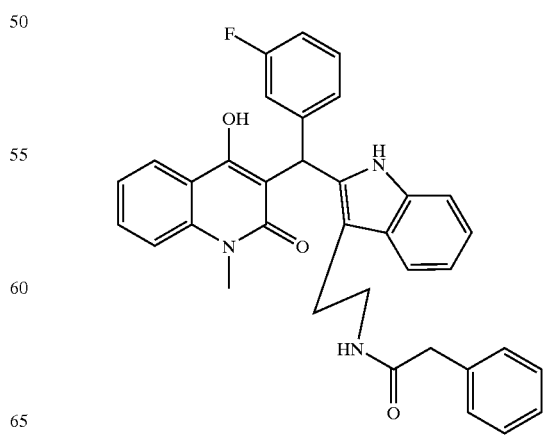

TABLE 2-30-continued
Compound No. 436
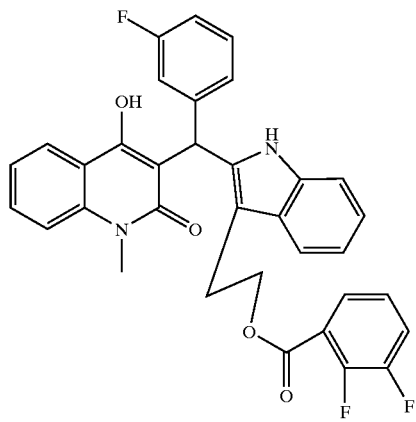
Compound No. 437
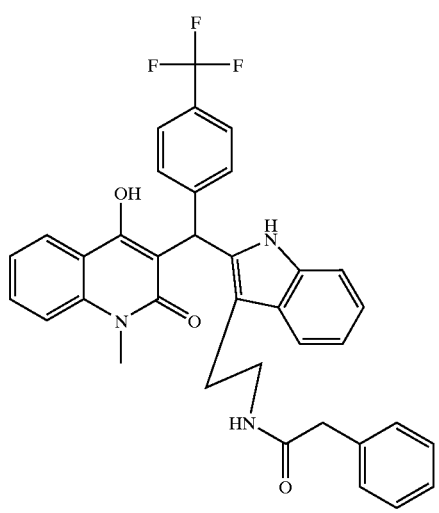
Compound No. 438
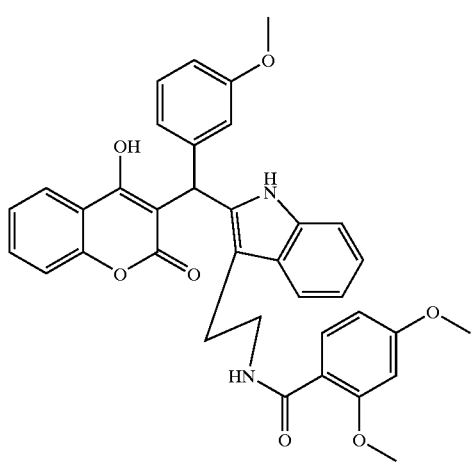
TABLE 2-30-continued
Compound No. 439
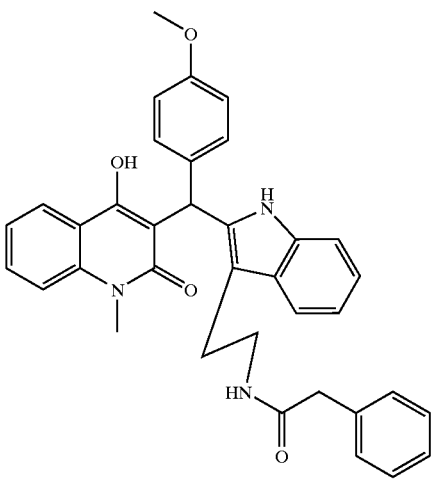
Compound No. 440
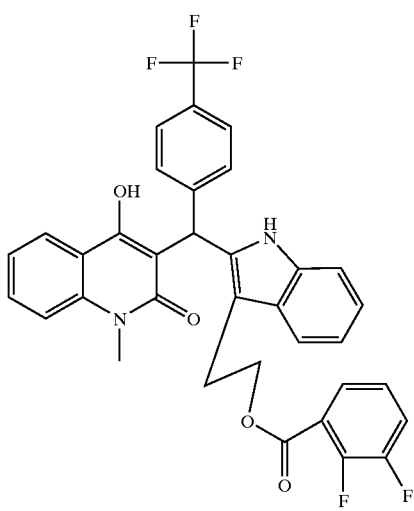
Compound No. 441
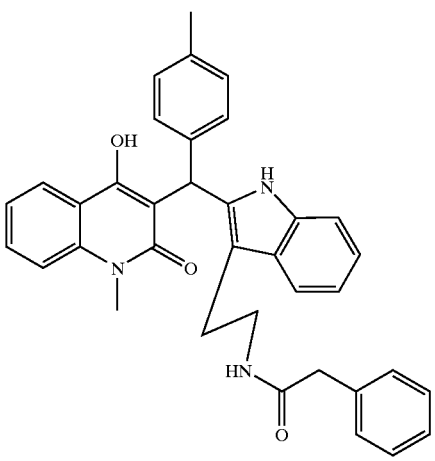

TABLE 2-30-continued
Compound No. 442
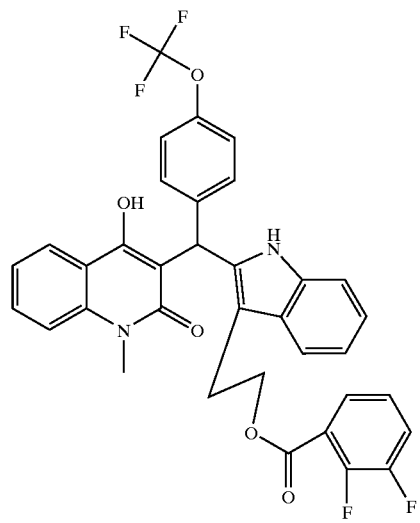
Compound No. 443
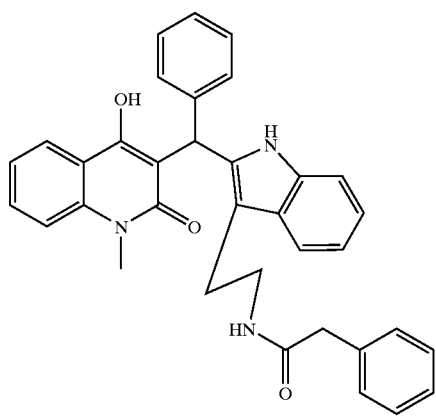
Compound No. 444
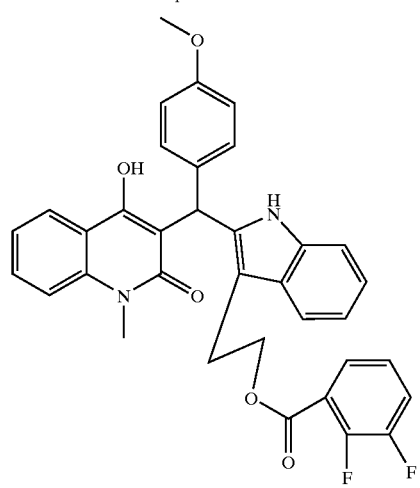
TABLE 2-30-continued
Compound No. 445
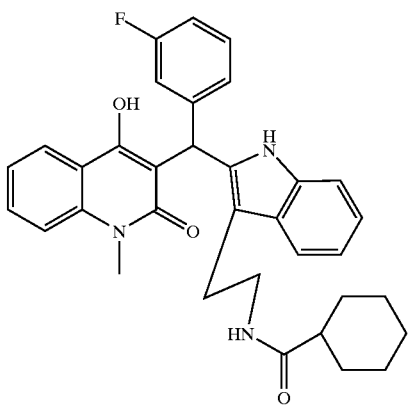
Compound No. 446
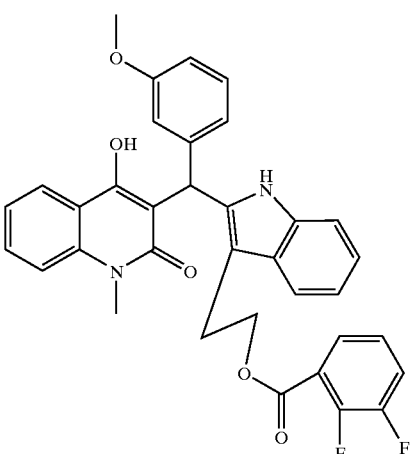
TABLE 2-31
Compound No. 447
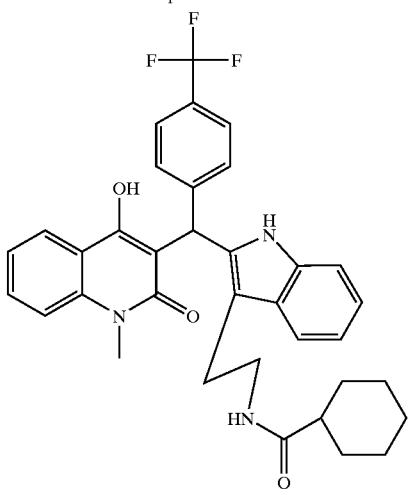

TABLE 2-31-continued
Compound No. 448
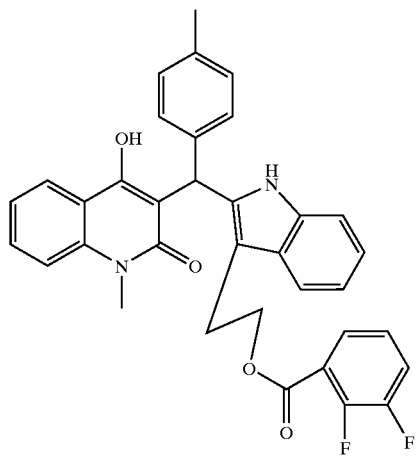
Compound No. 449
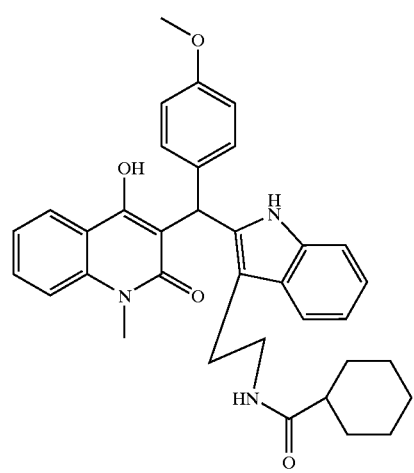
Compound No. 450
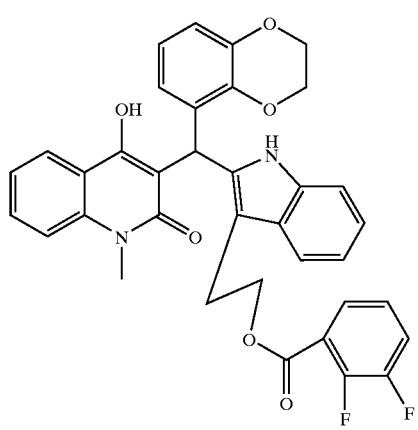
TABLE 2-31-continued
Compound No. 451
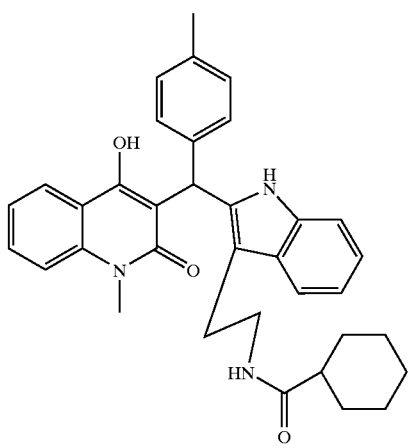
Compound No. 452
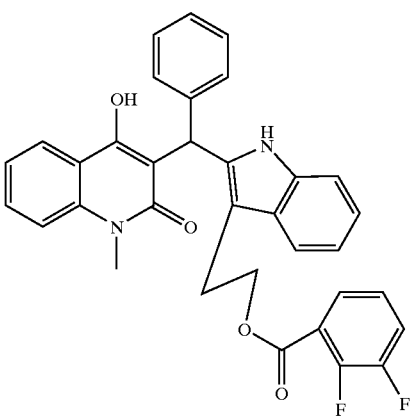
Compound No. 453
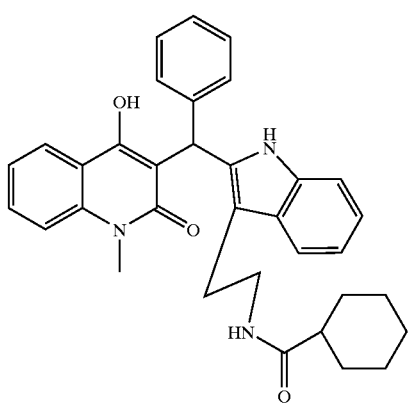

TABLE 2-31-continued
Compound No. 454
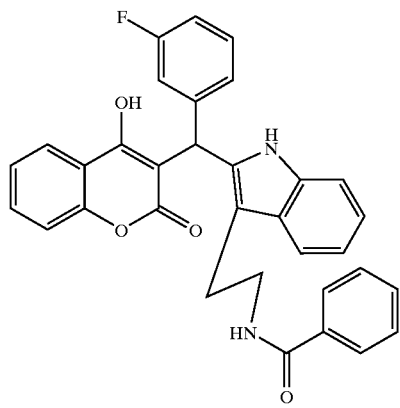
Compound No. 455
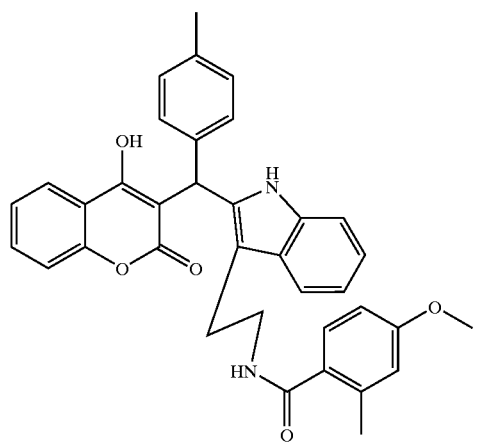
Compound No. 456
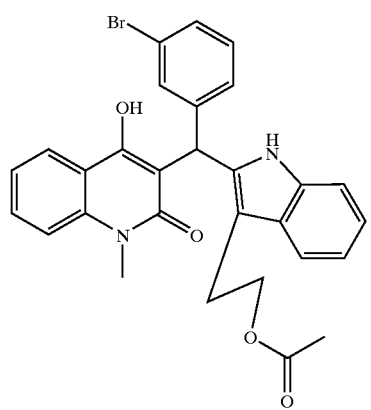
TABLE 2-31-continued
Compound No. 457
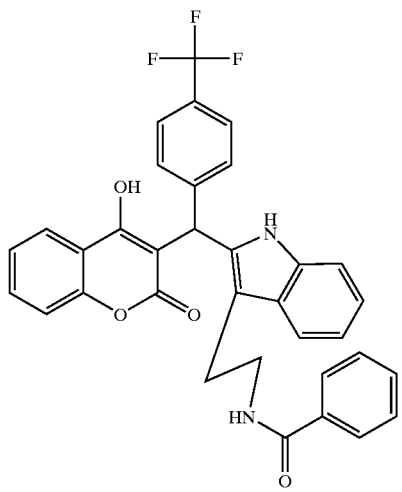
Compound No. 458
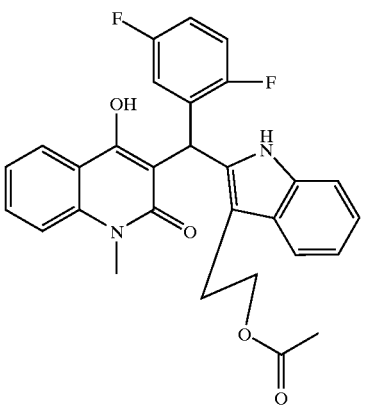
TABLE 2-32
Compound No. 459
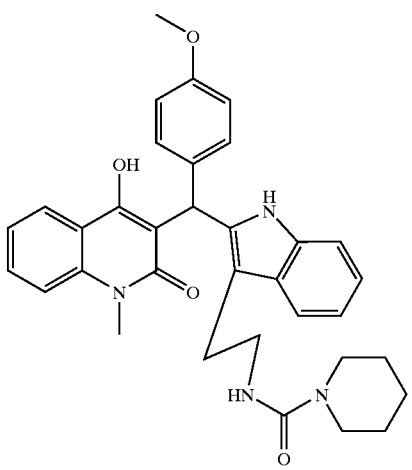

TABLE 2-32-continued
Compound No. 460
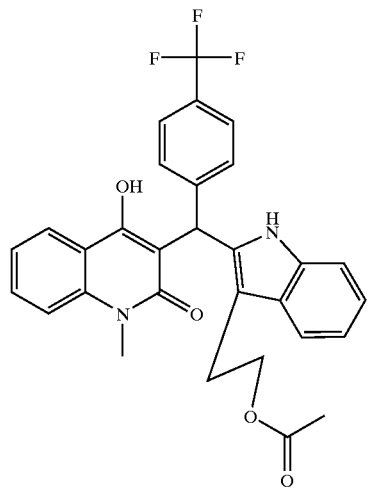
Compound No. 461
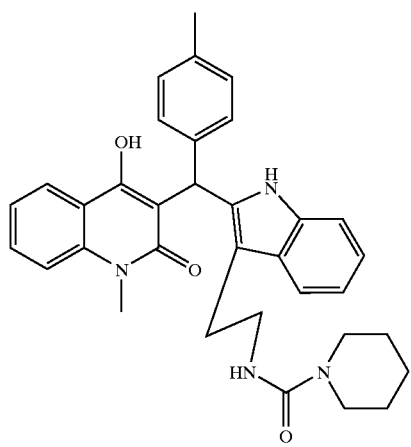
Compound No. 462
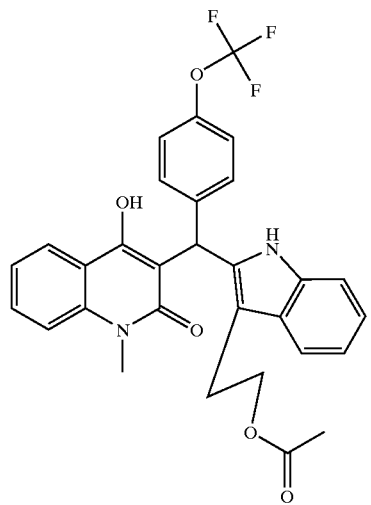
TABLE 2-32-continued
Compound No. 463
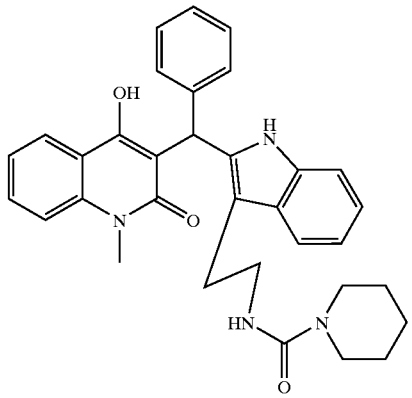
Compound No. 464
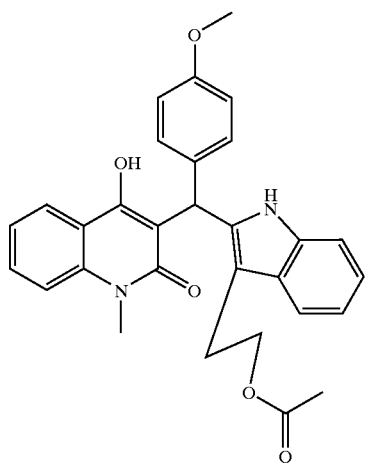
Compound No. 465
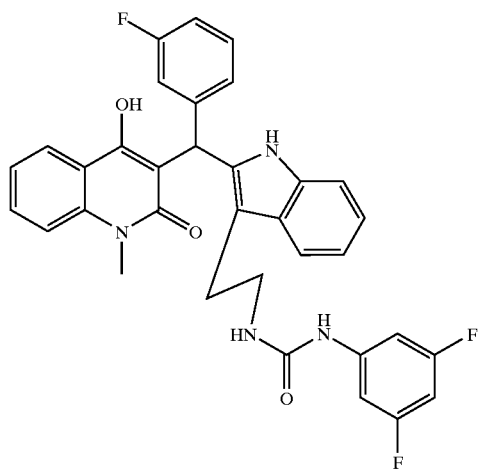

TABLE 2-32-continued
Compound No. 466
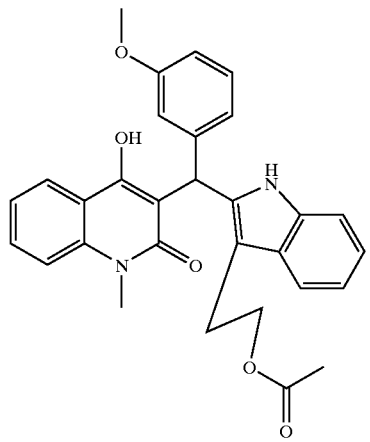
Compound No. 467
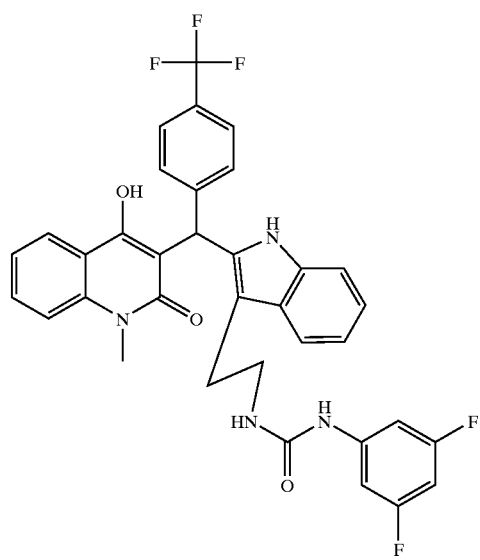
Compound No. 468
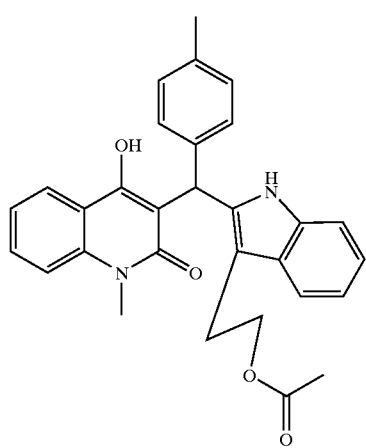
TABLE 2-32-continued
Compound No. 469
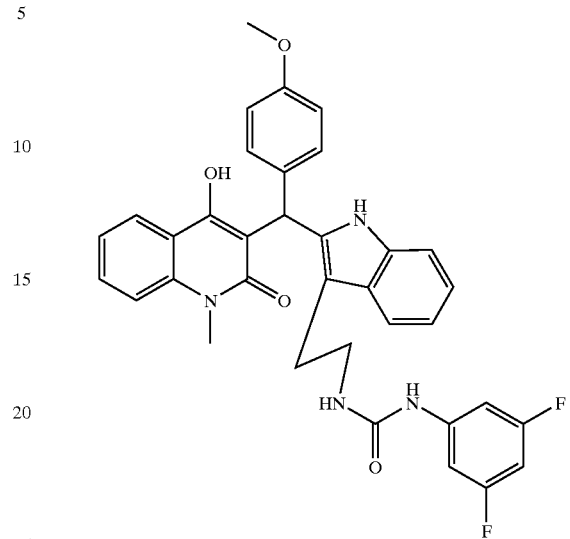
Compound No. 470
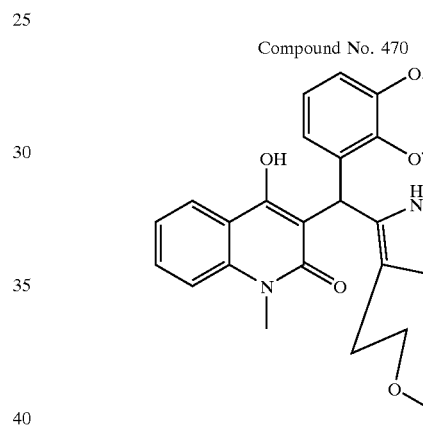
TABLE 2-33
Compound No. 471
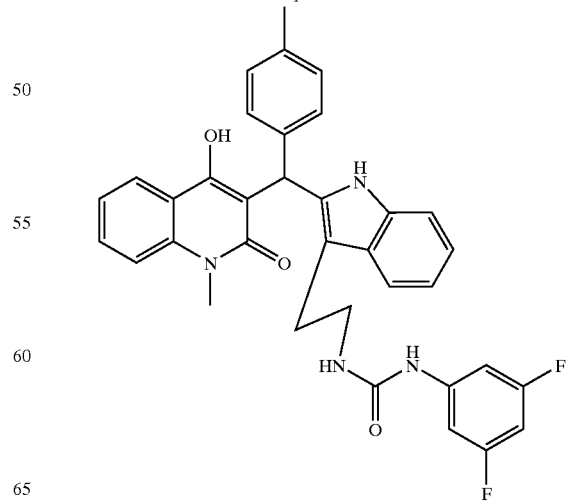

TABLE 2-33-continued
Compound No. 472
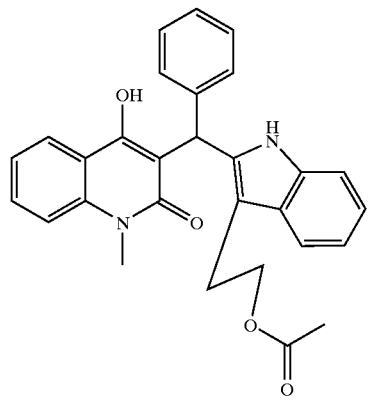
Compound No. 473
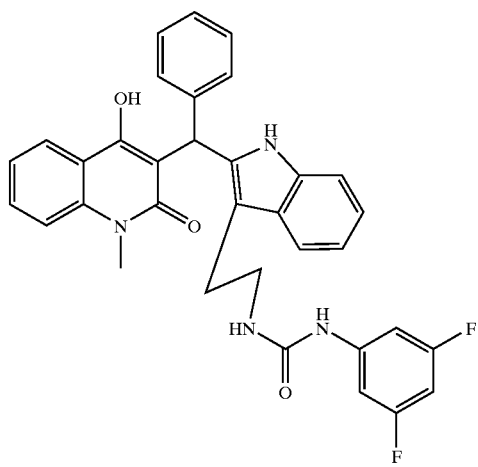
Compound No. 474
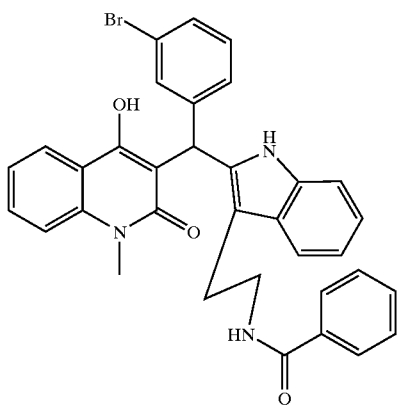
TABLE 2-33-continued
Compound No. 475
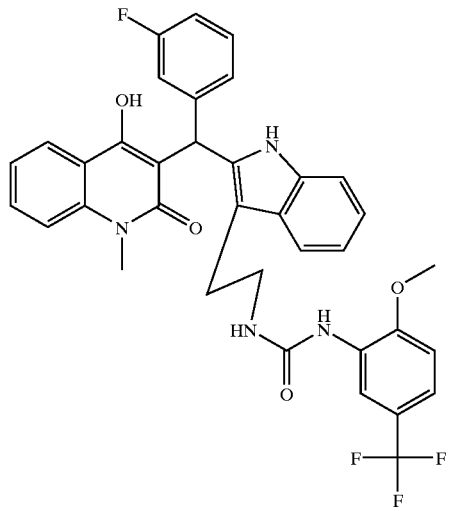
Compound No. 476
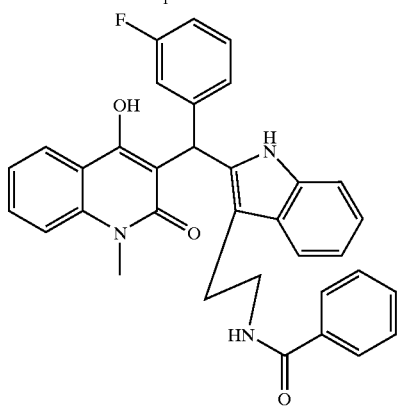
Compound No. 477
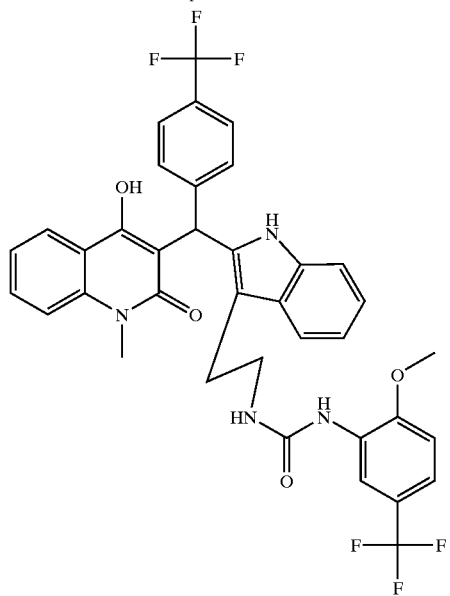

TABLE 2-33-continued
Compound No. 478
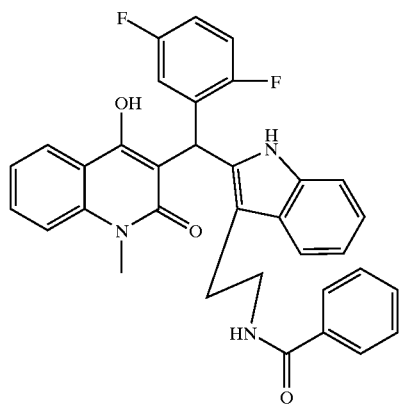
Compound No. 479
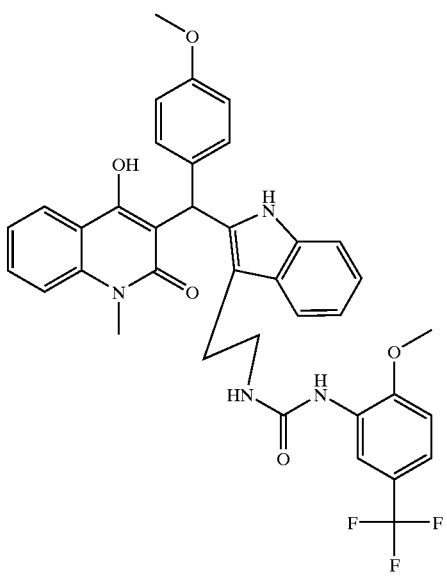
Compound No. 480
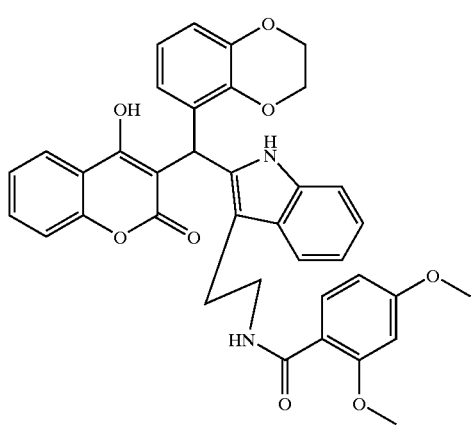
TABLE 2-33-continued
Compound No. 481
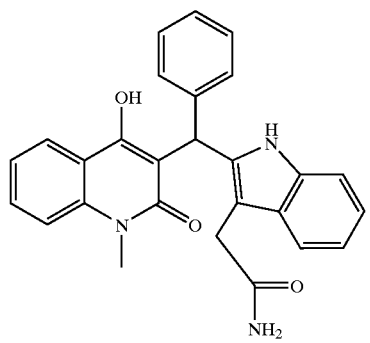
Compound No. 482
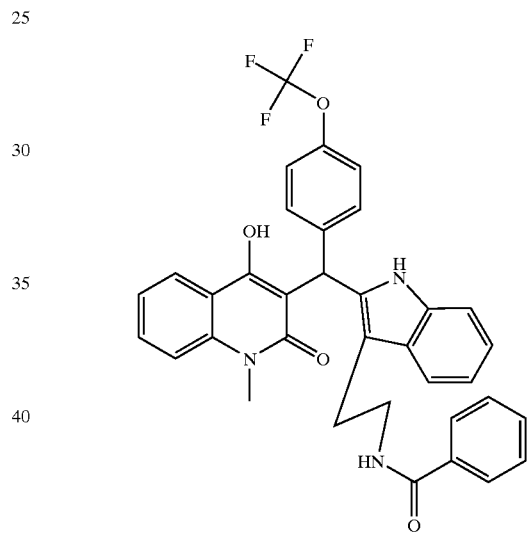
TABLE 2-34
Compound No. 483
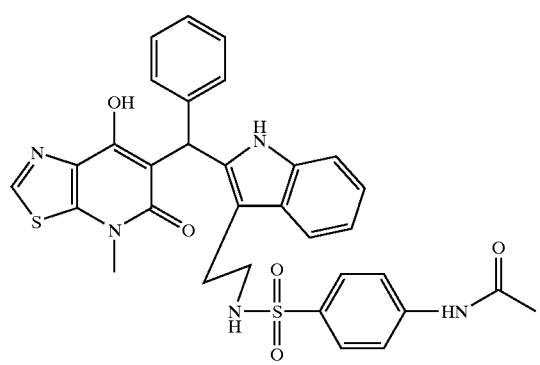

TABLE 2-34-continued
Compound No. 484
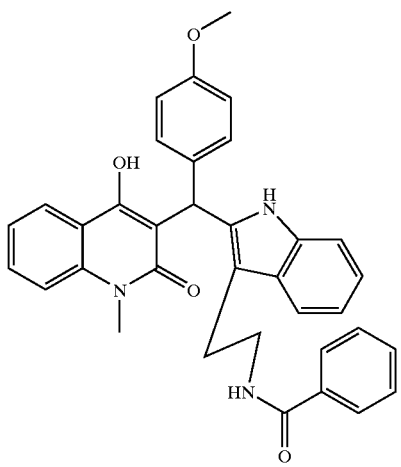
Compound No. 485
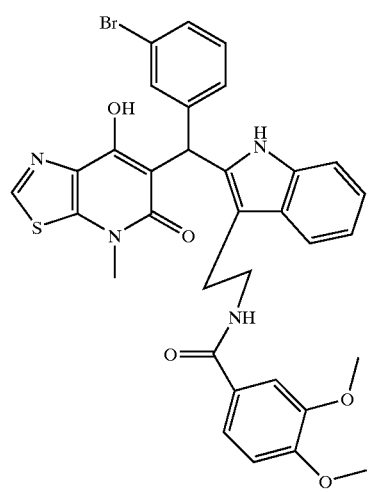
Compound No. 486
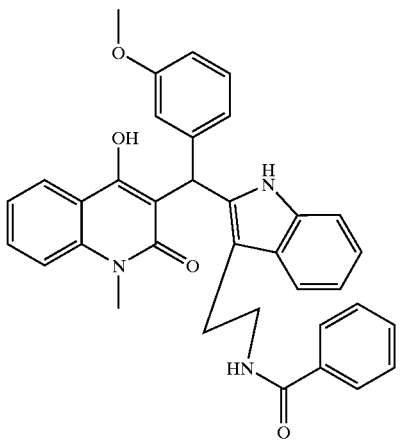
TABLE 2-34-continued
Compound No. 487
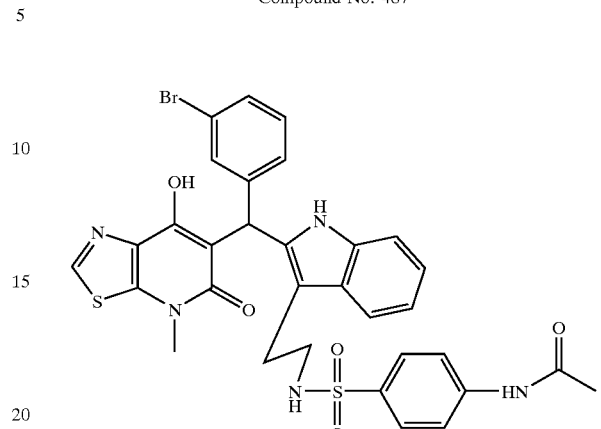
Compound No. 488
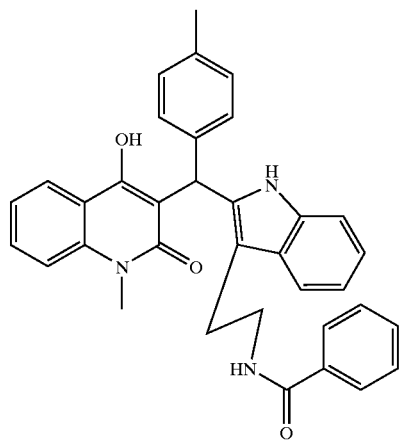
Compound No. 489
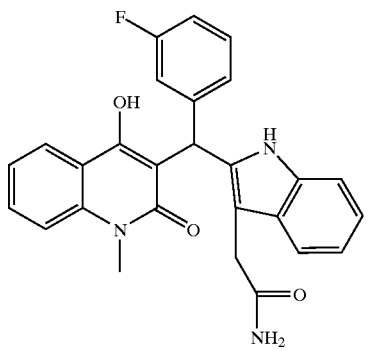

TABLE 2-34-continued
Compound No. 490
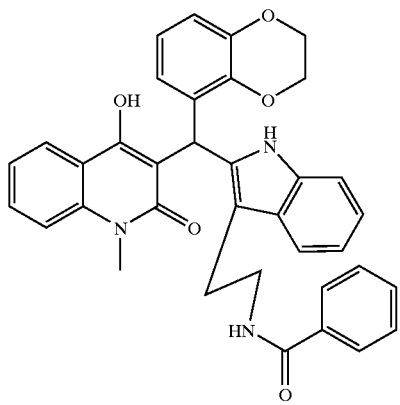
Compound No. 491
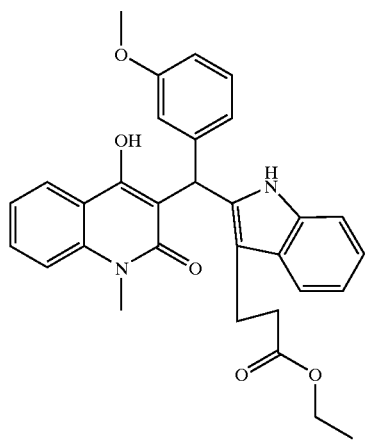
Compound No. 492
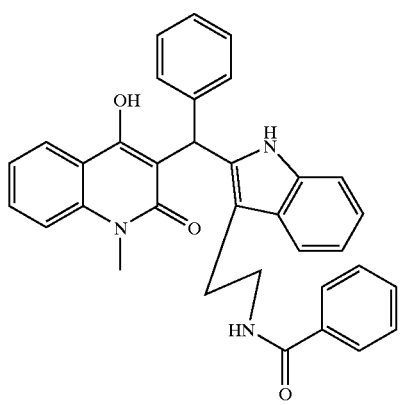
TABLE 2-34-continued
Compound No. 493
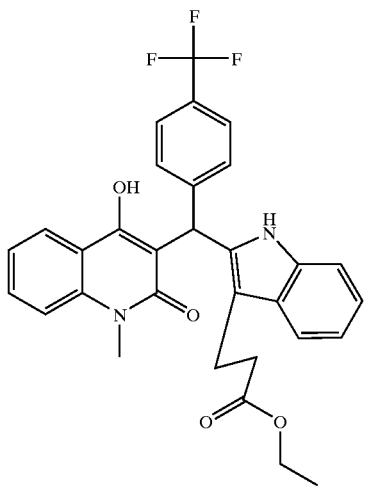
Compound No. 494
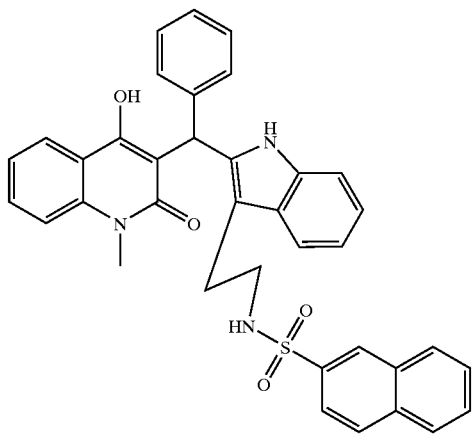
TABLE 2-35
Compound No. 495
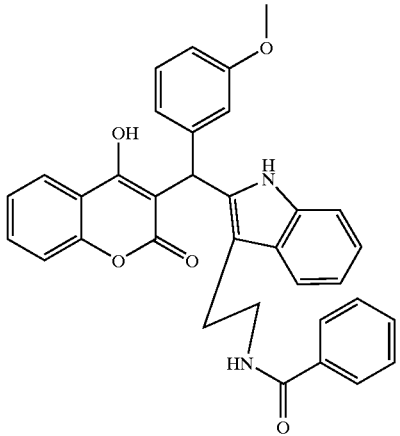

TABLE 2-35-continued
Compound No. 496
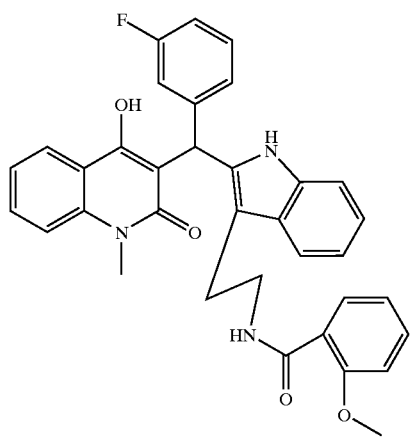
Compound No. 497
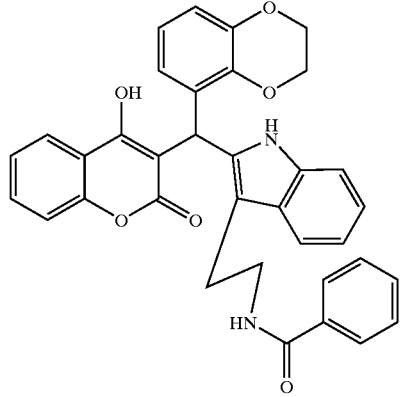
Compound No. 498
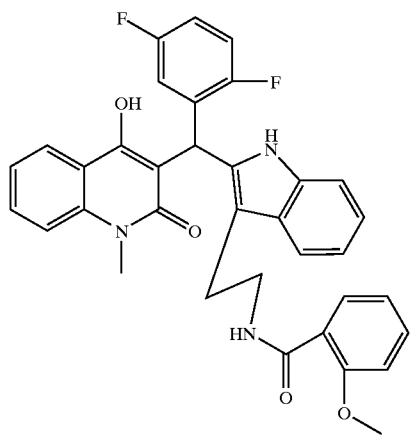
TABLE 2-35-continued
Compound No. 499
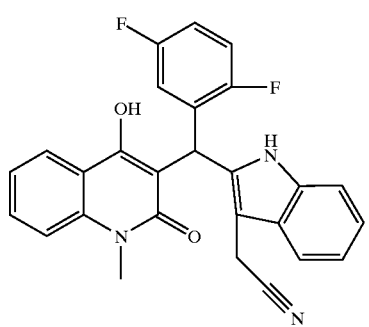
Compound No. 500
Compound No. 501
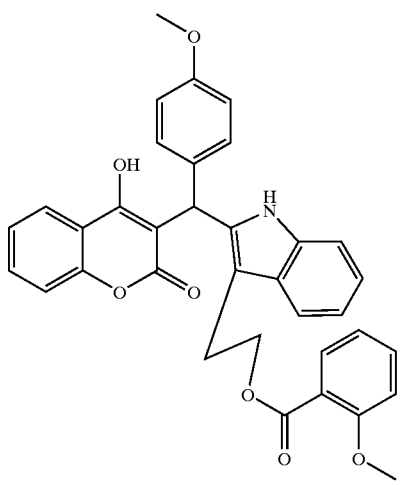

TABLE 2-35-continued
Compound No. 502
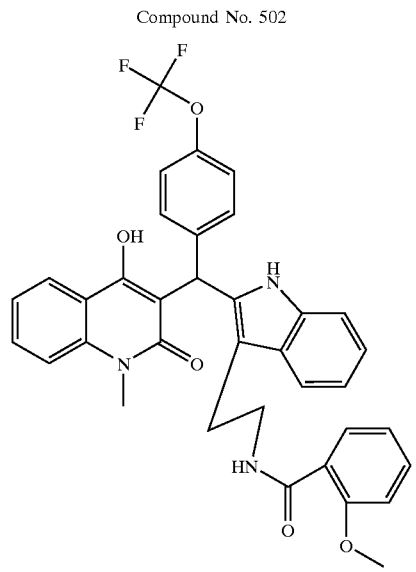
Compound No. 503
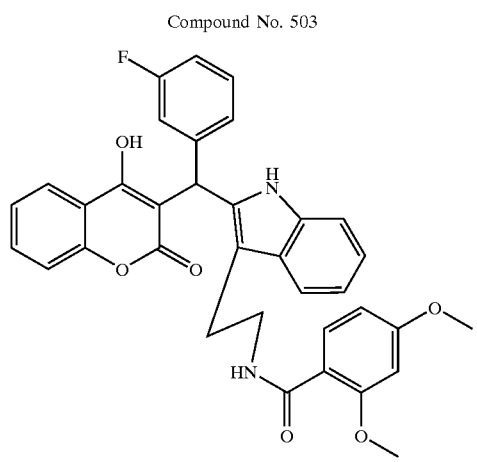
Compound No. 504
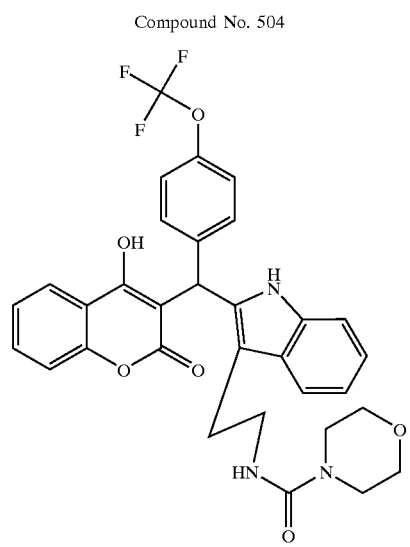
TABLE 2-35-continued
Compound No. 505
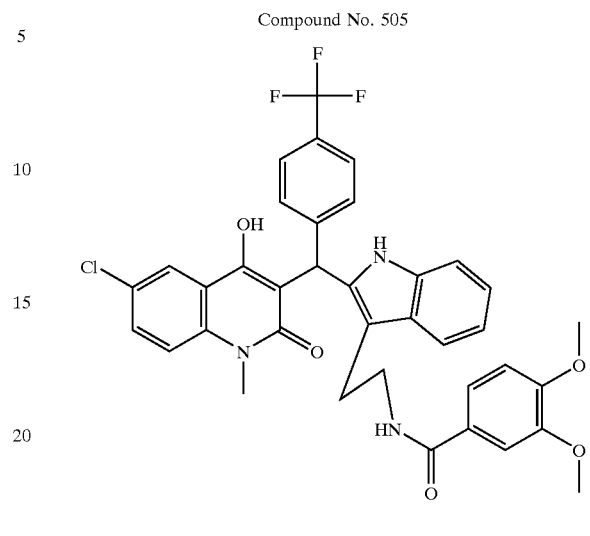
Compound No. 506
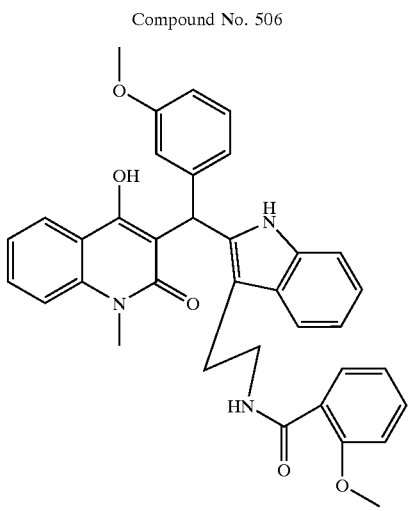
TABLE 2-36
Compound No. 507
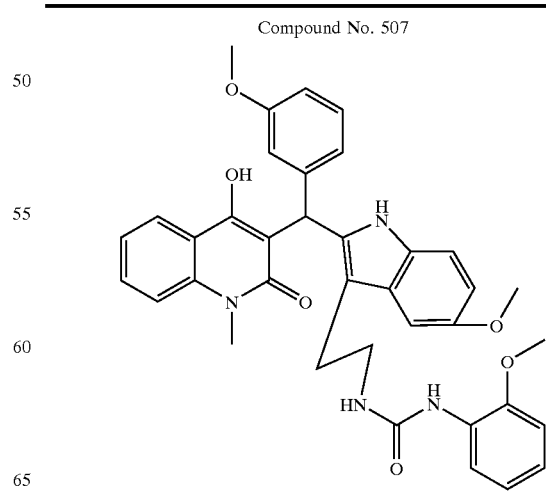

TABLE 2-36-continued
Compound No. 508
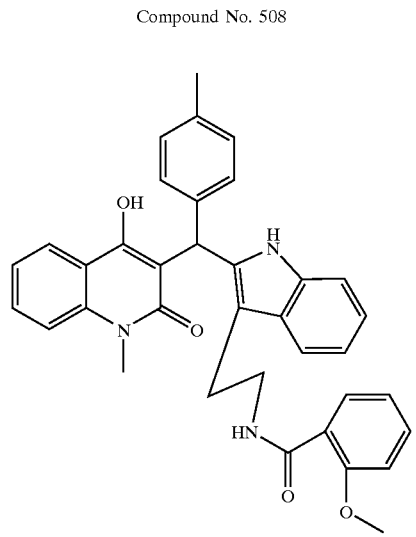
Compound No. 509
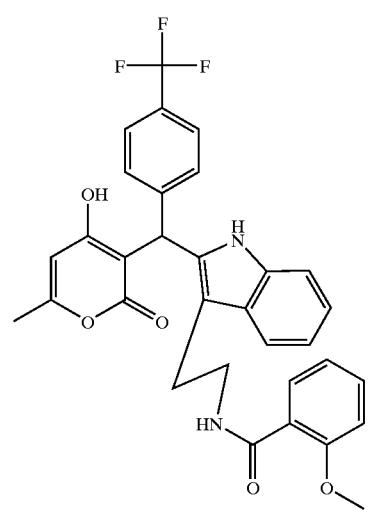
Compound No. 510
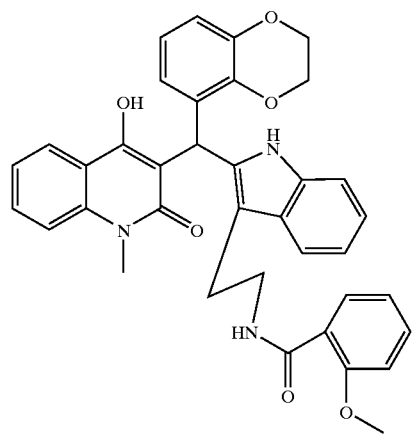
TABLE 2-36-continued
Compound No. 511
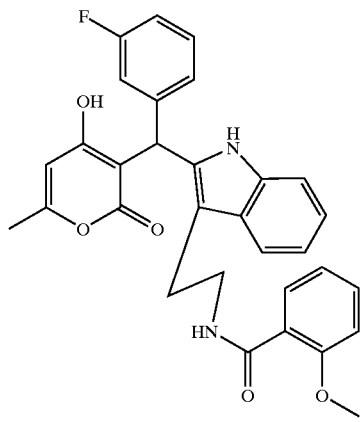
Compound No. 512
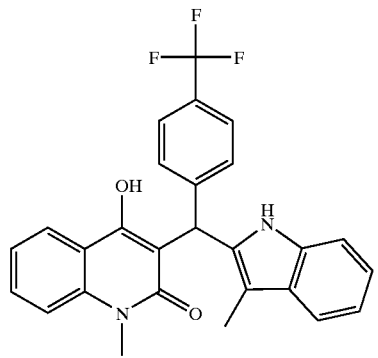
Compound No. 513
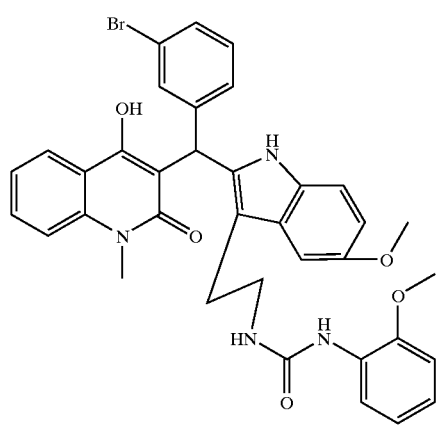

TABLE 2-36-continued
Compound No. 514
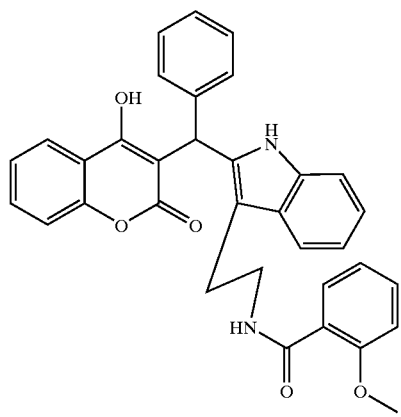
Compound No. 515
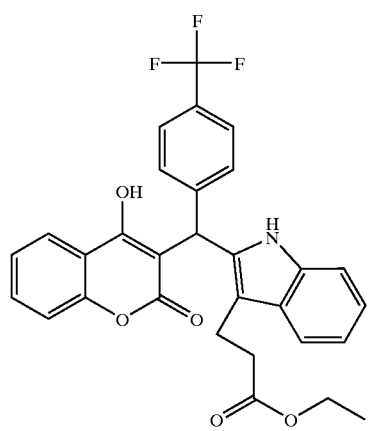
Compound No. 516
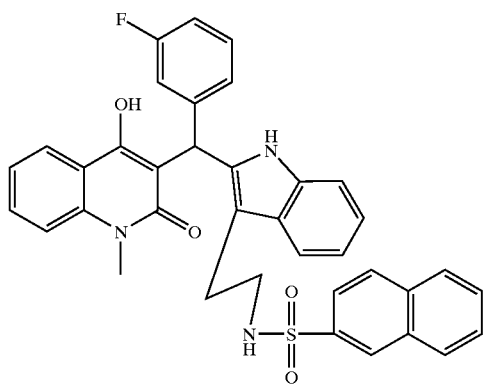
TABLE 2-36-continued
Compound No. 517
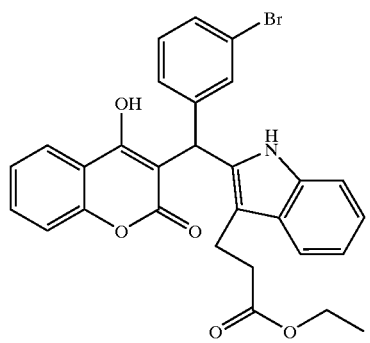
Compound No. 518
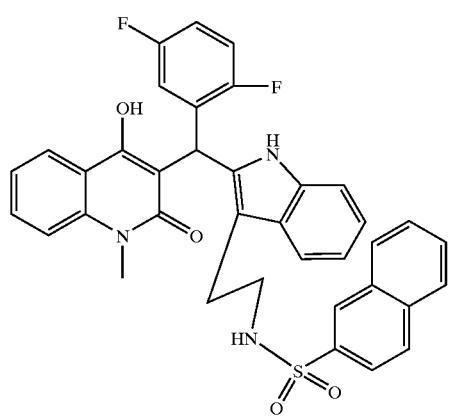
TABLE 2-37
Compound No. 519
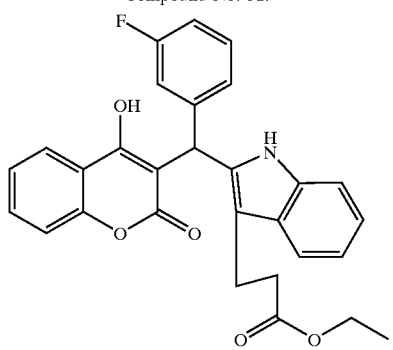
Compound No. 520
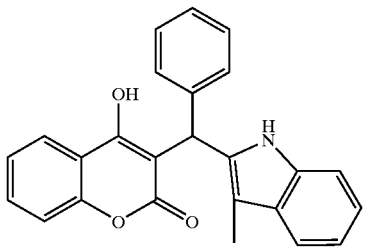

TABLE 2-37-continued
Compound No. 521
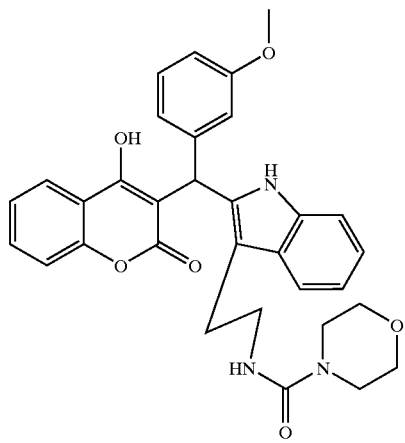
Compound No. 522
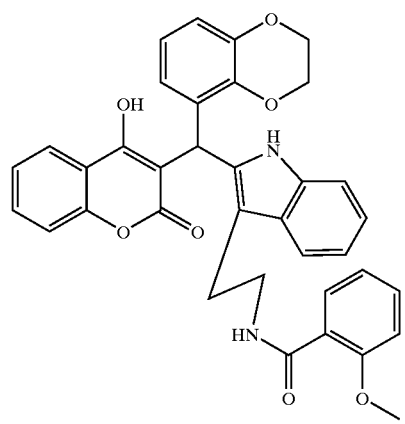
Compound No. 523
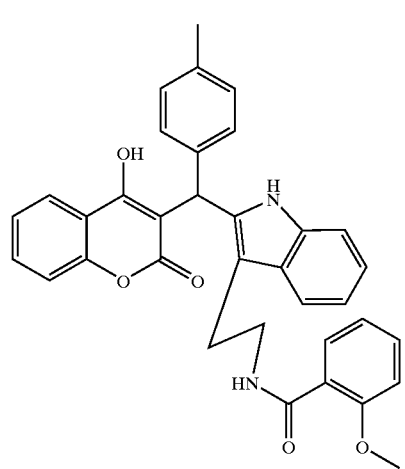
TABLE 2-37-continued
Compound No. 524
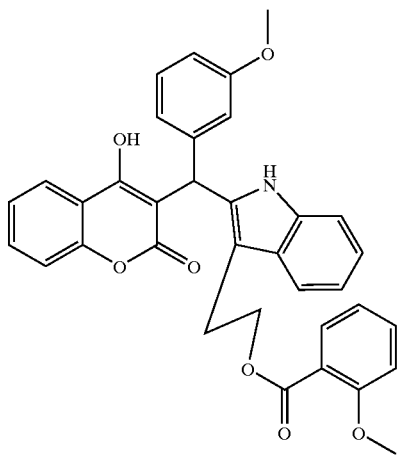
Compound No. 525
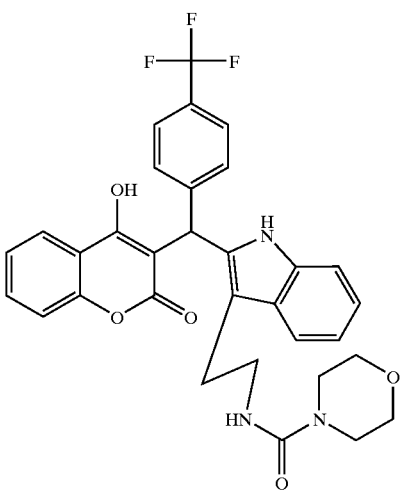
Compound No. 526
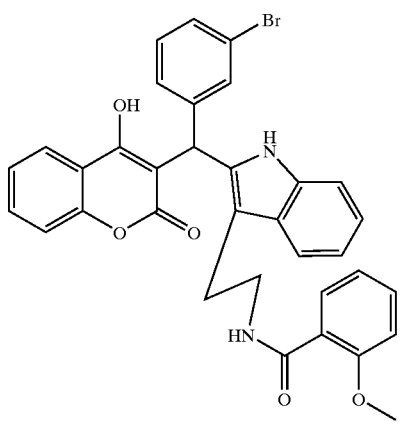

TABLE 2-37-continued
Compound No. 527
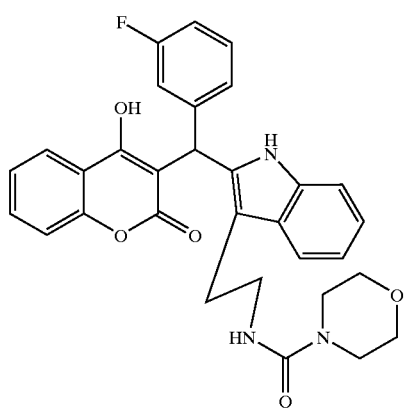
Compound No. 528
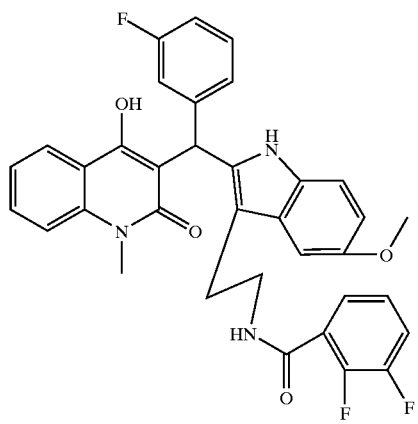
Compound No. 529
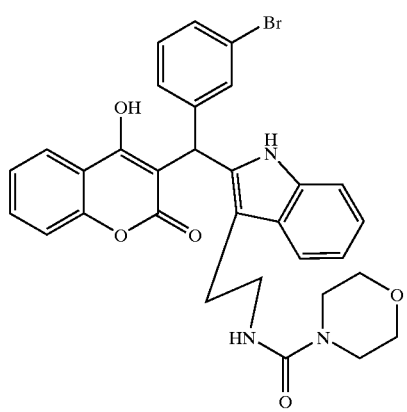
TABLE 2-37-continued
Compound No. 530
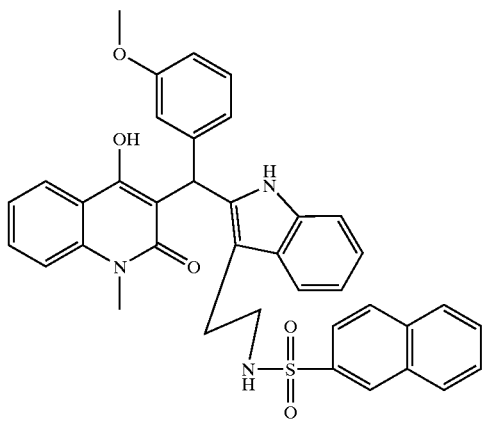
TABLE 2-38
Compound No. 531
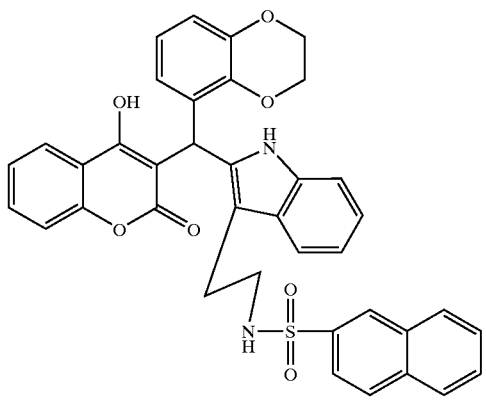
Compound No. 532
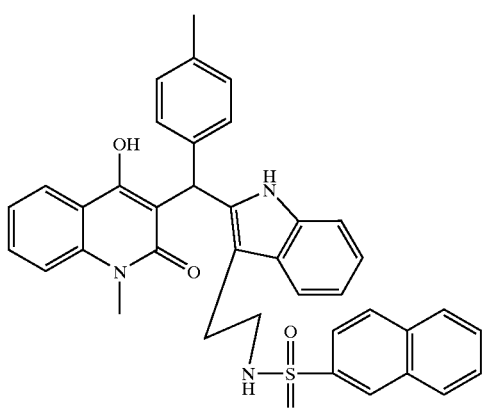

TABLE 2-38-continued
Compound No. 533
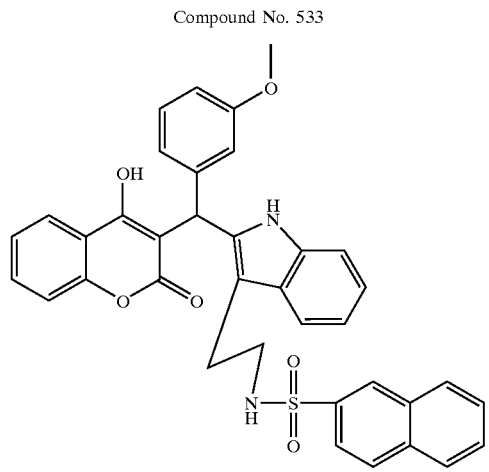
Compound No. 534
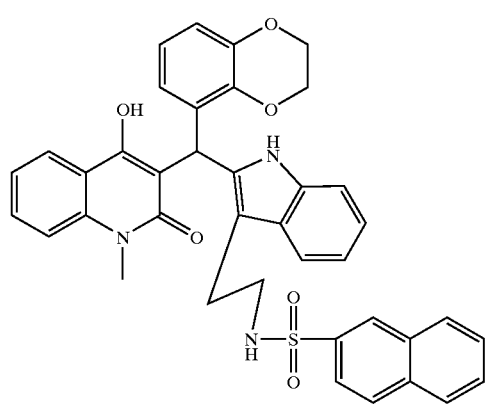
Compound No. 535
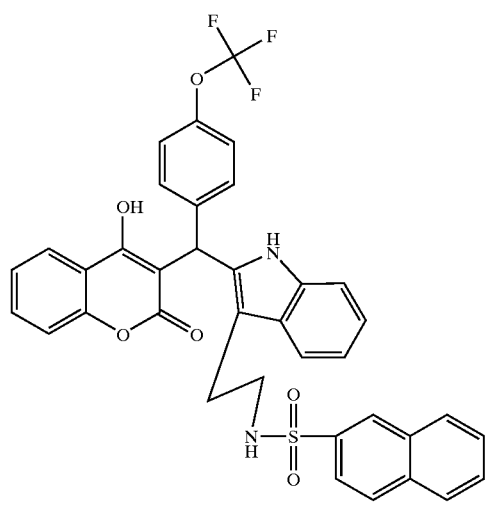
TABLE 2-38-continued
Compound No. 536
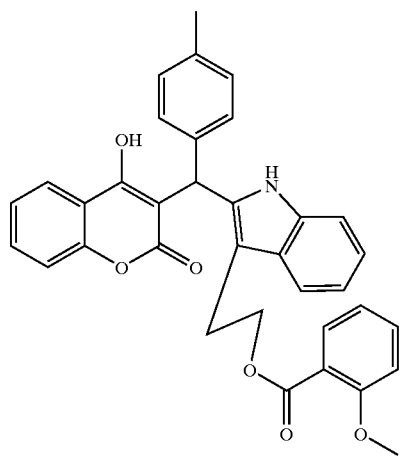
Compound No. 537
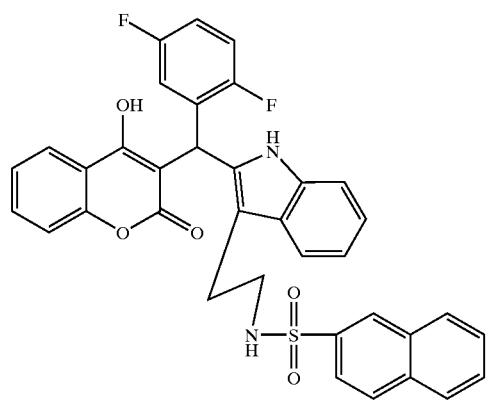
Compound No. 538
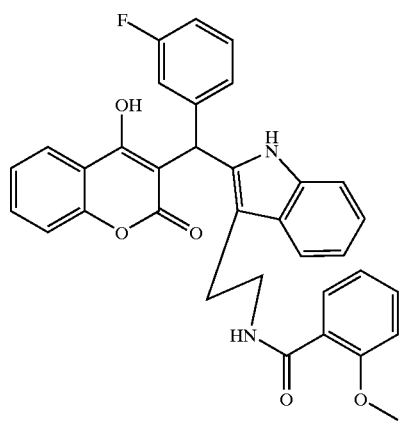

TABLE 2-38-continued
Compound No. 539
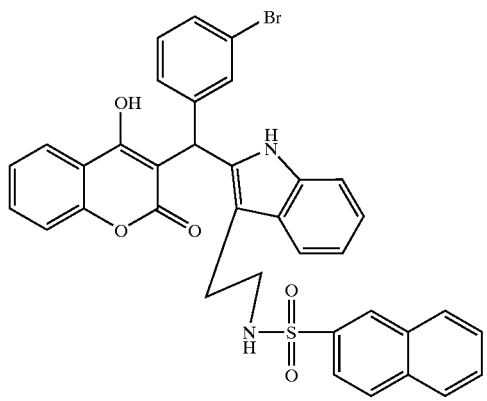
Compound No. 540
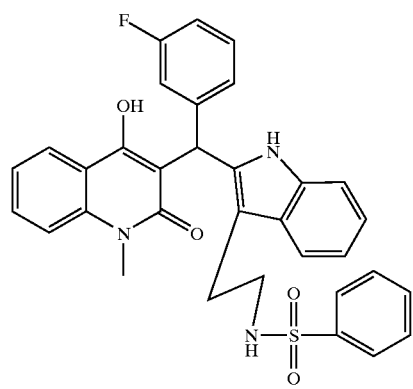
Compound No. 541
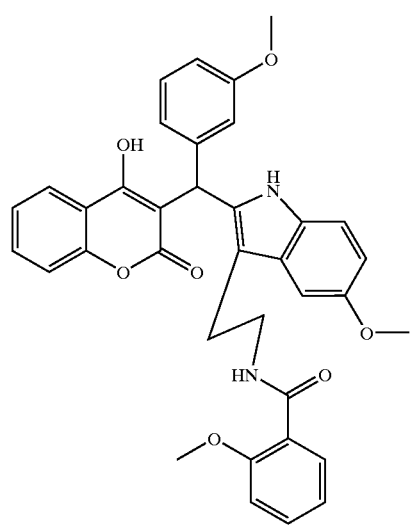
TABLE 2-38-continued
Compound No. 542
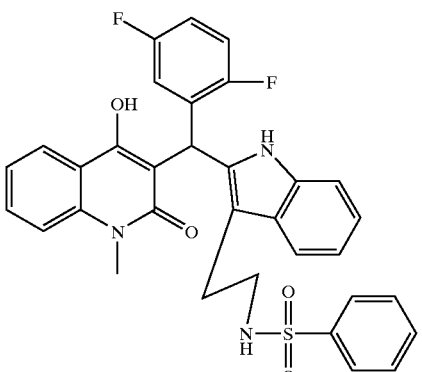
TABLE 2-39
Compound No. 543
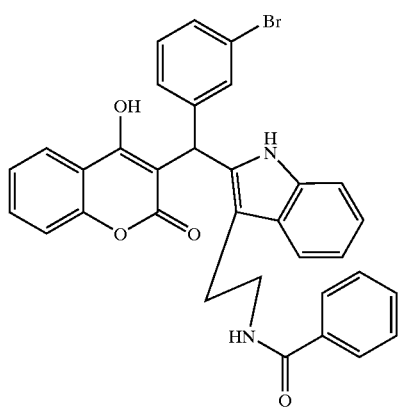
Compound No. 544
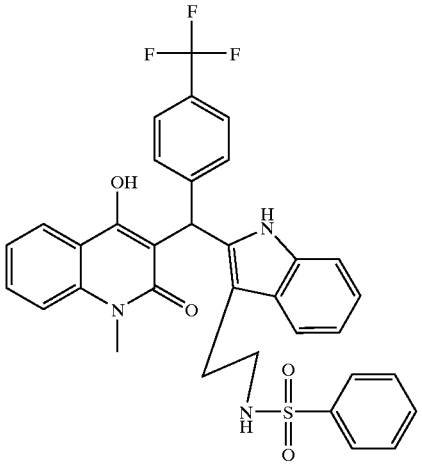

TABLE 2-39-continued
Compound No. 545
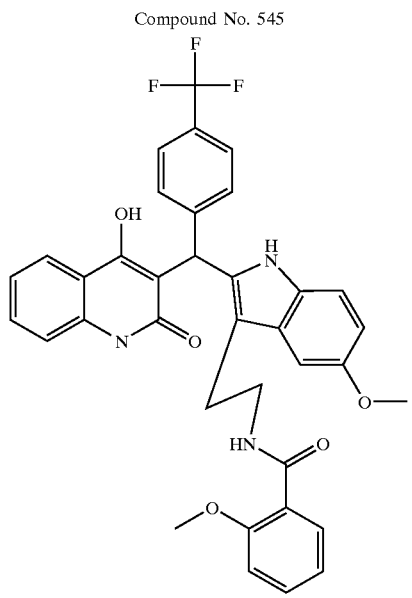
Compound No. 546
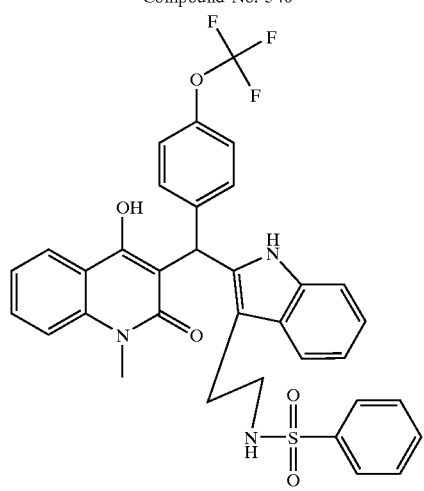
Compound No. 547
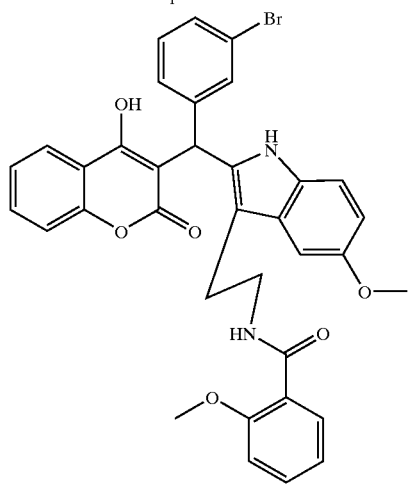
TABLE 2-39-continued
Compound No. 548
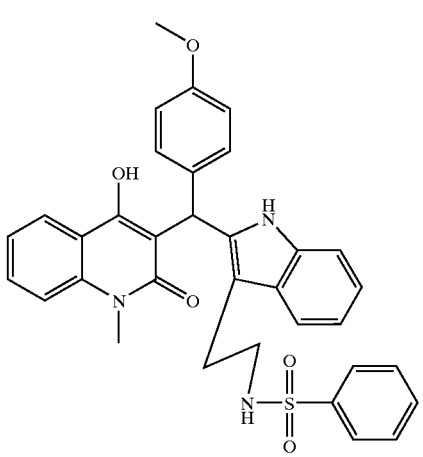
Compound No. 549
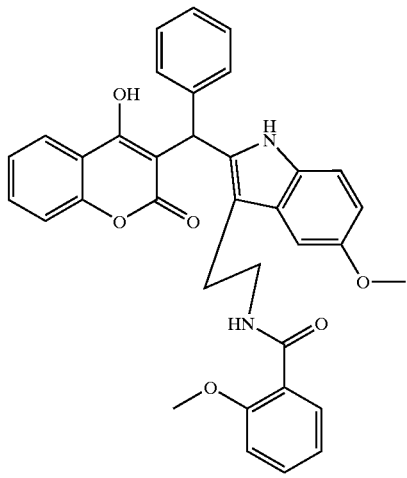
Compound No. 550
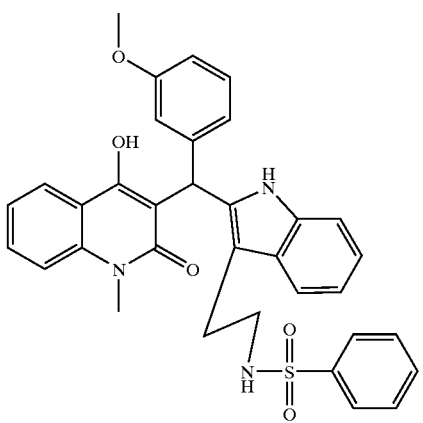

TABLE 2-39-continued
Compound No. 551
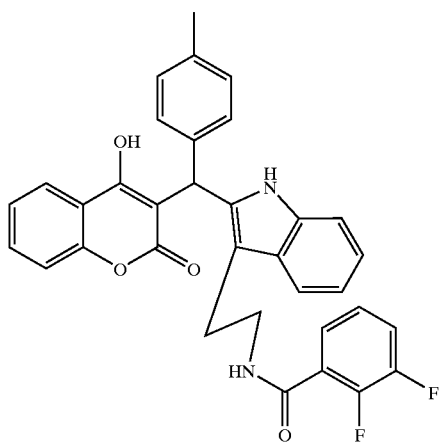
Compound No. 552
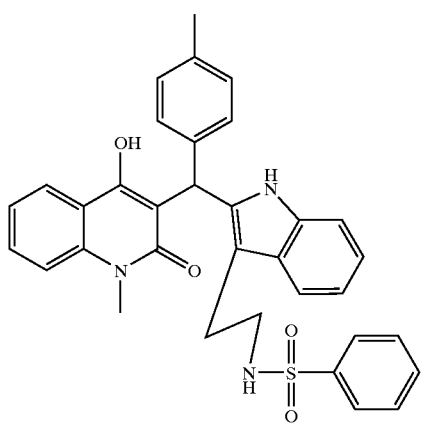
Compound No. 553
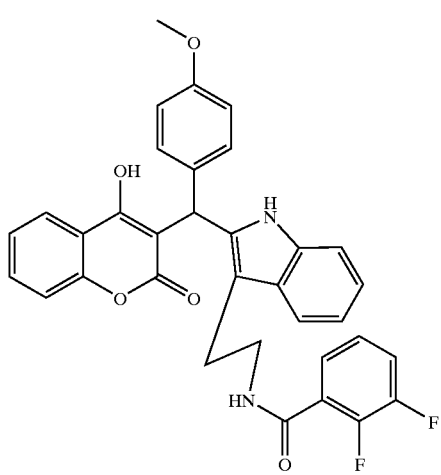
TABLE 2-39-continued
Compound No. 554
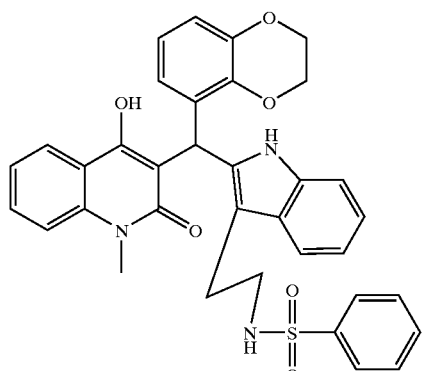
TABLE 2-40
Compound No. 555
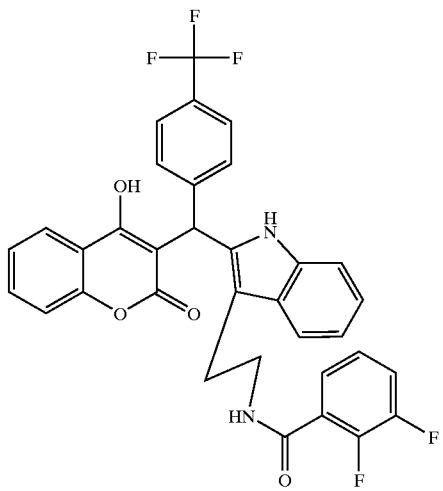
Compound No. 556
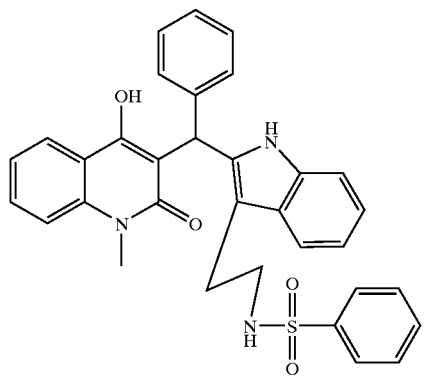

TABLE 2-40-continued
Compound No. 557
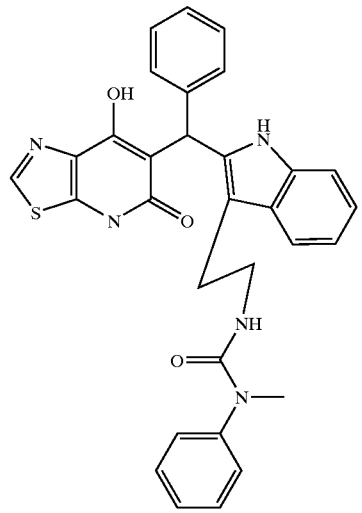
Compound No. 558
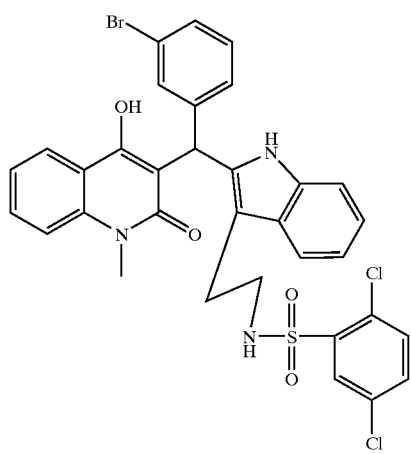
Compound No. 559
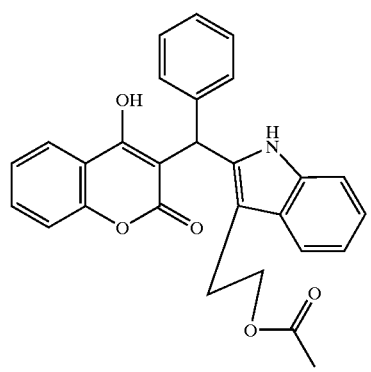
TABLE 2-40-continued
Compound No. 560
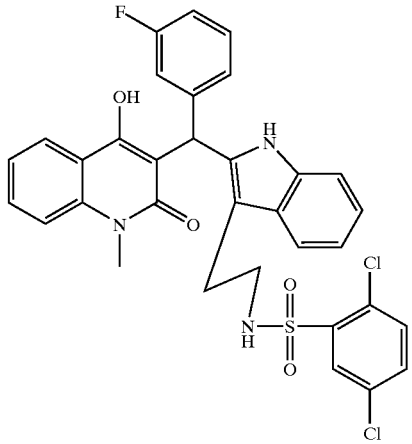
Compound No. 561
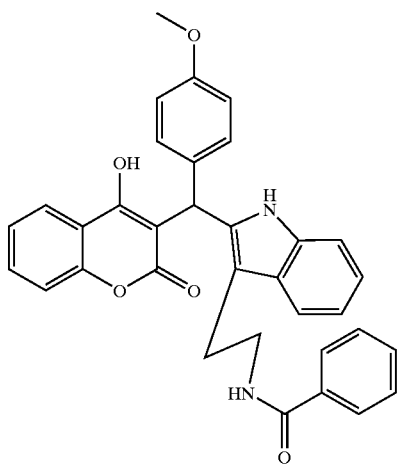
Compound No. 562
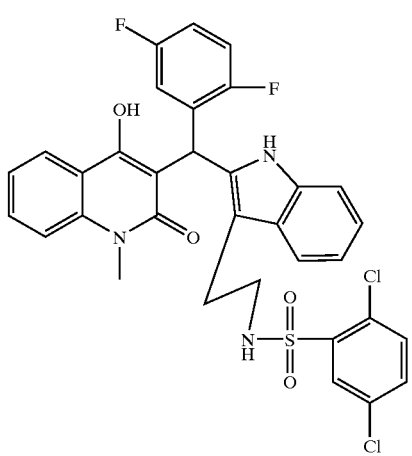

TABLE 2-40-continued
Compound No. 563
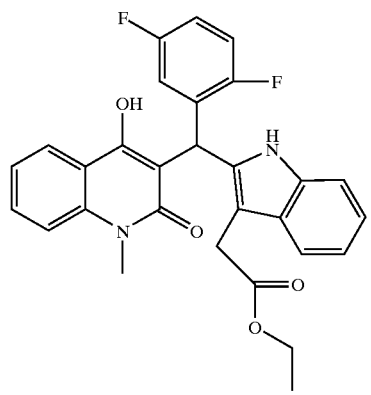
Compound No. 564
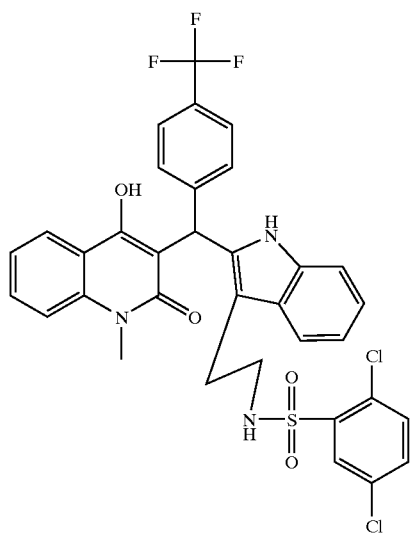
Compound No. 565
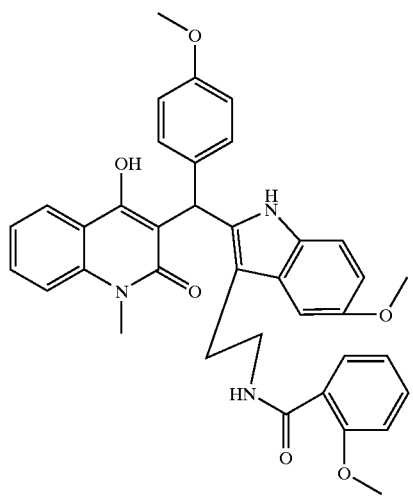
TABLE 2-40-continued
Compound No. 566
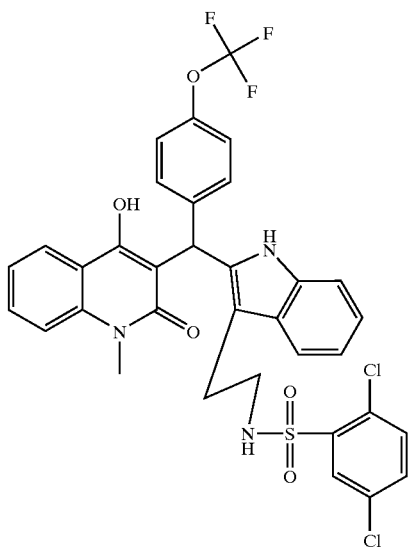
TABLE 2-41
Compound No. 567
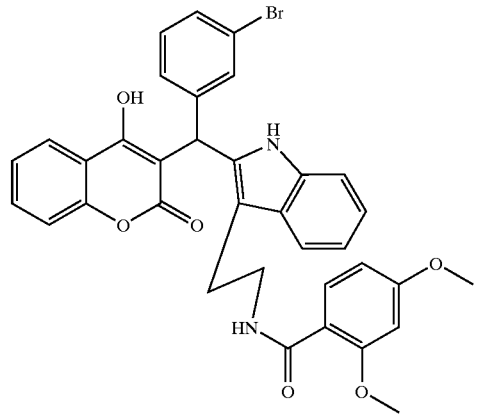
Compound No. 568
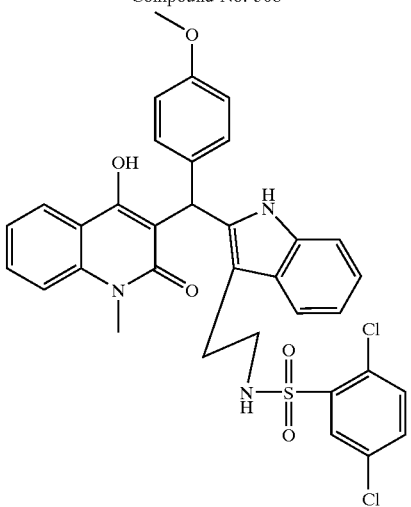

TABLE 2-41-continued
Compound No. 569
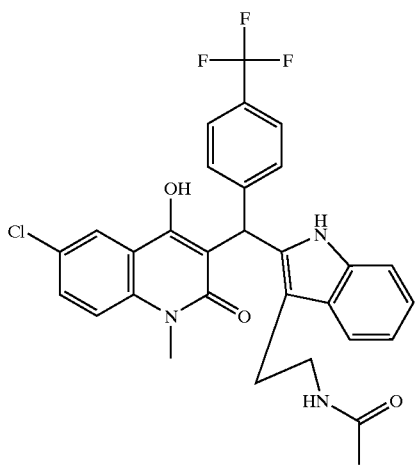
Compound No. 570
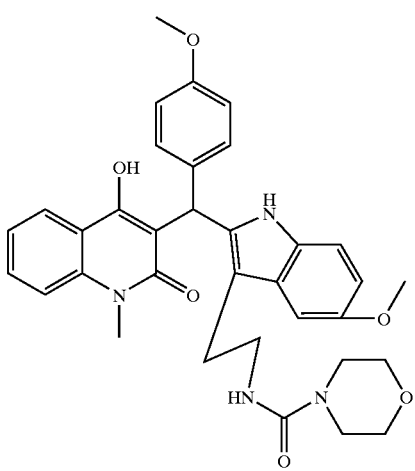
Compound No. 571
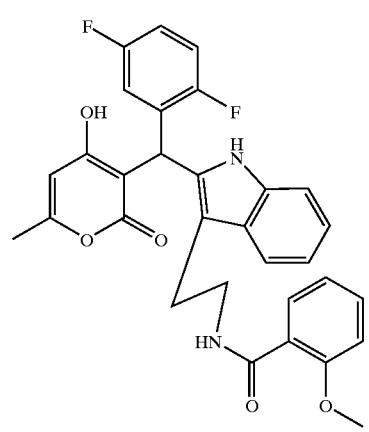
TABLE 2-41-continued
Compound No. 572
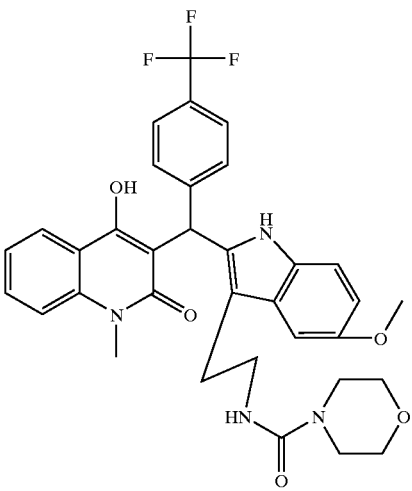
Compound No. 573
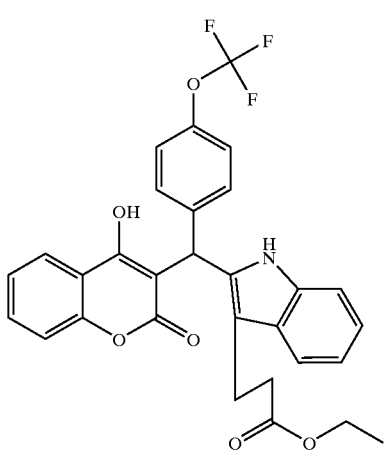
Compound No. 574
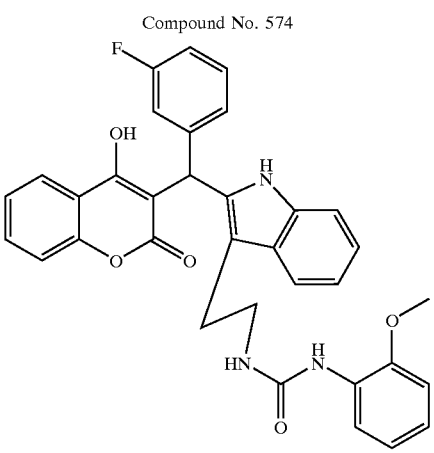

TABLE 2-41-continued
Compound No. 575
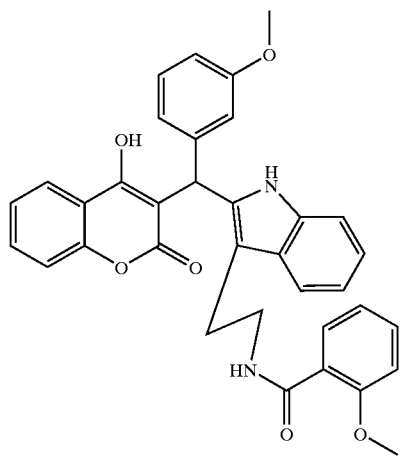
Compound No. 576
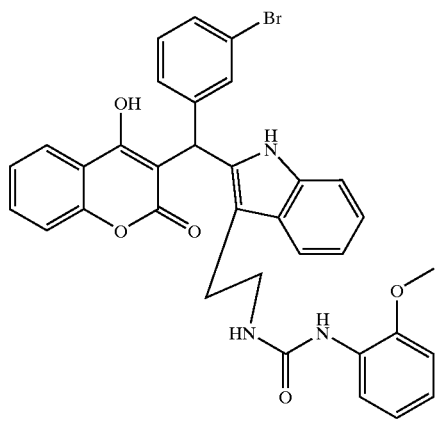
Compound No. 577
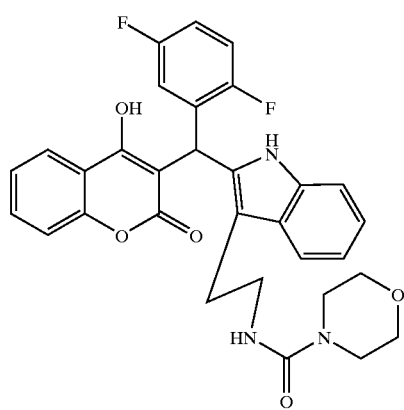
TABLE 2-41-continued
Compound No. 578
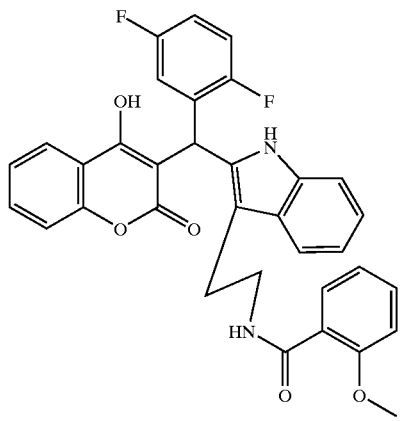
TABLE 2-42
Compound No. 579
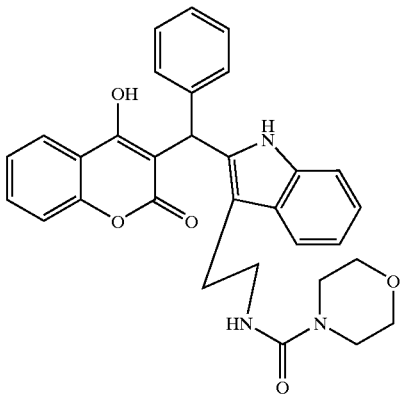
Compound No. 580
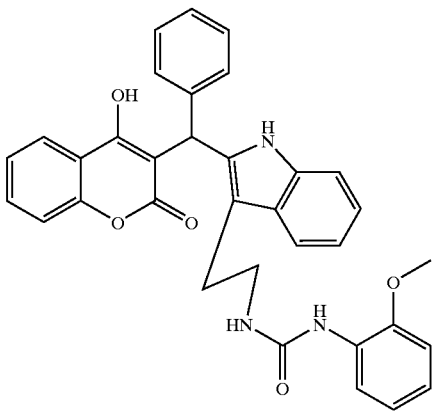

TABLE 2-42-continued
Compound No. 581
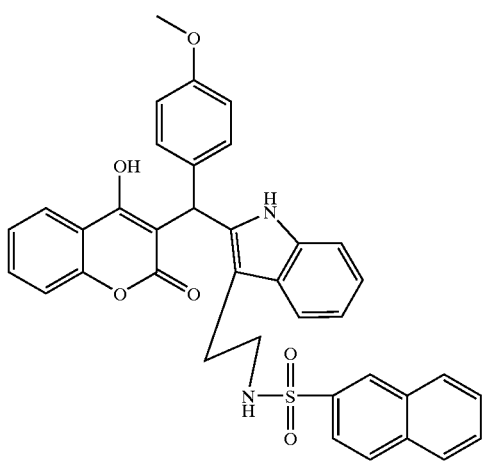
Compound No. 582
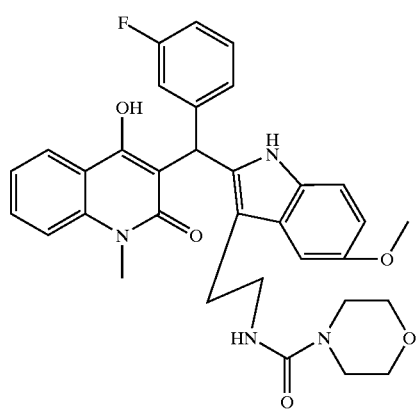
Compound No. 583
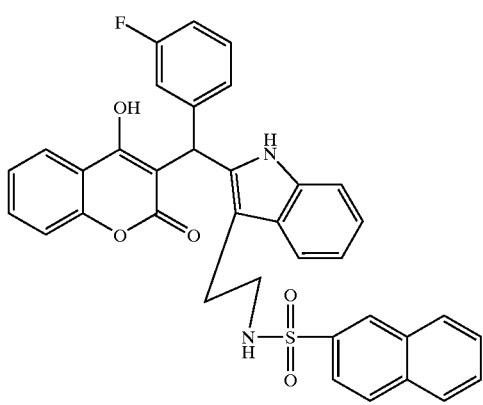
TABLE 2-42-continued
Compound No. 584
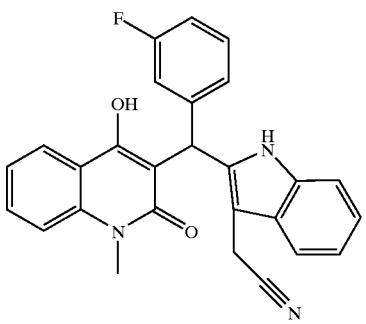
Compound No. 585
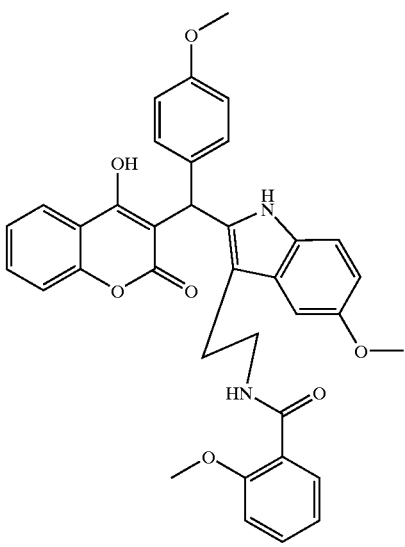
Compound No. 586
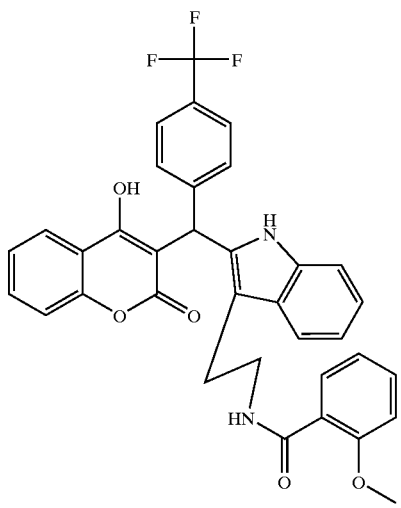

TABLE 2-42-continued
Compound No. 587
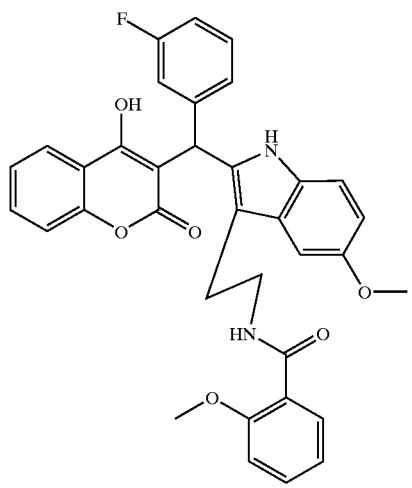
Compound No. 588
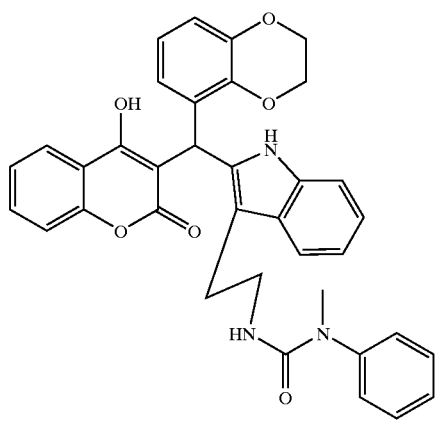
Compound No. 589
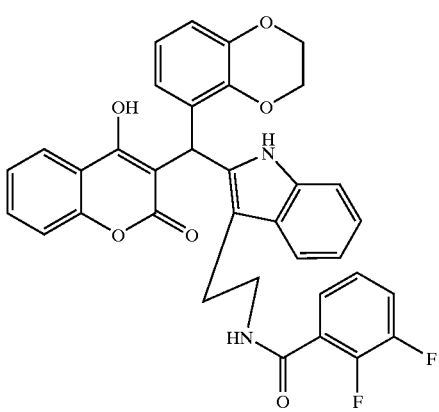
TABLE 2-42-continued
Compound No. 590
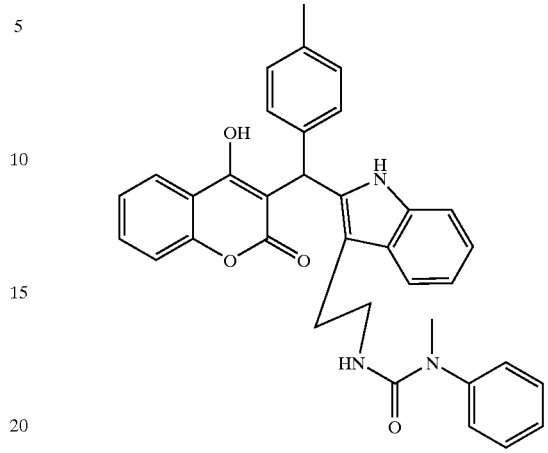
TABLE 2-43
Compound No. 591
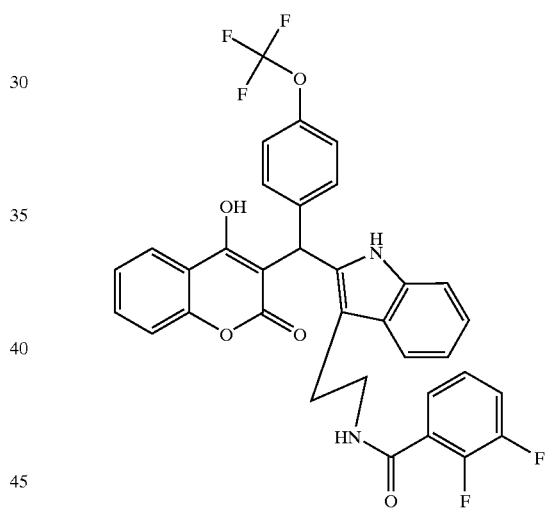
Compound No. 592
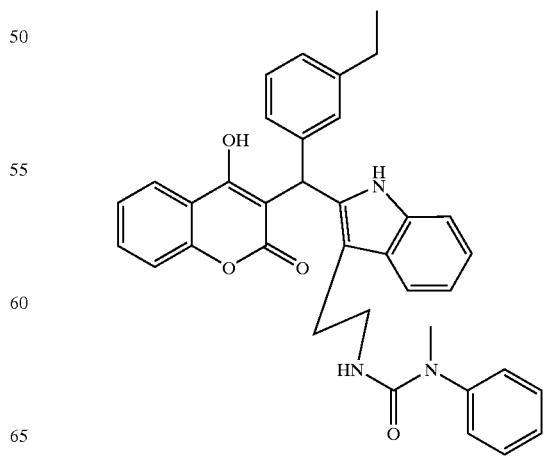

TABLE 2-43-continued
Compound No. 593
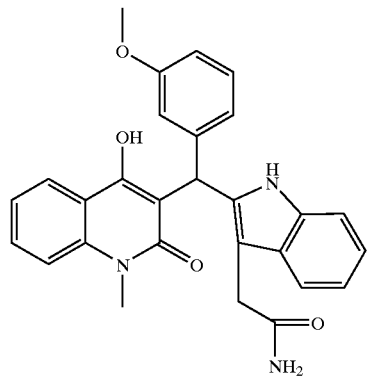
Compound No. 594
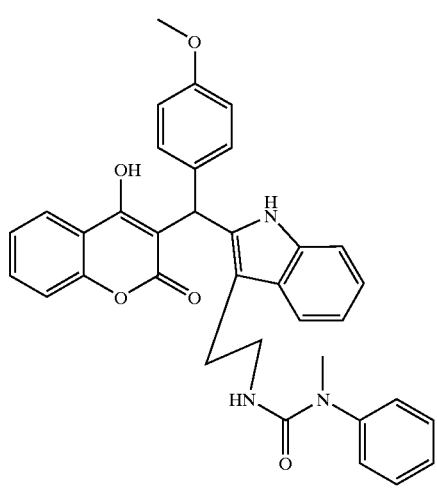
Compound No. 595
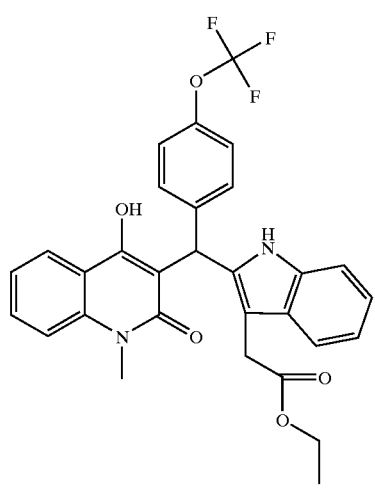
TABLE 2-43-continued
Compound No. 596
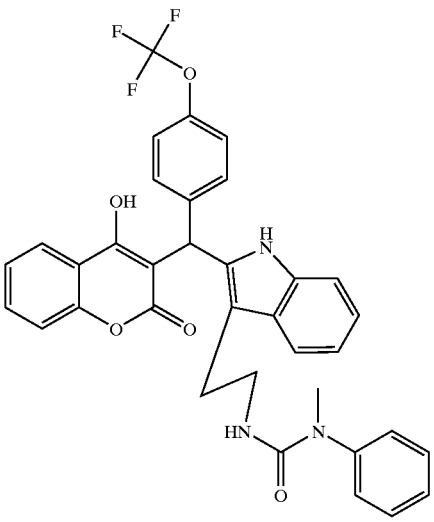
Compound No. 597
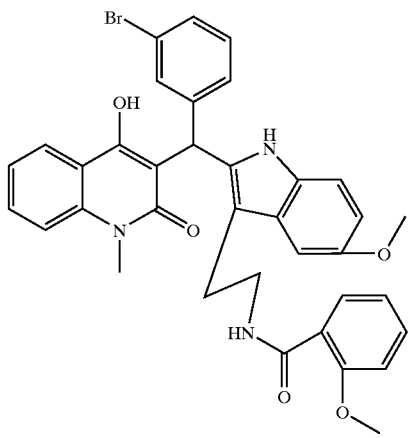
Compound No. 598
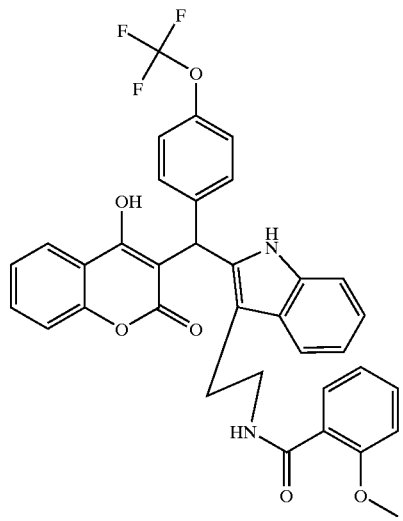

TABLE 2-43-continued
Compound No. 599
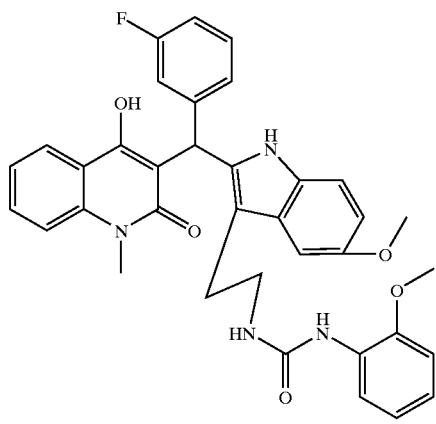
Compound No. 600
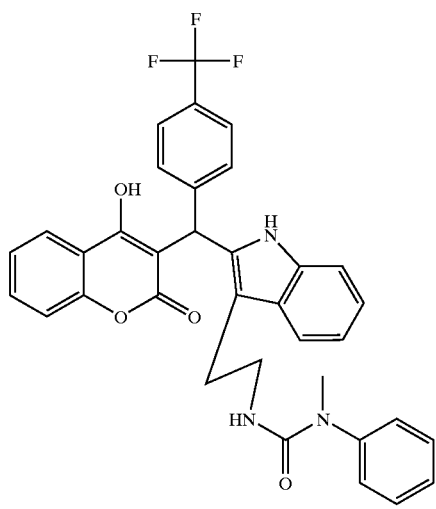
Compound No. 601
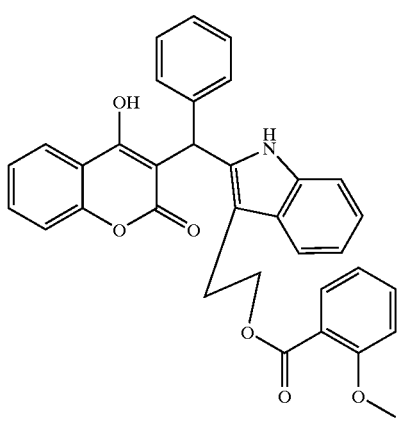
TABLE 2-43-continued
Compound No. 602
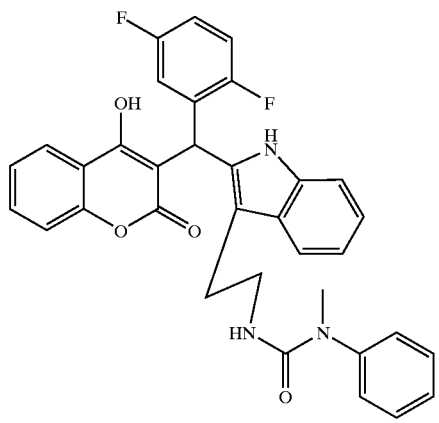
TABLE 2-44
Compound No. 603
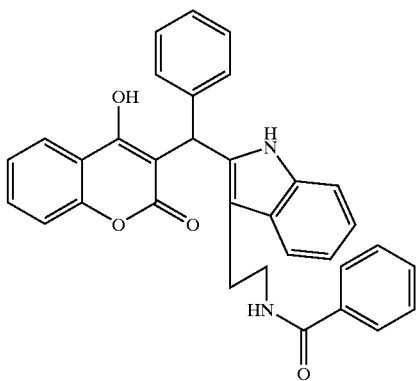
Compound No. 604
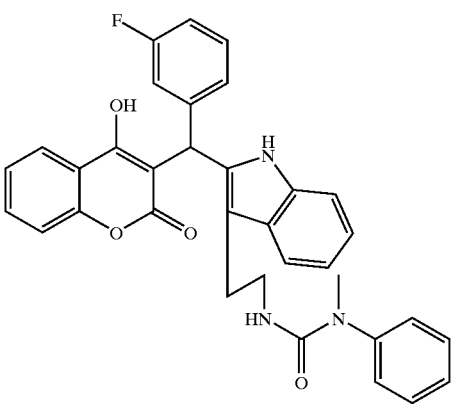

TABLE 2-44-continued
Compound No. 605
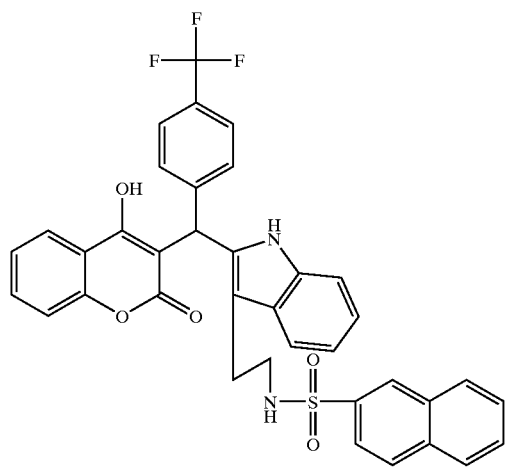
Compound No. 606
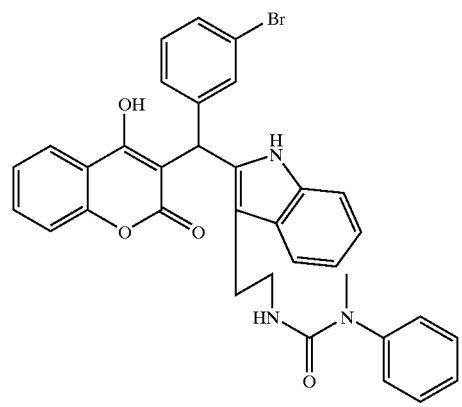
Compound No. 607
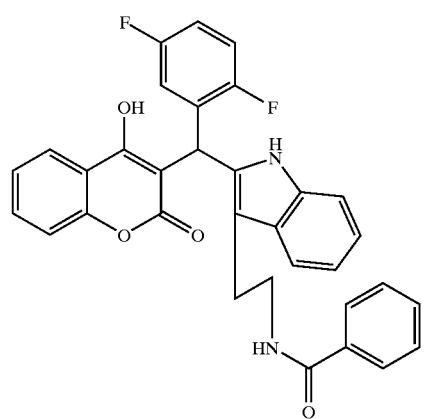
TABLE 2-44-continued
Compound No. 608
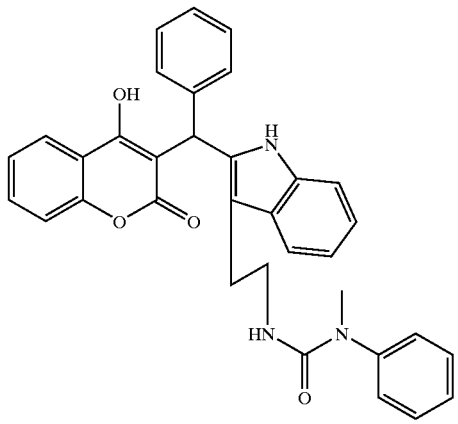
Compound No. 609
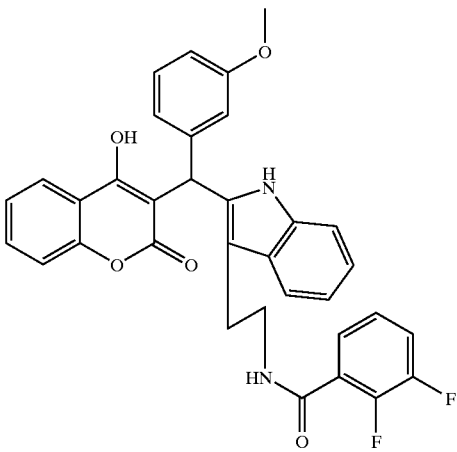
Compound No. 610
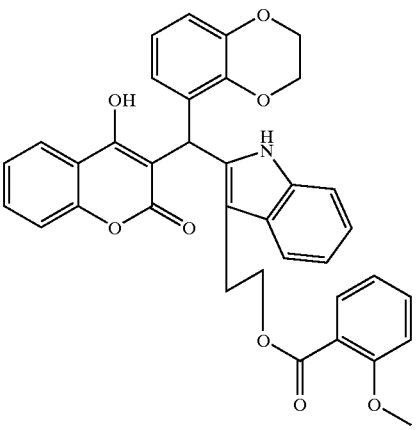

217

TABLE 2-44-continued

Compound No. 611

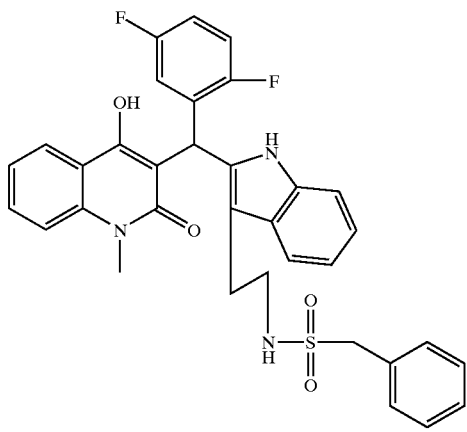

Compound No. 612

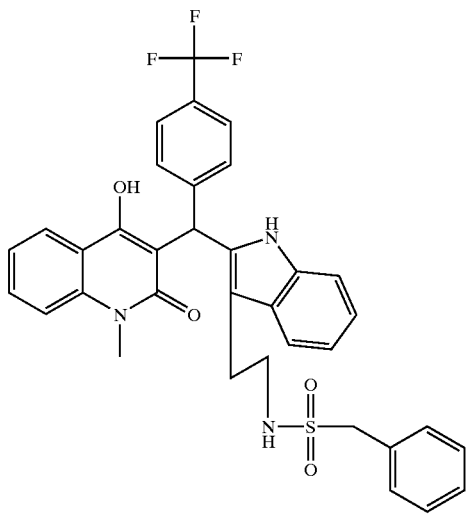

Compound No. 613

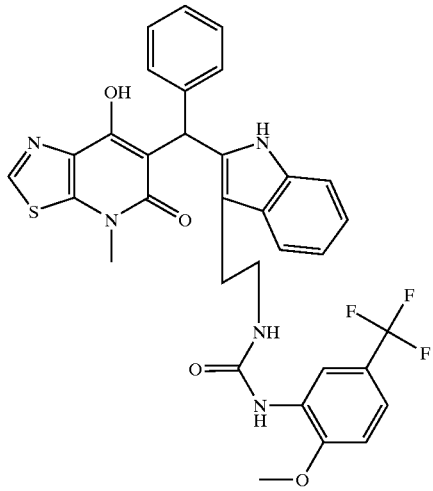

218

Now, there will be given Test Example which demonstrates the chymase inhibitory activity of some exemplary compounds chosen from the indole derivatives of the general formula (I) according to the first aspect of this invention.

TEST EXAMPLE 1

(a) The preparation of the enzyme chymase was carried out as follows. That is, a recombinant pro-type human chymase to be used had been prepared in accordance with the method of Urata et al's report ["J. Biol. Chem.", Vol.266, p.17173 (1991)]. Further, the chymase product as preliminarily purified was activated in accordance with the method of Murakami et al's report ["J. Biol. Chem.", Vol.270, p.2218 (1991)]. The resulting activated chymase product was purified with heparin Sepharose to afford an active-type human chymase.

(b) To 50 µl of Buffer A (comprising 0.5–3.0M NaCl and 50 mM tris-HCl, pH 8.0) containing 1–5 ng of the active-type human chymase as obtained by the above-mentioned methods, was added 2 µl of a solution in dimethylsulfide which contained an indole derivative of this invention as the substance to be tested. Then, to the resultant mixture, there was added 50 µl of Buffer A containing 0.5 mM of succinyl-alanyl-histidyl-prolyl-phenylalanyl-p-nitroanilide (a product of Backem Co.) as the substrate. The resulting reaction mixture was incubated at room temperature for 5 minutes. The chymase inhibitory activity was assessed by measuring the changes in the absorbance of a light at 405 nm of the resulting reaction solution with the passage of time. The chymase inhibitory activity of the indole derivatives tested of this invention was evaluated in term of $IC_{50}$ values (in molar concentration, M).

The indole derivatives of this invention as tested in this Example are the compounds of Compound No. 003, 021, 026, 027, 030, 076 and 078 shown in Table 1 above. The structural formulae of the compounds as tested are shown in the following Table 3.

TABLE 3

Compound No. 003

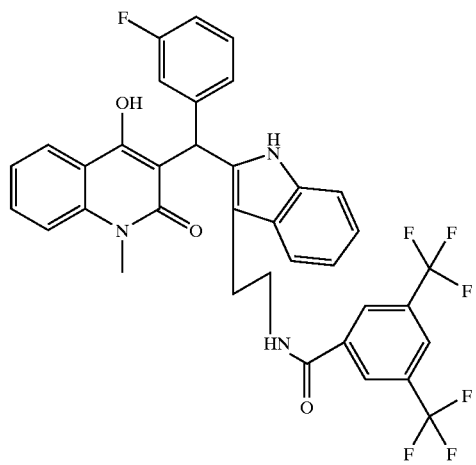

TABLE 3-continued
Compound No. 021
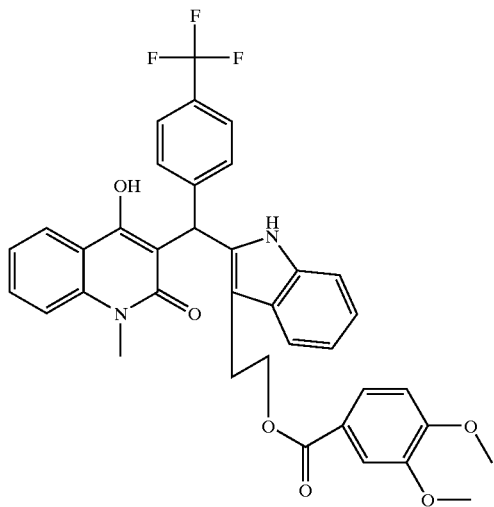
Compound No. 026
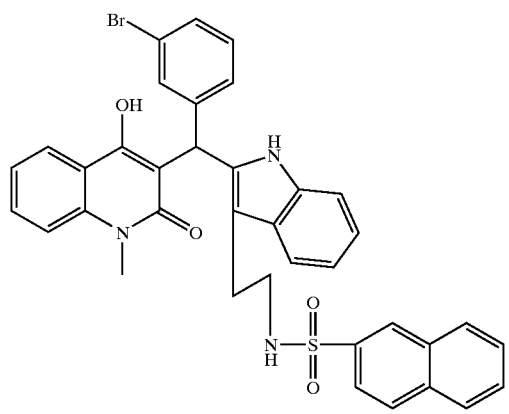
Compound No. 027
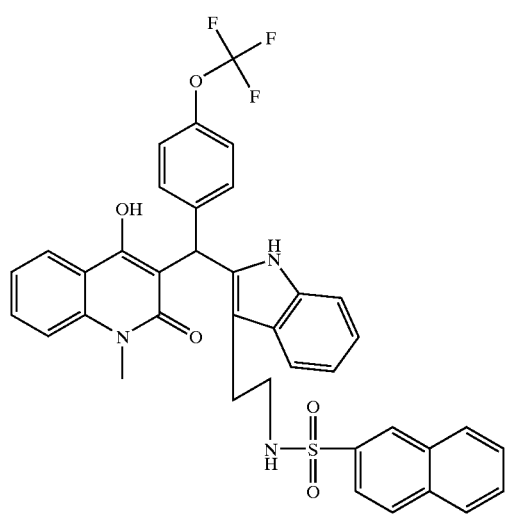
TABLE 3-continued
Compound No. 030
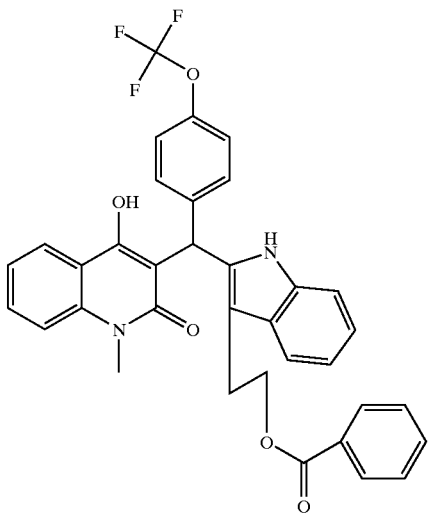
Compound No. 076
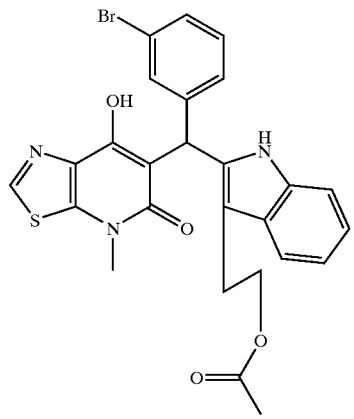
Compound No. 078
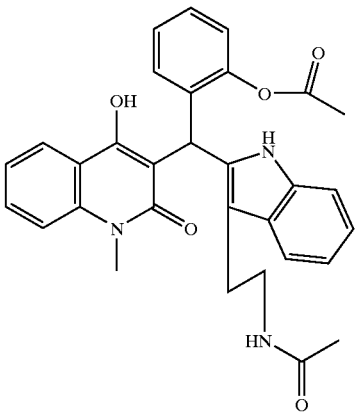

The results of the test so obtained are shown in the following Table 4.

TABLE 4

| Compound Tested (Compound No. in Table 1) | Chymase inhibitory activity $IC_{50}$ (molar concentration) |
| --- | --- |
| 003 | $2.64 \times 10^{-9}$ |
| 021 | $1.40 \times 10^{-9}$ |
| 026 | $4.39 \times 10^{-10}$ |
| 027 | $5.11 \times 10^{-9}$ |
| 030 | $5.87 \times 10^{-10}$ |
| 076 | $8.93 \times 10^{-10}$ |
| 078 | $1.86 \times 10^{-9}$ |

As demonstrated by the Test Example above, the indole derivatives of the general formula (I) according to the first aspect of this invention have a high chymase inhibitory activity and thus are useful as a chymase inhibitor and utilizable for therapeutic or prophylactic treatments of diseases in which a chymase participates.

According to a second aspect of this invention, therefore, there is provided a pharmaceutical composition comprising as an active ingredient at least one of the indole derivative of the general formula (I) or a pharmaceutically acceptable salt or a solvate thereof, in combination with a pharmaceutically acceptable carrier. The pharmaceutical composition according to the second aspect of this invention may be used for a therapeutic or prophylactic treatment of cardiac infarction, cardiomegaly, cardiac insufficiency, myocardosis, arteriosclerosis, hypertension, hemangioendtyrosis, peripheral cardiovascular disorder, renal insufficiency, inflammation, allergy, atopic dermatitis, rheumatism, asthma, or bronchitis.

Further, according to a third aspect of this invention, there is provided a chymase inhibitor characterized in that said inhibitor comprises as an active ingredient at least one of the indole derivative of the general formula (I) or a pharmaceutically acceptable salt or a solvate thereof.

Still further, according to a fourth aspect of this invention, there is provided a medicament to be used for therapeutic or prophylactic treatment of diseases in which an enzyme chymase participates, characterized in that said medicament comprises as an active ingredient at least one of the indole derivative of the general formula (I) or a pharmaceutically acceptable salt or a solvate thereof.

The indole derivative of the general formula (I) according to the first aspect of this invention and a pharmaceutically acceptable salt or a solvate thereof (particularly hydrate), as well as the indole derivative of the general formula (I) and a pharmaceutically acceptable salt or a solvate thereof usable as the active ingredient which are incorporated in the pharmaceutical composition of the second aspect of this invention, may be administered, orally or parenterally, to a patient having a disease to be cured or prevented. In cases where the indole derivative of this invention is parenterally administered, it can be administered by intravenous or intra-arterial injection or by intraperitoneal or intramuscular or other intra-tissular injection or by subcutaneous injection or by intramucosal administration or by application to skin.

The pharmaceutical composition according to the fourth aspect of this invention may be formulated, depending upon the route of its administrations, into an appropriate form for oral administration or into an appropriate form for parenteral administration. Concretely speaking, as an orally administrable preparation, there may be formulated tablets, capsules, pills, powder, granules, fine grains, syrup, emulsion, suspension, solution, aqueous solution and the like. As a parenterally administrable preparation, there may be formulated injection preparations such as those for intravenous, intramuscular or subcutaneous injection, ophthalmic solutions, collunarium, rectal suppository, as well as percutaneous absorbable preparations such as ointment, hard ointment or adhesive tapes, or an implant and so on.

A variety of the preparations above-mentioned may be formulated in a usual manner with incorporating therein excipient, disintegrator, binder, lubricant and/or coloring agent which are conventionally used. As a non-toxic excipient usable, there may be exemplified lactose, glucose, corn starch, sorbitol, crystalline cellulose, etc. As examples of a disintegrator, there may be mentioned starch, sodium alginate, gelatin, calcium carbonate, dextrin, etc. As a binder, there may be exemplified dimethyl cellulose, polyvinyl alcohol, polyvinyl ether, methyl cellulose, ethyl cellulose, gum arabic, hydroxypropyl cellulose, polyvinylpyrrolidone, etc. As typical examples of the lubricant, there may be mentioned talc, magnesium stearate, polyethylene glycol, hydrogenated oil, etc. As a coloring agent, there may be used, for example, Brilliant Blue, erythrosine, Tartrazine, etc.

Liquid preparations such as the solution, suspension, syrup and the like may be prepared in a usual manner with incorporating, in addition to the active ingredient, glycerol esters, alcohols, water, vegetable oils, etc. Capsule preparations may be prepared by filling the granules, powder or solution containing the active ingredient in soft or hard capsules.

In the injection preparations, there may be added, at need, a buffering agent (for example, acetate, citrate, phosphate, etc.), a pH adjuster (for example, sodium hydrogen carbonate, sodium hydroxide, hydrochloric acid, etc.) and may also be added, an antioxidant (for example, ascorbic acid, sodium sulfite, sodium pyrosulfite, etc.) as a stabilizer, or a preservative (for example, benzyl alcohol, chlorobutanol, p-hydroxybenzoic acid methyl ester, phenol, etc.).

In formulating the percutaneous absorbable preparations, the active ingredient may be mixed with oils, fats or petrolatum to form an ointment or may be mixed with an emulsifier to form a cream. In formulating the rectal suppository, the active ingredient may be mixed with a gelatin soft capsule material, followed by shaping the mixture into a suppository.

For the percutaneous preparations, they may be prepared in the form of a preparation made of a liquid or powdery composition containing the active ingredient. In the liquid preparation, there may be used, as the base, for example, water, saline solution, phosphate buffer, acetate buffer etc., and may further be added a surfactant, oxidation inhibitor, stabilizer, preservative, viscosity improver, and the like. In the powdery preparation, there may be used, as the base, for example, a water-absorbent base such as a water-soluble salt of polyacrylic acid, amylose, etc., or a barely water-soluble base such as cellulose, starch, etc. It is preferable to use a water-absorbent base. Further, into the powdery preparation, there may be incorporated, for example, an oxidation inhibitor, preservative, coloring agent, antiseptic agent, and the like. These liquid and powdery preparations for the percutaneous administration may also be applied to the skin, for example, by spray-coating.

For the ophthalmic solution preparations, they may be formulated in the form of an aqueous or non-aqueous eye drop preparation containing the indole derivative as the active ingredient. As a solvent to be used in such aqueous eye drop preparation, there may be used a sterilized purified water, physiological saline, and the like. In case where the sterilized purified water is used as the sole solvent, the eye drop preparation may take the form of an aqueous suspension with addition of a surface active agent, etc., or it may take the form of a solubilized preparations with using a non-ionic surface active agent as a solubilizing agent. In case where the ophthalmic preparation is administered by methods other than by the eye dropping, it may be administered as an eye ointment, coatable liquid preparation, insert preparationor or other.

Into the various preparations as above-mentioned, there may be added, if necessary, a pharmaceutically acceptable carrier, an isotonic agent, preservative, antiseptic agent, buffer, emulsifier, dispersant, stabilizer, or others. Further, in order to attain a sterilized or sterile preparation, it is also possible, during the processes of formulating the various preparations, to add a pharmaceutically acceptable germicide and/or to apply a pharmaceutically acceptable treatment of sterilization (such as filtration, heating, photo-irradiation).

The content of the active compound of this invention to be incorporated in the pharmaceutical composition according to the second aspect of this invention may depend upon the type of the preparations thereof, but it is usually in a range of 0.05–50% by weight, preferably in a range of 0.1–20% by weight, based on the weight of the composition.

The dosage of the indole derivative of this invention may be appropriately decided, depending upon each particular case, by taking into consideration the age, body weight, sex, difference in diseases, extent of symptoms and other parameters. For the oral administrations, the dosage is usually in a range of about 1–1000 mg/day for an adult, preferably 1–100 mg/day for an adult. For the parenteral administrations as made by intravenous, subcutaneous, intramuscular, percutaneous or intraperitoneal injection or in the form of collunarium, eye-drops, inhalants, etc., the dose of the indole derivative is usually 0.1–100 mg/day for an adult, preferably 0.3–50 mg/day for an adult.

Further, in case where the indole derivative, or the salt or solvate thereof (for example, hydrate) according to this invention is used as a prophylactic agent, it may be administered in advance in a usual manner, depending upon the symptoms of a disease to be protected.

As described hereinbefore, the indole derivative of the general formula (I) according to the first aspect of this invention may be synthesized by a multicomponent single step reaction of the three compounds consisting of the compound of the general formula (II), the compound of the general formula (III) and the compound of the general formula (IV) in the presence of a substance capable of acting as an acid.

According to a fifth aspect of this invention, therefore, there is provided a process for the preparation of the indole derivative represented by the following general formula (I)

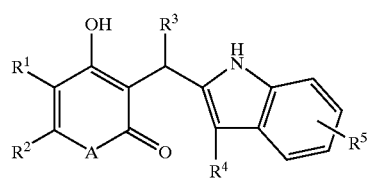

(I)

wherein A is an oxygen atom or a nitrogen atom to which nitrogen atom is bonded a hydrogen atom or such a $(C_1-C_{10})$ alkyl group which is, in turn, optionally substituted by a substituent selected from a halogen atom, a $(C_1-C_{10})$alkyl group, a $(C_1-C_{10})$alkoxy group and an acyl group, particularly an alkanoyl group or an aroyl group;

(i) $R^1$ and $R^2$ each stand for a hydrogen atom or an optionally substituted $(C_1-C_{10})$alkyl group, independently, or (ii) $R^1$ and $R^2$ as taken together form an optionally substituted $(C_5-C_{10})$cycloalkyl group or an optionally substituted $(C_6-C_{20})$aromatic ring, particularly a benzene ring, or (iii) $R^1$ and $R^2$ as taken together form an optionally substituted, saturated or unsaturated heterocycric ring containing one or more nitrogen, oxygen or sulfur atom(s), provided that the possible substituent(s) optionally present on the said optionally substituted alkyl group or cycloalkyl group or aromatic ring or heterocyclic ring may be one or more and is or are selected from a halogen atom, a $(C_1-C_{10})$ alkyl group and a $(C_1-C_{10})$alkoxy group;

$R^3$ stands for a hydrogen atom, an optionally substituted $(C_1-C_{10})$alkyl group, an optionally substituted $(C_5-C_{10})$ cycloalkyl group or an optionally substituted $(C_6-C_{20})$aryl group, particularly a phenyl group, or $R^3$ stands for an optionally substituted, saturated or unsaturated heterocyclic group containing one or more nitrogen, oxygen or sulfur atom(s), provided that the possible substituent(s) optionally present on the said optionally substituted alkyl group or cycloalkyl group or aryl group or heterocyclic group may be one or more and is or are selected from a halogen atom, a $(C_1-C_{10})$alkyl group, a $(C_1-C_{10})$alkoxy group, a halogenated $(C_1-C_{10})$alkyl group and a halogenated $(C_1-C_{10})$ alkoxy group, and that two or more of the said possible substituents as selected may be combined together to form one cyclic group;

$R^4$ stands for an optionally substituted $(C_1-C_{10})$alkyl group where the possible substituent(s) optionally present on the said alkyl group may be one or more and is or are selected from a hydroxyl group, an acyl group, particularly an alkanoyl group or an aroyl group, a $(C_1-C_{10})$ alkyloxycarbonyl group, a cyano group, an amino group, an acylamino group, particularly an alkanoylamino group or an aroylamino group, an acyloxy group, particularly an alkanoyloxy group, an ureido group and a sulfonylamino group, and where the said possible substituent(s) is or are optionally further substituted by one or more of a halogen atom, a $(C_1-C_{10})$alkyl group, a $(C_1-C_{10})$alkoxy group, a $(C_6-C_{20})$aryl group, particularly a phenyl group, an acyl group, particularly an alkanoyl group or an aroyl group, an acylamino group, a halogenated $(C_1-C_{10})$alkyl group and a halogenated $(C_1-C_{10})$alkoxy group;

$R^5$ stands for a hydrogen atom, a halogen atom, a $(C_1-C_{10})$alkyl group or a $(C_1-C_{10})$alkoxy group;

but with such provisos that, in the general formula (I), (i) when A is a methylated nitrogen atom and also $R^1$ and $R^2$ as taken together form a benzene ring in association with the ring-forming carbon atoms to which $R^1$ and $R^2$ are bonded, there is excluded the case where $R^3$ is hydrogen atom, $R^4$ is 2-acetaminoethyl group and $R^5$ is hydrogen atom;

(ii) when A is a methylated nitrogen atom and also $R^1$ and $R^2$ as taken together form a benzene ring in association with the ring-forming carbon atoms to which $R^1$ and $R^2$ are bonded, there is excluded the case where $R^3$ is 4-hydroxyphenyl group, $R^4$ is 2-acetaminoethyl group and $R^5$ is hydrogen atom;

(iii) a methylated nitrogen atom and also $R^1$ and $R^2$ as taken together form a benzene ring in association with the ring-forming carbon atoms to which $R^1$ and $R^2$ are bonded, there is excluded the case where $R^3$ is hydrogen atom, $R^4$ is 2-hydroxyethyl group and $R^5$ is hydrogen atom;

(iv) when A is a methylated nitrogen atom and also $R^1$ and $R^2$ as taken together form a benzene ring in association with the ring-forming carbon atoms to which $R^1$ and $R^2$ are bonded, there is excluded the case where $R^3$ is 4-hydroxyphenyl group, $R^4$ is 2-hydroxyethyl group and $R^5$ is hydrogen atom;

(v) when A is a methylated nitrogen atom and also $R^1$ and $R^2$ as taken together form a benzene ring in association with the ring-forming carbon atoms to which $R^1$ and $R^2$ are bonded, there is excluded the case where $R^3$ is phenyl group, $R^4$ is 2-acetaminoethyl group and $R^5$ is hydrogen atom; and (vi) when A is a methylated nitrogen atom and also $R^1$ and $R^2$ as taken together form a benzene ring in association with the ring-forming carbon atoms to which they are bonded, there is excluded the case where $R^3$ is phenyl group, $R^4$ is 2-hydroxyethyl group and $R^5$ is hydrogen atom; which process comprises a single step reaction of three components consisting of a compound of the following general formula (II)

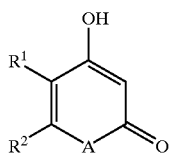

(II)

wherein A, $R^1$ and $R^2$ each have the same meanings as defined for the general formula (I) above, and an aldehyde compound of the general formula (III)

$$R^3-CHO \qquad (III)$$

wherein $R^3$ has the same meaning as defined for the general formula (I) above or a compound of the general formula (III')

$$R^3-CH=N-R^9 \qquad (III')$$

wherein $R^3$ has the same meaning as defined above and $R^9$ is an optionally substituted, straight or branched ($C_1$–$C_{10}$) alkyl group, an optionally substituted, straight or branched ($C_2$–$C_{10}$)alkenyl group, an optionally substituted, straight or branched ($C_2$–$C_{10}$)alkynyl group or an optionally substituted $C_6$ aryl or higher aryl group, and wherein the possible substituent(s) optionally present on the said optionally substituted alkyl group, alkenyl group, alkynyl group or aryl group is or are selected from a halogen atom, an amino group, nitro group, cyano group, an acyl group, particularly an alkanoyl group or an aroyl group, an optionally substituted, straight or branched ($C_1$–$C_{10}$)alkyl group, an optionally substituted ($C_3$–$C_{20}$)cycloalkyl group, an optionally substituted, straight or branched ($C_2$–$C_{10}$)alkenyl group, an optionally substituted, straight or branched ($C_2$–$C_{10}$) alkynyl group, an optionally substituted ($C_6$–$C_{20}$)aryl group, particularly a phenyl group, an acyloxy group, an optionally substituted, straight or branched ($C_1$–$C_{10}$)alkoxy group, an acyl group, particularly an alkanoyl group or aroyl group, an acylamino group, a carbamoyl group, an ureido group, a sulfonylamino group, an optionally substituted, straight or branched ($C_1$–$C_{10}$)alkyloxycarbonyl group, a carbamoyl group and an acyloxy group, as well as an indole compound of the general formula (IV)

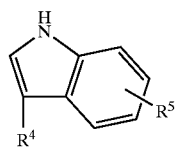

(IV)

wherein $R^4$ and $R^5$ each have the same meanings as defined for the general formula (I), in an organic solvent or in an aqueous solvent in the presence of a substance capable of acting as an acid, provided that, depending on the natures of the groups $R^1$ to $R^5$ of the compound of the formula (I) to be prepared, there are relevantly chosen a compound of the formula (II) bearing the relevantly corresponding $R^1$ and $R^2$, and a compound of the formula (III) or (III') bearing the relevantly corresponding $R^3$, as well as a compound of the formula (IV) bearing the relevantly corresponding $R^4$ and $R^5$, upon carrying out the reaction.

The compound of the general formula (II) which is to be used in the process according to the fifth aspect of this invention is preferably such one that is selected from a class of compound which have chemical structures and Compound Codes respectively shown in the following Table 5. The compounds shown in Table 5 are all already known, except the compound of Code A09.

TABLE 5

| Compound Code | Chemical Structure |
| --- | --- |
| A01 | ![structure] |
| A02 | ![structure] |
| A03 | ![structure] |
| A04 | ![structure] |
| A05 | ![structure] |

TABLE 5-continued

| Compound Code | Chemical Structure |
|---|---|
| A06 | 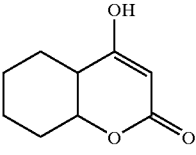 |
| A07 | 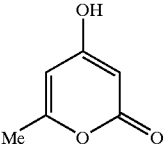 |
| A08 | 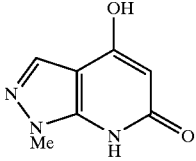 |
| A09 | 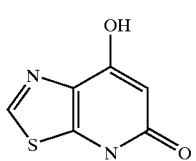 |

The aldehyde compound of the general formula (III) which is to be used in the process according to the fifth aspect of this invention is preferably such one that is selected from a class of aldehydes which have chemical structures and the Compound Codes shown respectively in the following Table 6. All the compounds shown in Table 6 are already known.

TABLE 6

| Compound Code | Chemical Structure |
|---|---|
| B01 | 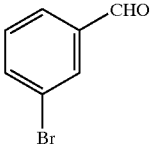 |
| B02 | 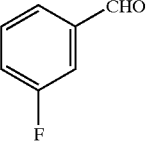 |
| B03 | 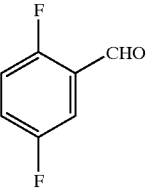 |
| B04 | 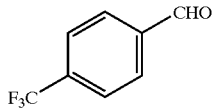 |
| B05 | 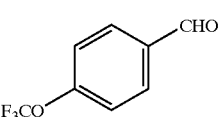 |
| B06 | 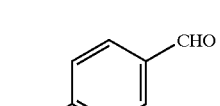 |
| B07 | 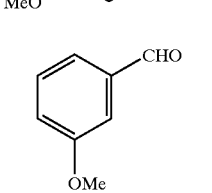 |
| B08 | 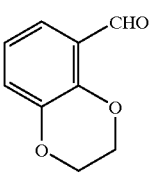 |
| B09 | 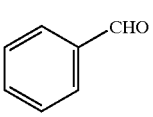 |
| B10 | 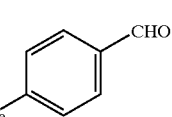 |
| B11 | 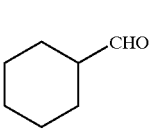 |
| B12 | 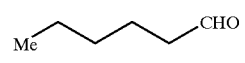 |
| B13 | 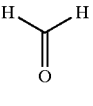 |
| B14 | 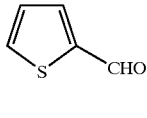 |
| B15 | 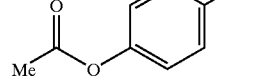 |

TABLE 6-continued

| Compound Code | Chemical Structure |
|---|---|
| B16 | 2-acetoxybenzaldehyde structure (benzene ring with CHO and O-C(=O)-Me) |

The indole compound of the general formula (IV) which is to be used in the process according to the fifth aspect of this invention is preferably such one that is selected from a class of already known indole derivatives which have chemical structures and Compound Codes respectively shown in the following two tables, Table 7a and Table 7b.

TABLE 7a

| Compound Code | Chemical Structure |
|---|---|
| C01 | indole-3-CH$_2$-C(=O)-OEt |
| C02 | indole-3-(CH$_2$)$_2$-O-C(=O)-(2,3-difluorophenyl) |
| C03 | indole-3-(CH$_2$)$_2$-O-C(=O)-(3,4-dimethoxyphenyl) |
| C04 | indole-3-(CH$_2$)$_2$-O-C(=O)-(2-methoxyphenyl) |
| C05 | indole-3-(CH$_2$)$_2$-O-C(=O)-phenyl |
| C06 | indole-3-(CH$_2$)$_2$-O-C(=O)-cyclohexyl |

TABLE 7a-continued

| Compound Code | Chemical Structure |
|---|---|
| C07 | indole-3-(CH$_2$)$_2$-O-C(=O)-(4-biphenyl) |
| C08 | indole-3-(CH$_2$)$_2$-O-C(=O)-(3,5-bis(trifluoromethyl)phenyl) |
| C09 | indole-3-(CH$_2$)$_2$-O-C(=O)-CH$_2$-phenyl |
| C10 | indole-3-(CH$_2$)$_2$-OAc |
| C11 | indole-3-(CH$_2$)$_2$-NH-C(=O)-piperidinyl |
| C12 | indole-3-(CH$_2$)$_2$-NH-C(=O)-N(Me)(phenyl) |
| C13 | indole-3-(CH$_2$)$_2$-NH-C(=O)-NH-(3,5-difluorophenyl) |
| C14 | indole-3-(CH$_2$)$_2$-NH-C(=O)-NH-(2-methoxy-5-trifluoromethylphenyl) |

TABLE 7a-continued

| Compound Code | Chemical Structure |
| --- | --- |
| C15 | 5-methyl-tryptamine morpholine urea |
| C16 | N-(2-(1H-indol-3-yl)ethyl)-2,3-difluorobenzamide |
| C17 | N-(2-(1H-indol-3-yl)ethyl)-2,4-dimethoxybenzamide |
| C18 | N-(2-(1H-indol-3-yl)ethyl)-3,4-dimethoxybenzamide |
| C19 | N-(2-(1H-indol-3-yl)ethyl)benzamide |
| C20 | N-(2-(1H-indol-3-yl)ethyl)-3,3-dimethylbutanamide |

TABLE 7b

| Compound Code | Chemical Structure |
| --- | --- |
| C21 | N-(2-(1H-indol-3-yl)ethyl)-[1,1'-biphenyl]-4-carboxamide |

TABLE 7b-continued

| Compound Code | Chemical Structure |
| --- | --- |
| C22 | N-(2-(1H-indol-3-yl)ethyl)-3,5-bis(trifluoromethyl)benzamide |
| C23 | N-(2-(1H-indol-3-yl)ethyl)-2-methoxybenzamide |
| C24 | N-acetyl tryptamine |
| C25 | N-(2-(5-methoxy-1H-indol-3-yl)ethyl)-2-methoxybenzamide |
| C26 | N-(2-(1H-indol-3-yl)ethyl)naphthalene-2-sulfonamide |
| C27 | N-(4-(N-(2-(1H-indol-3-yl)ethyl)sulfamoyl)phenyl)acetamide |
| C28 | N-(2-(1H-indol-3-yl)ethyl)benzenesulfonamide |
| C29 | N-(2-(1H-indol-3-yl)ethyl)-1-phenylmethanesulfonamide |
| C30 | N-(2-(1H-indol-3-yl)ethyl)butane-1-sulfonamide |

TABLE 7b-continued

| Compound Code | Chemical Structure |
|---|---|
| C31 | 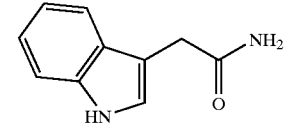 |
| C32 | 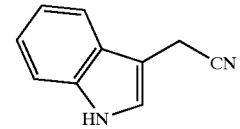 |
| C33 | 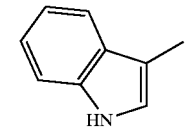 |
| C34 | 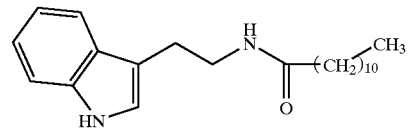 |
| C35 | 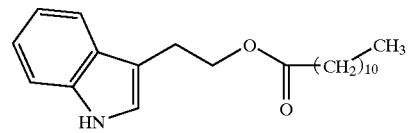 |

The process according to the fifth aspect of this invention does not embrace the process for the preparation of SF2809-I to VI substances having the formulae (A) to (F) which have been excluded from the scope of the indole derivative of the general formula (I).

Therefore, according to the fifth aspect of this invention, when 4-hydroxy-1-methyl-2-quinolinone of the formula (α)

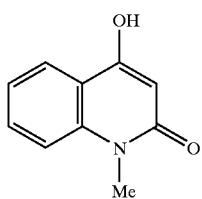

(α)

wherein Me denotes methyl group is used as the compound of the general formula (II) and also formaldehyde or 4-hydroxybenzaldehyde or benzaldehyde is used as the aldehyde compound of the general formula (III), it does not occur that 3-(2-acetaminoethyl)indole of the formula (β-1)

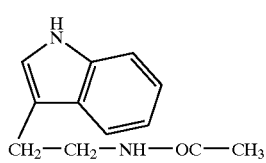

(β-1)

or 3-(2-hydroxyethyl)indole of the formula (β-2)

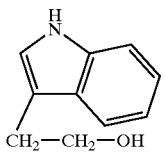

(β-2)

is selected as the indole compound of the formula (IV) to be used.

In the process according to the fifth aspect of this invention, the reaction as effected is shown by the following reaction equation (D).

Reaction Equation (D):

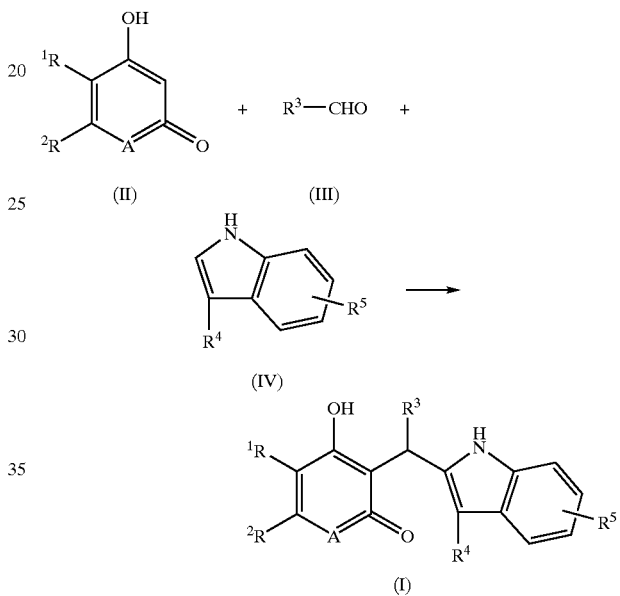

In the reaction equation above, $R^1$ to $R^5$ have the same meanings as defined in the general formula (I).

The process according to the fifth aspect of this invention is to be carried out in an organic solvent or an aqueous solvent in the presence of a substance capable of acting as an acid. The reaction may preferably be carried out in an anhydrous condition, but may also proceed in the presence of an amount of water. The reaction temperature may be in a range of from −78° C. to the boiling point of the solvent used. It is preferred that the reaction to produce the indole derivative of the general formula (I) according to this invention is carried out at a temperature of 60° C. to 100° C. for a reaction time of 1 hour to 48 hours.

Instead of the aldehyde of the general formula (III), there may be used such compound which is represented by the general formula (III')

$$R^3\text{---}CH\text{=}N\text{---}R^9 \qquad (\text{III}')$$

wherein $R^3$ has the same meaning as defined for the general formula (I) and $R^9$ is an optionally substituted, straight or branched $(C_1-C_{10})$alkyl group, an optionally substituted, straight or branched $(C_2-C_{10})$alkenyl group, an optionally substituted, straight or branched $(C_2-C_{10})$alkynyl group or an optionally substituted $C_6$ aryl or higher aryl group, and wherein the possible substituent(s) optionally present on the said optionally substituted alkyl group, alkenyl group, alkynyl group or aryl group is or are selected from a halogen atom, an amino group, nitro group, cyano group, an acyl group, particularly an alkanoyl group or an aroyl group, an optionally substituted, straight or branched ($C_1$–$C_{10}$)alkyl group, an optionally substituted ($C_3$–$C_{20}$)cycloalkyl group, an optionally substituted, straight or branched ($C_2$–$C_{10}$) alkenyl group, an optionally substituted, straight or branched ($C_2$–$C_{10}$)alkynyl group, an optionally substituted ($C_6$–$C_{20}$) aryl group, particularly a phenyl group, an acyloxy group, an optionally substituted, straight or branched ($C_1$–$C_{10}$)alkoxy group, an acyl group, particularly an alkanoyl group or aroyl group, an acylamino group, a carbamoyl group, an ureido group, a sulfonylamino group, an optionally substituted, straight or branched ($C_1$–$C_{10}$)alkyloxycarbonyl group, a carbamoyl group and an acyloxy group.

In this process, it is usual that the reaction as intended is carried out by dissolving simultaneously the compound of formula (II), the compound of formula (III) or (III') and the compound (IV) in an organic solvent, and conducting the reaction in the resulting solution. The molar ratio between the compound of formula (II), the compound of formula (III) or (III') and the compound (IV) to be subjected to the intended reaction may be chosen optionally as desired, but is preferably at a ratio of 2:3:2. As the reaction solvent, there may be used benzene, toluene, xylene, tetrahydrofuran, diethylether, dioxane, acetonitrile, chloroform, methylene chloride, acetic acid, formic acid, N,N-dimethylformamide, dimethylsulfoxide, and the like. Instead of the organic solvent, aqueous solvent such as water may also be used. The substance capable of acting as an acid may be used at an equimolar ratio to the compound of the general formula (III) used.

The substance capable of acting as an acid may be an organic acid, for example, a lower alkanoic acid such as acetic acid; a trihalogenated lower alkanoic acid such as trichloroacetic acid, trifluoroacetic acid, etc., p-toluenesulfonic acid, p-toluenesulfonic acid pyridinum, methanesulfonic acid, etc., or an inorganic acid, such as polyphosphoric acid, hydrochloric acid, sulfuric acid, nitric acid, etc. or Lewis acid, such as aluminium chloride, titanium tetrachloride, etc. There may also be used, as the substance capable of acting as an acid, "Polymer Supported Acid" which is supported on a solid phase such as polymers and can act as an acid upon the reaction intended. The use of acetic acid as the reaction medium is preferred because acetic acid is effective not only as the solvent, but also for the substance capable of acting as an acid.

When it is intended to produce the indole derivatives of the general formula (I) according to this invention by means of the process according to the fifth aspect of this invention, it is feasible that the compound of formula (II), the compound of formula (III) or (III'), and/or the compound of formula (IV)each having occasionally the substituent(s) which are reactive or functional, are protected at such reactive or functional site(s) with suitable protecting substituent(s). If such a protecting group is necessary for the blocking purpose, it is possible to utilize, for example, such protecting groups which are described in a book titled "Protecting Group in Organic Synthesis" written by T. W. Green and published in 1991 by John Wiley and Sons. The protecting group(s) as once introduced may be removed after completion of the reaction intended.

After the completion of the reaction, the compound of formula (I) desired can, in many cases, spontaneously deposit from the resulting reaction solution. The indole derivative as intended may be recovered by filtering the intended substance so deposited out of the reaction solution. If the intended substance is not yielded in such a deposited form, the indole derivative as intended may be recovered by subjecting the reaction solution to a post-treatment conventionally adopted in the usual chemical synthetic reactions, or by applying a usual purification method. For example, the isolation and purification of the intended indole derivative may be effected, for example, by operations for separation of liquids, distillation method, sublimation method, precipitation method, or crystallization method, or by normal phase or reversed phase column chromatography using silica gel or cellulose, preparative TLC method or HPLC method. Otherwise, the intended indole derivative may be recovered by a method of forming a salt thereof which is sparingly soluble in a solvent, followed by filtering off the deposited compound, or by a method of converting the intended indole derivative into its further derivative.

As a method for obtaining an optically active substance of the indole derivative of the general formula (I), there may be utilized a method of chemical synthesis wherein one or more of the starting compounds of formulae (II), (III), (IV) are used in the form of their optically active compounds. Otherwise, there may be utilized a synthesis method with using one or more of the starting compounds having an introduced asymmetric auxiliary group, a synthesis method with using a catalyst capable of introducing asymmetric site, a method of optical resolution comprising a preferential crystallization by utilizing the formation of a sparingly soluble, optically active salt, a method of optical resolution comprising use of a microorganism or enzyme, a method of optical resolution comprising chiral column chromatography, typically by HPLC, or a method of obtaining optically active substance comprising converting the racemic mixture into diastereomers, separating the diastereomers from each other, followed by converting each diastereomer again to an optically active compound as intended. Thus, by selecting appropriate method(s) from these above-mentioned methods or employing some selected methods in combination, the desired optically active substance of the indole derivative of the general formula (I) can be harvested.

The indole derivative which is once prepared by the process according to the fifth aspect of this invention may then be converted into another compound or compounds which can fall within the scope of this invention, by further chemically modifying their substituent(s) ($R^1$ to $R^5$) of said indole derivative.

As described hereinbefore, we have succeeded in producing by chemical synthesis process the SF2809-I to SF2809-VI substances which are described in the specification of PCT Application No. PCT/JP99/06738.

According to a sixth aspect of this invention, therefore, there is provided a process for the preparation of SF2809-I substance represented by the formula (A)

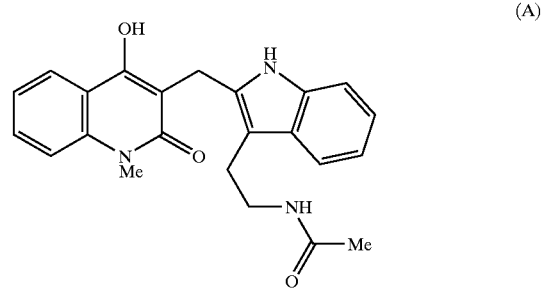

(A)

which comprises a single step reaction of three components consisting of 4-hydroxy-1-methyl-2-quinolinone of the formula (α)

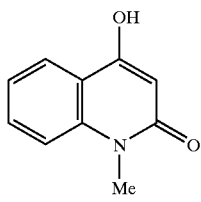

and formaldehyde of the formula (γ-1)

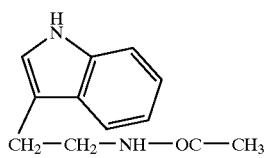

and 3-(2-acetaminoethyl)indole of the formula (β-1)

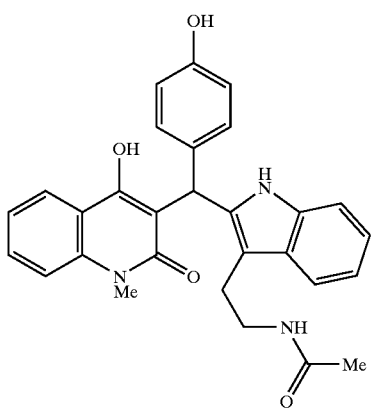

in an organic solvent or an aqueous solvent in the presence of a substance capable of acting as an acid.

According to a seventh aspect of this invention, there is provided a process for the preparation of SF2809-II substance represented by the formula (B)

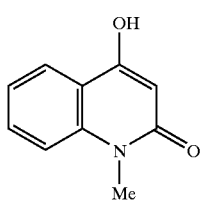

which comprises a single step reaction of three components consisting of 4-hydroxy-1-methyl-2-quinolinone of the formula (α)

(α)

and 4-hydroxybenzaldehyde of the formula (γ-2)

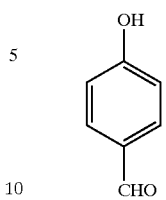

and 3-(2-acetaminoethyl)indole of the formula (β-1)

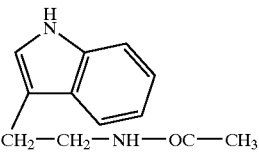

in an organic solvent or an aqueous solvent in the presence of a substance capable of acting as an acid.

According to an eighth aspect of this invention, there is provided a process for the preparation of SF2809-III substance represented by the formula (C)

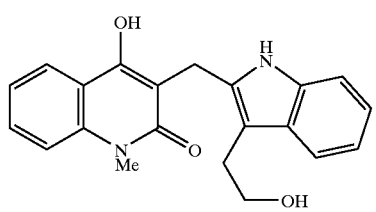

which comprises a single step reaction of three components consisting of 4-hydroxy-1-methyl-2-quinolinone of the formula (α)

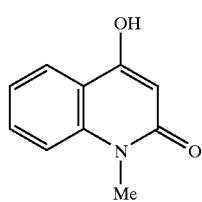

and formaldehyde of the formula (γ-1)

HCHO    (γ-1)

and 3-(2-hydroxyethyl)indole of the formula (β-2)

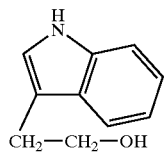

in an organic solvent or an aqueous solvent in the presence of a substance capable of acting as an acid.

According to a ninth aspect of this invention, there is provided a process for the preparation of SF2809-IV substance represented by the formula (D)

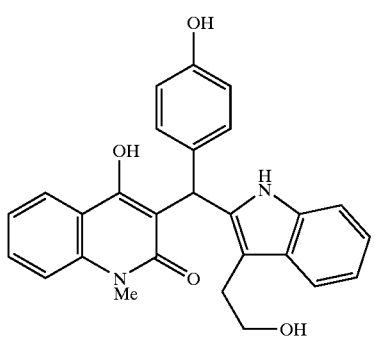
(D)

which comprises a single step reaction of three components consisting of 4-hydroxy-1-methyl-2-quinolinone of the formula (α)

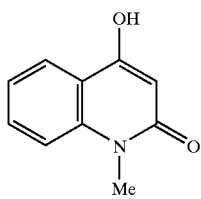
(α)

and 4-hydroxybenzaldehyde of the formula (γ-2)

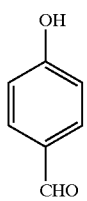
(γ-2)

and 3-(2-hydroxyethyl)indole or the Formula (β-2)

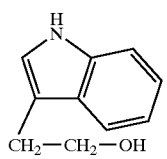
(β-2)

in an organic solvent or an aqueous solvent in the presence of a substance capable of acting as an acid.

According to a tenth aspect of this invention, there is provided a process for the preparation SF2809-V substance represented by the formula (E)

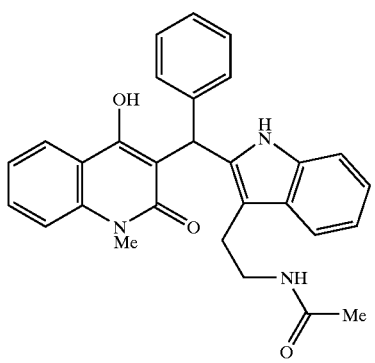
(E)

which comprises a single step reaction of three components consisting of 4-hydroxy-1-methyl-2-quinolinone of the formula (α)

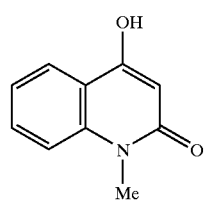
(α)

and benzaldehyde of the formula (γ-3)

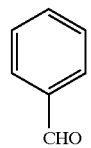
(γ-3)

and 3-(2-acetaminoethyl)indole of the formula (β-1)

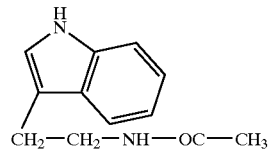
(β-1)

in an organic solvent or an aqueous solvent in the presence of a substance capable of acting as an acid.

Further, according to an eleventh aspect of this invention, there is provided a process for the preparation of SF2809-VI substance represented by the formula (F)

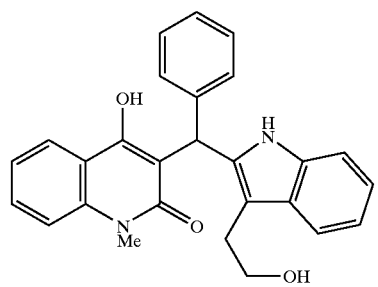
(F)

which comprises a single step reaction of three components consisting of 4-hydroxy-1-methyl-2-quinolinone of the formula (α)

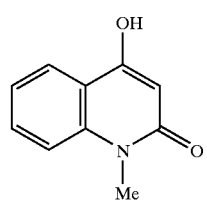
(α)

and benzaldehyde of the formula (γ-3)

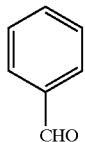

and 3-(2-acetaminoethyl)indole of the formula (β-1)

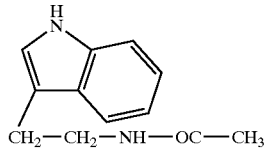

in an organic solvent or an aqueous solvent in the presence of a substance capable of acting as an acid.

Each of the aforesaid processes according to the sixth to the eleventh aspects of this invention may be conducted in the same manner as described fully hereinbefore for the process according to the fifth aspect of this invention.

BEST MODE FOR CARRYING OUT THE INVENTION

The process for the preparation of some typical compounds among the indole derivatives of the general formula (I) according to this invention will now be illustrated with reference to the following Referential Example and Examples. However, this invention is in no way limited to these Examples.

REFERENTIAL EXAMPLE 1

Preparation of 7-hydroxy-4-methyl-4H-thiazolo[5,4-b]-pyridin-5-one of the Formula (IIa)

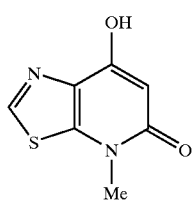

(corresponding to the compound shown in the Table 5 as Compound Code A09)

To a solution of methyl 5-methylaminothiazol-4-carboxylate (5.0 g, 29 mmol) in methylene chloride (50 ml), were added bromo-tris(pyridino)phosphonium hexafluorophosphate (15.6 g, 34.8 mmol), diisopropylethylamine (12.7 ml, 72.6 mmol) and mono-t-butyl malonate (5.4 ml, 34.8 mmol) under ice cooling. The resulting reaction mixture was then stirred for 10 minutes and was further stirred at room temperature overnight. To the reaction mixture, were further added bromo-tris(pyridino)phosphonium hexafluorophosphate (10.5 g), diisopropylethylamine (9.78 ml) and mono-t-butyl malonate (3.4 ml), and the resulting mixture was stirred at room temperature for 6 hours.

The resulting reaction solution was washed with water and then dried over anhydrous magnesium sulfate, and the dried solution was distilled to remove the solvent therefrom.

The residue obtained was purified by a silica gel chromatography (as developed with n-hexane-ethyl acetate=1:1), to afford an oily substance (5.0 g). This oily substance (5.0 g) was dissolved in an ethanol (10 ml) and the ethanolic solution was added to an ethanolic solution of sodium ethoxide which had been prepared from metallic sodium (1.1 g) and anhydrous ethanol (300 ml). The resulting mixture was heated under reflux for 12 hours. After the resulting reaction solution was cooled to room temperature, a volume of concentrated hydrochloric acid (30 ml) was added slowly thereto, and the resulting mixture was heated under reflux for 2 hours. Thus, there was deposited a solid substance from the reaction solution as formed. This deposit was filtered off and the filtrate so obtained was concentrated. The deposit formed in the resulting concentrate was separated by filtration therefrom, and the resulting deposit solid was suspended in water. Then, the aqueous suspension was stirred for 30 minutes. The resulting aqueous suspension was filtered to give a solid substance, and the resultant solid was dried at 50° C. overnight. There was thus obtained the titled compound of the above formula (IIa) (1.3 g, yield 25%) as a novel compound.

$^1$H-NMR (DMSO-d6) δ: 3.50 (3H, s), 5.74 (1H, s), 8.85 (1H, s), 11.44 (1H, s)

Mass spectrum (TSP): m/z 183 (M$^+$+1)

The reaction step effected by the above process may be expressed by the following reaction equation.

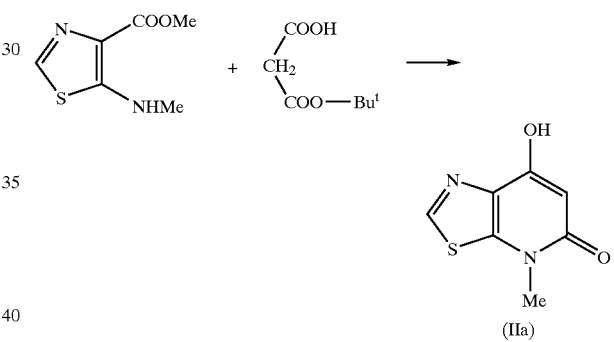

In the above equation, -Bu$^t$ stands for tertiary butyl group.

EXAMPLE 1

Preparation of the Compound of the Following Formula (I-003)

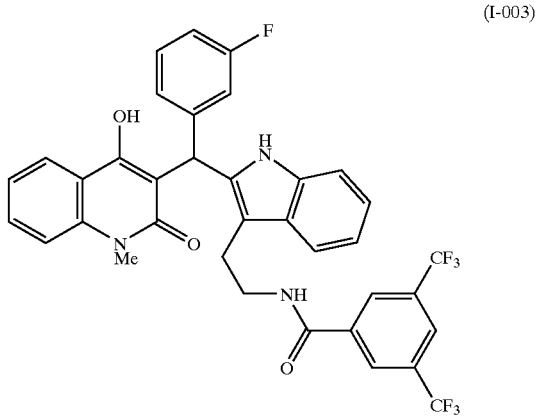

(corresponding to the compound given in Table 1-1 as Compound No.003)

To to acetic acid (3 ml) were added 4-hydroxy-1-methyl-2-quinolinone of the formula (α)

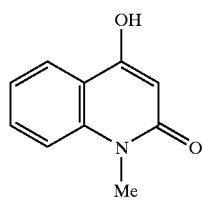
(α)

[the compound given in Table 5 as Compound Code A01 and belonging to compound of the general formula (II)] (35 mg; 200 μmol), 3-fluorobenzaldehyde of the formula (γ-4)

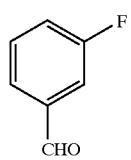
(γ-4)

[the compound given in Table 6 as Compound Code B02 and belonging to compound of the general formula (III)] (32 μl; 300 μmol) and 3-[2-(3,5-di-trifluoromethylbenzoyl)aminoethyl] indole of the following (β-3)

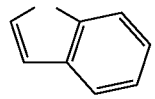

[the compound given in Table 7b as Compound Code C22 and belonging to compound of the general formula (IV)] (80 mg; 200 μmol).

Acetic acid used as above could act not only as the organic solvent for the reaction medium, but also for a substance which is capable of acting as an acid. The resulting solution (namely, the reaction mixture) was stirred at 65° C. for 20 hours. After the completion of the reaction, the resulting reaction solution was concentrated. The resulting residue was purified by a silica gel column chromatography (as gradiently developed with chloroform–methanol=1:0 to 60:1). Thus, there was obtained the titled compound of the above formula (I-003) (86 mg; yield 63%).

Examples 2 to 81

Similarly to the process of Example 1 above, there was produced each of the compounds of Compound Nos. 004 to 014 given in Table 1-1 above; compounds of Compound Nos. 015 to 026 given in Table 1-2; compounds of Compound Nos. 027 to 038 given in Table 1-3; compounds of Compound Nos. 039 to 050 given in Table 1-4; compounds of Compound Nos. 051 to 062 given in Table 1-5; compounds of Compound Nos. 063 to 074 given in Table 1-6; and compounds of Compound Nos. 075 to 083 given in Table 1-7.

In Table 8-1 to Table 8-7 given hereinafter, there are summarily shown Compound Nos. (see Table 1-1 to Table 1-7) of the indole derivatives of the formula (I) as produced in the above Example 1 and in the present Examples 2 to 81, their molecular formulae, their theoretical molecular weights and their found values of the mass spectra data (m/z values).

In Table 8-1 to Table 8-7, there are also listed the three starting compounds which were used as the multicomponents for the single step reaction to produce each of the intended compounds of the general formula (I) and which each are indicated by Compound Nos. in the following Tables 8-1 to 8-7. Thus, in the following tables, the three starting compounds as used, that is, the compound of the general formula (II), compound of the general formula (III) and compound of the general formula (IV) as used in each Example are respectively indicated by Compound Code (A01 to A09) as shown in Table 5, by Compound Code (B01 to B16) as shown in Table 6, and by Compound Code (C01 to C35) as shown in Table 7a to Table 7b given hereinbefore.

TABLE 8-1

| | Compound of formula (I) as produced | | | | Starting compounds as used | | |
|---|---|---|---|---|---|---|---|
| Example No. | Compound No. | Molecular formula | Theoretical Molecular weight | Mass spectrum Found values (m/z) | Compound code for compound of formula (II) | Compound code for compound of formula (III) | Compound code for compound of formula (IV) |
| 1 | 003 | $C_{36}H_{26}F_7N_3O_3$ | 681 | 682(M + H$^+$) | A01 | B02 | C22 |
| 2 | 004 | $C_{36}H_{31}F_3N_4O_4$ | 640 | 641(M + H$^+$) | A01 | B05 | C12 |
| 3 | 005 | $C_{36}H_{34}N_4O_4$ | 586 | 587(M + H$^+$) | A01 | B06 | C12 |
| 4 | 006 | $C_{36}H_{32}BrN_3O_5$ | 666 | 668(M + H$^+$) | A01 | B01 | C18 |
| 5 | 007 | $C_{36}H_{32}FN_3O_5$ | 605 | 606(M + H$^+$) | A01 | B02 | C18 |
| 6 | 008 | $C_{36}H_{33}N_3O_5$ | 587 | 588(M + H$^+$) | A01 | B09 | C18 |
| 7 | 009 | $C_{34}H_{26}BrF_2N_3O_5$ | 642 | 644(M + H$^+$) | A01 | B01 | C16 |
| 8 | 010 | $C_{34}H_{26}F_3N_3O_3$ | 581 | 582(M + H$^+$) | A01 | B02 | C16 |
| 9 | 011 | $C_{40}H_{32}BrN_3O_5$ | 682 | 644(M + H$^+$) | A01 | B01 | C21 |
| 10 | 012 | $C_{33}H_{33}BrN_4O_5$ | 613 | 615(M + H$^+$) | A01 | B01 | C11 |
| 11 | 013 | $C_{33}H_{33}F_2N_4O_5$ | 552 | 553(M + H$^+$) | A01 | B02 | C11 |
| 12 | 014 | $C_{33}H_{32}F_2N_4O_5$ | 570 | 570(M + H$^+$) | A01 | B03 | C11 |

TABLE 8-2

| | Compound of formula (I) as produced | | | | Starting compounds as used | | |
|---|---|---|---|---|---|---|---|
| Example No. | Compound No. | Molecular formula | Theoretical Molecular weight | Mass spectrum Found values (m/z) | Compound code for compound of formula (II) | Compound code for compound of formula (III) | Compound code for compound of formula (IV) |
| 13 | 015 | $C_{34}H_{33}F_3N_4O_3$ | 602 | 603(M + H$^+$) | A01 | B04 | C11 |
| 14 | 016 | $C_{34}H_{27}BrF_2N_4O_3$ | 657 | 659(M + H$^+$) | A01 | B01 | C13 |
| 15 | 017 | $C_{36}H_{25}F_7N_2O_4$ | 682 | 683(M + H$^+$) | A01 | B02 | C08 |
| 16 | 018 | $C_{38}H_{26}F_6N_2O_6$ | 722 | 723(M + H$^+$) | A01 | B08 | C08 |
| 17 | 019 | $C_{36}H_{26}F_6N_2O_4$ | 664 | 665(M + H$^+$) | A01 | B09 | C08 |
| 18 | 020 | $C_{40}H_{32}N_2O_4$ | 604 | 605(M + H$^+$) | A01 | B09 | C07 |
| 19 | 021 | $C_{37}H_{31}F_3N_2O_6$ | 656 | 657(M + H$^+$) | A01 | B04 | C03 |
| 20 | 022 | $C_{34}H_{23}BrF_2N_2O_4$ | 643 | 645(M + H$^+$) | A01 | B01 | C02 |
| 21 | 023 | $C_{34}H_{24}F_4N_2O_4$ | 600 | 601(M + H$^+$) | A01 | B03 | C02 |
| 22 | 024 | $C_{29}H_{25}FN_2O_4$ | 484 | 485(M + H$^+$) | A01 | B02 | C10 |
| 23 | 025 | $C_{35}H_{28}F_3N_3O_3$ | 595 | 596(M + H$^+$) | A01 | B04 | C19 |
| 24 | 026 | $C_{37}H_{30}BrN_3O_4S$ | 692 | 693(M + H$^+$) | A01 | B01 | C26 |

TABLE 8-3

| | Compound of formula (I) as produced | | | | Starting compounds as used | | |
|---|---|---|---|---|---|---|---|
| Example No. | Compound No. | Molecular formula | Theoretical Molecular weight | Mass spectrum Found values (m/z) | Compound code for compound of formula (II) | Compound code for compound of formula (III) | Compound code for compound of formula (IV) |
| 25 | 027 | $C_{38}H_{30}F_3N_3O_5S$ | 697 | 698(M + H$^+$) | A01 | B05 | C26 |
| 26 | 028 | $C_{34}H_{27}BrN_2O_4$ | 607 | 609(M + H$^+$) | A01 | B01 | C05 |
| 27 | 029 | $C_{35}H_{27}F_3N_2O_4$ | 596 | 597(M + H$^+$) | A01 | B04 | C05 |
| 28 | 030 | $C_{35}H_{27}F_3N_2O_5$ | 612 | 613(M + H$^+$) | A01 | B05 | C05 |
| 29 | 031 | $C_{34}H_{33}BrN_2O_4$ | 613 | 615(M + H$^+$) | A01 | B01 | C06 |
| 30 | 032 | $C_{35}H_{33}F_3N_2O_4$ | 602 | 603(M + H$^+$) | A01 | B04 | C06 |
| 31 | 033 | $C_{36}H_{29}BrN_2O_4$ | 621 | 623(M + H$^+$) | A01 | B01 | C09 |
| 32 | 034 | $C_{36}H_{29}F_3N_2O_4$ | 610 | 611(M + H$^+$) | A01 | B04 | C09 |
| 33 | 035 | $C_{36}H_{29}F_3N_2O_5$ | 626 | 627(M + H$^+$) | A01 | B05 | C09 |
| 34 | 036 | $C_{37}H_{12}N_2O_6$ | 600 | 601(M + H$^+$) | A01 | B08 | C09 |
| 35 | 037 | $C_{33}H_{33}BrN_2O_4$ | 601 | 603(M + H$^+$) | A01 | B01 | C20 |
| 36 | 038 | $C_{33}H_{28}BrN_3O_4S$ | 642 | 644(M + H$^+$) | A01 | B01 | C28 |

TABLE 8-4

| | Compound of formula (I) as produced | | | | Starting compounds as used | | |
|---|---|---|---|---|---|---|---|
| Example No. | Compound No. | Molecular formula | Theoretical Molecular weight | Mass spectrum Found values (m/z) | Compound code for compound of formula (II) | Compound code for compound of formula (III) | Compound code for compound of formula (IV) |
| 37 | 039 | $C_{34}H_{30}BrO_4S$ | 656 | 658(M + H$^+$) | A01 | B01 | C29 |
| 38 | 040 | $C_{35}H_{31}BrN_4O_5S$ | 699 | 701(M + H$^+$) | A01 | B01 | C27 |
| 39 | 041 | $C_{33}H_{34}N_4O_4$ | 550 | 551(M + H$^+$) | A01 | B09 | C15 |
| 40 | 042 | $C_{31}H_{32}F_3N_3O_5$ | 655 | 656(M + H$^+$) | A01 | B04 | C25 |
| 41 | 043 | $C_{37}H_{35}N_3O_6$ | 617 | 618(M + H$^+$) | A01 | B07 | C25 |
| 42 | 044 | $C_{29}H_{25}BrN_2O_4$ | 545 | 547(M + H$^+$) | A01 | B01 | C01 |
| 43 | 045 | $C_{27}H_{22}BrN_3O_3$ | 516 | 518(M + H$^+$) | A01 | B01 | C31 |
| 44 | 046 | $C_{27}H_{20}BrN_3O_2$ | 498 | 500(M + H$^+$) | A01 | B01 | C32 |
| 45 | 047 | $C_{36}H_{30}N_2O_5$ | 574 | 547(M + H$^+$) | A05 | B09 | C17 |
| 46 | 048 | $C_{30}H_{27}NO_5$ | 481 | 481(M + H$^+$) | A05 | B10 | C01 |
| 47 | 049 | $C_{31}H_{27}BrN_2O_5$ | 587 | 589(M + H$^+$) | A07 | B01 | C23 |
| 48 | 050 | $C_{26}H_{25}N_3O_3$ | 451 | 425(M + H$^+$) | A04 | B09 | C24 |

TABLE 8-5

| | Compound of formula (I) as produced | | | | Starting compounds as used | | |
|---|---|---|---|---|---|---|---|
| Example No. | Compound No. | Molecular formula | Theoretical Molecular weight | Mass spectrum Found values (m/z) | Compound code for compound of formula (II) | Compound code for compound of formula (III) | Compound code for compound of formula (IV) |
| 49 | 051 | $C_{29}H_{33}N_3O_3$ | 471 | 472(M + H$^+$) | A01 | B11 | C24 |
| 50 | 052 | $C_{30}H_{29}N_3O_3$ | 479 | 479(M + H$^+$) | A01 | B10 | C24 |
| 51 | 053 | $C_{30}H_{25}F_3N_3O_3$ | 533 | 534(M + H$^+$) | A01 | B15 | C24 |

TABLE 8-5-continued

| | Compound of formula (I) as produced | | | | Starting compounds as used | | |
|---|---|---|---|---|---|---|---|
| Example No. | Compound No. | Molecular formula | Theoretical Molecular weight | Mass spectrum Found values (m/z) | Compound code for compound of formula (II) | Compound code for compound of formula (III) | Compound code for compound of formula (IV) |
| 52 | 054 | $C_{27}H_{25}N_3O_3S$ | 471 | 472(M + H$^+$) | A01 | B14 | C24 |
| 53 | 055 | $C_{31}H_{33}N_3O_4S$ | 543 | 544(M + H$^+$) | A01 | B09 | C30 |
| 54 | 056 | $C_{39}H_{46}N_2O_4$ | 606 | 607(M + H$^+$) | A01 | B09 | C35 |
| 55 | 057 | $C_{36}H_{32}N_2O_6$ | 588 | 589(M + H$^+$) | A01 | B06 | C04 |
| 56 | 058 | $C_{26}H_{22}N_2O_2$ | 394 | 395(M + H$^+$) | A01 | B09 | C33 |
| 57 | 059 | $C_{36}H_{31}ClN_2O_6$ | 622 | 623(M + H$^+$) | A02 | B09 | C03 |
| 58 | 060 | $C_{36}H_{30}ClF_3N_4O_4$ | 674 | 675(M + H$^+$) | A02 | B09 | C14 |
| 59 | 061 | $C_{39}H_{47}N_3O_3$ | 743 | 606(M + H$^+$) | A01 | B09 | C34 |
| 60 | 062 | $C_{30}H_{25}ClF_3N_3O_4$ | 583 | 584(M + H$^+$) | A02 | B05 | C24 |

TABLE 8-6

| | Compound of formula (I) as produced | | | | Starting compounds as used | | |
|---|---|---|---|---|---|---|---|
| Example No. | Compound No. | Molecular formula | Theoretical Molecular weight | Mass spectrum Found values (m/z) | Compound code for compound of formula (II) | Compound code for compound of formula (III) | Compound code for compound of formula (IV) |
| 61 | 063 | $C_{33}H_{33}NO_7$ | 579 | 580(M + H$^+$) | A06 | B09 | C03 |
| 62 | 064 | $C_{38}H_{32}F_3N_3O_5$ | 631 | 632(M + H$^+$) | A06 | B09 | C14 |
| 63 | 065 | $C_{28}H_{27}BrN_2O_4$ | 535 | 535(M + H$^+$) | A06 | B01 | C24 |
| 64 | 066 | $C_{36}H_{31}BrN_2O_5S$ | 683 | 683(M + H$^+$) | A06 | B01 | C26 |
| 65 | 067 | $C_{33}H_{29}N_3O_6S$ | 595 | 595(M + H$^+$) | A09 | B09 | C03 |
| 66 | 068 | $C_{33}H_{27}BrF_3N_5O_4S$ | 726 | 728(M + H$^+$) | A09 | B01 | C14 |
| 67 | 069 | $C_{34}H_{27}BrN_4O_4S_2$ | 699 | 701(M + H$^+$) | A09 | B01 | C26 |
| 68 | 070 | $C_{26}H_{33}N_3O_3$ | 459 | 460(M + H$^+$) | A01 | B12 | C24 |
| 69 | 071 | $C_{41}H_{32}F_3N_3O_4$ | 687 | 688(M + H$^+$) | A01 | B05 | C21 |
| 70 | 072 | $C_{34}H_{29}N_5O_4S$ | 603 | 604(M + H$^+$) | A08 | B09 | C26 |
| 71 | 073 | $C_{26}H_{23}BrN_4O_4$ | 535 | 536(M + H$^+$) | A08 | B01 | C10 |
| 72 | 074 | $C_{25}H_{24}BrN_5O_3$ | 534 | 499(M − 2H$_2$O$^+$) | A08 | B01 | C24 |

TABLE 8-7

| | Compound of formula (I) as produced | | | | Starting compounds as used | | |
|---|---|---|---|---|---|---|---|
| Example No. | Compound No. | Molecular formula | Theoretical Molecular weight | Mass spectrum Found values (m/z) | Compound code for compound of formula (II) | Compound code for compound of formula (III) | Compound code for compound of formula (IV) |
| 73 | 075 | $C_{33}H_{30}N_4O_5S$ | 595 | 596(M + H$^+$) | A09 | B09 | C18 |
| 74 | 076 | $C_{26}H_{22}BrN_3O_4S$ | 552 | 554(M + H$^+$) | A09 | B01 | C10 |
| 75 | 077 | $C_{26}H_{23}N_3O_4S$ | 474 | 474(M + H$^+$) | A09 | B09 | C10 |
| 76 | 078 | $C_{31}H_{29}N_3O_5$ | 523 | 524(M + H$^+$) | A01 | B16 | C24 |
| 77 | 079 | $C_{33}H_{28}BrN_3O_6S$ | 674 | 676(M + H$^+$) | A09 | B01 | C24 |
| 78 | 080 | $C_{25}H_{26}N_3O_3$ | 415 | 415(M + H$^+$) | A03 | B09 | C24 |
| 79 | 081 | $C_{27}H_{28}N_4O_3S$ | 472 | 473(M + H$^+$) | A09 | B09 | C24 |
| 80 | 082 | $C_{30}H_{31}N_5O_3S$ | 541 | 542(M + H$^+$) | A09 | B09 | C11 |
| 81 | 083 | $C_{31}H_{26}N_4O_3S$ | 534 | 535(M + H$^+$) | A09 | B09 | C19 |

In Examples 2 to 81, the respective compounds of the formulae (II), (III) and (IV) used as the starting compounds were dissolved together simultaneously in a volume of acetic acid and the intended reaction was effected in the resulting solution in acetic acid. The yields of the resulting product compounds of the general formula (I), namely the compounds of Compound Nos. 004 to 083 were 80% to 10%.

In cases where the product compound of the formula (I) contained a bromine atom or bromine atoms, its mass spectrum pattern as measured showed the observed two ion peaks which were near the ion peak value equal to the theoretical molecular weight of the product compound. These two ion peaks were attributable to the isotopes of the bromine atom of the said product. The numerical figures which are given in Table 8 as the found values of the mass spectra data denote the ion peak of a higher intensity among the two ion peaks.

EXAMPLE 82

This Example illustrates an example of the production of SF2809-I substance of the following formula (A)

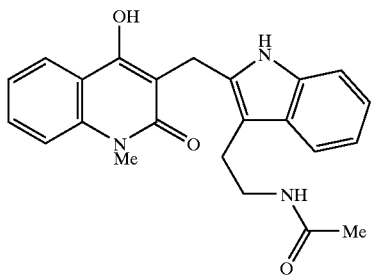

(A)

by the process according to the sixth aspect of this invention.

To acetic acid (10 ml) were added 4-hydroxy-1-methyl-2-quinolinone of the following formula (α)

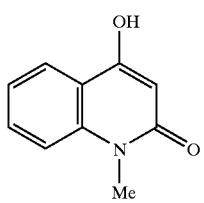

(α)

(the compound of Compound Code A01 given in Table 5) (350 mg; 2.0 mmol) and formaldehyde of the formula (γ-1)

HCHO  (γ-1)

(the compound of Compound Code B13 given in Table 6)(75 mg; 30 mmol) and 3-(2-acetaminoethyl)indole of the formula (β-1)

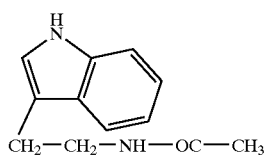

(β-1)

[compound of Compound Code C24 given in Table 7b](404 mg; 2.0 mmol). The resulting solution in acetic acid was heated on an oil bath at 80° C. for 12 hours under stirring.

After the completion of the reaction, the resulting reaction solution was concentrated under reduced pressure. The resulting residue was purified by a silica gel column chromatography (as developed with chloroform-methanol, 1:0 to 60:1, by gradient development). There was obtained the target compound, SF2809-I substance (65 mg; Yield 8.3%). All the physical property data of SF2809-I substance as obtained in this Example were coincident with those of SF2809-I substance which was obtained by the fermentation process as described in the specification of No. PCT Application No. PCT/JP99/06738.

EXAMPLE 83

This Example illustrates an example of the production of SF2809-V substance of the following formula (E)

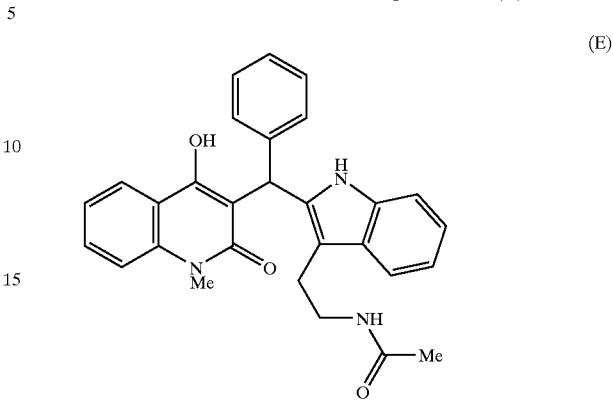

(E)

by the process according to the tenth aspect of this invention.

To acetic acid (500 ml) were added 4-hydroxy-1-methyl-2-quinolinone of the formula (α) above (the compound of Compound Code A01 given in Table 5)(10.5 g; 60 mmol) and benzaldehyde of the formula (γ-3)

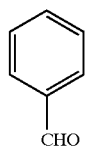

(γ-3)

CHO (the compound of Compound Code B09 given in Table 6)(9.56 g; 90 mmol) and 3-(2-acetaminoethyl)indole of the formula (β-1) above (the compound of Compound Code C24 given in Table 7b)(12.12 g; 60 mmol).

The resulting solution in acetic acid was heated on an oil bath at 70–80° C. for 19 hours under stirring. The resulting reaction solution was allowed to stand to cool down to room temperature. Thereafter, the crystals as deposited from the cooled reaction solution were separated by suction-filtration. Upon washing the so separated crystals twice with methanol, SF2809-V substance was obtained in the form of colorless fine crystalline powder (21.3 g; yield 75%). All the physical property data of SF2809-V substance as obtained in this Example were coincident with those of SF2809-V substance which are shown in the specification of PCT Application No. PCT/JP99/06738.

Industrial Applicability

According to this invention, the indole derivative of the general formula (I) above-mentioned can be obtained by a chemical synthetic process in a facile and efficient way. The indole derivative of the general formula (I) has a high chymase inhibitory activity and hence is useful for a therapeutic or prophylactic treatment for a variety of diseases in which the enzyme chymase participates, for example, diseases of circulatory system such as hypertension and cardiac insufficiency, as well as allergosis such as asthma, rheumatism and atopic dermatitis.

What is claimed is:

1. An indole derivative represented by the following formula (I)

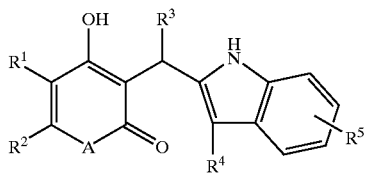

or a pharmaceutically acceptable salt of or a solvate thereof, wherein:

A is an oxygen atom or a nitrogen atom which is bonded to a hydrogen atom or to a $(C_1-C_{10})$alkyl group which is, in turn, optionally substituted by a substituent selected from the group consisting of a halogen atom, a $(C_1-C_{10})$alkyl group, a $(C_1-C_{10})$alkoxy group and an acyl group;

(i) $R^1$ and $R^2$ each stand for a hydrogen atom or an optionally substituted $(C_1-C_{10})$alkyl group, independently, or (ii) $R^1$ and $R^2$ as taken together form an optionally substituted $(C_5-C_{10})$cycloalkyl group or an optionally substituted $(C_6-C_{20})$aromatic ring, or (iii) $R^1$ and $R^2$ as taken together form an optionally substituted, saturated or unsaturated heterocycric ring containing one or more nitrogen, oxygen or sulfur atom(s), wherein substituent(s) optionally present on the optionally substituted alkyl group or cycloalkyl group or aromatic ring or heterocyclic ring may be one or more and is or are selected from the group consisting of a halogen atom, a $(C_1-C_{10})$alkyl group and a $(C_1-C_{10})$alkoxy group;

$R^3$ stands for a hydrogen atom, an optionally substituted $(C_1-C_{10})$alkyl group, an optionally substituted $(C_5-C_{10})$cycloalkyl group or an optionally substituted $(C_6-C_{20})$aryl group, or $R^3$ stands for an optionally substituted, saturated or unsaturated heterocyclic group containing one or more nitrogen, oxygen or sulfur atom(s), wherein the substituent(s) optionally present on the optionally substituted alkyl group or cycloalkyl group or aryl group or heterocyclic group may be one or more and is or are selected from the group consisting of a halogen atom, a $(C_1-C_{10})$alkyl group, a $(C_1-C_{10})$alkoxy group, a halogenated $(C_1-C_{10})$alkyl group and a halogenated $(C_1-C_{10})$alkoxy group and wherein two or more of the substituents as selected may be combined together to form one cyclic group;

$R_4$ stands for an optionally substituted $(C_1-C_{10})$alkyl group wherein the substituent(s) optionally present on said alkyl group may be one or more and is or are selected from the group consisting of a hydroxyl group, an acyl group, a $(C_1-C_{10})$alkyloxy-carbonyl group, a cyano group, an amino group, an acylamino group, an acyloxy group, an ureido group and a sulfonylamino group, and wherein the substituent(s) is or are optionally further substituted by one or more of a halogen atom, a $(C_1-C_{10})$alkyl group, a $(C_1-C_{10})$alkoxy group, a $(C_6-C_{20})$aryl group, an acyl group, an acylamino group, a halogenated $(C_1-C_{10})$alkyl group and a halogenated $(C_1-C_{10})$alkoxy group;

$R^5$ stands for a hydrogen atom, a halogen atom, a $(C_1-C_{10})$alkyl group or a $(C_1-C_{10})$alkoxy group;

but with such provisos that, in the formula (1):

(i) when A is a methylated nitrogen atom and $R^1$ and $R^2$ as taken together form a benzene ring in association with the ring-forming carbon atoms to which $R^1$ and $R^2$ are bonded, there is excluded the case where $R^3$ is hydrogen atom, $R_4$ is 2-acetaminoethyl group and $R^5$ is hydrogen atom;

(ii) when A is a methylated nitrogen atom and $R^1$ and $R^2$ as taken together form a benzene ring in association with the ring-forming carbon atoms to which $R^1$ and $R^2$ are bonded, there is excluded the case where $R^3$ is 4-hydroxyphenyl group, $R_4$ is 2-acetaminoethyl group and $R^5$ is hydrogen atom;

(iii) when A is a methylated nitrogen atom and $R^1$ and $R^2$ as taken together form a benzene ring in association with the ring-forming carbon atoms to which $R^1$ and $R^2$ are bonded, there is excluded the case where $R^3$ is hydrogen atom, $R_4$ is 2-hydroxyethyl group and $R^5$ is hydrogen atom;

(iv) when A is a methylated nitrogen atom and $R^1$ and $R^2$ as taken together form a benzene ring in association with the ring-forming carbon atoms to which $R^1$ and $R^2$ are bonded, there is excluded the case where $R^3$ is 4-hydroxyphenyl group, $R_4$ is 2-hydroxyethyl group and $R^5$ is hydrogen atom;

(v) when A is a methylated nitrogen atom and $R^1$ and $R^2$ as taken together form a benzene ring in association with the ring-forming carbon atoms to which $R^1$ and $R^2$ are bonded, there is excluded the case where $R^3$ is phenyl group, $R_4$ is 2-acetaminoethyl group and $R^5$ is hydrogen atom; and (vi) when A is a methylated nitrogen atom and also $R^1$ and $R^2$ as taken together form a benzene ring in association with the ring-forming carbon atoms to which $R^1$ and $R^2$ are bonded, there is excluded the case where $R^3$ is phenyl group, $R_4$ is 2-hydroxyethyl group and $R^5$ is hydrogen atom.

2. The indole derivative or a pharmaceutically acceptable salt or solvate thereof as claimed in claim 1 which is a compound represented by the formula (Ia)

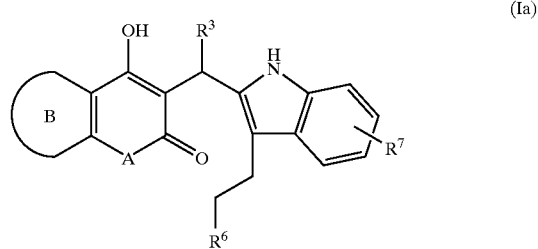

wherein:

A has the same meaning as defined in claim 1;

B stands for a cyclic group, which cyclic group B either stands for an optionally substituted $(C_6-C_{20})$aromatic ring, or the cyclic group B stands for an optionally substituted, saturated or unsaturated heterocyclic ring containing one or more nitrogen, oxygen or sulfur atom(s), wherein the substituent(s) optionally present on the optionally substituted aromatic ring or heterocyclic ring is or are selected from the group consisting of a halogen atom, a $(C_1–C_{10})$alkyl group, a $(C_1–C_{10})$ alkoxy group, a halogenated $(C_1–C_{10})$alkyl group and a halogenated $(C_1–C_{10})$alkoxy group and the substituent(s) may be either single or plural ones;

$R^3$ has the same meaning as defined in claim 1;

$R_6$ stands for a hydroxyl group, an optionally substituted acyl group, an optionally substituted $(C_1–C_{10})$ alkyloxy-carbonyl group, a cyano group, an optionally substituted amino group, an optionally substituted acyloxy group, an optionally substituted ureido group or an optionally substituted sulfonylamino group, wherein the substituent(s) optionally present on the optionally substituted groups is or are selected from the group consisting of a halogen atom, a $(C_1–C_{10})$alkyl group, a $(C_1–C_{10})$alkoxy group, a $(C_6–C_{20})$aryl group, an acyl group, an acylamino group, a halogenated $(C_1–C_{10})$ alkyl group, a halogenated $(C_1–C_{10})$alkoxy group and a halogenated acyl group;

$R^7$ stands for a hydrogen atom, a halogen atom, a $(C_1–C_6)$ alkyl group or a $(C_1–C_6)$alkoxy group;

but with such provisos that, in the formula (Ia), (i) when A is a methylated nitrogen atom and B is a benzene ring, there is excluded the case where $R^3$ is hydrogen atom, $R_6$ is acetamino group and $R^7$ is hydrogen atom;

(ii) when A is a methylated nitrogen atom and B is a benzene ring, there is excluded the case where $R^3$ is 4-hydroxyphenyl group, $R_6$ is acetamino group and $R^7$ is hydrogen atom;

(iii) when A is a methylated nitrogen atom and B is a benzene ring, there is excluded the case where $R^3$ is hydrogen atom, $R_6$ is hydroxyl group and $R^7$ is hydrogen atom;

(iv) when A is a methylated nitrogen atom and B is a benzene ring, there is excluded the case where $R^3$ is 4-hydroxyiphenyl group, $R_6$ is hydroxyl group and $R^7$ is hydrogen atom;

(v) when A is a methylated nitrogen atom and B is a benzene ring, there is excluded the case where $R^3$ is phenyl group, $R_6$ is acetamino group and $R^7$ is hydrogen atom; and (vi) when A is a methylated nitrogen atom and B is a benzene ring, there is excluded the case where $R^3$ is phenyl group, $R_6$ is hydroxyl group and $R^7$ is hydrogen atom.

3. The indole derivative or a pharmaceutically acceptable salt or a solvate thereof as claimed in claim 1, which is a compound represented by the formula (Ib)

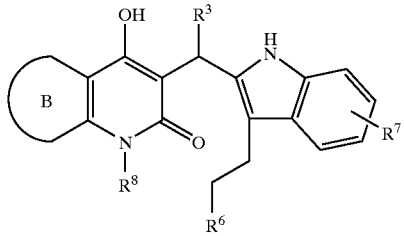

(Ib)

wherein:

B stands for a cyclic group, which cyclic group B either stands for an optionally substituted $(C_6–C_{20})$aromatic ring, or the cyclic group B stands for an optionally substituted, saturated or unsaturated heterocyclic ring containing one or more nitrogen, oxygen or sulfur atom(s), wherein the substituent(s) optionally present on the optionally substituted aromatic ring or heterocyclic ring is or are selected from the group consisting of a halogen atom, a $(C_1–C_{10})$alkyl group, a $(C_1–C_{10})$ alkoxy group, a halogenated $(C_1–C_{10})$alkyl group and a halogenated $(C_1–C_{10})$alkoxy group and the substituent(s) may be either single or plural ones;

$R^3$ has the same meaning as defined in claim 1;

$R^6$ stands for a hydroxyl group, an optionally substituted acyl group, an optionally substituted $(C_1–C_{10})$ alkyloxy-carbonyl group, a cyano group, an optionally substituted amino group, an optionally substituted acyloxy group, an optionally substituted ureido group or an optionally substituted sulfonylamino group, wherein the substituent(s) optionally present on the optionally substituted groups is or are selected from the group consisting of a halogen atom, a $(C_1–C_{10})$alkyl group, a $(C_1–C_{10})$alkoxy group, a $(C_6–C_{20})$aryl group, an acyl group, an acylamino group, a halogenated $(C_1–C_{10})$ alkyl group, a halogenated $(C_1–C_{10})$alkoxy group and a halogenated acyl group;

$R^7$ stands for a hydrogen atom, a halogen atom, a $(C_1–C_6)$ alkyl group or a $(C_1–C_6)$alkoxy group;

$R^8$ stands for a hydrogen atom or a straight or branched $(C_1–C_{10})$alkyl group;

but with such provisos that in the formula (1b):

(i) when B is a benzene ring and $R^8$ is methyl group, there is excluded the case where $R^3$ is hydrogen atom, $R^6$ is acetamino group and $R^7$ is hydrogen atom;

(ii) when B is a benzene ring and $R^8$ is methyl group, there is excluded the case where $R^3$ is 4-hydroxyphenyl group, $R^6$ is acetamino group and $R^7$ is hydrogen atom;

(iii) when B is a benzene ring and $R^8$ is methyl group, there is excluded the case where $R^3$ is hydrogen atom, $R^6$ is hydroxyl group and $R^7$ is hydrogen atom;

(iv) when B is a benzene ring and $R^8$ is methyl group, there is excluded the case where $R^3$ is 4-hydroxyphenyl group, $R^6$ is hydroxyl group and $R^7$ is hydrogen atom;

(v) when B is a benzene ring and $R^8$ is methyl group, there is excluded the case where $R^3$ is phenyl group, $R^6$ is acetamido group and $R^7$ is hydrogen atom; and (vi) when B is a benzene ring and $R^8$ is methyl group, there is excluded the case where $R^3$ is phenyl group, $R^6$ is hydroxyl group and $R^7$ is hydrogen atom.

4. The compound as claimed in claim 1, wherein the compound is one of the following formulas:
Compound No. 005
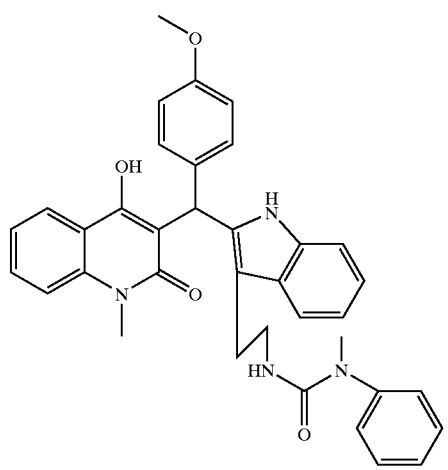
Compound No. 006
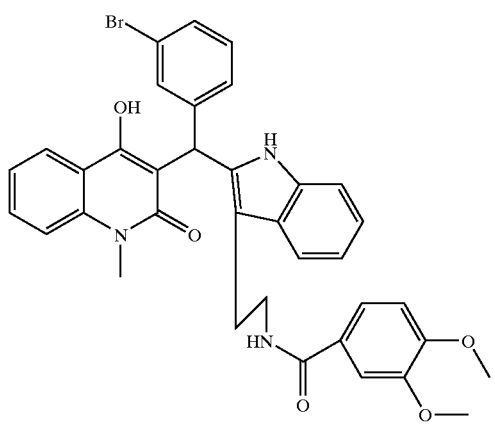
Compound No. 007
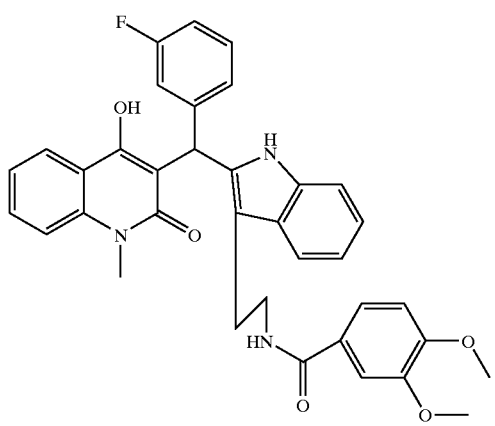
Compound No. 008
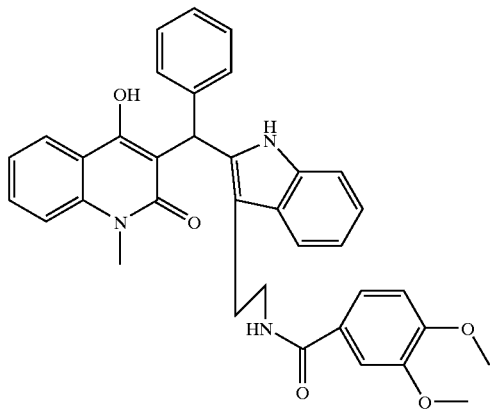
Compound No. 009
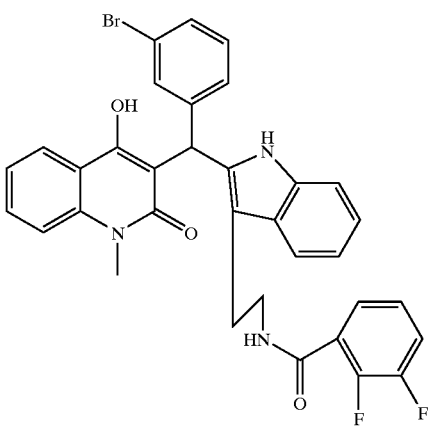
Compound No. 010
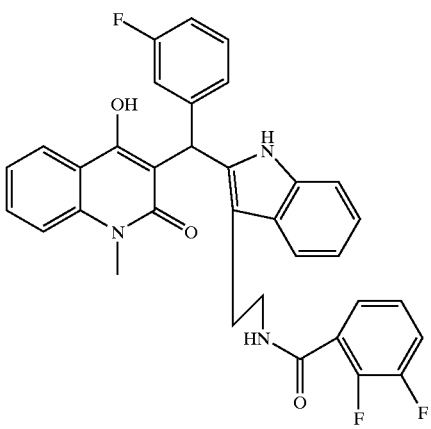

Compound No. 011
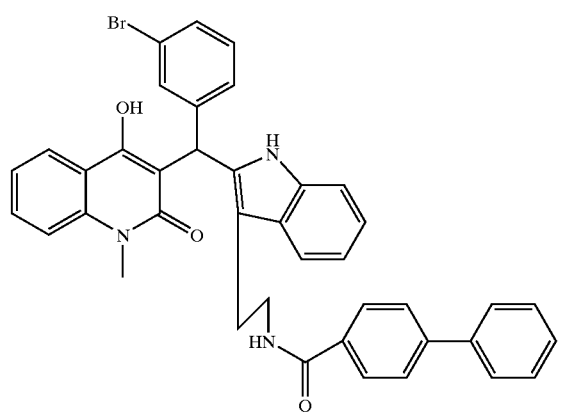
Compound No. 012
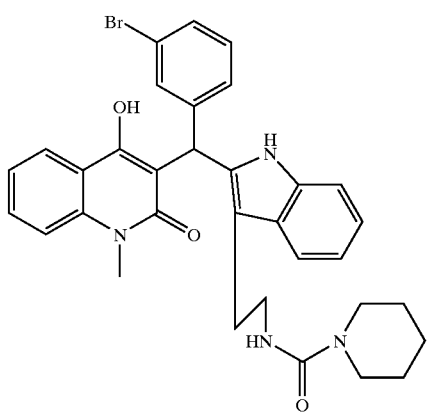
Compound No. 013
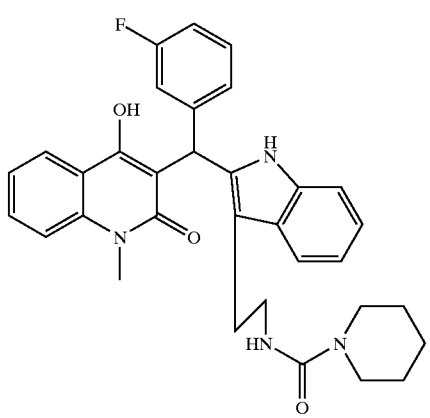
Compound No. 014
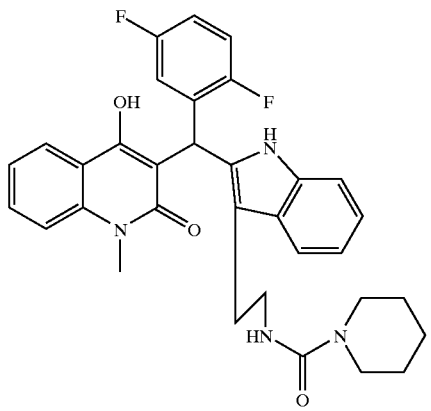
Compound No. 015
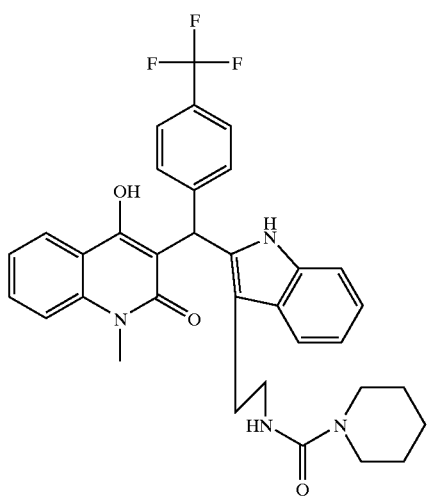
Compound No. 016
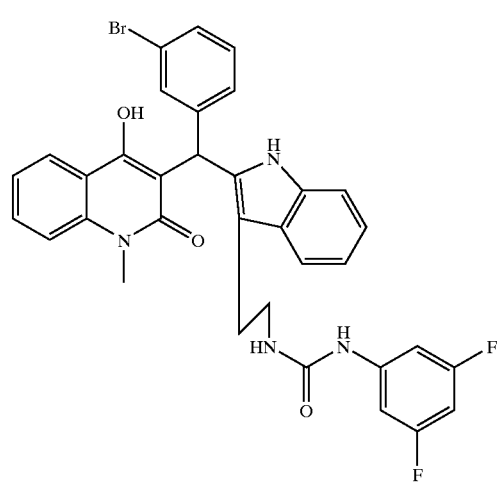

-continued
Compound No. 017
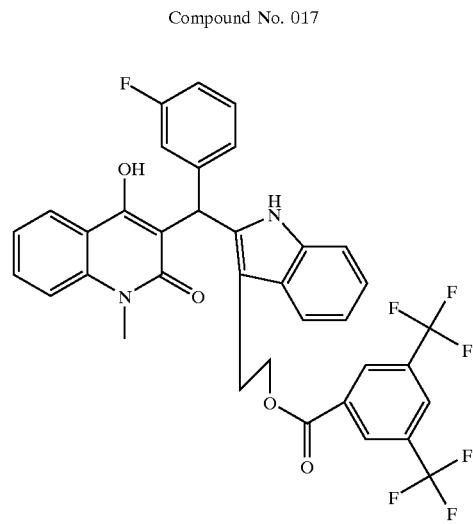
Compound No. 018
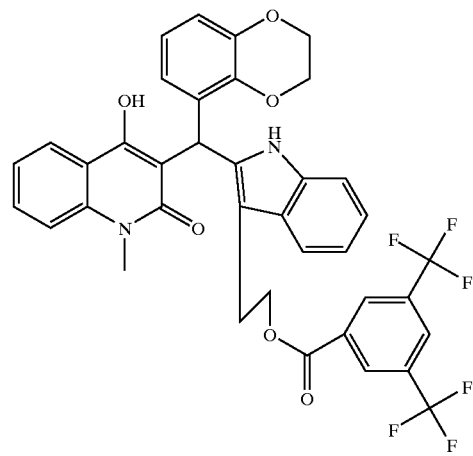
Compound No. 019
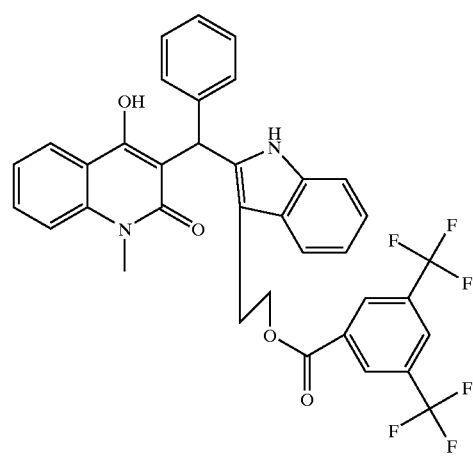
-continued
Compound No. 020
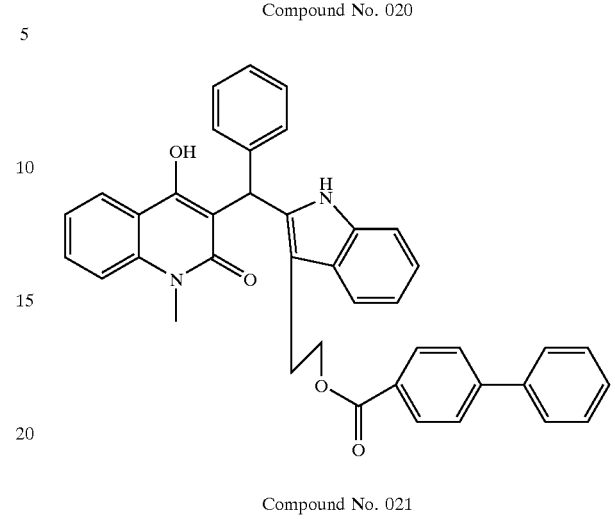
Compound No. 021
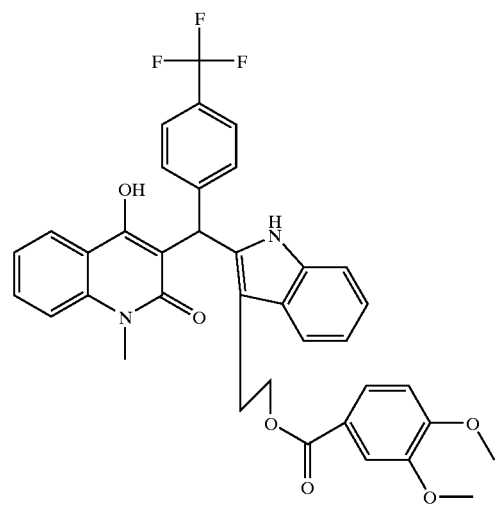
Compound No. 022
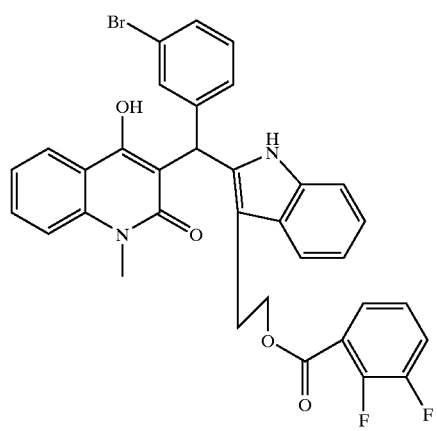

-continued
Compound No. 023
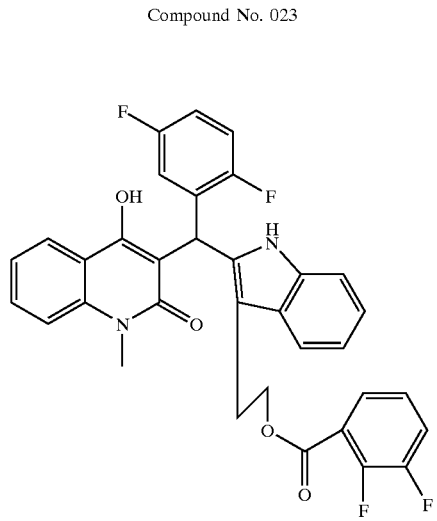
Compound No. 024
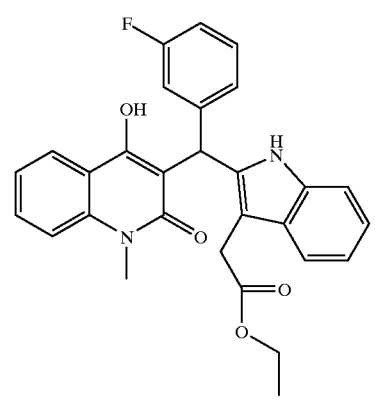
Compound No. 025
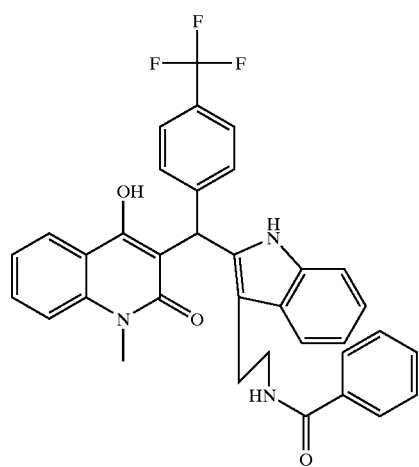
-continued
Compound No. 026
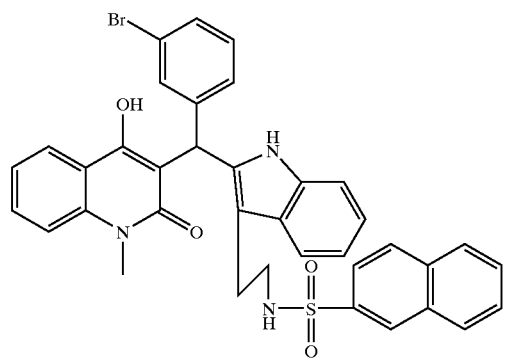
Compound No. 027
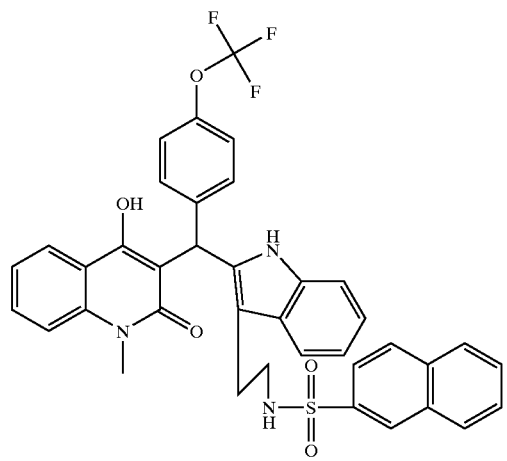
Compound No. 028
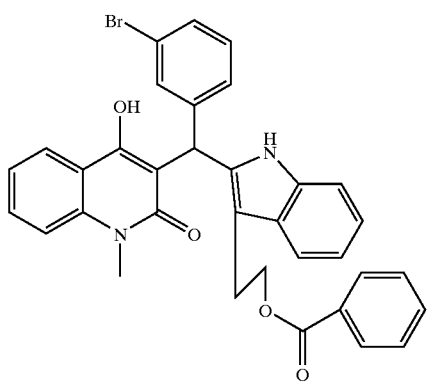

-continued
Compound No. 029
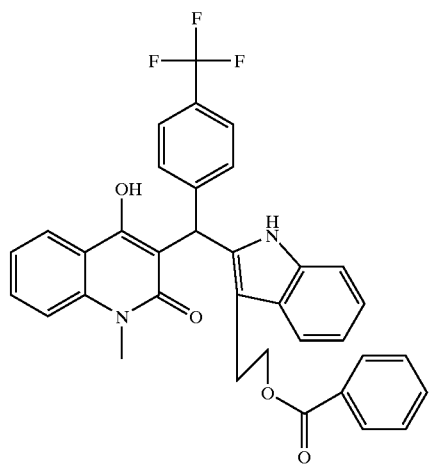
Compound No. 030
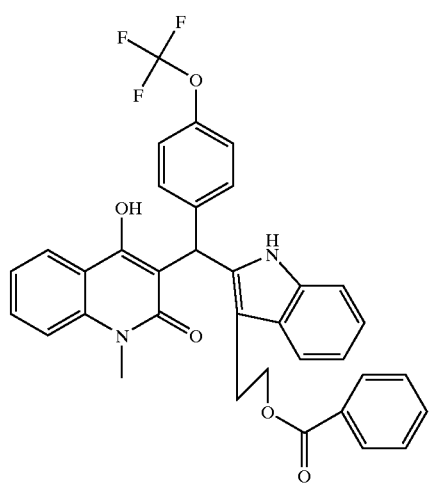
Compound No. 031
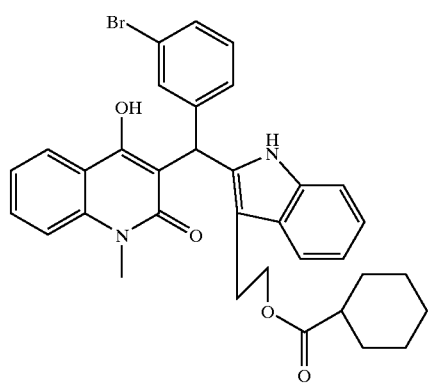
-continued
Compound No. 032
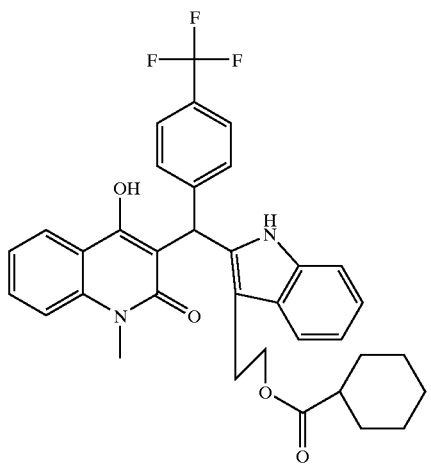
Compound No. 033
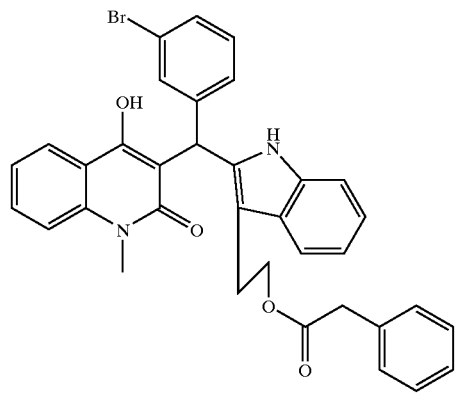
Compound No. 034
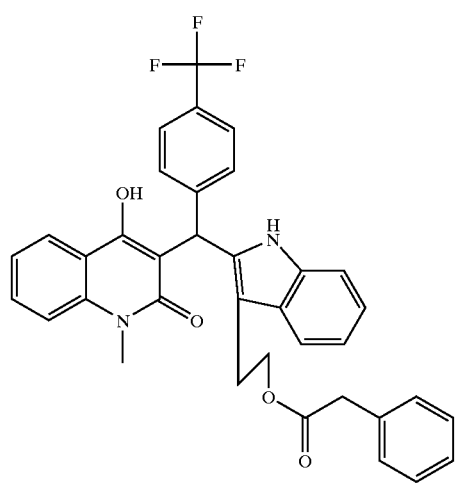

-continued
Compound No. 035
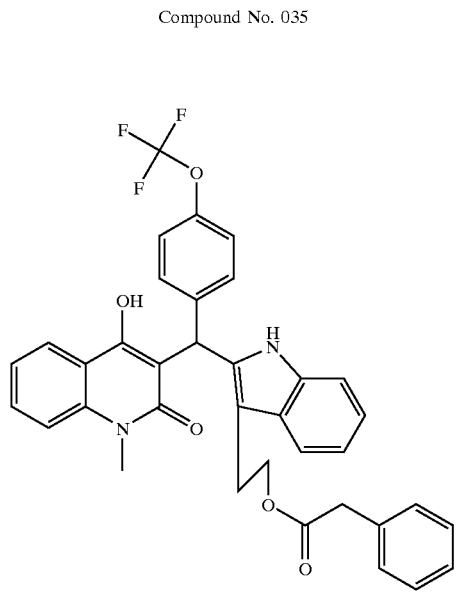
Compound No. 036
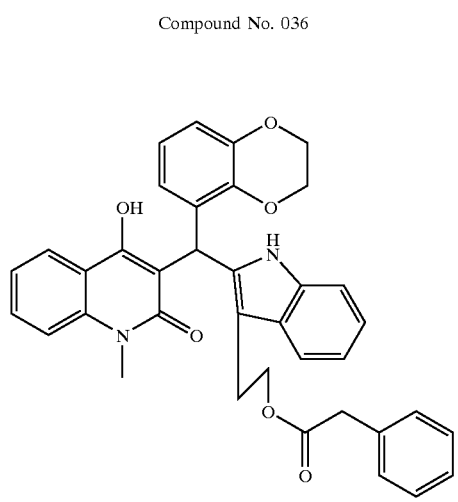
Compound No. 037
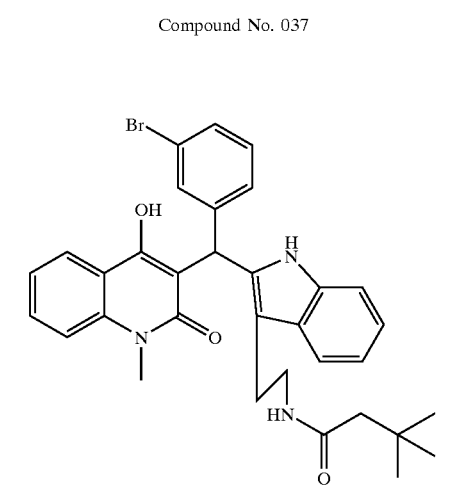
-continued
Compound No. 038
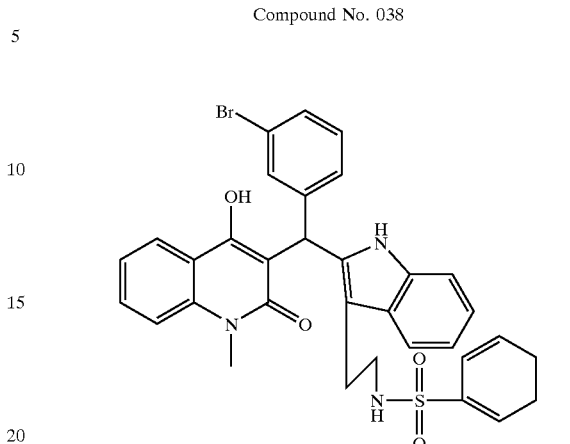
Compound No. 039
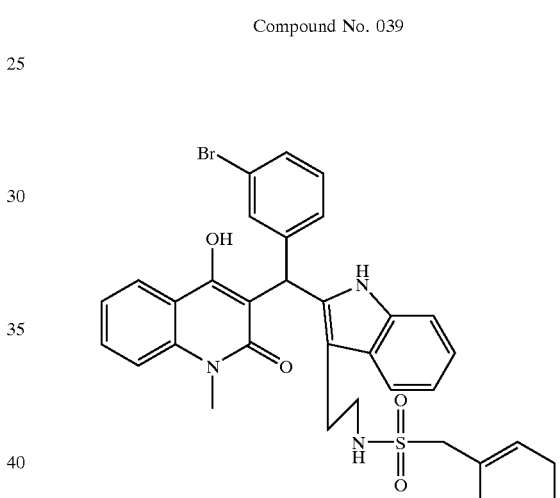
Compound No. 040
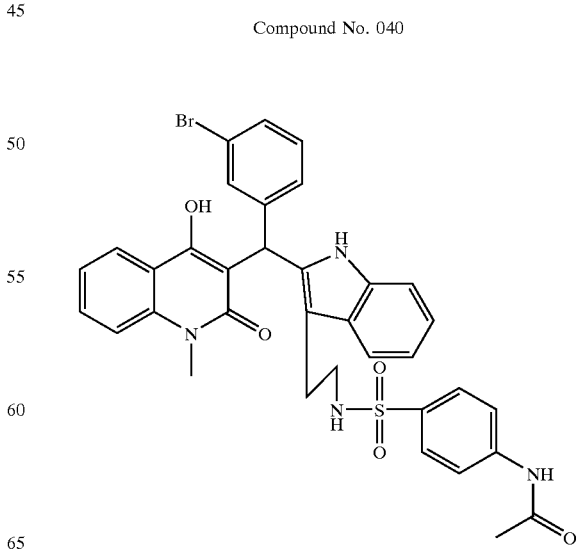

-continued
Compound No. 041
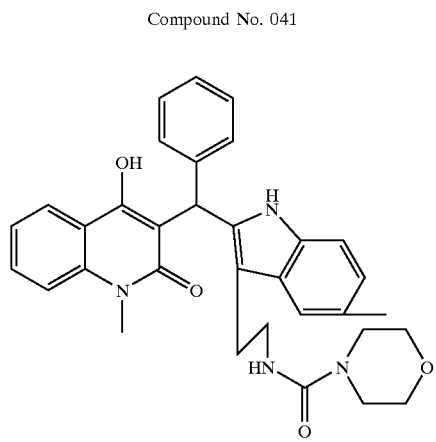
Compound No. 042
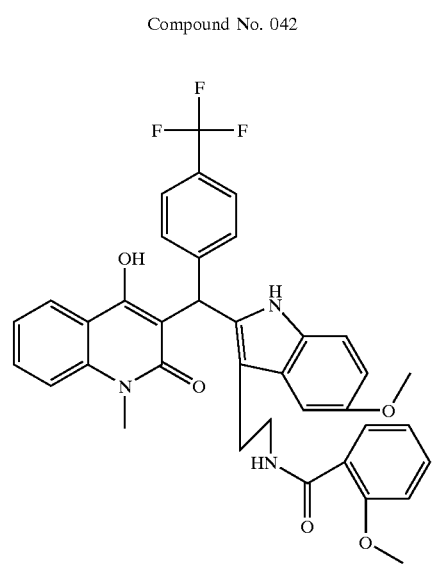
Compound No. 043
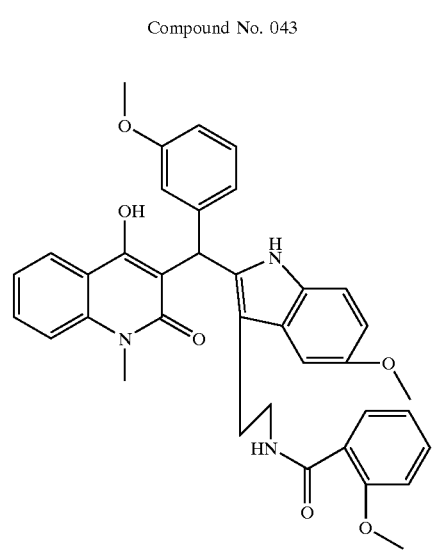
-continued
Compound No. 044
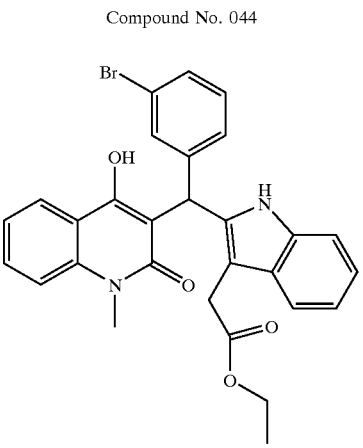
Compound No. 045
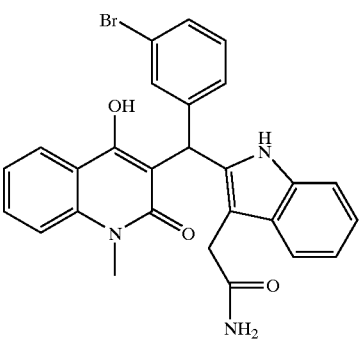
Compound No. 046
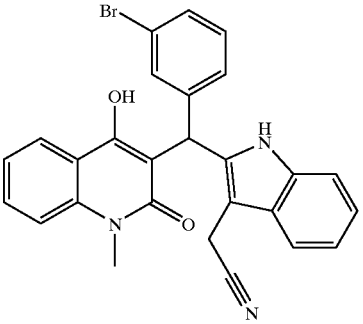
Compound No. 047
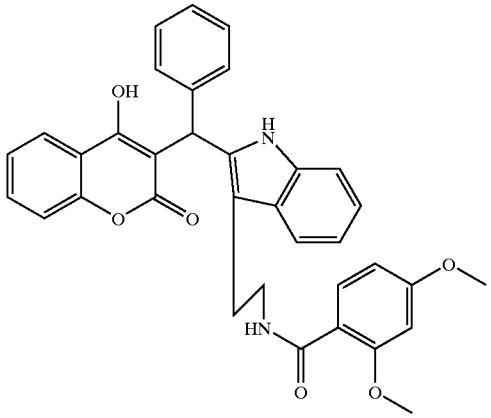

-continued
Compound No. 048
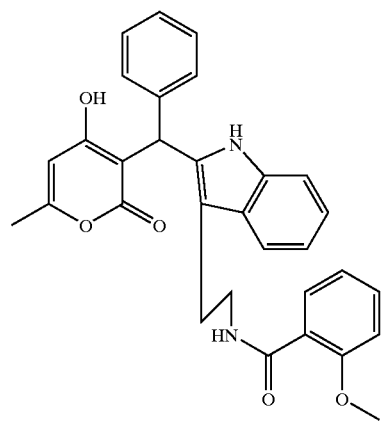
Compound No. 049
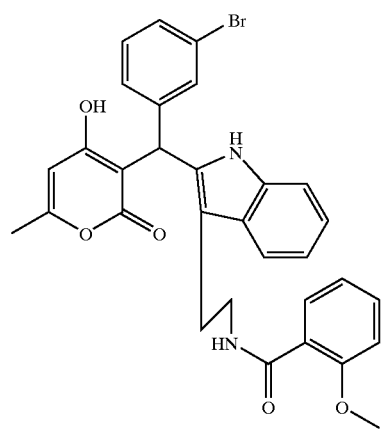
Compound No. 050
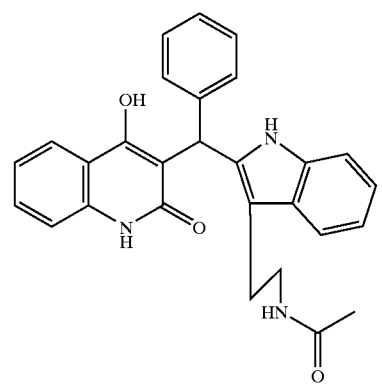
-continued
Compound No. 051
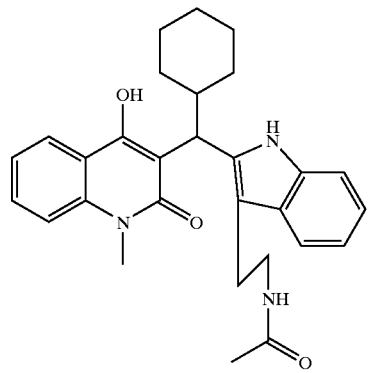
Compound No. 052
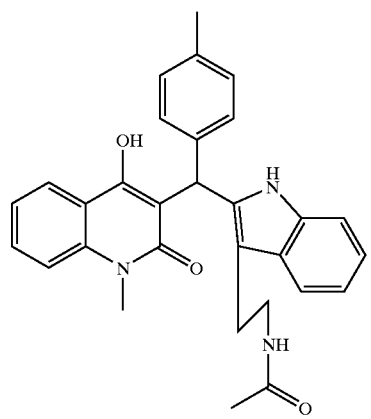
Compound No. 053
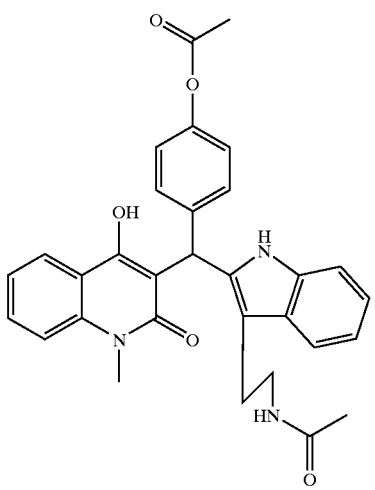

-continued
Compound No. 054
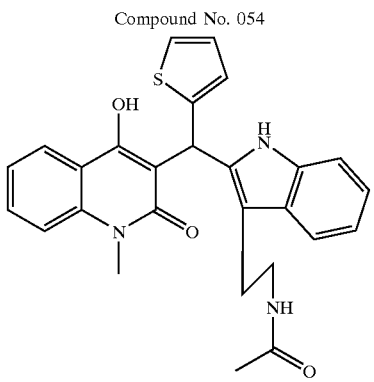
Compound No. 055
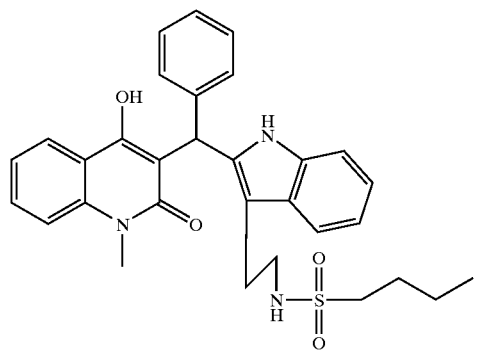
Compound No. 056
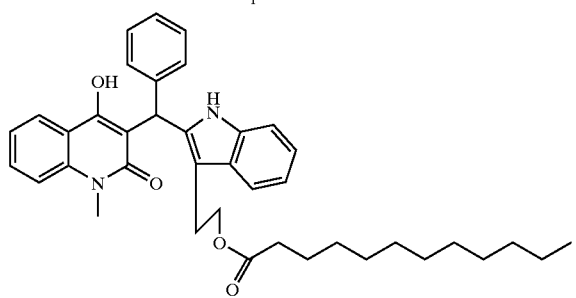
Compound No. 057
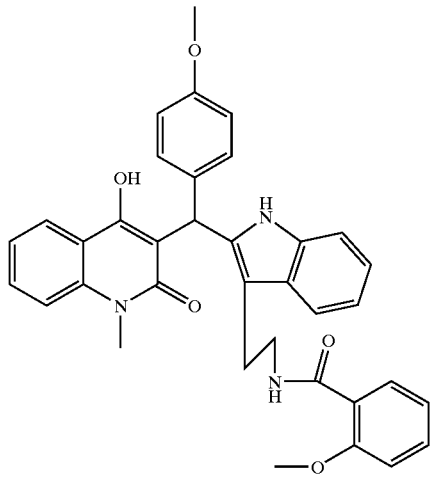
-continued
Compound No. 058
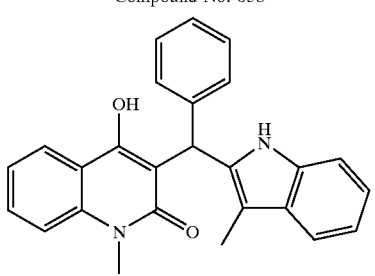
Compound No. 059
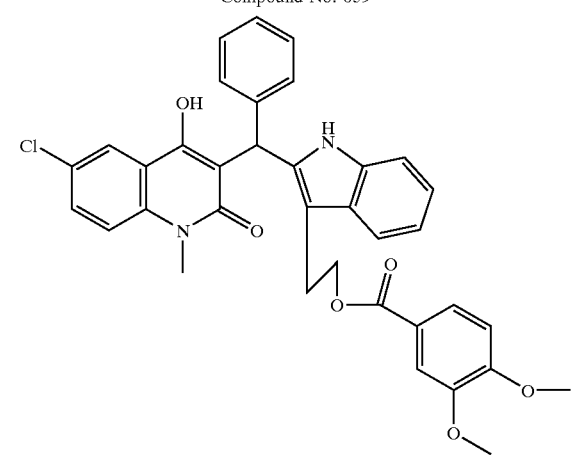
Compound No. 060
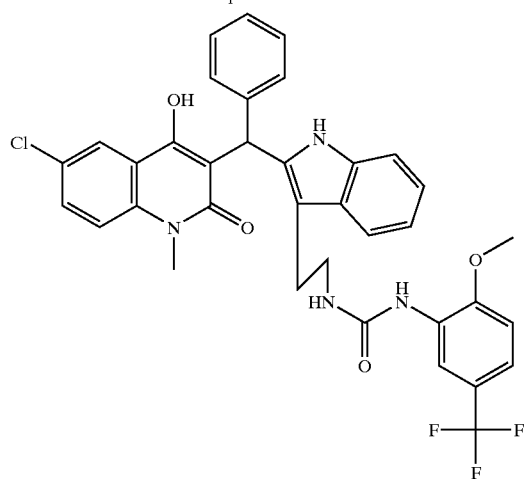
Compound No. 061
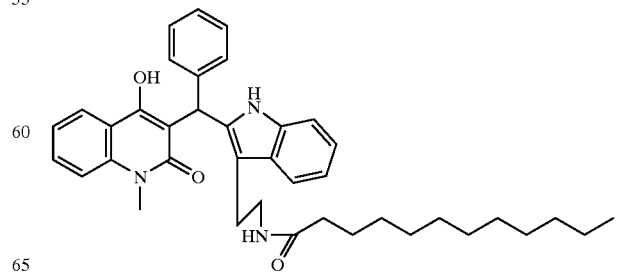

-continued
Compound No. 062
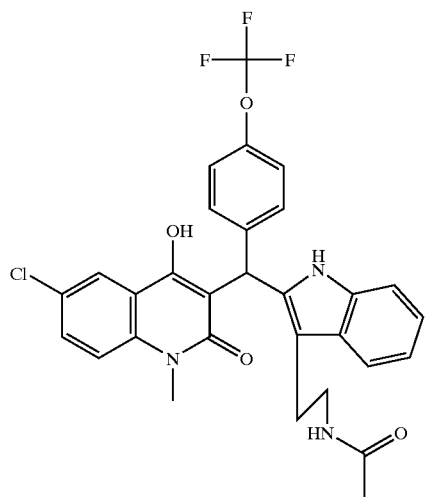
Compound No. 063
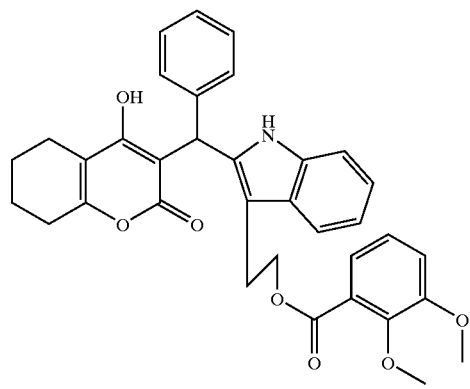
Compound No. 064
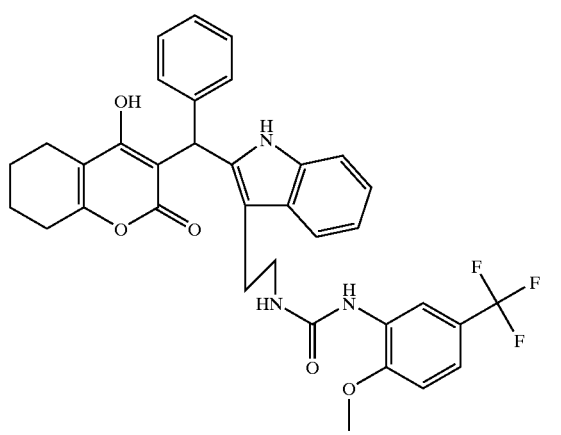
-continued
Compound No. 065
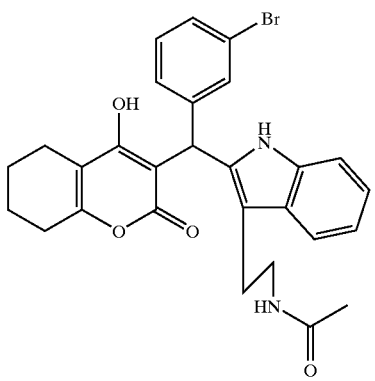
Compound No. 066
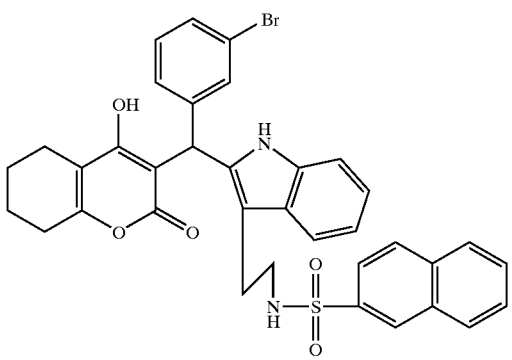
Compound No. 067
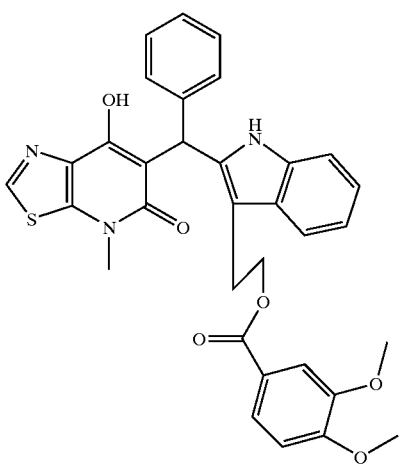

-continued
Compound No. 068
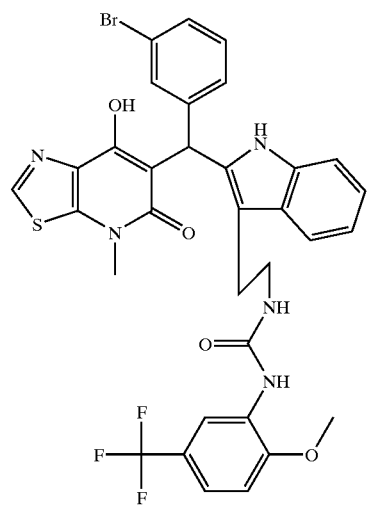
Compound No. 069
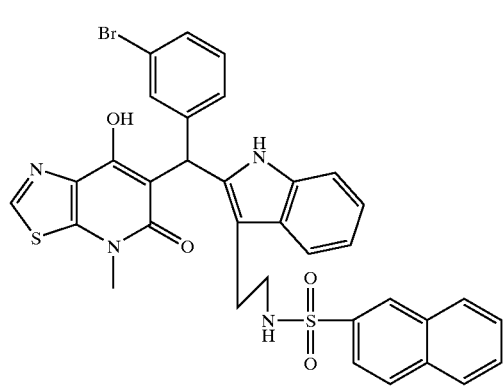
Compound No. 070
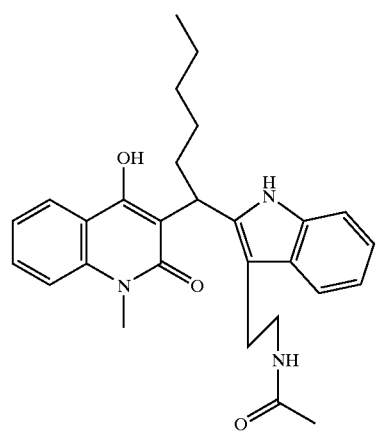
-continued
Compound No. 071
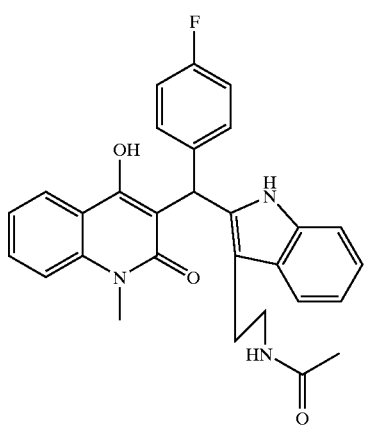
Compound No. 072
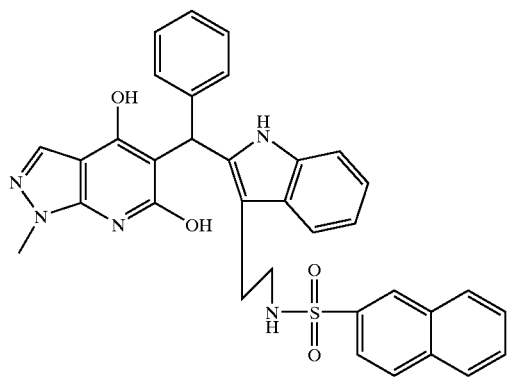
Compound No. 073
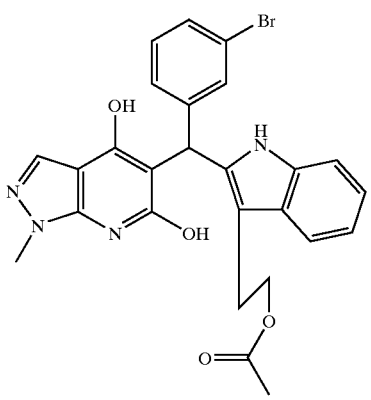

-continued
Compound No. 074
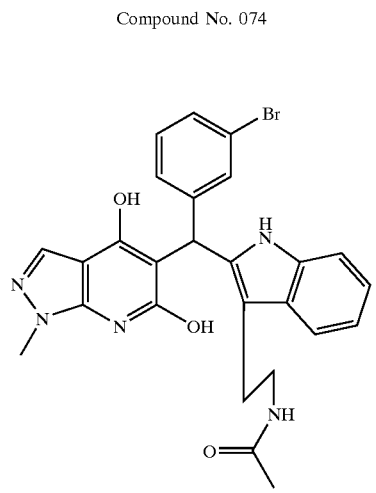
Compound No. 075
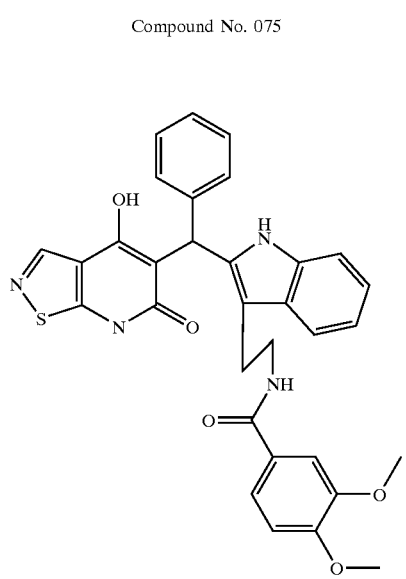
Compound No. 076
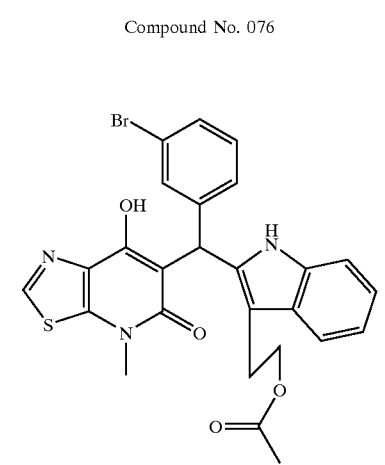
-continued
Compound No. 077
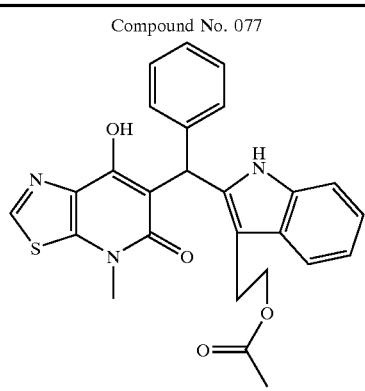
Compound No. 078
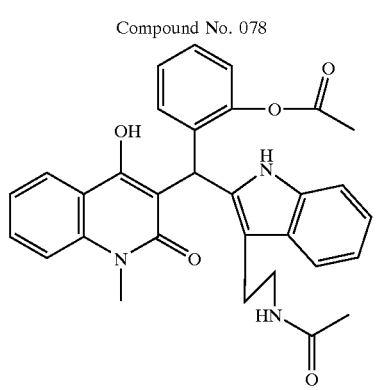
Compound No. 079
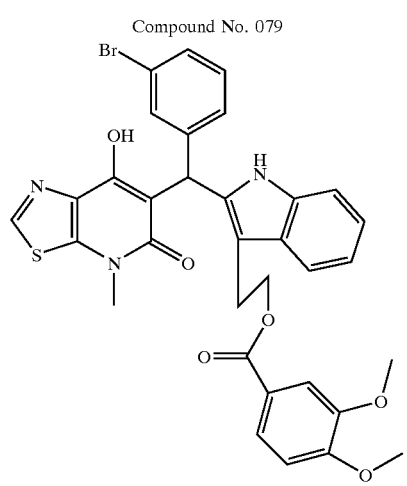
Compound No. 080
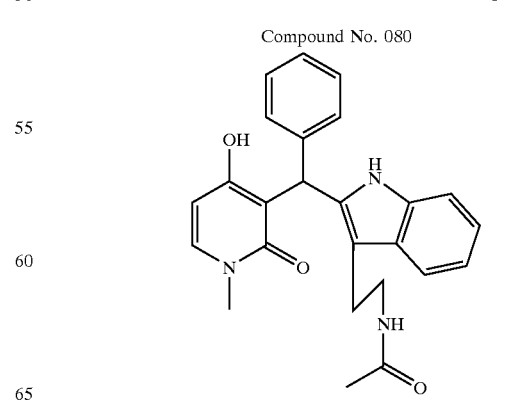

Compound No. 081

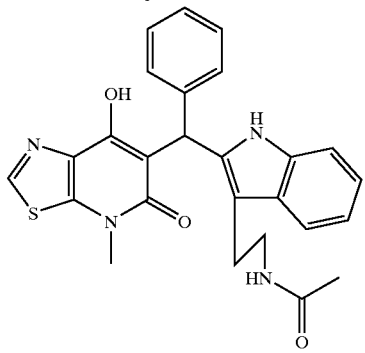

Compound No. 082

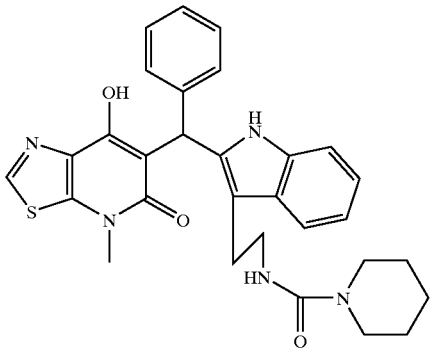

Compound No. 083

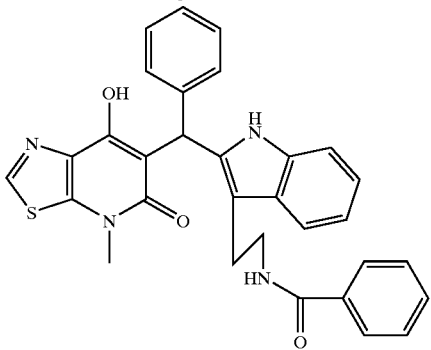

5. A pharmaceutical composition comprising as an active ingredient at least one of the indole derivative of the formula (I) as claimed in claim 1, or a pharmaceutically acceptable salt or a solvate thereof, in combination with a pharmaceutically acceptable carrier or carriers.

6. A pharmaceutical composition as claimed in claim 5, adapted for use as a therapeutic or prophylactic treatment of cardiac infarction, cardiomegaly, cardiac insufficiency, mycardosis, arteriosclerosis, hypertension, hemangioendotyrosis, periphery cardiovascular disorder, renal insufficiency, inflammation, allergy, atopic dermatitis, rheumatism, asthma, or bronchitis.

7. A composition comprising an indole derivative of the formula (I) as claimed in claim 1, or a pharmaceutically acceptable salt or a solvate thereof, said composition adapted for use as a chymase inhibitor.

8. A process for the preparation of an indole derivative which is a compound as claimed in claim 1 and represented by the formula (I)

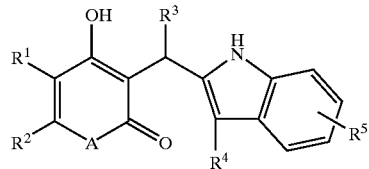

(I)

wherein A is an oxygen atom or a nitrogen atom which is bonded to a hydrogen atom or to a $(C_1-C_{10})$alkyl group which is, in turn, optionally substituted by a substituent selected from a halogen atom, a $(C_1-C_{10})$alkyl group, a $(C_1-C_{10})$alkoxy group and an acyl group;
  (i) $R^1$ and $R^2$ each stand for a hydrogen atom or an optionally substituted $(C_1-C_{10})$alkyl group, independently, or (ii) $R^1$ and $R^2$ as taken together form an optionally substituted $(C_5-C_{10})$cycloalkyl group or an optionally substituted $(C_6-C_{20})$aromatic ring, or (iii) $R^1$ and $R^2$ as taken together form an optionally substituted, saturated or unsaturated heterocycric ring containing one or more nitrogen, oxygen or sulfur atom(s), wherein the substituent(s) optionally present on the optionally substituted alkyl group or cycloalkyl group or aromatic ring or heterocyclic ring may be one or more and is or are selected from the group consisting of a halogen atom, a $(C_1-C_{10})$alkyl group and a $(C_1-C_{10})$alkoxy group;

$R^3$ stands for a hydrogen atom, an optionally substituted $(C_1-C_{10})$alkyl group, an optionally substituted $(C_5-C_{10})$cycloalkyl group or an optionally substituted $(C_6-C_{20})$aryl group, or $R^3$ stands for an optionally substituted, saturated or unsaturated heterocyclic group containing one or more nitrogen, oxygen or sulfur atom(s), wherein the substituent(s) optionally present on the optionally substituted alkyl group or cycloalkyl group or aryl group or heterocyclic group may be one or more and is or are selected from the group consisting of a halogen atom, a $(C_1-C_{10})$alkyl group, a $(C_1-C_{10})$alkoxy group, a halogenated $(C_1-C_{10})$alkyl group and a halogenated $(C_1-C_{10})$alkoxy group, and wherein two or more of the substituents as selected may be combined together to form one cyclic group;

$R_4$ stands for an optionally substituted $(C_1-C_{10})$alkyl group wherein the substituent(s) optionally present on the alkyl group may be one or more and is or are selected from the group consisting of a hydroxyl group, an acyl group, a $(C_1-C_{10})$alkyloxy-carbonyl group, a cyano group, an amino group, an acylamino group, an acyloxy group, an ureido group and a sulfonylamino group, and wherein the substituent(s) is or are optionally further substituted by one or more of a halogen atom, a $(C_1-C_{10})$alkyl group, a $(C_1-C_{10})$alkoxy group, a $(C_6-C_{20})$aryl group, an acyl group, an acylamino group, a halogenated $(C_1-C_{10})$alkyl group and a halogenated $(C_1-C_{10})$alkoxy group;

$R^5$ stands for a hydrogen atom, a halogen atom, a $(C_1-C_{10})$alkyl group or a $(C_1-C_{10})$alkoxy group;

but with such provisos that, in the formula (I):
  (i) when A is a methylated nitrogen atom and $R^1$ and $R^2$ as taken together form a benzene ring in association with the ring-forming carbon atoms to which $R^1$ and $R^2$ are bonded, there is excluded the case where $R^3$ is hydrogen atom, $R^4$ is 2-acetaminoethyl group and $R^5$ is hydrogen atom;
  (ii) when A is a methylated nitrogen atom and $R^1$ and $R^2$ as taken together form a benzene ring in association with the ring-forming carbon atoms to which $R^1$ and $R^2$ are bonded, there is excluded the case where $R^3$ is 4-hydroxyphenyl group, $R^4$ is 2-acetaminoethyl group and $R^5$ is hydrogen atom;

(iii) when A is a methylated nitrogen atom and $R^1$ and $R^2$ as taken together form a benzene ring in association with the ring-forming carbon atoms to which $R^1$ and are bonded, there is excluded the case where $R^3$ is hydrogen atom, $R^4$ is 2-hydroxyethyl group and $R^5$ is hydrogen atom;

(iv) when A is a methylated nitrogen atom and $R^1$ and $R^2$ as taken together form a benzene ring in association with the ring-forming carbon atoms to which $R^1$ and are bonded, there is excluded the case where $R^3$ is 4-hydroxyphenyl group, $R^4$ is 2-hydroxyethyl group and $R^5$ is hydrogen atom;

(v) when A is a methylated nitrogen atom and $R^1$ and $R^2$ as taken together form a benzene ring in association with the ring-forming carbon atoms to which $R^1$ and $R^2$ are bonded, there is excluded the case where $R^3$ is phenyl group, $R^4$ is 2-acetaminoethyl group and $R^5$ is hydrogen atom; and (vi) when A is a methylated nitrogen atom and $R^1$ and $R^2$ as taken together form a benzene ring in association with the ring-forming carbon atoms to which they are bonded, there is excluded the case where $R^3$ is phenyl group, $R^4$ is 2-hydroxyethyl group and $R^5$ is hydrogen atom;

said process comprising a single step reaction of three components (a)–(c) consisting of:

(a) a compound of the formula (II)

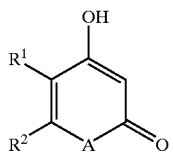

(II)

wherein A, $R^1$ and $R^2$ each have the same meanings as defined for the formula (I) above;

(b) an aldehyde compound of the formula (III) or formula (III') where:

$R^3$—CHO  (III)

wherein $R^3$ has the same meaning as defined for the formula (I) above and where:

$R^3$—CH=N—$R^9$  (III')

wherein $R^3$ has the same meaning as defined above, and $R^9$ is an optionally substituted, straight or branched $(C_1-C_{10})$alkyl group, an optionally substituted, straight or branched $(C_2-C_{10})$alkenyl group, an optionally substituted, straight or branched $(C_2-C_{10})$alkynyl group or an optionally substituted $C_6$ aryl or higher aryl group, and wherein the substituent(s) optionally present on the optionally substituted alkyl group, alkenyl group, alkynyl group or aryl group is or are selected from the group consisting of a halogen atom, an amino group, nitro group, a cyano group, an acyl group, an optionally substituted, straight or branched $(C_1-C_{10})$ alkyl group, an optionally substituted $(C_3-C_{20})$ cycloalkyl group, an optionally substituted, straight or branched $(C_2-C^{10})$alkenyl group, an optionally substituted, straight or branched $(C_2-C_{10})$alkynyl group, an optionally substituted $(C_6-C_{20})$aryl group, an acyloxy group, an optionally substituted, straight or branched $(C_1-C_{10})$alkoxy group, an acyl group, an acylamino group, a carbamoyl group, an ureido group, a sulfonylamino group, an optionally substituted, straight or branched $(C_1-C_{10})$alkyloxycarbonyl group, a carbamoyl group, an acyloxy group; and (c) an indole compound of the formula (IV)

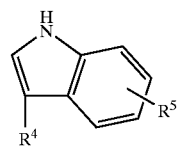

(IV)

wherein $R_4$ and $R^5$ each have the same meanings as defined for the formula (I), in an organic solvent or in an aqueous solvent in the presence of a substance capable of acting as an acid, with proviso such that, depending on the natures of the groups $R^1$ to $R^5$ of the compound of the formula (I) to be prepared, there are relevantly chosen a component (a) compound of the formula (II) bearing the relevantly corresponding $R^1$ and $R^2$, and a component (b) compound of the formula (III) or (III') bearing the relevantly corresponding $R^3$, and a component (c) compound of the formula (IV) bearing the relevantly corresponding $R^4$ and $R^5$, upon carrying out the reaction.

9. The process as claimed in claim 8, wherein the component (a) compound of the formula (II) is one of the following formulas:

| Compound Code | Chemical Structure |
|---|---|
| A01 | 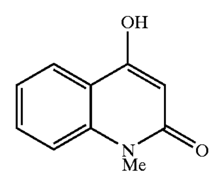 |
| A02 | 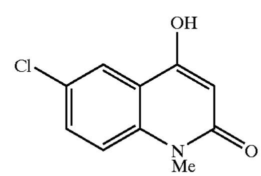 |
| A03 | 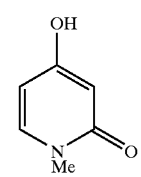 |

-continued
| Compound Code | Chemical Structure |
|---|---|
| A04 | 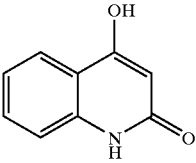 |
| A05 | 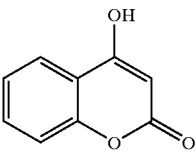 |
| A06 | 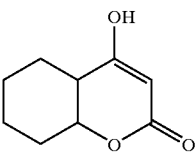 |
| A07 | 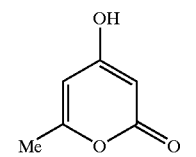 |
| A08 | 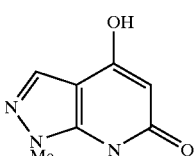 |
| A09 | 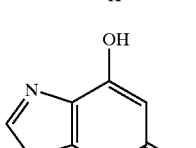 |
10. The process as claimed in claim 8, wherein the component (b) aldehyde compound of the formula (III) is a compound selected from the aldehydes which have the following formulas:
| Compound Code | Chemical Structure |
|---|---|
| B01 | 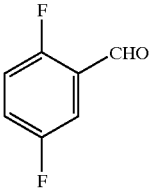 |
| B02 | 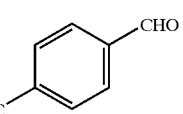 |
-continued
| Compound Code | Chemical Structure |
|---|---|
| B03 | 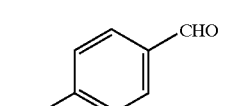 |
| B04 | 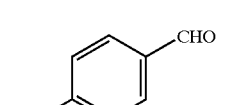 |
| B05 | 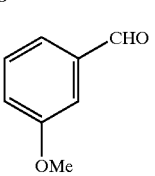 |
| B06 | 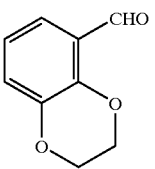 |
| B07 | 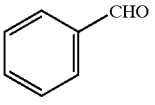 |
| B08 | 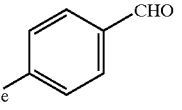 |
| B09 | 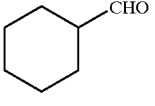 |
| B10 | 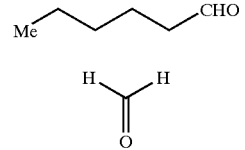 |
| B11 | 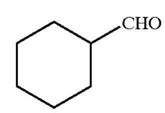 |
| B12 | 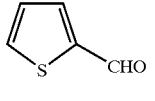 |
| B13 | 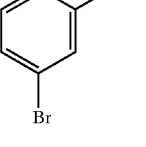 |
| B14 | 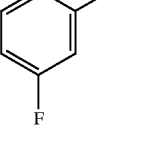 |

11. The process as claimed in claim 8, wherein the component (c) indole compound of the formula (IV) is a compound selected from the indoles which have the following formulas:

-continued
| Compound Code | Chemical Structure |
|---|---|
| C14 | 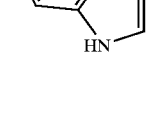 |
| C15 | 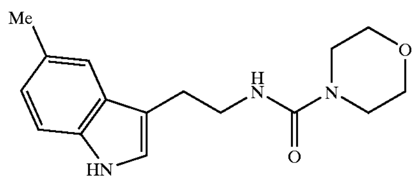 |
| C16 | 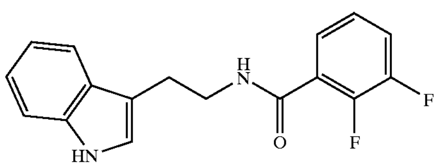 |
| C17 | 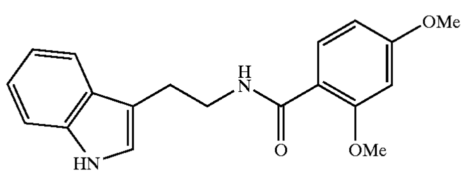 |
| C18 | 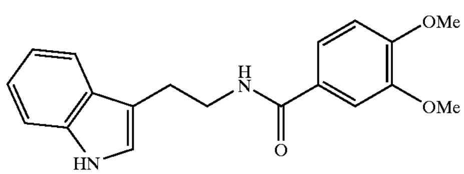 |
| C19 | 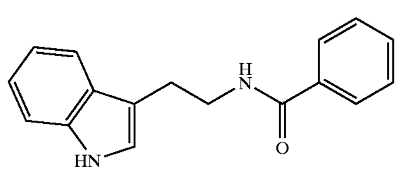 |
| C20 | 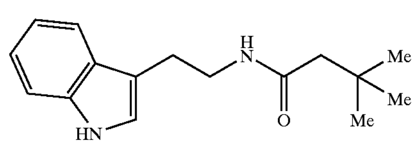 |
| C21 | 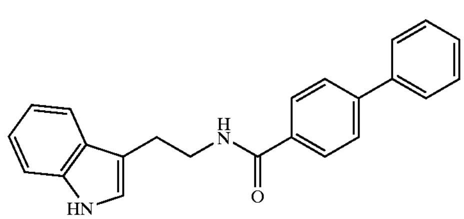 |
-continued
| Compound Code | Chemical Structure |
|---|---|
| C22 | 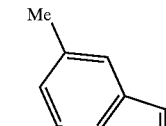 |
| C23 | 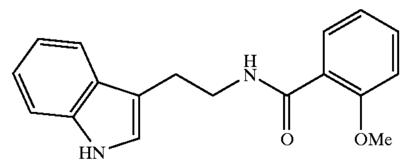 |
| C24 | 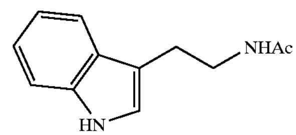 |
| C25 | 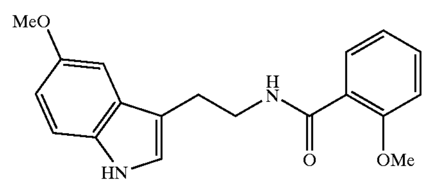 |
| C26 | 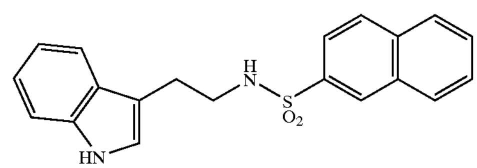 |
| C27 | 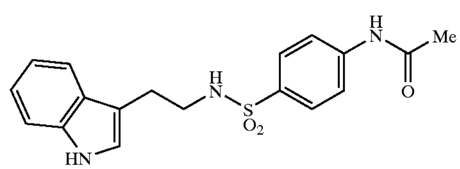 |
| C28 | 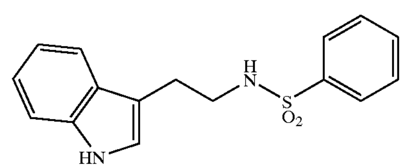 |
| C29 | 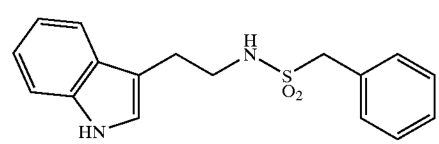 |
| C30 | 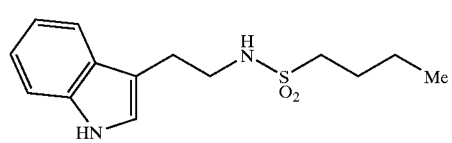 |

-continued

| Compound Code | Chemical Structure |
|---|---|
| C31 | 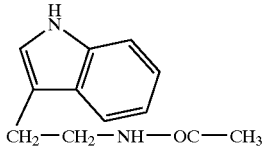 |
| C32 | 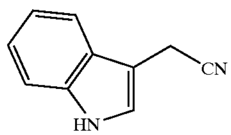 |
| C33 | 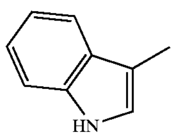 |
| C34 | 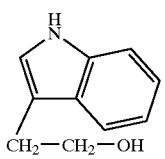 |
| C35 | 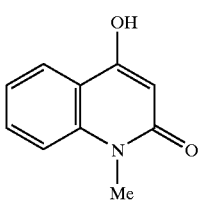 |

12. The process as claimed in claim 8, wherein the component (c) indole compound of the formula (IV) is neither 3-(2-acetaminoethyl)indole of the formula (β-1)

(β-1)

nor 3-(2-hydroxyethyl)indole of the formula (β-2)

(β-2)

in the case when component (a) is (i) 4-hydroxy-1-methyl-2-quinolinone of the formula (α)

(α)

where Me stands for methyl group and concurrently (ii) component (b) the aldehyde compound is formaldehyde or 4-hydroxybenzaldehyde or benzaldehyde.

13. A process for the preparation of a compound named as SF2809-I substance and having formula (A)

(A)

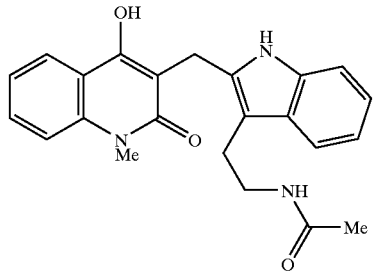

said process comprising reacting three components (a)–(c) in a single step reaction, the three components consisting of (a) 4-hydroxy-1-methyl-2-quinolinone of the formula (α)

(α)

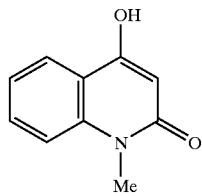

(b) formaldehyde of the formula (γ-1)

HCHO      (γ-1)

and (c) 3-(2-acetaminoethyl)indole of the formula (β-1)

(β-1)

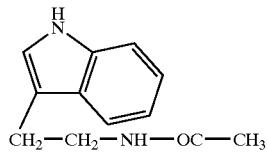

with the three components (a)–(c) in an organic solvent or an aqueous solvent in the presence of a substance capable of acting as an acid.

14. A process for the preparation of a compound named as SF2809-II substance and having formula (B)

(B)

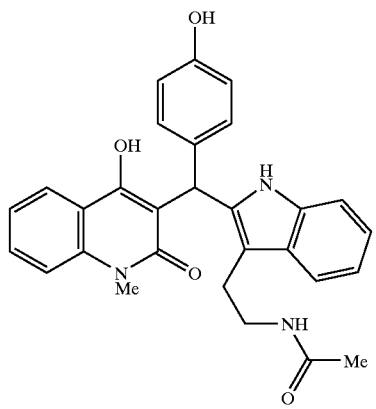

said process comprising reacting three components (a)–(c) in a single step, the three components consisting of (a) 4-hydroxy-1-methyl-2-quinolinone of the formula (α)

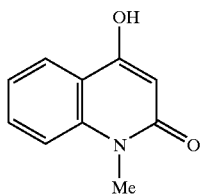

(α)

(b) 4-hydroxybenzaldehyde of the formula (β-2)

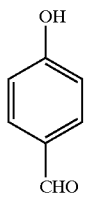

(γ-2)

and
(c) 3-(2-acetaminoethyl)indole of the formula (β-1)

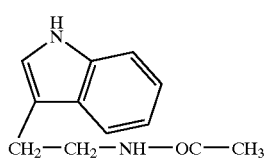

(β-1)

wherein the three components are in an organic solvent or an aqueous solvent in the presence of a substance capable of acting as an acid.

15. A process for the preparation of a compound named as SF2809-III substance and having formula (C)

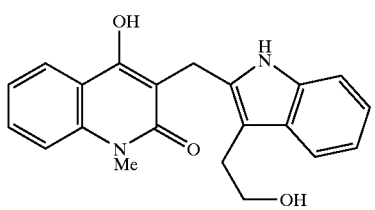

(C)

said process comprising reacting three components (a)–(c) in a single step reaction, the three components consisting of (a) 4-hydroxy-1-methyl-2-quinolinone of the formula (α)

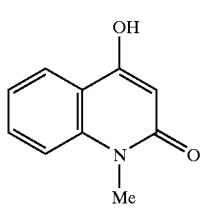

(α)

(b) formaldehyde of the formula (γ-1)

(γ-1)

and
(c) 3-(2-hydroxyethyl)indole of the formula (β-2)

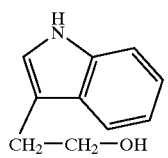

(β-2)

wherein the three components are in an organic solvent or an aqueous solvent in the presence of a substance capable of acting as an acid.

16. A process for the preparation of a compound named as SF2809-IV substance and having formula (D)

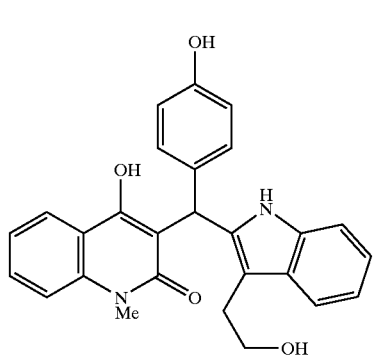

(D)

said process comprising reacting three components (a)–(c), in a single step reaction, the three components consisting of (a) 4-hydroxy-1-methyl-2-quinolinone of the formula (a)

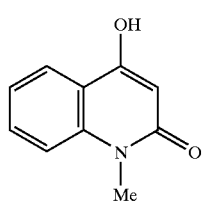

(α)

(b) 4-hydroxybenzaldehyde of the formula (γ-2)

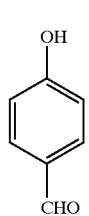

(γ-2)

and (c) 3-(2-hydroxyethyl)indole of the formula (β-2)

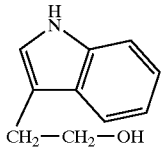
(β-2)

wherein the three are in an organic solvent or an aqueous solvent in the presence of a substance capable of acting as an acid.

17. A process for the preparation of a compound named as SF2809-V substance and having formula (E)

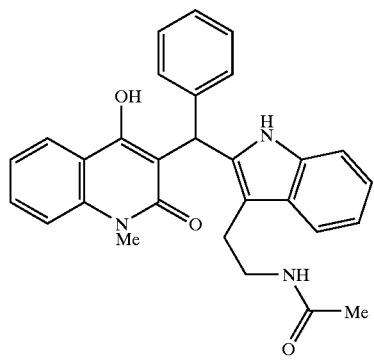
(E)

said process comprising reacting three components (a)–(c) in a single step reaction, the three components consisting of (a) 4-hydroxy-1-methyl-2-quinolinone of the formula (α)

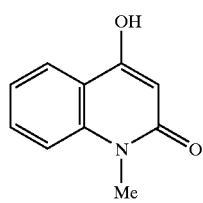
(α)

(b) benzaldehyde of the formula (γ-3)

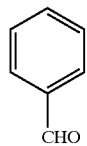
(γ-3)

and
(c) 3-(2-acetaminoethyl)indole of the formula (β-1)

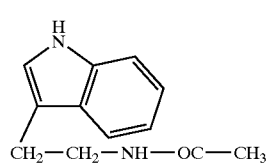
(β-1)

wherein the three components are in an organic solvent or an aqueous solvent in the presence of a substance capable of acting as an acid.

18. A process for the preparation of a compound named as SF2809-VI substance and having formula (F)

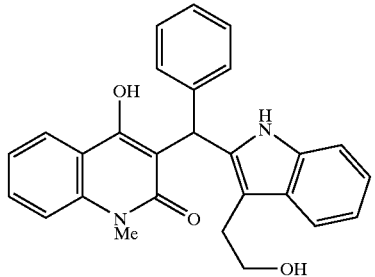
(F)

said process comprising reacting three components (a)–(c) in a single step reaction, the three components consisting of (a) 4-hydroxy-1-methyl-2-quinolinone of the formula (α)

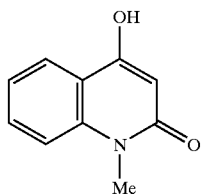
(α)

(b) benzaldehyde of the formula (γ-3)

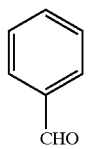
(γ-3)

and
(c) 3-(2-acetaminoethyl)indole of the formula (β-1)

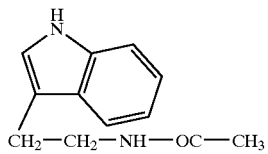
(β-1)

wherein the three are in an organic solvent or an aqueous solvent in the presence of a substance capable of acting as an acid.

* * * * *

UNITED STATES PATENT AND TRADEMARK OFFICE
CERTIFICATE OF CORRECTION

PATENT NO.        : 6,852,734 B2
APPLICATION NO. : 10/275111
DATED             : February 8, 2005
INVENTOR(S)       : Yamamoto et al.

It is certified that error appears in the above-identified patent and that said Letters Patent is hereby corrected as shown below:

On the title page, field (75), change "Hariyama" to --Harimaya--, and "Yanagisawa" to --Fujihira--.

Signed and Sealed this

Twelfth Day of September, 2006

JON W. DUDAS
*Director of the United States Patent and Trademark Office*